(12) United States Patent
Banai et al.

(10) Patent No.: US 8,722,411 B2
(45) Date of Patent: May 13, 2014

(54) BRUCELLA PHAGE POLYNUCLEOTIDES AND USES THEREOF

(75) Inventors: Menachem Banai, Mevasseret Zion (IL); Valeria Strada, Haifa (IL); Svetlana Bardenstein, Ramla (IL); Itzhak Ben-Asouli, Kfar-HaNagid (IL); Farhat Osman, Sakhnin (IL)

(73) Assignee: The State of Israel, Ministry of Agriculture & Rural Development, Kimron Veterinary Institute, Beit-Dagan (IL)

( * ) Notice: Subject to any disclaimer, the term of this patent is extended or adjusted under 35 U.S.C. 154(b) by 0 days.

(21) Appl. No.: 13/500,360

(22) PCT Filed: Oct. 7, 2010

(86) PCT No.: PCT/IL2010/000812
§ 371 (c)(1),
(2), (4) Date: Apr. 5, 2012

(87) PCT Pub. No.: WO2011/042901
PCT Pub. Date: Apr. 14, 2011

(65) Prior Publication Data
US 2012/0208280 A1    Aug. 16, 2012

Related U.S. Application Data

(60) Provisional application No. 61/272,574, filed on Oct. 7, 2009.

(51) Int. Cl.
*C12N 15/74*    (2006.01)
*C12N 15/33*    (2006.01)
*C12N 1/21*     (2006.01)

(52) U.S. Cl.
USPC .......... 435/471; 435/5; 435/252.3; 435/320.1

(58) Field of Classification Search
None
See application file for complete search history.

(56) References Cited

U.S. PATENT DOCUMENTS

| 7,833,706 B2 * | 11/2010 | Begovich et al. ............ 435/6.14 |
| 2003/0017449 A1 | 1/2003 | Adams et al. |
| 2006/0292135 A1 | 12/2006 | Loomis et al. |
| 2007/0202115 A1 | 8/2007 | Bullerdiek |
| 2009/0068638 A1 | 3/2009 | Shabani et al. |
| 2009/0155768 A1 | 6/2009 | Scholl et al. |

FOREIGN PATENT DOCUMENTS

WO    WO 2011/042901    4/2011

OTHER PUBLICATIONS

International Preliminary Report on Patentability Dated Apr. 19, 2012 From the International Beureau of WIPO RE. Application No. PCT/IL2010/000812.
International Search Report and the Written Opinion Dated Aug. 9, 2011 From the International Searching Authority Re: PCT/IL2010/00812.
Invitation to Pay Additional Fees Dated May 18, 2011 From the International Searching Authority Re. Application No. PCT/IL2010/00812.
Chain et al. "*Ochrobactrum anthropi* ATCC 49188 Chromosome 1, Complete Sequence", GenBank Direct Submission CP000758.1, Retrieved From the Internet, Apr. 24, 2008, Locus 'Oant_0025', Nucleotides 25982-26617.
Kuhn et al. "Bacteriophage Felix 01 Red Gene, Complete CDs; and Unknown Genes", GenBank Nucleotide, Accession No. AF071201.
Rigby et al. "Properties and Partial Genetic Characterization of Nepean Phage and Other Lytic Phages of *Brucella* Species", Canadian Journal of Veterinary Research, 53(3): 319-325, Jul. 1989.
Zhu et al. "Molecular Characterization of Tb, A New Approach for an Ancient Brucellaphage", International Journal of Molecular Sciences, 10: 2999-3011, 2009.
Notification to Pay the Restoration Fee for Unity Dated Feb. 7, 2014 From the State Intellectual Property Office of the People's Republic of China Re. Application No. 201080055381.3 and Its Summary in English.

* cited by examiner

*Primary Examiner* — Padma V Baskar

(57) ABSTRACT

An isolated polynucleotide is disclosed which comprises a nucleic acid sequence of a *Brucella* phage, the nucleic acid sequence being specific to the *Brucella* phage and comprising a sequence selected from the group consisting of SEQ ID NOs: 387-393. An exemplary polynucleotide sequence is one which comprises at least 100 consecutive nucleotides of a nucleic acid sequence as set forth in SEQ ID NO: 396. Uses of such sequences are further disclosed.

9 Claims, 5 Drawing Sheets
(4 of 5 Drawing Sheet(s) Filed in Color)

US 8,722,411 B2

BRUCELLA PHAGE POLYNUCLEOTIDES AND USES THEREOF

RELATED APPLICATIONS

This application is a National Phase of PCT Patent Application No. PCT/IL2010/000812 having International filing date of Oct. 7, 2010, which claims the benefit of priority of U.S. Provisional Patent Application No. 61/272,574 filed on Oct. 7, 2009. The contents of the above applications are all incorporated herein by reference.

FIELD AND BACKGROUND OF THE INVENTION

The present invention, in some embodiments thereof, relates to *Brucella* phage nucleic acid sequences and uses thereof.

*Brucella* are Gram negative, small coccobacilli bacteria. They are animal pathogens causing abortions in the natural hosts, in the latest period of pregnancy. Genus *Brucella* includes 10 species divided to smooth and rough outer membrane LPS bearing organisms. Three smooth *Brucella* species, (*B. melitensis, B. abortus* and *B. suis*) associated with small ruminant, bovid and swine brucellosis, respectively, are zoonotic to humans. Less frequently, *B. ceti* and *B. pinnipedialis* associated with marine mammal brucellosis have been documented as causative agents of human brucellosis. In addition, *B. canis* that is associated with canine brucellosis is a rough organism that causes human infection. The disease in humans is presented as undulant fever also known as Malta fever, and it may sequel to a chronic disease or manifestation of meningitis, osteomyelitis, endocarditis and other complications. In rare occasions the disease may become fatal.

*Brucella* phages are bacterial viruses specific to *Brucella* species. A review of *Brucella* phages and their taxonomical relatedness was published in 1981. All contemporarily known *Brucella* phages were shown to comprise a similar icosahedral head and short tail morphology belonging to the family Podoviradae. The studied phages were shown to be closely related according to antigenic and physiological properties and resistance to chemical and physical agents. These findings have led the authors to include the summarized variants within a single species and propose phage Tb as type virus (Ackerman, H.-W., Simon, F., and Verger, J.-M. 1981. Intervirology 16: 1-7).

*Brucella* phages have linear double stranded DNA in size around 38 kilo base pairs. Restriction enzyme digestion analyses of phages Tb, Fi, Wb, Iz and R/C have shown similarity amongst the DNAs and little evidence has been found for lysogenic existence of the phages or presence of plasmid forms in the hosts.

Previous studies have established guanosine—cytosine content of 45.3-46.7% in phage Tb whereas a higher percentage of 48.9% was anticipated in other phages.

Use of phages as therapeutic agents of a pathogenic disease has been indicated by several researchers (Brussow, H. 2005. Microbiol. 151: 2133-2140; Summers, W. C. 2001. Ann. Rev. Microbiol. 55: 437-451).

In addition, *Brucella* phages have been employed in *Brucella* typing and a phage susceptibility test has become instrumental in classification and establishing a taxonomical tree of genus *Brucella*. Specifically, it was suggested that division of genus *Brucella* into nomen-species is partly justified according to their species specific phage susceptibilities that also correlated well with host affiliation of the strains. *Brucella* phages have been divided into 7 groups according to their infectivity to *Brucella* spp. Phage Izatnagar ($Iz_1$) represents group 6 that is infective to all smooth *Brucella* nomenspecies and partly to rough strains (Corbel and Tolari, 1988, Res Vet Sci; 44: 45-49).

Zhu et al., 2009 [ Int. J. Mol. Sci. 10: 2999-3011] teaches a partial sequence for the Tb (Tbilisi) *Brucella* phage.

Rigby et al., 1989 [ Can J Vet Res. 53: 319-325] teaches a partial sequence for Nepean phage and other lytic phages of *Brucella* species.

U.S. Patent No. 20030017449 teaches detection of *Brucella* using *Brucella* phage.

SUMMARY OF THE INVENTION

According to an aspect of some embodiments of the present invention there is provided an isolated polynucleotide comprising a nucleic acid sequence of a *Brucella* phage, the nucleic acid sequence being specific to the *Brucella* phage and comprising a sequence selected from the group consisting of SEQ ID NOs: 396 and 387-393.

According to an aspect of some embodiments of the present invention there is provided an isolated polynucleotide being at least 15 nucleotides in length which hybridizes to the isolated polynucleotide of the present invention.

According to an aspect of some embodiments of the present invention there is provided a method of down-regulating expression of a gene of interest in a bacteria, the method comprising transforming bacteria with a nucleic acid construct which comprises a *Brucella* phage regulatory sequence, thereby down-regulating expression of the gene of interest.

According to an aspect of some embodiments of the present invention there is provided a nucleic acid construct comprising at least 100 nucleotides of a nucleic acid sequence as set forth in SEQ ID NO: 396.

According to an aspect of some embodiments of the present invention there is provided a nucleic acid construct comprising:

i. a polynucleotide encoding a gene of interest operationally fused to a *Brucella* promoter;

ii. a first *Brucella* phage sequence fused to a 5' end of the promoter, the first sequence comprising at least 100 nucleotides of a nucleic acid sequence as set forth in SEQ ID NO: 394; and iii. a second *Brucella* phage sequence fused to a 3' end of the gene of interest, the second sequence comprising at least 100 nucleotides of a nucleic acid sequence as set forth in SEQ ID NO: 395.

According to an aspect of some embodiments of the present invention there is provided a recombinant *Brucella* phage which identifies *Brucella* bacteria by outputting a detectable signal.

According to an aspect of some embodiments of the present invention there is provided an isolated *Brucella* bacterial cell comprising the recombinant *Brucella* phage of the present invention.

According to an aspect of some embodiments of the present invention there is provided a method of diagnosing a *Brucella* infection in a subject, the method comprising contacting a sample of the subject with the recombinant *Brucella* phage of the present invention, thereby diagnosing the *Brucella* infection.

According to an aspect of some embodiments of the present invention there is provided a method of diagnosing a *Brucella* infection in a subject, the method comprising contacting a sample of the subject with the isolated *Brucella* bacterial cells of the present invention, thereby diagnosing the *Brucella* infection.

According to some embodiments of the invention, the isolated polynucleotide comprises at least 100 consecutive nucleotides of a nucleic acid sequence as set forth in SEQ ID NO: 396.

According to some embodiments of the invention, the isolated polynucleotide comprises the sequence as set forth in SEQ ID NO: 396.

According to some embodiments of the invention, the isolated polynucleotide comprises a nucleic acid sequence as set forth in SEQ ID NOs: 387-393.

According to some embodiments of the invention, the isolated polynucleotide has the nucleic acid sequence as set forth in SEQ ID NO: 1.

According to some embodiments of the invention, the isolated polynucleotide comprises at least one nucleic acid sequence being selected from the group consisting of SEQ ID NO: 394 and 395 in a forward or reverse orientation.

According to some embodiments of the invention, the isolated polynucleotide further comprises a heterologous nucleic acid sequence and a heterologous promoter sequence which directs expression of the heterologous nucleic acid sequence.

According to some embodiments of the invention, the nucleic acid sequence comprises a transcriptional regulatory region.

According to some embodiments of the invention, the transcriptional regulatory region comprises a *brucella* phage promoter.

According to some embodiments of the invention, the isolate polynucleotide comprises a sequence as set forth in SEQ ID NOs: 2-386.

According to some embodiments of the invention, the heterologous nucleic acid sequence encodes a detectable moiety.

According to some embodiments of the invention, the heterologous nucleic acid sequence encodes a polypeptide which is lethal to *Brucella*.

According to some embodiments of the invention, the bacteria comprises *Brucella* bacteria.

According to some embodiments of the invention, a strain of the *Brucella* bacteria comprises *B. Suis* or *B. melitensis*.

According to some embodiments of the invention, the gene is endogenous to the bacteria.

According to some embodiments of the invention, the gene is endogenous to a phage of the bacteria.

According to some embodiments of the invention, the regulatory sequence comprises at least 100 nucleotides of a nucleic acid sequence as set forth in SEQ ID NO: 396.

According to some embodiments of the invention, the regulatory sequence comprises the sequence as set forth in SEQ ID NO: 396.

According to some embodiments of the invention, the regulatory sequence further comprises the sequence as set forth in SEQ ID NO: 397.

According to some embodiments of the invention, the regulatory sequence is flanked by a transposon sequence.

According to some embodiments of the invention, the nucleic acid construct comprises a nucleic acid sequence as set forth in SEQ ID NO: 396.

According to some embodiments of the invention, the nucleic acid sequence is flanked by a transposon sequence.

According to some embodiments of the invention, the gene of interest encodes a therapeutic polypeptide.

According to some embodiments of the invention, the gene of interest encodes a detectable moiety.

According to some embodiments of the invention, the gene of interest is comprised in a Lux operon.

According to some embodiments of the invention, the detectable signal is a luminescent signal.

According to some embodiments of the invention, the recombinant *Brucella* phage comprise lytic activity.

According to some embodiments of the invention, a genome of the phage comprises a polynucleotide sequence which encodes the detectable signal.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

Figure 1:
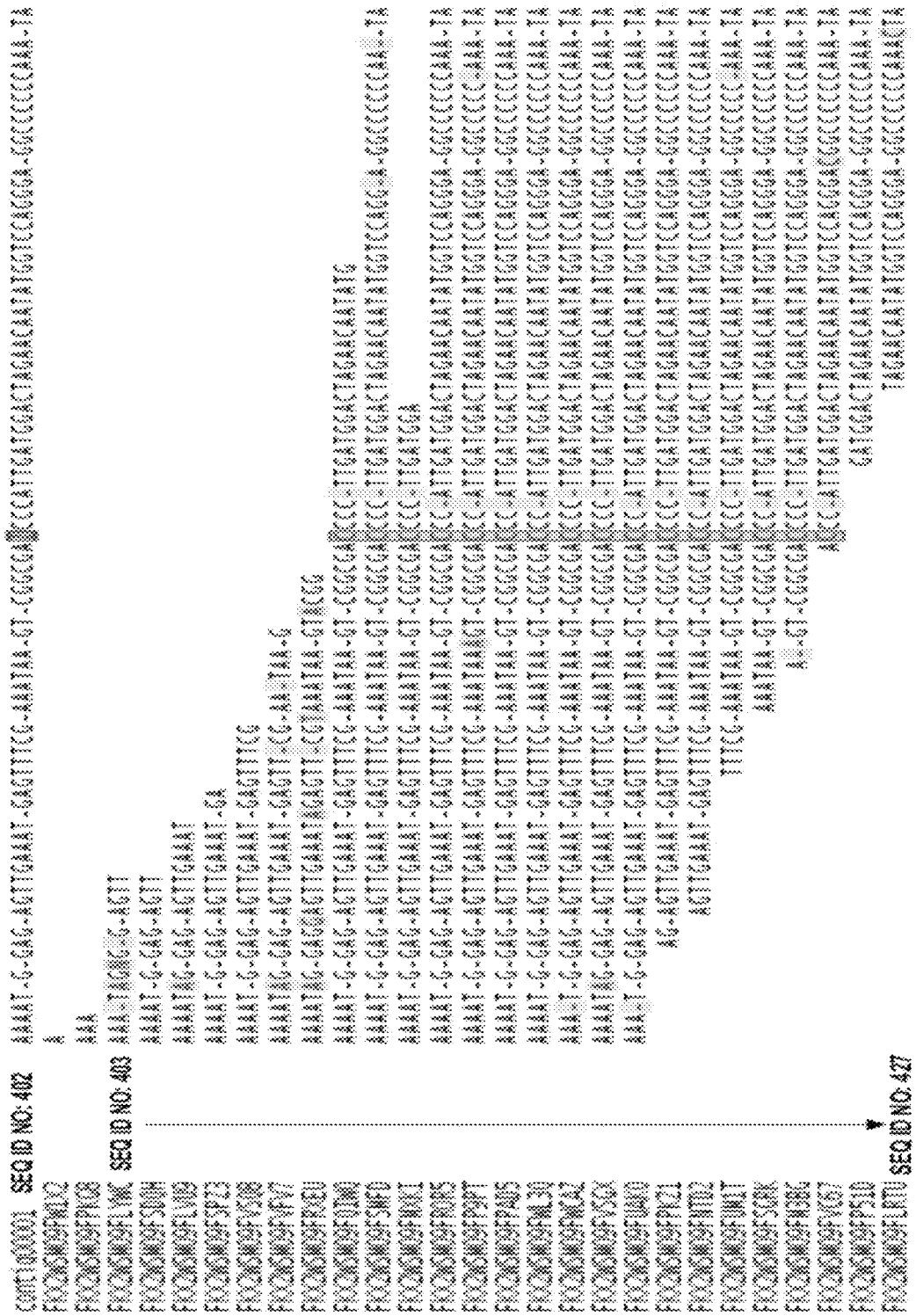

FIG. 1 shows read sequences that corroborate on the specific consensus largest contigue of 38255 nucleotides identified by the sequencing machine. It can be seen that C and A are each distributed equally in 8 contigues at nucleotides 5549 and 5550 leaving a gap of a single nucleotide in one or the other position. This indicates an SNP (or heterozygote) in position 5549 between C and A, respectively. In each construct, N is correctly identified as C.

Figure 2:
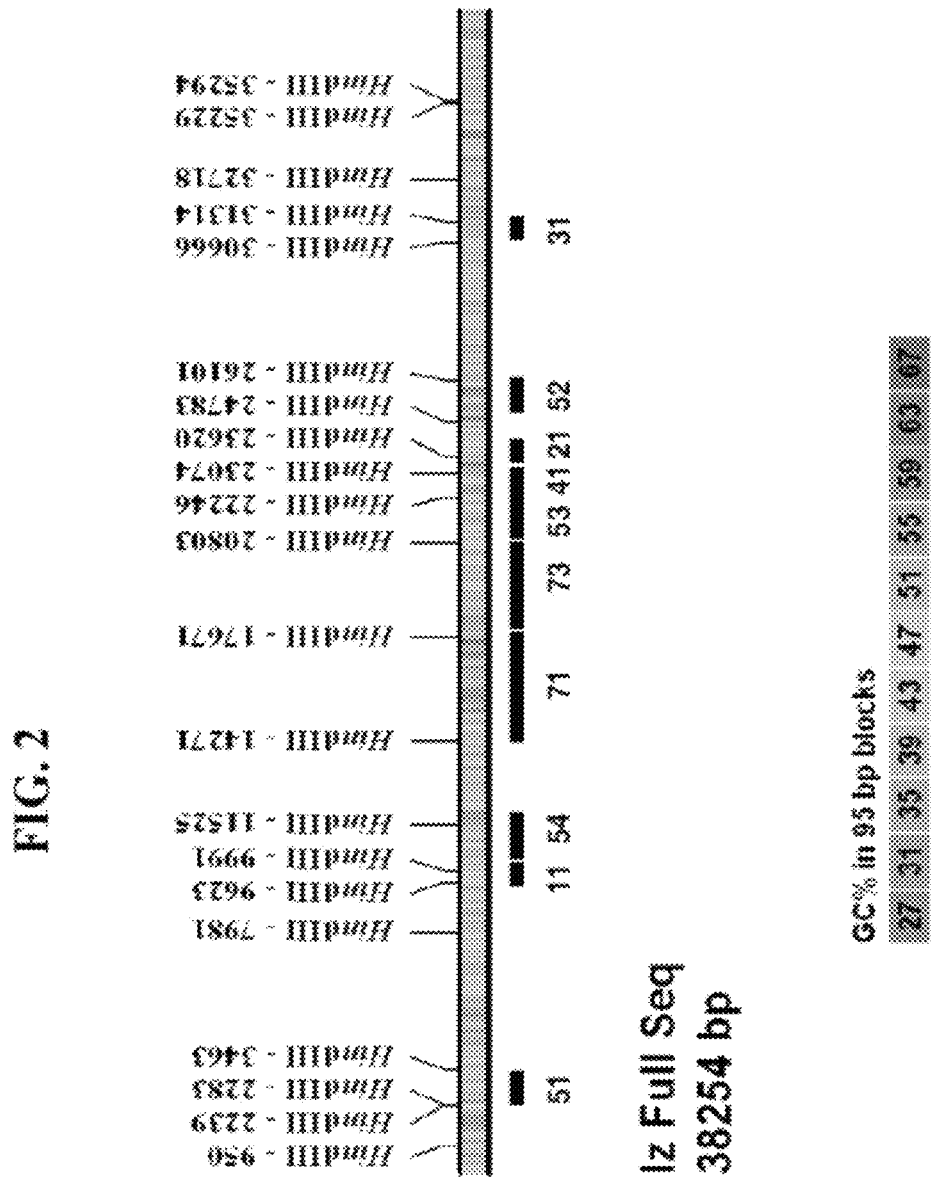

FIG. 2 depicts 9 phage $Iz_1$ DNA fragments that have been successfully sub-cloned into plasmid pBS. These fragments hybridized with whole Phage $Iz_1$ genomic DNA and nucleotide sequencing confirmed their accurate sequence that was identical to the overlapping sequences in the complete phage genome.

Figure 3A:
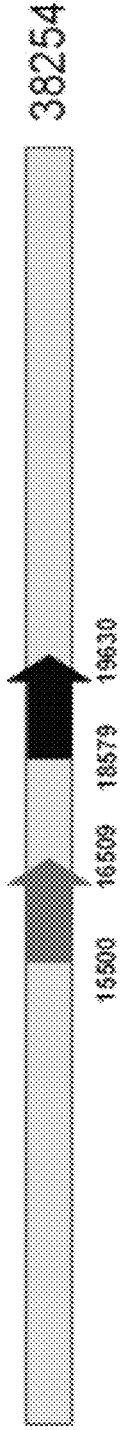
Figure 3B:
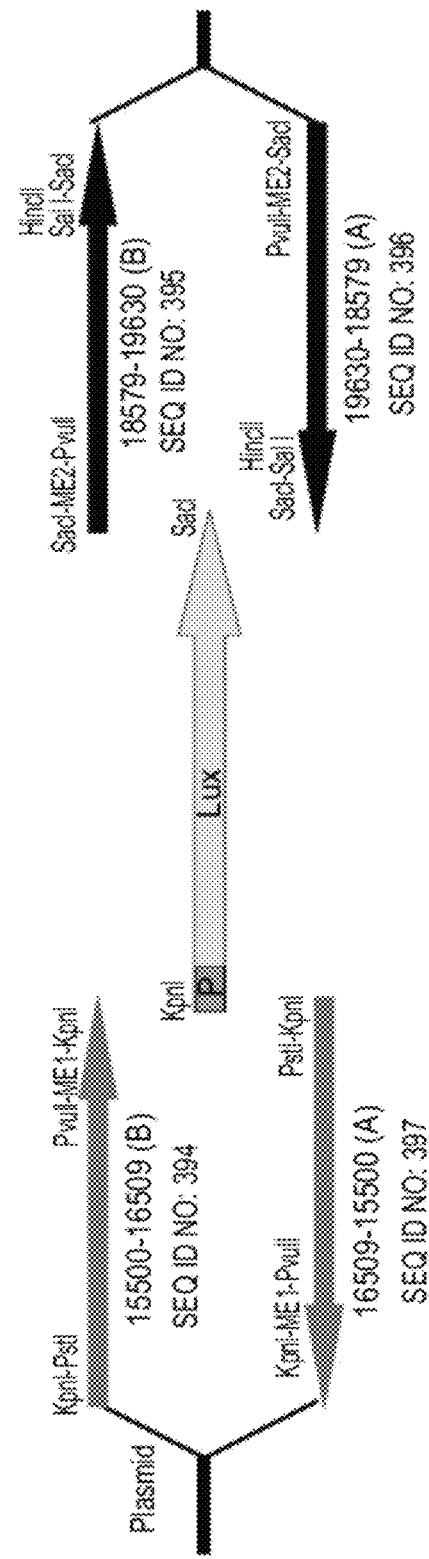

FIGS. 3A-B are schematic diagrams illustrating two plasmid constructs based on *Brucella* plasmid pBBR1mcs-4.1-Il1053Lux$_{CDABE}$. The constructs include Phage $L_1$ DNA fragments that extend between nucleotides 15500 to 16509 and 18579 to 19630 and one of Tn5 mosaic ends added in the correct orientation to their 3' and 5' ends. These engineered fragments were cloned up- and downstream of Lux, respectively, in two orientations.

Figure 4:
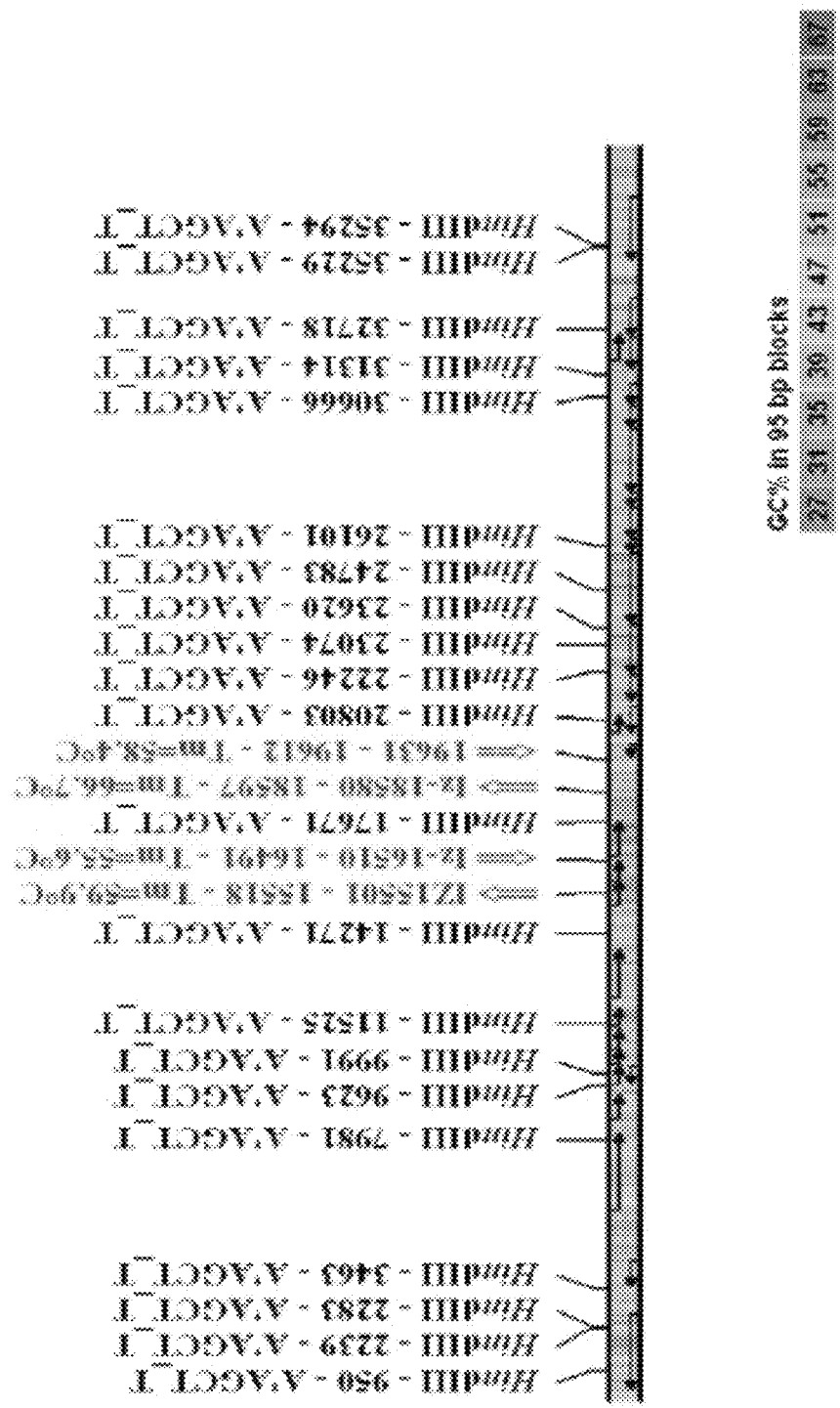

FIG. 4 is a schematic diagram illustrating the position of the primers used to construct the plasmid constructs depicted in FIG. 3B.

Figure 5:
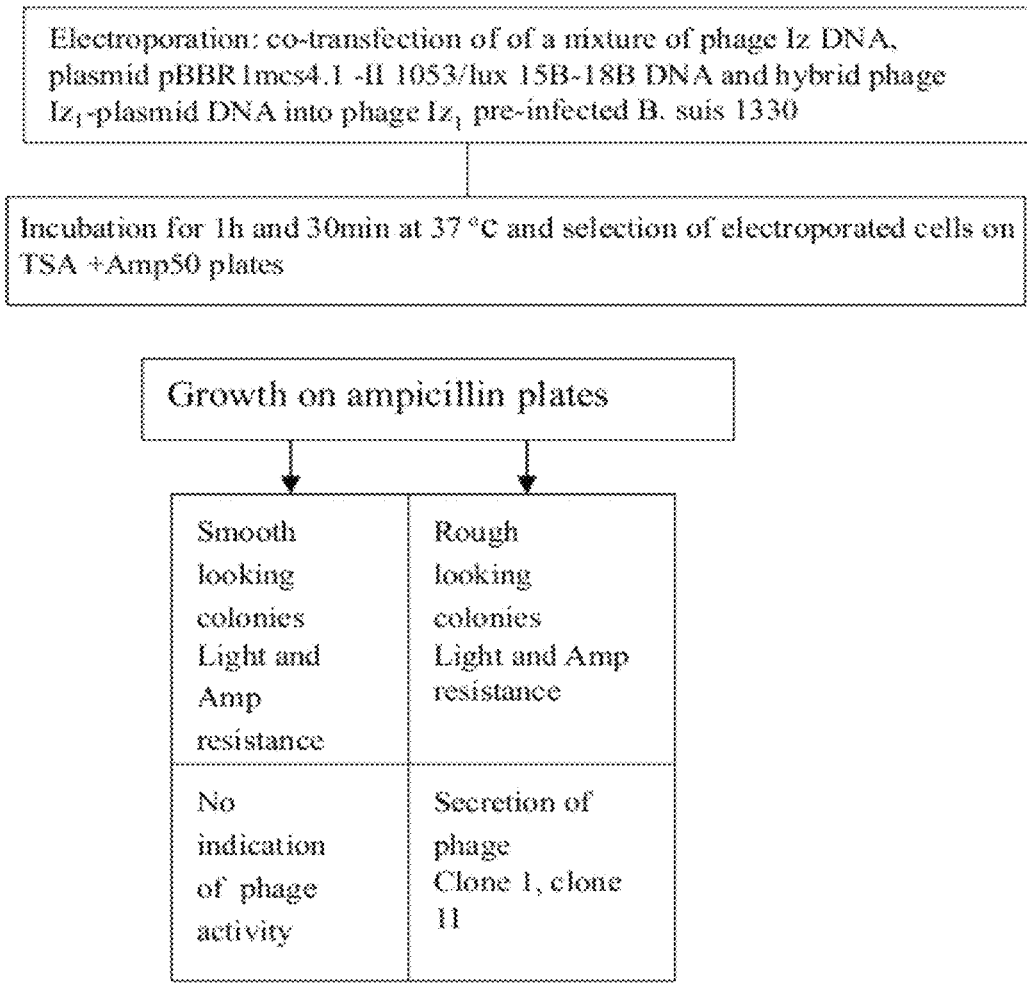

FIG. 5 is a flow diagram illustrating the steps taken to generate a *Brucella* phage carrier clone.

DESCRIPTION OF SPECIFIC EMBODIMENTS OF THE INVENTION

The present invention, in some embodiments thereof, relates to *Brucella* phage nucleic acid sequences and uses thereof.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

The *Brucella* species are important zoonotic pathogens affecting a wide variety of mammals. In agriculturally important domestic animals, these bacteria cause abortion and infertility, and they are of serious economic concern worldwide. *Brucella* species that infect humans cause an undulating fever, which if untreated, can manifest as orchitis, osteoarthritis, spondylitis, endocarditis, and neurological disorders. In rare events it may be fatal.

The present inventors have sequenced the entire genome (38,254 base pairs) of the *Brucella* phage $Iz_1$ as a genotype representative of all other *Brucella* phages. Two genomic *Brucella* phage $Iz_1$ populations were identified, differing between C or A at nucleotide 5549. BLAST analysis of this sequence revealed 6 regions of homology with *Ochrobactrum anthropi* ATCC 49188 chromosome 1—see Table 2 in the Examples section herein below. Subtraction of these sequences from the sequence of the full length genome, leads the inventors to the discovery of novel polynucleotide sequences which are specific to *Brucella* phage (e.g. SEQ ID NOs: 387-393).

The information gleaned from the sequence has allowed the inventors to identify apparent sequence of minimal presence of ORFs, which can be used for inserting genes of interest (for example, those encoding detectable moieties) into the phage, without affecting its lytic activity. Thus, development of a recombinant *Brucella* phage has been sought based on recombinational replacement of this site in the phage genome with a detectable signal (e.g. Lux operon). Due to the outputting of this signal, such a phage could be used to identify *Brucella* bacteria. Phage carrier *Brucella* clones were generated in which phage $Iz_1$ coresided in the cells in presence of plasmid pBBR1mcs4.1-II1053/Lux$_{CDABE}$/15B-18B (FIG. 3B), providing unlimited opportunities for recombinational events to occur between the Lux operon on the plasmid DNA and the *Brucella* phage DNA.

In addition, the present inventors have identified regulatory regions in the phage which possess regulatory function and were shown to be capable of down-regulating light expression endowed by the plasmid indicating potential implementation of such a gene regulation mechanism within *Brucella* bacteria.

Thus, for example, the present inventors identified a fragment of phage DNA which can down-regulate a gene operatively linked thereto (SEQ ID NO: 396; 19630-18579) following transformation into *Brucella* bacteria. When this sequence was transformed into *Brucella* bacteria, together with an additional phage DNA fragment (SEQ ID NO: 397; 16509-15500), it conferred different lethal activities on *Brucella* species, being the most lethal to lethal to the *B. abortus* strain 544, less severely lethal to *B. melitensis* and non-lethal to the *B. suis* strain of *Brucella*. Correspondingly, the down-regulatory activity of this fragment was also shown to be species specific.

Knowledge of phage regulatory regions should add to computational identification of additional unrecognized regulatory sequences within the genome of *Brucella*. This approach has already been demonstrated in the legume endosymbiont *Sinorhizobium meliloti* (delVal C, et al., Mol Microbiol 2007; 66: 1080-1091), that is belonging to the alpha-proteobacteria class, as also *Agrobactrum tumefaciens*, the causative agent of crown-gall disease in plants and *Brucella*, indicating close relatedness and therefore possible shared functions between these organisms (Inon de Iannino N, et al., J Bacteriol 1998; 180: 4392-4400).

Thus, according to one aspect of the present invention, there is provided an isolated polynucleotide comprising a nucleic acid sequence of a *Brucella* phage, the nucleic acid sequence being specific to the *Brucella* phage and comprising a sequence selected from the group consisting of SEQ ID NOs: 387-393.

As used herein, the term "phage" (synonymous with the term "bacteriophage" refers to a virus that selectively infects prokaryotes—such as bacteria. Many bacteriophages are specific to a particular genus or species or strain of cell.

The phage is typically a lytic bacteriophage.

A lytic bacteriophage is one that follows the lytic pathway through completion of the lytic cycle, rather than entering the lysogenic pathway. A lytic bacteriophage undergoes viral replication leading to lysis of the cell membrane, destruction of the cell, and release of progeny bacteriophage particles capable of infecting other cells.

A lysogenic bacteriophage is one capable of entering the lysogenic pathway, in which the bacteriophage becomes a dormant, passive part of the cell's genome through prior to completion of its lytic cycle.

According to one embodiment, the phage is a Tb type phage, for example Phage $Iz_1$.

A sequence specific to a *Brucella* phage is one which is present in the phage and not present in other organisms—i.e. unique to *Brucella*. Since the sequence of the *Brucella* phage genome is now known, *Brucella* phage specific sequences may be identified using BLAST or other similar programs.

According to one embodiment, the *Brucella* phage specific sequence does not comprise more than 70% identity with another nucleic acid sequence as verified using a sequence alignment software such as BLAST analysis.

According to one embodiment, the *Brucella* phage specific sequence does not comprise more than 60% identity with another nucleic acid sequence as verified using a sequence alignment software such as BLAST analysis.

As used herein the phrase "an isolated polynucleotide" refers to a single or double stranded nucleic acid sequences which is isolated and provided in the form of an RNA sequence, a complementary polynucleotide sequence (cDNA), a genomic polynucleotide sequence and/or a composite polynucleotide sequences (e.g., a combination of the above).

As used herein the phrase "complementary polynucleotide sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic polynucleotide sequence" refers to a sequence derived (isolated) from a chromosome and thus it represents a contiguous portion of a chromosome.

As used herein the phrase "composite polynucleotide sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

According to one embodiment, the isolated polynucleotide comprises at least 15, at least 20, at least 40, at least 50, at least 100, at least 200, at least 500 or at least 1000 consecutive nucleotides of the sequences as set forth in SEQ ID NOs: 387-393.

Thus, the polynucleotides of the present invention may be from 15-38,254 nucleotides long.

It will be appreciated that homologues of the sequences described hereinabove are also envisaged by the present invention. Accordingly, the polynucleotides of this aspect of the present invention may have a nucleic acid sequence at least 50%, at least 55%, at least 60%, at least 65%, at least 70%, at least 75%, at least 80%, at least 85%, at least 87%, at least 89%, at least 90% at least 91%, at least 93%, at least 95% or more say 100% identical to the sequences derived from SEQ ID NOs: 387-393, as determined using BlastN software of the National Center of Biotechnology Information (NCBI) using default parameters.

Thus, the present invention encompasses nucleic acid sequences described hereinabove; fragments thereof, sequences hybridizable therewith, sequences in the opposite orientation thereto, sequences homologous thereto, sequences encoding similar polypeptides with different codon usage, altered sequences characterized by mutations, such as deletion, insertion or substitution of one or more nucleotides, either naturally occurring or man induced, either randomly or in a targeted fashion.

Exemplary polynucleotides contemplated by the present invention are those that comprise the nucleic acid sequence as set forth in SEQ ID NOs: 1 and 387-393.

Other exemplary polynucleotides contemplated by the present invention are those that comprise regulatory regions within the sequences as set forth in SEQ ID NOs: 387-393, such as at least 100 consecutive nucleotides of the regulatory region as set forth in SEQ ID NO: 395 shown by the present inventors to possess down-regulating activity of a gene operationally linked thereto, when inserted in the opposite orientation (i.e. SEQ ID NO: 396). Another regulatory sequence includes SEQ ID NO: 394, both in the forward or reverse orientation. This is also present in the complete phage genome possibly affecting regulatory functions of phage $Iz_1$ genes.

Using bioinformatic tools, the present inventors identified additional regulatory regions within the full length sequence of the phage genome which may serve as promoter sequences (i.e. transcriptional regulatory regions) in the phage (SEQ ID NOs: 2-386). Such promoter sequences may be placed upstream of a heterologous nucleic acid sequence so as to promote transcription thereof. Moreover, the downregulatory activity might be used to identify important chemicals that change the activity of the transcriptional regulatory regions, thereby facilitating development of novel drugs.

Other sequences which encode putative polypeptides are also provided and also considered to be in the realm of the present invention. Such sequences are provided in Table 1 herein below. Polynucleotide sequences encoding such polypeptides may be used for various purposes. Thus, for instance a polynucleotide sequence encoding a putative lysin or holin may be used to selectively kill *Brucella* cells. The advantages of lysin-based therapy are numerous: they can be prepared with high purity and possess high specific activity; they exhibit rapid lethal action; they are nontoxic; and apparently, antibodies that form against these proteins do not neutralize their lytic activity. Lastly, no bacterial resistance develops to these proteins, probably because they possess multiple domains for cell wall binding and hydrolysis.

Examples of additional important polypeptides are:

1. Secretory proteins including flagellar proteins (secretion Type III, This apparatus is related to the injectisome used by many gram-negative pathogens and symbionts to transfer effector proteins into host cells) and VirB (Type IV, The translocation of DNA across biological membranes is an essential process for many living organisms. In bacteria, type IV secretion systems (T4SS) are used to deliver DNA as well as protein substrates from donor to target cells. The T4SS are structurally complex machines assembled from a dozen or more membrane proteins in response to environmental signals The translocation of DNA across biological membranes is an essential process for many living organisms. In bacteria, type IV secretion systems (T4SS) are used to deliver DNA as well as protein substrates from donor to target cells. The T4SS are structurally complex machines assembled from a dozen or more membrane proteins in response to environmental signals)

2. Phage integrase—catalyses the site specific integration and excision of the bacteriophage in the lysogenic cycle.

3. Toxins, phospholipase—degrade phospholipids, protease—degrade proteins.

TABLE 1

| Subject id | Description | % identity | alignment length | Mis matches | gap openings | q. start | q. end |
|---|---|---|---|---|---|---|---|
| ref\|YP_672794.1\| | hypothetical protein Meso_0225 [*Mesorhizobium* sp. BNC1] | 52.46 | 812 | 347 | 13 | 37128 | 34810 |
| ref\|YP_672803.1\| | hypothetical protein Meso_0234 [*Mesorhizobium* sp. BNC1] | 47.39 | 652 | 336 | 11 | 29673 | 27739 |
| ref\|YP_672798.1\| | hypothetical protein Meso_0229 [*Mesorhizobium* sp. BNC1] | 79.76 | 336 | 68 | 0 | 32487 | 31480 |
| ref\|NP_102255.1\| | hypothetical protein mll0462 [Mesorhizobium loti MAFF303099] | 35.80 | 810 | 501 | 16 | 37143 | 34771 |
| ref\|ZP_06361176.1\| | conserved hypothetical protein [*Rhodopseudomonas palustris* DX-1] | 36.76 | 759 | 443 | 13 | 37074 | 34909 |

TABLE 1-continued

| Subject id | Description | % identity | alignment length | Mis matches | gap openings | q. start | q. end |
|---|---|---|---|---|---|---|---|
| ref\|YP_672806.1\| | hypothetical protein Meso_0237 [*Mesorhizobium* sp. BNC1] | 69.35 | 323 | 97 | 2 | 27275 | 26313 |
| ref\|YP_224275.1\| | hypothetical protein LPPPVgp44 [*Listonella* phage phiHSIC] | 33.16 | 781 | 474 | 17 | 5921 | 8119 |
| ref\|YP_672793.1\| | phage uncharacterized protein [*Mesorhizobium* sp. BNC1] | 58.62 | 348 | 136 | 10 | 1378 | 359 |
| ref\|YP_672793.1\| | phage uncharacterized protein [*Mesorhizobium* sp. BNC1] | 35.58 | 104 | 63 | 3 | 2737 | 2438 |
| ref\|YP_224270.1\| | putative helicase [*Listonella* phage phiHSIC] | 41.36 | 515 | 280 | 6 | 12291 | 13769 |
| ref\|YP_224270.1\| | putative helicase [*Listonella* phage phiHSIC] | 52.63 | 76 | 36 | 0 | 12089 | 12316 |
| ref\|YP_224270.1\| | putative helicase [*Listonella* phage phiHSIC] | 63.33 | 30 | 11 | 0 | 11996 | 12085 |
| ref\|YP_468629.1\| | hypothetical protein RHE_CH01094 [*Rhizobium etli* CFN 42] | 33.23 | 641 | 391 | 9 | 37125 | 35314 |
| ref\|YP_002280249.1\| | hypothetical protein Rleg2_0727 [*Rhizobium leguminosarum* bv. *trifolii*] | 31.65 | 654 | 397 | 6 | 37125 | 35314 |
| ref\|YP_769515.1\| | hypothetical protein RL3937 [*Rhizobium leguminosarum* bv. *viciae* 3841] | 31.65 | 654 | 393 | 11 | 37050 | 35251 |
| ref\|ZP_06361168.1\| | conserved hypothetical protein [*Rhodopseudomonas palustris* DX-1] | 40.16 | 371 | 221 | 4 | 28854 | 27745 |
| ref\|ZP_06361168.1\| | conserved hypothetical protein [*Rhodopseudomonas palustris* DX-1] | 44.32 | 176 | 93 | 3 | 29652 | 29140 |
| ref\|ZP_02961020.1\| | hypothetical protein PROSTU_03006 [*Providencia stuartii* ATCC 25827] | 37.97 | 403 | 244 | 7 | 12315 | 13505 |
| ref\|ZP_02961020.1\| | hypothetical protein PROSTU_03006 [*Providencia stuartii* ATCC 25827] | 43.52 | 108 | 61 | 1 | 11993 | 12316 |
| rer\|ZP_01234562.1\| | putative ATP-dependent helicase [*Vibrio angustum* S14] | 36.39 | 404 | 250 | 7 | 12315 | 13505 |
| ref\|ZP_01234562.1\| | putative ATP-dependent helicase [*Vibrio angustum* S14] | 41.82 | 110 | 64 | 1 | 11996 | 12325 |
| ref\|YP_002263457.1\| | putative helicase (DEAD/DEAH box helicase) [*Aliivibrio salmonicida*] | 38.17 | 393 | 237 | 7 | 12297 | 13457 |
| ref\|YP_002263457.1\| | putative helicase (DEAD/DEAH box helicase) [*Aliivibrio salmonicida*] | 44.44 | 108 | 60 | 1 | 11996 | 12319 |
| ref\|YP_002155626.1\| | DNA or RNA helicase [*Vibrio fischeri* MJ11] | 37.47 | 403 | 246 | 7 | 12315 | 13505 |
| ref\|YP_002155626.1\| | DNA or RNA helicase [*Vibrio fischeri* MJ11] | 43.52 | 108 | 61 | 1 | 11996 | 12319 |
| ref\|YP_204247.1\| | ATP-dependet helicase [*Vibrio fischeri* ES114] | 37.47 | 403 | 246 | 7 | 12315 | 13505 |

TABLE 1-continued

| Subject id | Description | % identity | alignment length | Mis matches | gap openings | q. start | q. end |
|---|---|---|---|---|---|---|---|
| ref|YP_204247.1| | ATP-dependet helicase [*Vibrio fischeri* ES114] | 43.52 | 108 | 61 | 1 | 11996 | 12319 |
| ref|YP_003333937.1| | type III restriction protein res subunit [*Dickeya dadantii* Ech586] | 38.71 | 403 | 241 | 7 | 12315 | 13505 |
| ref|YP_003333937.1| | type III restriction protein res subunit [*Dickeya dadantii* Ech586] | 45.83 | 96 | 52 | 1 | 11996 | 12283 |
| ref|ZP_02195032.1| | helicase-related protein [*Vibrio* sp. AND4] | 36.45 | 428 | 265 | 9 | 12315 | 13577 |
| ref|ZP_02195032.1| | helicase-related protein [*Vibrio* sp. AND4] | 40.91 | 110 | 65 | 1 | 11996 | 12325 |
| ref|ZP_01160173.1| | putative ATP-dependent helicase [*Photobacterium* sp. SKA34] | 35.64 | 404 | 253 | 7 | 12315 | 13505 |
| ref|ZP_01160173.1| | putative ATP-dependent helicase [*Photobacterium* sp. SKA34] | 41.82 | 110 | 64 | 1 | 11996 | 12325 |
| ref|ZP_06125419.1| | putative helicase, ATP-dependent [*Providencia rettgeri* DSM 1131] | 35.80 | 405 | 254 | 7 | 12309 | 13505 |
| ref|ZP_06125419.1| | putative helicase, ATP-dependent [*Providencia rettgeri* DSM 1131] | 44.44 | 108 | 60 | 1 | 11993 | 12316 |
| ref|ZP_03345188.1| | putative helicase [*Salmonella enterica* subsp. *enterica* serovar Typhi | 37.22 | 403 | 247 | 7 | 12315 | 13505 |
| ref|ZP_03345188.1| | putative helicase [*Salmonella enterica* subsp. *enterica* serovar Typhi | 42.73 | 110 | 63 | 1 | 11996 | 12325 |
| ref|ZP_02667261.1| | putative helicase [*Salmonella enterica* subsp. *enterica* serovar | 37.98 | 387 | 234 | 6 | 12315 | 13457 |
| ref|ZP_02667261.1| | putative helicase [*Salmonella enterica* subsp. *enterica* serovar | 42.73 | 110 | 63 | 1 | 11996 | 12325 |
| ref|YP_149939.1| | putative helicase [*Salmonella enterica* subsp. *enterica* serovar | 37.98 | 387 | 234 | 6 | 12315 | 13457 |
| ref|YP_149939.1| | putative helicase [*Salmonella enterica* subsp. *enterica* serovar | 42.73 | 110 | 63 | 1 | 11996 | 12325 |
| ref|ZP_06155453.1| | putative ATP-dependent helicase [*Photobacterium damselae* subsp. | 36.34 | 388 | 240 | 6 | 12315 | 13457 |
| ref|ZP_06155453.1| | putative ATP-dependent helicase [*Photobacterium damselae* subsp. | 40.91 | 110 | 65 | 1 | 11996 | 12325 |
| ref|ZP_03220222.1| | putative helicase [*Salmonella enterica* subsp. *enterica* serovar Javiana | 37.98 | 387 | 234 | 6 | 12315 | 13457 |
| ref|ZP_03220222.1| | putative helicase [*Salmonella enterica* subsp. *enterica* serovar Javiana | 42.73 | 110 | 63 | 1 | 11996 | 12325 |
| ref|YP_001587034.1| | hypothetical protein SPAB_00777 [*Salmonella enterica* subsp. *enterica* | 37.73 | 387 | 235 | 6 | 12315 | 13457 |
| ref|YP_001587034.1| | hypothetical protein SPAB_00777 [*Salmonella enterica* subsp. *enterica* | 42.73 | 110 | 63 | 1 | 11996 | 12325 |

TABLE 1-continued

| Subject id | Description | % identity | alignment length | Mis matches | gap openings | q. start | q. end |
|---|---|---|---|---|---|---|---|
| ref\|YP_002244308.1\| | putative helicase [*Salmonella enterica* subsp. *enterica* serovar | 37.73 | 387 | 235 | 6 | 12315 | 13457 |
| ref\|YP_002244308.1\| | putative helicase [*Salmonella enterica* subsp. *enterica* serovar | 42.73 | 110 | 63 | 1 | 11996 | 12325 |
| ref\|YP_002227157.1\| | putative helicase [*Salmonella enterica* subsp. *enterica* serovar | 37.73 | 387 | 235 | 6 | 12315 | 13457 |
| ref\|YP_002227157.1\| | putative helicase [*Salmonella enterica* subsp. *enterica* serovar | 42.73 | 110 | 63 | 1 | 11996 | 12325 |
| ref\|ZP_03213834.1\| | putative helicase [*Salmonella enterica* subsp. *enterica* serovar Virchow | 37.73 | 387 | 235 | 6 | 12315 | 13457 |
| ref\|ZP_03213834.1\| | putative helicase [*Salmonella enterica* subsp. *enterica* serovar Virchow | 42.73 | 110 | 63 | 1 | 11996 | 12325 |
| ref\|NP_456781.1\| | putative helicase [*Salmonella enterica* subsp. *enterica* serovar Typhi | 37.73 | 387 | 235 | 6 | 12315 | 13457 |
| ref\|NP_456781.1\| | putative helicase [*Salmonella enterica* subsp. *enterica* serovar Typhi | 42.73 | 110 | 63 | 1 | 11996 | 12325 |
| ref\|YP_002147196.1\| | putative helicase [*Salmonella enterica* subsp. *enterica* serovar Agona | 37.73 | 387 | 235 | 6 | 12315 | 13457 |
| ref\|YP_002147196.1\| | putative helicase [*Salmonella enterica* subsp. *enterica* serovar Agona | 42.73 | 110 | 63 | 1 | 11996 | 12325 |
| ref\|ZP_02654653.1\| | putative helicase [*Salmonella enterica* subsp. *enterica* serovar Kentucky | 37.73 | 387 | 235 | 6 | 12315 | 13457 |
| ref\|ZP_02654653.1\| | putative helicase [*Salmonella enterica* subsp. *enterica* serovar Kentucky | 42.73 | 110 | 63 | 1 | 11996 | 12325 |
| ref\|ZP_06639525.1\| | conserved hypothetical protein [*Serratia odorifera* DSM 4582] | 37.87 | 404 | 245 | 7 | 12312 | 13505 |
| ref\|ZP_06639525.1\| | conserved hypothetical protein [*Serratia odorifera* DSM 4582] | 41.12 | 107 | 63 | 1 | 11996 | 12316 |
| ref\|YP_003211214.1\| | Uncharacterized protein yejH [*Cronobacter turicensis* z3032] | 37.97 | 403 | 244 | 7 | 12315 | 13505 |
| ref\|YP_003211214.1\| | Uncharacterized protein yejH [*Cronobacter turicensis* z3032] | 42.59 | 108 | 62 | 1 | 11996 | 12319 |
| ref\|ZP_05877188.1\| | helicase-related protein [*Vibrio furnissii* CIP 102972] | 35.28 | 428 | 270 | 9 | 12315 | 13577 |
| ref\|ZP_05877188.1\| | helicase-related protein [*Vibrio furnissii* CIP 102972] | 41.82 | 110 | 64 | 1 | 11996 | 12325 |
| ref\|ZP_02683731.1\| | putative helicase [*Salmonella enterica* subsp. *enterica* serovar Hadar | 37.47 | 387 | 236 | 6 | 12315 | 13457 |
| ref\|ZP_02683731.1\| | putative helicase [*Salmonella enterica* subsp. *enterica* serovar Hadar | 42.73 | 110 | 63 | 1 | 11996 | 12325 |
| ref\|YP_129752.1\| | putative ATP-dependent helicase [*Photobacterium profundum* SS9] | 35.31 | 405 | 255 | 7 | 12312 | 13505 |

TABLE 1-continued

| Subject id | Description | % identity | alignment length | Mis matches | gap openings | q. start | q. end |
|---|---|---|---|---|---|---|---|
| ref|YP_129752.1| | putative ATP-dependent helicase [*Photobacterium profundum* SS9] | 41.12 | 107 | 63 | 1 | 11996 | 12316 |
| ref|YP_003365861.1| | putative helicase [*Citrobacter rodentium* ICC168] | 37.47 | 403 | 246 | 7 | 12315 | 13505 |
| ref|YP_003365861.1| | putative helicase [*Citrobacter rodentium* ICC168] | 43.52 | 108 | 61 | 1 | 11996 | 12319 |
| ref|YP_217227.1| | putative ATP-dependent helicase [*Salmonella enterica* subsp. *enterica* | 37.47 | 387 | 236 | 6 | 12315 | 13457 |
| ref|YP_217227.1| | putative ATP-dependent helicase [*Salmonella enterica* subsp. *enterica* | 42.73 | 110 | 63 | 1 | 11996 | 12325 |
| ref|YP_001401684.1| | putative helicase [*Yersinia pseudotuberculosis* IP 31758] | 37.87 | 404 | 245 | 7 | 12312 | 13505 |
| ref|YP_001401684.1| | putative helicase [*Yersinia pseudotuberculosis* IP 31758] | 40.19 | 107 | 64 | 1 | 11996 | 12316 |
| ref|NP_670218.1| | ATP-dependent helicase [*Yersinia pestis* KIM 10] | 37.87 | 404 | 245 | 7 | 12312 | 13505 |
| ref|NP_670218.1| | ATP-dependent helicase [*Yersinia pestis* KIM 10] | 40.19 | 107 | 64 | 1 | 11996 | 12316 |
| ref|YP_001445844.1| | hypothetical protein VIBHAR_02656 [*Vibrio harveyi* ATCC BAA-1116] | 35.75 | 428 | 268 | 9 | 12315 | 13577 |
| ref|YP_001445844.1| | hypothetical protein VIBHAR_02656 [*Vibrio harveyi* ATCC BAA-1116] | 41.82 | 110 | 64 | 1 | 11996 | 12325 |
| ref|NP_934217.1| | DNA or RNA helicase [*Vibrio vulnificus* YJ016] | 36.60 | 388 | 239 | 7 | 12315 | 13457 |
| ref|NP_934217.1| | DNA or RNA helicase [*Vibrio vulnificus* YJ016] | 41.82 | 110 | 64 | 1 | 11996 | 12325 |
| ref|ZP_01218531.1| | putative ATP-dependent helicase [*Photobacterium profundum* 3TCK] | 35.31 | 405 | 255 | 7 | 12312 | 13505 |
| ref|ZP_01218531.1| | putative ATP-dependent helicase [*Photobacterium profundum* 3TCK] | 41.12 | 107 | 63 | 1 | 11996 | 12316 |
| ref|YP_069832.1| | putative DEAD box helicase family protein [*Yersinia pseudotuberculosis* | 37.87 | 404 | 245 | 7 | 12312 | 13505 |
| ref|YP_069832.1| | putative DEAD box helicase family protein [*Yersinia pseudotuberculosis* | 40.19 | 107 | 64 | 1 | 11996 | 12316 |
| ref|ZP_04619081.1| | hypothetical protein yaldo0001_20880 [*Yersinia aldovae* ATCC 35236] | 37.87 | 404 | 245 | 7 | 12312 | 13505 |
| ref|ZP_04619081.1| | hypothetical protein yaldo0001_20880 [*Yersinia aldovae* ATCC 35236] | 40.19 | 107 | 64 | 1 | 11996 | 12316 |
| ref|ZP_04633499.1| | hypothetical protein yfred0001_40330 [*Yersinia frederiksenii* ATCC | 38.37 | 404 | 243 | 7 | 12312 | 13505 |
| ref|ZP_04633499.1| | hypothetical protein yfred0001_40330 | 40.19 | 107 | 64 | 1 | 11996 | 12316 |

TABLE 1-continued

| Subject id | Description | % identity | alignment length | Mis matches | gap openings | q. start | q. end |
|---|---|---|---|---|---|---|---|
| ref|ZP_04616780.1| | hypothetical protein yruck0001_10270 [*Yersinia frederiksenii* ATCC *Yersinia ruckeri* ATCC 29473] | 38.12 | 404 | 244 | 7 | 12312 | 13505 |
| ref|ZP_04616780.1| | hypothetical protein yruck0001_10270 [*Yersinia ruckeri* ATCC 29473] | 42.06 | 107 | 62 | 1 | 11996 | 12316 |
| ref|ZP_06053624.1| | putative ATP-dependent helicase [*Grimontia hollisae* CIP 101886] | 36.97 | 403 | 248 | 7 | 12315 | 13505 |
| ref|ZP_06053624.1| | putative ATP-dependent helicase [*Grimontia hollisae* CIP 101886] | 39.81 | 108 | 65 | 1 | 11996 | 12319 |
| ref|ZP_02661469.1| | putative helicase [*Salmonella enterica* subsp. *enterica* serovar | 37.47 | 387 | 236 | 6 | 12315 | 13457 |
| ref|ZP_02661469.1| | putative helicase [*Salmonella enterica* subsp. *enterica* serovar | 42.73 | 110 | 63 | 1 | 11996 | 12325 |
| ref|ZP_06048813.1| | helicase-related protein [*Vibrio cholerae* CT 5369-93] | 34.58 | 454 | 290 | 10 | 12315 | 13655 |
| ref|ZP_06048813.1| | helicase-related protein [*Vibrio cholerae* CT 5369-93] | 40.91 | 110 | 65 | 1 | 11996 | 12325 |
| ref|ZP_05926045.1| | helicase-related protein [*Vibrio* sp. RC341] | 34.80 | 454 | 289 | 10 | 12315 | 13655 |
| ref|ZP_05926045.1| | helicase-related protein [*Vibrio* sp. RC341] | 40.91 | 110 | 65 | 1 | 11996 | 12325 |
| ref|ZP_04562718.1| | conserved hypothetical protein [*Citrobacter* sp. 30_2] | 36.36 | 407 | 253 | 7 | 12315 | 13517 |
| ref|ZP_04562718.1| | conserved hypothetical protein [*Citrobacter* sp. 30_2] | 42.59 | 108 | 62 | 1 | 11996 | 12319 |
| ref|YP_003017214.1| | type III restriction protein res subunit [*Pectobacterium carotovorum* | 36.97 | 403 | 248 | 7 | 12315 | 13505 |
| ref|YP_003017214.1| | type III restriction protein res subunit [*Pectobacterium carotovorum* | 41.12 | 107 | 63 | 1 | 11996 | 12316 |
| ref|ZP_06080609.1| | helicase-related protein [*Vibrio* sp. RC586] | 34.80 | 454 | 289 | 10 | 12315 | 13655 |
| ref|ZP_06080609.1| | helicase-related protein [*Vibrio* sp. RC586] | 40.91 | 110 | 65 | 1 | 11996 | 12325 |
| ref|ZP_05968474.1| | putative helicase, ATP-dependent [*Enterobacter cancerogenus* ATCC 35316] | 37.47 | 403 | 246 | 7 | 12315 | 13505 |
| ref|ZP_05968474.1| | putative helicase, ATP-dependent [*Enterobacter cancerogenus* ATCC 35316] | 40.91 | 110 | 65 | 1 | 11996 | 12325 |
| ref|ZP_03049176.1| | putative helicase [*Escherichia coli* E110019] | 37.47 | 387 | 236 | 6 | 12315 | 13457 |
| ref|ZP_03049176.1| | putative helicase [*Escherichia coli* E110019] | 43.52 | 108 | 61 | 1 | 11996 | 12319 |
| ref|ZP_06191030.1| | type III restriction protein res subunit [*Serratia odorifera* 4Rx13] | 37.62 | 404 | 246 | 7 | 12312 | 13505 |

TABLE 1-continued

| Subject id | Description | % identity | alignment length | Mis matches | gap openings | q. start | q. end |
|---|---|---|---|---|---|---|---|
| ref\|ZP_06191030.1\| | type III restriction protein res subunit [*Serratia odorifera* 4Rx13] | 41.12 | 107 | 63 | 1 | 11996 | 12316 |
| ref\|NP_797593.1\| | helicase-related protein [*Vibrio parahaemolyticus* RIMD 2210633] | 35.98 | 428 | 267 | 9 | 12315 | 13577 |
| ref\|NP_797593.1\| | helicase-related protein [*Vibrio parahaemolyticus* RIMD 2210633] | 40.91 | 110 | 65 | 1 | 11996 | 12325 |
| ref\|ZP_06352119.2\| | putative helicase, ATP-dependent [*Citrobacter youngae* ATCC 29220] | 36.61 | 407 | 252 | 7 | 12315 | 13517 |
| ref\|ZP_06352119.2\| | putative helicase, ATP-dependent [*Citrobacter youngae* ATCC 29220] | 42.59 | 108 | 62 | 1 | 11996 | 12319 |
| ref\|ZP_04613347.1\| | hypothetical protein yrohd0001_26030 [*Yersinia rohdei* ATCC 43380] | 38.12 | 404 | 244 | 7 | 12312 | 13505 |
| ref\|ZP_04613347.1\| | hypothetical protein yrohd0001_26030 [*Yersinia rohdei* ATCC 43380] | 40.19 | 107 | 64 | 1 | 11996 | 12316 |
| ref\|ZP_05719867.1\| | helicase-related protein [*Vibrio mimicus* VM603] | 37.11 | 388 | 237 | 7 | 12315 | 13457 |
| ref\|ZP_05719867.1\| | helicase-related protein [*Vibrio mimicus* VM603] | 40.91 | 110 | 65 | 1 | 11996 | 12325 |
| dbj\|BAI55606.1\| | putative ATP-dependent helicase [*Escherichia coli* SE15] | 37.73 | 387 | 235 | 6 | 12315 | 13457 |
| dbj\|BAI55606.1\| | putative ATP-dependent helicase [*Escherichia coli* SE15] | 43.52 | 108 | 61 | 1 | 11996 | 12319 |
| ref\|YP_001569729.1\| | hypothetical protein SARI_00664 [*Salmonella enterica* subsp. *arizonae*] | 37.73 | 387 | 235 | 6 | 12315 | 13457 |
| ref\|YP_001569729.1\| | hypothetical protein SARI_00664 [*Salmonella enterica* subsp. *arizonae*] | 42.59 | 108 | 62 | 1 | 11996 | 12319 |
| ref\|YP_001452182.1\| | hypothetical protein CKO_00592 [*Citrobacter koseri* ATCC BAA-895] | 36.97 | 403 | 248 | 7 | 12315 | 13505 |
| ref\|YP_001452182.1\| | hypothetical protein CKO_00592 [*Citrobacter koseri* ATCC BAA-895] | 43.52 | 108 | 61 | 1 | 11996 | 12319 |
| ref\|YP_001479479.1\| | type III restriction protein res subunit [*Serratia proteamaculans* 568] | 37.62 | 404 | 246 | 7 | 12312 | 13505 |
| ref\|YP_001479479.1\| | type III restriction protein res subunit [*Serratia proteamaculans* 568] | 41.12 | 107 | 63 | 1 | 11996 | 12316 |
| ref\|ZP_01978844.1\| | DNA or RNA helicase [*Vibrio cholerae* MZO-2] | 34.58 | 454 | 290 | 10 | 12315 | 13655 |
| ref\|ZP_01978844.1\| | DNA or RNA helicase [*Vibrio cholerae* MZO-2] | 40.91 | 110 | 65 | 1 | 11996 | 12325 |
| ref\|ZP_06039032.1\| | helicase-related protein [*Vibrio mimicus* MB-451] | 37.11 | 388 | 237 | 7 | 12315 | 13457 |

TABLE 1-continued

| Subject id | Description | % identity | alignment length | Mis matches | gap openings | q. start | q. end |
|---|---|---|---|---|---|---|---|
| ref\|ZP_06039032.1\| | helicase-related protein [*Vibrio mimicus* MB-451] | 40.91 | 110 | 65 | 1 | 11996 | 12325 |
| ref\|YP_670125.1\| | hypothetical protein ECP_2225 [*Escherichia coli* 536] | 37.73 | 387 | 235 | 6 | 12315 | 13457 |
| ref\|YP_670125.1\| | hypothetical protein ECP_2225 [*Escherichia coli* 536] | 43.52 | 108 | 61 | 1 | 11996 | 12319 |
| ref\|YP_003286407.1\| | helicase-related protein [*Vibrio* sp. Ex25] | 35.51 | 428 | 269 | 9 | 12315 | 13577 |
| ref\|YP_003286407.1\| | helicase-related protein [*Vibrio* sp. Ex25] | 41.82 | 110 | 64 | 1 | 11996 | 12325 |
| ref\|ZP_04960385.1\| | ATP-dependent RNA helicase, DEAD/DEAH box family [*Vibrio cholerae*] | 34.36 | 454 | 291 | 10 | 12315 | 13655 |
| ref\|ZP_04960385.1\| | ATP-dependent RNA helicase, DEAD/DEAH box family [*Vibrio cholerae*] | 40.91 | 110 | 65 | 1 | 11996 | 12325 |
| ref\|YP_001005731.1\| | putative DEAD box helicase family protein [*Yersinia enterocolitica*] | 38.12 | 404 | 244 | 7 | 12312 | 13505 |
| ref\|YP_001005731.1\| | putative DEAD box helicase family protein [*Yersinia enterocolitica*] | 40.19 | 107 | 64 | 1 | 11996 | 12316 |
| ref\|ZP_04418721.1\| | helicase-related protein [*Vibrio cholerae* 12129(1)] | 34.36 | 454 | 291 | 10 | 12315 | 13655 |
| ref\|ZP_04418721.1\| | helicase-related protein [*Vibrio cholerae* 12129(1)] | 40.91 | 110 | 65 | 1 | 11996 | 12325 |
| ref\|ZP_04410188.1\| | helicase-related protein [*Vibrio cholerae* TM 11079-80] | 34.36 | 454 | 291 | 10 | 12315 | 13655 |
| ref\|ZP_04410188.1\| | helicase-related protein [*Vibrio cholerae* TM 11079-80] | 40.91 | 110 | 65 | 1 | 11996 | 12325 |
| ref\|ZP_01950681.1\| | ATP-dependent RNA helicase, DEAD/DEAH box family [*Vibrio cholerae* 1587] | 34.36 | 454 | 291 | 10 | 12315 | 13655 |
| ref\|ZP_01950681.1\| | ATP-dependent RNA helicase, DEAD/DEAH box family [*Vibrio cholerae* 1587] | 40.91 | 110 | 65 | 1 | 11996 | 12325 |
| ref\|YP_001463537.1\| | putative helicase [*Escherichia coli* E24377A] | 37.47 | 387 | 236 | 6 | 12315 | 13457 |
| ref\|YP_001463537.1\| | putative helicase [*Escherichia coli* E24377A] | 43.52 | 108 | 61 | 1 | 11996 | 12319 |
| ref\|YP_689683.1\| | putative ATP-dependent helicase [*Shigella flexneri* 5 str. 8401] | 37.47 | 387 | 236 | 6 | 12315 | 13457 |
| ref\|YP_689683.1\| | putative ATP-dependent helicase [*Shigella flexneri* 5 str. 8401] | 43.52 | 108 | 61 | 1 | 11996 | 12319 |
| ref\|NP_416689.1\| | predicted ATP-dependent DNA or RNA helicase [*Escherichia coli* str. K-12 | 37.47 | 387 | 236 | 6 | 12315 | 13457 |

TABLE 1-continued

| Subject id | Description | % identity | alignment length | Mis matches | gap openings | q. start | q. end |
|---|---|---|---|---|---|---|---|
| ref|NP_416689.1| | predicted ATP-dependent DNA or RNA helicase [*Escherichia coli* str. K-12] | 43.52 | 108 | 61 | 1 | 11996 | 12319 |
| ref|YP_003468785.1| | putative ATP-dependent helicase with nucleoside triP hydrolase domain | 36.22 | 392 | 244 | 6 | 12315 | 13472 |
| ref|YP_003468785.1| | putative ATP-dependent helicase with nucleoside triP hydrolase domain | 41.12 | 107 | 63 | 1 | 11996 | 12316 |
| ref|ZP_04404492.1| | helicase-related protein [*Vibrio cholerae* TMA 21] | 34.36 | 454 | 291 | 10 | 12315 | 13655 |
| ref|ZP_04404492.1| | helicase-related protein [*Vibrio cholerae* TMA 21] | 40.91 | 110 | 65 | 1 | 11996 | 12325 |
| ref|ZP_04005046.1| | ATP-dependent helicase [*Escherichia coli* 83972] | 37.73 | 387 | 235 | 6 | 12315 | 13457 |
| ref|ZP_04005046.1| | ATP-dependent helicase [*Escherichia coli* 83972] | 42.59 | 108 | 62 | 1 | 11996 | 12319 |
| ref|ZP_01983341.1| | putative DNA or RNA helicase [*Vibrio cholerae* 623-39] | 34.36 | 454 | 291 | 10 | 12315 | 13655 |
| ref|ZP_01983341.1| | putative DNA or RNA helicase [*Vibrio cholerae* 623-39] | 40.91 | 110 | 65 | 1 | 11996 | 12325 |
| ref|ZP_06033549.1| | helicase-related protein [*Vibrio mimicus* VM223] | 37.11 | 388 | 237 | 7 | 12315 | 13457 |
| ref|ZP_06033549.1| | helicase-related protein [*Vibrio mimicus* VM223] | 40.91 | 110 | 65 | 1 | 11996 | 12325 |
| ref|NP_754607.1| | hypothetical protein c2721 [*Escherichia coli* CFT073] | 37.73 | 387 | 235 | 6 | 12315 | 13457 |
| ref|NP_754607.1| | hypothetical protein c2721 [*Escherichia coli* CFT073] | 42.59 | 108 | 62 | 1 | 11996 | 12319 |
| ref|YP_001437156.1| | hypothetical protein ESA_01052 [*Cronobacter sakazakii* ATCC BAA-894] | 37.47 | 403 | 246 | 7 | 12315 | 13505 |
| ref|YP_001437156.1| | hypothetical protein ESA_01052 [*Cronobacter sakazakii* ATCC BAA-894] | 42.59 | 108 | 62 | 1 | 11996 | 12319 |
| ref|YP_001458984.1| | putative helicase [*Escherichia coli* HS] | 37.47 | 387 | 236 | 6 | 12315 | 13457 |
| ref|YP_001458984.1| | putative helicase [*Escherichia coli* HS] | 43.52 | 108 | 61 | 1 | 11996 | 12319 |
| ref|ZP_06654124.1| | helicase [*Escherichia coli* B354] | 37.47 | 387 | 236 | 6 | 12315 | 13457 |
| ref|ZP_06654124.1| | helicase [*Escherichia coli* B354] | 43.52 | 108 | 61 | 1 | 11996 | 12319 |
| ref|ZP_06658113.1| | helicase [*Escherichia coli* B185] | 37.47 | 387 | 236 | 6 | 12315 | 13457 |
| ref|ZP_06658113.1| | helicase [*Escherichia coli* B185] | 43.52 | 108 | 61 | 1 | 11996 | 12319 |
| ref|YP_002408285.1| | putative nucleic acid ATP-dependent helicase [*Escherichia coli* IAI39] | 37.47 | 387 | 236 | 6 | 12315 | 13457 |
| ref|YP_002408285.1| | putative nucleic acid ATP-dependent helicase [*Escherichia coli* IAI39] | 43.52 | 108 | 61 | 1 | 11996 | 12319 |
| ref|NP_288767.1| | putative ATP-dependent helicase [*Escherichia coli* O157:H7 EDL933] | 37.47 | 387 | 236 | 6 | 12315 | 13457 |
| ref|NP_288767.1| | putative ATP-dependent helicase | 43.52 | 108 | 61 | 1 | 11996 | 12319 |

TABLE 1-continued

| Subject id | Description | % identity | alignment length | Mis matches | gap openings | q. start | q. end |
|---|---|---|---|---|---|---|---|
| | [*Escherichia coli* O157:H7 EDL933] | | | | | | |
| ref|ZP_05945679.1| | helicase-related protein [*Vibrio orientalis* CIP 102891] | 34.62 | 439 | 280 | 9 | 12315 | 13610 |
| ref|ZP_05945679.1| | helicase-related protein [*Vibrio orientalis* CIP 102891] | 40.91 | 110 | 65 | 1 | 11996 | 12325 |
| ref|ZP_05435996.1| | predicted ATP-dependet helicase [*Escherichia* sp. 4_1_40B] | 37.47 | 387 | 236 | 6 | 12315 | 13457 |
| ref|ZP_05435996.1| | predicted ATP-dependet helicase [*Escherichia* sp. 4_1_40B] | 43.52 | 108 | 61 | 1 | 11996 | 12319 |
| ref|YP_002398545.1| | putative nucleic acid ATP-dependent helicase [*Escherichia coli* ED1a] | 37.47 | 387 | 236 | 6 | 12315 | 13457 |
| ref|YP_002398545.1| | putative nucleic acid ATP-dependent helicase [*Escherichia coli* ED1a] | 43.52 | 108 | 61 | 1 | 11996 | 12319 |
| ref|YP_002329837.1| | predicted ATP-dependet helicase [*Escherichia coli* O127:H6 str. | 37.47 | 387 | 236 | 6 | 12315 | 13457 |
| ref|YP_002329837.1| | predicted ATP-dependet helicase [*Escherichia coli* O127:H6 str. | 43.52 | 108 | 61 | 1 | 11996 | 12319 |
| emb|CBG35250.1| | putative helicase [*Escherichia coli* 042] | 37.47 | 387 | 236 | 6 | 12315 | 13457 |
| emb|CBG35250.1| | putative helicase [*Escherichia coli* 042] | 43.52 | 108 | 61 | 1 | 11996 | 12319 |
| ref|YP_311124.1| | putative ATP-dependent helicase [*Shigella sonnei* Ss046] | 37.21 | 387 | 237 | 6 | 12315 | 13457 |
| ref|YP_311124.1| | putative ATP-dependent helicase [*Shigella sonnei* Ss046] | 44.44 | 108 | 60 | 1 | 11996 | 12319 |
| ref|ZP_06182173.1| | helicase-related protein [*Vibrio alginolyticus* 40B] | 35.05 | 428 | 271 | 9 | 12315 | 13577 |
| ref|ZP_06182173.1| | helicase-related protein [*Vibrio alginolyticus* 40B] | 41.82 | 110 | 164 | 1 | 11996 | 12325 |
| ref|YP_002383391.1| | putative nucleic acid ATP-dependent helicase [*Escherichia fergusonii* | 37.47 | 387 | 236 | 6 | 12315 | 13457 |
| ref|YP_002383391.1| | putative nucleic acid ATP dependent helicase [*Escherichia fergusonii* | 43.52 | 108 | 61 | 1 | 11996 | 12319 |
| ref|ZP_01956145.1| | DNA or RNA helicase [*Vibrio cholerae* MZO-3] | 36.86 | 388 | 238 | 7 | 12315 | 13457 |
| ref|ZP_01956145.1| | DNA or RNA helicase [*Vibrio cholerae* MZO-3] | 40.91 | 110 | 65 | 1 | 11996 | 12325 |
| ref|ZP_04413136.1| | helicase-related protein [*Vibrio cholerae* bv. *albensis* VL426] | 34.36 | 454 | 291 | 10 | 12315 | 13655 |
| ref|ZP_04413136.1| | helicase-related protein [*Vibrio cholerae* bv. *albensis* VL426] | 40.91 | 110 | 65 | 1 | 11996 | 12325 |
| ref|YP_003259295.1| | type III restriction protein res subunit [*Pectobacterium wasabiae* | 36.72 | 403 | 249 | 7 | 12315 | 13505 |

TABLE 1-continued

| Subject id | Description | % identity | alignment length | Mis matches | gap openings | q. start | q. end |
|---|---|---|---|---|---|---|---|
| ref\|YP_003259295.1\| | type III restriction protein res subunit [*Pectobacterium wasabiae* | 40.19 | 107 | 64 | 1 | 11996 | 12316 |
| emb\|CBK87212.1\| | DNA or RNA helicases of superfamily II [*Enterobacter cloacae* NCTC 9394] | 36.63 | 404 | 250 | 7 | 12312 | 13505 |
| emb\|CBK87212.1\| | DNA or RNA helicases of superfamily II [*Enterobacter cloacae* NCTC 9394] | 40.91 | 110 | 65 | 1 | 11996 | 12325 |
| ref\|YP_402562.1\| | putative ATP-dependent helicase [*Shigella dysenteriae* Sd197] | 37.47 | 387 | 236 | 6 | 12315 | 13457 |
| ref\|YP_402562.1\| | putative ATP-dependent helicase [*Shigella dysenteriae* Sd197] | 42.59 | 108 | 62 | 1 | 11996 | 12319 |
| gb\|ACI81269.1\| | putative ATP-dependent helicase [*Escherichia coli*] | 37.21 | 387 | 237 | 6 | 12315 | 13457 |
| gb\|ACI81269.1\| | putative ATP-dependent helicase [*Escherichia coli*] | 43.52 | 108 | 61 | 1 | 11996 | 12319 |
| ref\|YP_960220.1\| | type III restriction enzyme, res subunit [*Marinobacter aquaeolei* VT8] | 36.76 | 408 | 247 | 10 | 12315 | 13505 |
| ref\|YP_960220.1\| | type III restriction enzyme, res subunit [*Marinobacter aquaeolei* VT8] | 37.96 | 108 | 67 | 1 | 11996 | 12319 |
| ref\|ZP_01681930.1\| | ATP-dependent RNA helicase, DEAD/DEAH box family [*Vibrio cholerae* V52] | 34.14 | 454 | 292 | 10 | 12315 | 13655 |
| ref\|ZP_01681930.1\| | ATP-dependent RNA helicase, DEAD/DEAH box family [*Vibrio cholerae* V52] | 40.91 | 110 | 65 | 1 | 11996 | 12325 |
| ref\|NP_231273.1\| | helicase-related protein [*Vibrio cholerae* O1 biovar El Tor str. N16961] | 34.14 | 454 | 292 | 10 | 12315 | 13655 |
| ref\|NP_231273.1\| | helicase-related protein [*Vibrio cholerae* O1 biovar El Tor str. N16961] | 40.91 | 110 | 65 | 1 | 11996 | 12325 |
| ref\|ZP_04397756.1\| | helicase-related protein [*Vibrio cholerae* BX 330286] | 34.14 | 454 | 292 | 10 | 12315 | 13655 |
| ref\|ZP_04397756.1\| | helicase-related protein [*Vibrio cholerae* BX 330286] | 40.91 | 110 | 65 | 1 | 11996 | 12325 |
| ref\|ZP_03066501.1\| | putative helicase [*Shigella dysenteriae* 1012] | 37.21 | 387 | 237 | 6 | 12315 | 13457 |
| ref\|ZP_03066501.1\| | putative helicase [*Shigella dysenteriae* 1012] | 43.52 | 108 | 61 | 1 | 11996 | 12319 |
| ref\|YP_001744380.1\| | putative helicase [*Escherichia coli* SMS-3-5] | 37.47 | 387 | 236 | 6 | 12315 | 13457 |
| ref\|YP_001744380.1\| | putative helicase [*Escherichia coli* SMS-3-5] | 43.52 | 108 | 61 | 1 | 11996 | 12319 |
| ref\|NP_708083.1\| | putative ATP-dependent helicase [*Shigella flexneri* 2a str. 301] | 37.21 | 387 | 237 | 6 | 12315 | 13457 |

TABLE 1-continued

| Subject id | Description | % identity | alignment length | Mis matches | gap openings | q. start | q. end |
|---|---|---|---|---|---|---|---|
| ref|NP_708083.1| | putative ATP-dependent helicase [*Shigella flexneri* 2a str. 301] | 43.52 | 108 | 61 | 1 | 11996 | 12319 |
| ref|ZP_03842064.1| | helicase [*Proteus mirabilis* ATCC 29906] | 36.99 | 392 | 241 | 6 | 12315 | 13472 |
| ref|ZP_03842064.1| | helicase [*Proteus mirabilis* ATCC 29906] | 42.59 | 108 | 62 | 1 | 11996 | 12319 |
| ref|YP_002150583.1| | helicase [*Proteus mirabilis* HI4320] | 36.99 | 392 | 241 | 6 | 12315 | 13472 |
| ref|YP_002150583.1| | helicase [*Proteus mirabilis* HI4320] | 42.59 | 108 | 62 | 1 | 11996 | 12319 |
| ref|YP_003296361.1| | DNA or RNA helicases of superfamily II [*Edwardsiella tarda* EIB202] | 38.24 | 387 | 233 | 6 | 12315 | 13457 |
| ref|YP_003296361.1| | DNA or RNA helicases of superfamily II [*Edwardsiella tarda* EIB202] | 42.06 | 107 | 62 | 1 | 11996 | 12316 |
| ref|ZP_02827406.1| | putative helicase [*Escherichia coli* O157:H7 str. EC508] | 37.47 | 387 | 236 | 6 | 12315 | 13457 |
| ref|ZP_02827406.1| | putative helicase [*Escherichia coli* O157:H7 str. EC508] | 43.52 | 108 | 61 | 1 | 11996 | 12319 |
| ref|ZP_04637851.1| | hypothetical protein yinte0001_11550 [*Yersinia intermedia* ATCC 29909] | 38.12 | 404 | 244 | 7 | 12312 | 13505 |
| ref|ZP_04637851.1| | hypothetical protein yinte0001_11550 [*Yersinia intermedia* ATCC 29909] | 40.19 | 107 | 64 | 1 | 11996 | 12316 |
| ref|ZP_01078151.1| | putative helicase [*Marinomonas* sp. MED121] | 33.55 | 453 | 295 | 8 | 12315 | 13655 |
| ref|ZP_01078151.1| | putative helicase [*Marinomonas* sp. MED121] | 41.28 | 109 | 64 | 1 | 11993 | 12319 |
| ref|YP_001177496.1| | type III restriction enzyme, res subunit [*Enterobacter* sp. 638] | 36.63 | 404 | 250 | 7 | 12312 | 13505 |
| ref|YP_001177496.1| | type III restriction enzyme, res subunit [*Enterobacter* sp. 638] | 40.91 | 110 | 65 | 1 | 11996 | 12325 |
| ref|ZP_03027279.1| | putative helicase [*Escherichia coli* B7A] | 37.21 | 387 | 237 | 6 | 12315 | 13457 |
| ref|ZP_03027279.1| | putative helicase [*Escherichia coli* B7A] | 43.52 | 108 | 61 | 1 | 11996 | 12319 |
| ref|ZP_04622971.1| | hypothetical protein ykris0001_4070 [*Yersinia kristensenii* ATCC 33638] | 37.62 | 404 | 246 | 7 | 12312 | 13505 |
| ref|ZP_04622971.1| | hypothetical protein ykris0001_4070 [*Yersinia kristensenii* ATCC 33638] | 40.19 | 107 | 64 | 1 | 11996 | 12316 |
| ref|YP_003531677.1| | Uncharacterized protein yejH [*Erwinia amylovora* CFBP1430] | 36.86 | 407 | 251 | 8 | 12315 | 13517 |
| ref|YP_003531677.1| | Uncharacterized protein yejH [*Erwinia amylovora* CFBP1430] | 44.86 | 107 | 59 | 1 | 11996 | 12316 |
| ref|YP_050835.1| | putative helicase [*Pectobacterium atrosepticum* SCRI1043] | 36.99 | 392 | 241 | 6 | 12315 | 13472 |
| ref|YP_050835.1| | putative helicase [*Pectobacterium atrosepticum* SCRI1043] | 41.12 | 107 | 63 | 1 | 11996 | 12316 |

TABLE 1-continued

| Subject id | Description | % identity | alignment length | Mis matches | gap openings | q. start | q. end |
|---|---|---|---|---|---|---|---|
| ref|ZP_06715404.1| | putative helicase, ATP-dependent [*Edwardsiella tarda* ATCC 23685] | 36.72 | 403 | 249 | 7 | 12315 | 13505 |
| ref|ZP_06715404.1| | putative helicase, ATP-dependent [*Edwardsiella tarda* ATCC 23685] | 42.99 | 107 | 61 | 1 | 11996 | 12316 |
| ref|ZP_01066377.1| | helicase-related protein [*Vibrio* sp. MED222] | 34.35 | 428 | 274 | 9 | 12315 | 13577 |
| ref|ZP_01066377.1| | helicase-related protein [*Vibrio* sp. MED222] | 40.00 | 110 | 66 | 1 | 11996 | 12325 |
| ref|ZP_05887740.1| | helicase-related protein [*Vibrio coralliilyticus* ATCC BAA-450] | 34.50 | 429 | 274 | 9 | 12315 | 13580 |
| ref|ZP_05887740.1| | helicase-related protein [*Vibrio coralliilyticus* ATCC BAA-450] | 41.82 | 110 | 64 | 1 | 11996 | 12325 |
| ref|ZP_01991276.1| | DNA or RNA helicase [*Vibrio parahaemolyticus* AQ3810] | 37.40 | 385 | 234 | 7 | 12315 | 13448 |
| ref|ZP_01991276.1| | DNA or RNA helicase [*Vibrio parahaemolyticus* AQ3810] | 40.91 | 110 | 65 | 1 | 11996 | 12325 |
| ref|YP_003494744.1| | type III restriction protein res subunit [*Thioalkalivibrio* sp. K90mix] | 37.08 | 391 | 230 | 12 | 12312 | 13436 |
| ref|YP_003494744.1| | type III restriction protein res subunit [*Thioalkalivibrio* sp. K90mix] | 47.27 | 110 | 52 | 2 | 11999 | 12310 |
| ref|YP_003520872.1| | YejH [*Pantoea ananatis* LMG 20103] | 34.98 | 466 | 288 | 12 | 12312 | 13664 |
| ref|YP_003520872.1| | YejH [*Pantoea ananatis* LMG 20103] | 40.37 | 109 | 65 | 1 | 11996 | 12322 |
| ref|YP_408545.1| | putative ATP-dependent helicase [*Shigella boydii* Sb227] | 37.21 | 387 | 237 | 6 | 12315 | 13457 |
| ref|YP_408545.1| | putative ATP-dependent helicase [*Shigella boydii* Sb227] | 43.52 | 108 | 61 | 1 | 11996 | 12319 |
| emb|CBA72544.1| | helicase [*Arsenophonus nasoniae*] | 37.47 | 387 | 236 | 6 | 12315 | 13457 |
| emb|CBA72544.1| | helicase [*Arsenophonus nasoniae*] | 41.12 | 107 | 63 | 1 | 11996 | 12316 |
| gb|ADF63037.1| | putative helicase [*Enterobacter cloacae* subsp. *cloacae* ATCC 13047] | 36.88 | 404 | 249 | 7 | 12312 | 13505 |
| gb|ADF63037.1| | putative helicase [*Enterobacter cloacae* subsp. *cloacae* ATCC 13047] | 40.91 | 110 | 65 | 1 | 11996 | 12325 |
| ref|YP_001336265.1| | putative ATP-dependent helicase [*Klebsiella pneumoniae* subsp. | 37.72 | 403 | 245 | 7 | 12315 | 13505 |
| ref|YP_001336265.1| | putative ATP-dependent helicase [*Klebsiella pneumoniae* subsp. | 40.91 | 110 | 65 | 1 | 11996 | 12325 |
| ref|YP_002648342.1| | Putative ATP-dependent helicase [*Erwinia pyrifoliae* Ep1/96] | 36.12 | 407 | 254 | 8 | 12315 | 13517 |

TABLE 1-continued

| Subject id | Description | % identity | alignment length | Mis matches | gap openings | q. start | q. end |
|---|---|---|---|---|---|---|---|
| ref\|YP_002648342.1\| | Putative ATP-dependent helicase [*Erwinia pyrifoliae* Ep1/96] | 45.79 | 107 | 58 | 1 | 11996 | 12316 |
| ref\|YP_002237396.1\| | putative helicase [*Klebsiella pneumoniae* 342] | 37.72 | 403 | 245 | 7 | 12315 | 13505 |
| ref\|YP_002237396.1\| | putative helicase [*Klebsiella pneumoniae* 342] | 40.91 | 110 | 65 | 1 | 11996 | 12325 |
| ref\|ZP_01616973.1\| | putative ATP-dependent helicase [marine gamma proteobacterium HTCC2143] | 33.85 | 455 | 292 | 11 | 12315 | 13652 |
| ref\|ZP_01616973.1\| | putative ATP-dependent helicase [marine gamma proteobacterium HTCC2143] | 42.06 | 107 | 62 | 1 | 11996 | 12316 |
| ref\|ZP_01893164.1\| | putative ATP-dependent helicase with nucleoside triP hydrolase domain | 35.28 | 411 | 252 | 8 | 12315 | 13505 |
| ref\|ZP_01893164.1\| | putative ATP-dependent helicase with nucleoside triP hydrolase domain | 38.89 | 108 | 66 | 1 | 11996 | 12319 |
| ref\|ZP_03320542.1\| | hypothetical protein PROVALCAL_03503 [*Providencia alcalifaciens* DSM | 34.83 | 422 | 269 | 8 | 12315 | 13562 |
| ref\|ZP_03320542.1\| | hypothetical protein PROVALCAL_03503 [*Providencia alcalifaciens* DSM | 41.82 | 110 | 64 | 1 | 11996 | 12325 |
| ref\|ZP_03825744.1\| | putative helicase [*Pectobacterium carotovorum* subsp. *brasiliensis* | 36.72 | 403 | 249 | 7 | 12315 | 13505 |
| ref\|ZP_03825744.1\| | putative helicase [*Pectobacterium carotovorum* subsp. *brasiliensis* | 40.19 | 107 | 64 | 1 | 11996 | 12316 |
| ref\|ZP_01166590.1\| | putative ATP-dependent helicase [*Oceanospirillum* sp. MED92] | 35.41 | 401 | 251 | 8 | 12294 | 13472 |
| ref\|ZP_01166590.1\| | putative ATP-dependent helicase [*Oceanospirillum* sp. MED92] | 37.17 | 113 | 71 | 1 | 11978 | 12316 |
| ref\|ZP_06547896.1\| | DNA or RNA helicase, superfamily II [*Klebsiella* sp. 1_1_55] | 37.72 | 403 | 245 | 7 | 12315 | 13505 |
| ref\|ZP_06547896.1\| | DNA or RNA helicase, superfamily II [*Klebsiella* sp. 1_1_55] | 40.91 | 110 | 65 | 1 | 11996 | 12325 |
| ref\|YP_003040502.1\| | hypothetical protein PAU_01666 [*Photorhabdus asymbiotica*] | 35.06 | 405 | 255 | 7 | 12315 | 13505 |
| ref\|YP_003040502.1\| | hypothetical protein PAU_01666 [*Photorhabdus asymbiotica*] | 40.91 | 110 | 65 | 1 | 11996 | 12325 |
| ref\|ZP_04628275.1\| | hypothetical protein yberc0001_27060 [*Yersinia bercovieri* ATCC 43970] | 37.87 | 404 | 245 | 7 | 12312 | 13505 |
| ref\|ZP_04628275.1\| | hypothetical protein yberc0001_27060 [*Yersinia bercovieri* ATCC 43970] | 39.25 | 107 | 65 | 1 | 11996 | 12316 |

TABLE 1-continued

| Subject id | Description | % identity | alignment length | Mis matches | gap openings | q. start | q. end |
|---|---|---|---|---|---|---|---|
| ref\|YP_002311188.1\| | Helicase: Type III restriction enzyme, res subunit: DEAD/DEAH box | 36.12 | 407 | 254 | 7 | 12315 | 13517 |
| ref\|YP_002311188.1\| | Helicase: Type III restriction enzyme, res subunit: DEAD/DEAH box | 42.86 | 105 | 60 | 2 | 11996 | 12310 |
| ref\|ZP_00992578.1\| | helicase-related protein [*Vibrio splendidus* 12B01] | 34.11 | 428 | 275 | 9 | 12315 | 13577 |
| ref\|ZP_00992578.1\| | helicase-related protein [*Vibrio splendidus* 12B01] | 40.00 | 110 | 66 | 1 | 11996 | 12325 |
| ref\|YP_002417462.1\| | helicase-like protein [*Vibrio splendidus* LGP32] | 33.64 | 428 | 277 | 9 | 12315 | 13577 |
| ref\|YP_002417462.1\| | helicase-like protein [*Vibrio splendidus* LGP32] | 40.00 | 110 | 166 | 1 | 11996 | 12325 |
| ref\|ZP_04640356.1\| | hypothetical protein ymoll0001_26590 [*Yersinia mollaretii* ATCC 43969] | 37.62 | 404 | 246 | 7 | 12312 | 13505 |
| ref\|ZP_04640356.1\| | hypothetical protein ymoll0001_26590 [*Yersinia mollaretii* ATCC 43969] | 39.25 | 107 | 65 | 1 | 11996 | 12316 |
| ref\|NP_930102.1\| | hypothetical protein plu2868 [*Photorhabdus luminescens* subsp. *laumondii* | 35.24 | 403 | 255 | 7 | 12315 | 13505 |
| ref\|NP_930102.1\| | hypothetical protein plu2868 [*Photorhabdus luminescens* subsp. *laumondii* | 40.00 | 110 | 66 | 1 | 11996 | 12325 |
| ref\|YP_001473601.1\| | type III restriction enzyme, res subunit [*Shewanella sediminis* HAW-EB3] | 36.12 | 407 | 254 | 7 | 12315 | 13517 |
| ref\|YP_001473601.1\| | type III restriction enzyme, res subunit [*Shewanella sediminis* HAW-EB3] | 39.45 | 109 | 66 | 2 | 11996 | 12322 |
| ref\|YP_750157.1\| | type III restriction enzyme, res subunit [*Shewanella frigidimarina* | 35.33 | 484 | 297 | 16 | 12315 | 13718 |
| ref\|YP_750157.1\| | type III restriction enzyme, res subunit [*Shewanella frigidimarina* | 36.70 | 109 | 69 | 2 | 11996 | 12322 |
| ref\|YP_001502414.1\| | type III restriction protein res subunit [*Shewanella pealeana* ATCC | 33.68 | 484 | 303 | 12 | 12315 | 13712 |
| ref\|YP_001502414.1\| | type III restriction protein res subunit [*Shewanella pealeana* ATCC | 40.95 | 105 | 62 | 2 | 11996 | 12310 |
| ref\|ZP_01738006.1\| | putative ATP-dependent helicase with nucleoside trip hydrolase domain | 34.55 | 411 | 255 | 8 | 12315 | 13505 |
| ref\|ZP_01738006.1\| | putative ATP-dependent helicase with nucleoside trip hydrolase domain | 39.81 | 108 | 65 | 1 | 11996 | 12319 |
| ref\|YP_572900.1\| | type III restriction enzyme, res subunit [*Chromohalobacter salexigens* | 36.75 | 400 | 230 | 10 | 12327 | 13457 |
| ref\|YP_572900.1\| | type III restriction enzyme, res subunit | 41.67 | 108 | 63 | 1 | 11996 | 12319 |

TABLE 1-continued

| Subject id | Description | % identity | alignment length | Mis matches | gap openings | q. start | q. end |
|---|---|---|---|---|---|---|---|
| ref|ZP_01217250.1| | [*Chromohalobacter salexigens*] putative ATP-dependent helicase [*Psychromonas* sp. CNPT3] | 34.11 | 428 | 276 | 8 | 12315 | 13580 |
| ref|ZP_01217250.1| | putative ATP-dependent helicase [*Psychromonas* sp. CNPT3] | 40.91 | 110 | 65 | 1 | 11996 | 12325 |
| ref|ZP_01614134.1| | putative ATP-dependent helicase with nucleoside triP hydrolase domain | 36.62 | 385 | 238 | 6 | 12321 | 13457 |
| ref|ZP_01614134.1| | putative ATP-dependent helicase with nucleoside triP hydrolase domain | 42.31 | 104 | 60 | 1 | 11996 | 12307 |
| ref|ZP_01815643.1| | DNA or RNA helicase [*Vibrionales bacterium* SWAT-3] | 33.88 | 428 | 276 | 9 | 12315 | 13577 |
| ref|ZP_01815043.1| | DNA or RNA helicase [*Vibrionales bacterium* SWAT-3] | 40.00 | 110 | 66 | 1 | 11996 | 12325 |
| ref|ZP_05119245.1| | ATP-dependent rna helicase, dead/deah box family [*Vibrio* | 35.31 | 388 | 244 | 7 | 12315 | 13457 |
| ref|ZP_05119245.1| | ATP-dependent rna helicase, dead/deah box family [*Vibrio* | 41.82 | 110 | 64 | 1 | 11996 | 12325 |
| ref|NP_718328.1| | helicase [*Shewanella oneidensis* MR-1] | 34.38 | 413 | 262 | 8 | 12315 | 13526 |
| ref|NP_718328.1| | helicase [*Shewanella oneidensis* MR-1] | 46.07 | 89 | 48 | 1 | 11993 | 12259 |
| ref|ZP_03806120.1| | hypothetical protein PROPEN_04520 [*Proteus penneri* ATCC 35198] | 36.22 | 392 | 244 | 6 | 12315 | 13472 |
| ref|ZP_03806120.1| | hypothetical protein PROPEN_04520 [*Proteus penneri* ATCC 35198] | 40.19 | 107 | 64 | 1 | 11996 | 12316 |
| ref|ZP_02158478.1| | helicase [*Shewanella benthica* KT99] | 35.63 | 407 | 256 | 7 | 12315 | 13517 |
| ref|ZP_02158478.1| | helicase [*Shewanella benthica* KT99] | 37.61 | 109 | 68 | 2 | 11996 | 12322 |
| ref|YP_003556546.1| | helicase [*Shewanella violacea* DSS12] | 35.14 | 407 | 258 | 7 | 12315 | 13517 |
| ref|YP_003556546.1| | helicase [*Shewanella violacea* DSS12] | 38.53 | 109 | 67 | 2 | 11996 | 12322 |
| ref|ZP_05730923.1| | type III restriction protein res subunit [*Pantoea* sp. At-9b] | 36.63 | 404 | 249 | 9 | 12315 | 13505 |
| ref|ZP_05730923.1| | type III restriction protein res subunit [*Pantoea* sp. At-9b] | 42.99 | 107 | 61 | 1 | 11996 | 12316 |
| ref|YP_870159.1| | type III restriction enzyme, res subunit [*Shewanella* sp. ANA-3] | 34.87 | 413 | 260 | 8 | 12315 | 135261 |
| ref|YP_870159.1| | type III restriction enzyme, res subunit [*Shewanella* sp. ANA-3] | 46.59 | 88 | 47 | 1 | 11996 | 12259 |
| ref|YP_734491.1| | type III restriction enzyme, res subunit [*Shewanella* sp. MR-4] | 34.62 | 413 | 261 | 8 | 12315 | 135261 |
| ref|YP_734491.1| | type III restriction enzyme, res subunit [*Shewanella* sp. MR-4] | 46.59 | 88 | 47 | 1 | 11996 | 122591 |
| ref|YP_002987959.1| | type III restriction protein res subunit [*Dickeya dadantii* Ech703] | 37.50 | 392 | 239 | 6 | 12315 | 13472 |
| ref|YP_002987959.1| | type III restriction protein res subunit | 40.19 | 107 | 64 | 1 | 11996 | 12316 |

TABLE 1-continued

| Subject id | Description | % identity | alignment length | Mis matches | gap openings | q. start | q. end |
|---|---|---|---|---|---|---|---|
| | [*Dickeya dadantii* Ech703] | | | | | | |
| ref|YP_738477.1| | type III restriction enzyme, res subunit [*Shewanella* sp. MR-7] | 34.38 | 413 | 262 | 8 | 12315 | 13526 |
| ref|YP_738477.1| | type III restriction enzyme, res subunit [*Shewanella* sp. MR-7] | 46.59 | 88 | 47 | 1 | 11996 | 12259 |
| ref|YP_001907200.1| | Putative ATP-dependent helicase [*Erwinia tasmaniensis* Et1/99] | 35.63 | 407 | 256 | 8 | 12315 | 135171 |
| ref|YP_001907200.1| | Putative ATP-dependent helicase [*Erwinia tasmaniensis* Et1/99] | 42.06 | 107 | 62 | 1 | 11996 | 12316 |
| ref|ZP_04919702.1| | IS4 ORF [*Vibrio cholerae* V51] | 34.36 | 454 | 291 | 10 | 12315 | 13655 |
| ref|ZP_04919702.1| | IS4 ORF [*Vibrio cholerae* V51] | 37.25 | 102 | 64 | 1 | 12020 | 12325 |
| ref|YP_001673921.1| | type III restriction protein res subunit [*Shewanella halifaxensis*] | 35.63 | 407 | 256 | 7 | 12315 | 13517 |
| ref|YP_001673921.1| | type III restriction protein res subunit [*Shewanella halifaxensis*] | 43.18 | 88 | 50 | 1 | 11996 | 12259 |
| ref|YP_942721.1| | type III restriction enzyme, res subunit [*Psychromonas ingrahamii* 37] | 34.24 | 403 | 259 | 7 | 12315 | 13505 |
| ref|YP_942721.1| | type III restriction enzyme, res subunit [*Psychromonas ingrahamii* 37] | 41.28 | 109 | 64 | 1 | 11996 | 12322 |
| ref|YP_857132.1| | putative helicase, ATP-dependent [*Aeromonas hydrophila* subsp. | 35.22 | 389 | 244 | 7 | 12315 | 13457 |
| ref|YP_857132.1| | putative helicase, ATP-dependent [*Aeromonas hydrophila* subsp. | 44.44 | 108 | 60 | 1 | 11993 | 12316 |
| ref|ZP_02901914.1| | putative helicase [*Escherichia albertii* TW07627] | 37.47 | 387 | 236 | 6 | 12315 | 13457 |
| ref|ZP_02901914.1| | putative helicase [*Escherichia albertii* TW07627] | 38.00 | 100 | 62 | 1 | 12020 | 12319 |
| ref|YP_001554221.1| | type III restriction protein res subunit [*Shewanella baltica* OS195] | 35.35 | 413 | 258 | 8 | 12315 | 13526 |
| ref|YP_001554221.1| | type III restriction protein res subunit [*Shewanella baltica* OS195] | 38.53 | 109 | 67 | 1 | 11996 | 12322 |
| ref|YP_963049.1| | type III restriction enzyme, res subunit [*Shewanella* sp. W3-18-1] | 34.87 | 413 | 260 | 8 | 12315 | 13526 |
| ref|YP_963049.1| | type III restriction enzyme, res subunit [*Shewanella* sp. W3-18-1] | 42.55 | 94 | 54 | 1 | 11978 | 12259 |
| ref|YP_002358450.1| | type III restriction protein res subunit [*Shewanella baltica* OS223] | 35.11 | 413 | 259 | 8 | 12315 | 13526 |
| ref|YP_002358450.1| | type III restriction protein res subunit [*Shewanella baltica* OS223] | 43.01 | 93 | 53 | 1 | 11996 | 12274 |
| ref|ZP_01707328.1| | type III restriction enzyme, res subunit | 34.87 | 413 | 260 | 8 | 12315 | 13526 |

TABLE 1-continued

| Subject id | Description | % identity | alignment length | Mis matches | gap openings | q. start | q. end |
|---|---|---|---|---|---|---|---|
| ref\|ZP_01707328.1\| | type III restriction enzyme, res subunit [*Shewanella putrefaciens* 200] | 42.55 | 94 | 54 | 1 | 11978 | 12259 |
| ref\|YP_001183870.1\| | type III restriction enzyme, res subunit [*Shewanella putrefaciens*] | 34.87 | 413 | 260 | 8 | 12315 | 13526 |
| ref\|YP_001183870.1\| | type III restriction enzyme, res subunit [*Shewanella putrefaciens*] | 42.55 | 94 | 54 | 1 | 11978 | 12259 |
| ref\|YP_001050129.1\| | type III restriction protein res subunit [*Shewanella baltica* OS155] | 35.11 | 413 | 259 | 8 | 12315 | 13526 |
| ref\|YP_001050129.1\| | type III restriction protein res subunit [*Shewanella baltica* OS155] | 43.01 | 93 | 53 | 1 | 11996 | 12274 |
| ref\|YP_001365953.1\| | type III restriction protein res subunit [*Shewanella baltica* OS185] | 35.35 | 413 | 258 | 8 | 12315 | 13526 |
| ref\|YP_001365953.1\| | type III restriction protein res subunit [*Shewanella baltica* OS185] | 38.53 | 109 | 67 | 1 | 11996 | 12322 |
| ref\|YP_001093658.1\| | type III restriction enzyme, res subunit [*Shewanella loihica* PV-4] | 36.12 | 407 | 254 | 8 | 12315 | 13517 |
| ref\|YP_001093658.1\| | type III restriction enzyme, res subunit [*Shewanella loihica* PV-4] | 40.37 | 109 | 65 | 1 | 11996 | 12322 |
| ref\|YP_563094.1\| | type III restriction enzyme, res subunit [*Shewanella denitrificans*] | 35.81 | 430 | 263 | 11 | 12315 | 13565 |
| ref\|YP_563094.1\| | type III restriction enzyme, res subunit [*Shewanella denitrificans*] | 38.53 | 109 | 67 | 2 | 11996 | 12322 |
| ref\|YP_001761097.1\| | type III restriction protein res subunit [*Shewanella woodyi* ATCC 51908] | 34.40 | 407 | 261 | 8 | 12315 | 13517 |
| ref\|YP_001761097.1\| | type III restriction protein res subunit [*Shewanella woodyi* ATCC 51908] | 41.51 | 106 | 62 | 2 | 11996 | 12313 |
| ref\|YP_001141517.1\| | ATP-dependent helicase [*Aeromonas salmonicida* subsp. *salmonicida* A449] | 35.22 | 389 | 244 | 6 | 12315 | 13457 |
| ref\|YP_001141517.1\| | ATP-dependent helicase [*Aeromonas salmonicida* subsp. *salmonicida* A449] | 44.44 | 108 | 60 | 1 | 11993 | 12316 |
| ref\|YP_340484.1\| | ATP-dependent helicase [*Pseudoalteromonas haloplanktis* TAC125] | 35.00 | 440 | 280 | 10 | 12321 | 13622 |
| ref\|YP_340484.1\| | ATP-dependent helicase [*Pseudoalteromonas haloplanktis* TAC125] | 43.21 | 81 | 46 | 1 | 12065 | 12307 |
| ref\|YP_002934010.1\| | hypothetical protein NT01EI_2606 [*Edwardsiella ictaluri* 93-146] | 37.57 | 362 | 220 | 6 | 12315 | 13382 |
| ref\|YP_002934010.1\| | hypothetical protein NT01EI_2606 | 42.06 | 107 | 62 | 1 | 11996 | 12316 |

TABLE 1-continued

| Subject id | Description | % identity | alignment length | Mis matches | gap openings | q. start | q. end |
|---|---|---|---|---|---|---|---|
| ref|YP_001341391.1| | type III restriction protein res subunit [*Edwardsiella ictaluri* 93-146] [*Marinomonas* sp. MWYL1] | 34.19 | 389 | 248 | 7 | 12315 | 13457 |
| ref|YP_001341391.1| | type III restriction protein res subunit [*Marinomonas* sp. MWYL1] | 36.70 | 109 | 69 | 1 | 11996 | 12322 |
| ref|YP_663012.1| | type III restriction enzyme, res subunit [*Pseudoalteromonas atlantica*] | 32.92 | 407 | 254 | 8 | 12294 | 13457 |
| ref|YP_663012.1| | type III restriction enzyme, res subunit [*Pseudoalteromonas atlantica*] | 38.89 | 108 | 66 | 1 | 11993 | 12316 |
| ref|ZP_02335655.1| | putative helicase [*Yersinia pestis* FV-1] | 37.87 | 404 | 245 | 7 | 12312 | 13505 |
| ref|ZP_02335655.1| | putative helicase [*Yersinia pestis* FV-1] | 34.72 | 72 | 47 | 1 | 12101 | 12316 |
| ref|YP_003547295.1| | type III restriction protein res subunit [*Coraliomargarita akajimensis*] | 33.41 | 431 | 277 | 12 | 12315 | 13577 |
| ref|YP_003547295.1| | type III restriction protein res subunit [*Coraliomargarita akajimensis*] | 45.83 | 96 | 52 | 2 | 11996 | 12283 |
| ref|YP_927955.1| | helicase [*Shewanella amazonensis* SB2B] | 35.19 | 395 | 250 | 9 | 12315 | 13481 |
| ref|YP_927955.1| | helicase [*Shewanella amazonensis* SB2B] | 36.70 | 109 | 69 | 1 | 11996 | 12322 |
| ref|NP_970398.1| | putative ATP-dependent helicase [*Bdellovibrio bacteriovorus* HD100] | 34.53 | 391 | 246 | 10 | 12315 | 13457 |
| ref|NP_970398.1| | putative ATP-dependent helicase [*Bdellovibrio bacteriovorus* HD100] | 45.83 | 96 | 52 | 1 | 11996 | 12283 |
| ref|ZP_03829927.1| | putative helicase [*Pectobacterium carotovorum* subsp. *carotovorum* WPP14] | 36.48 | 403 | 250 | 7 | 12315 | 13505 |
| ref|ZP_03829927.1| | putative helicase [*Pectobacterium carotovorum* subsp. *carotovorum* WPP14] | 34.72 | 72 | 47 | 1 | 12101 | 12316 |
| gb|AAA16381.1| | yejH [*Escherichia coli*] | 38.51 | 296 | 176 | 4 | 12315 | 13184 |
| gb|AAA16381.1| | yejH [*Escherichia coli*] | 43.52 | 108 | 61 | 1 | 11996 | 12319 |
| ref|ZP_01899439.1| | putative ATP-dependent helicase with nucleoside triP hydrolasedomain | 36.81 | 383 | 236 | 8 | 12327 | 13457 |
| ref|ZP_01899439.1| | putative ATP-dependent helicase with nucleoside triP hydrolasedomain | 30.99 | 71 | 49 | 1 | 12104 | 12316 |
| ref|ZP_01132472.1| | putative ATP-dependent helicase with nucleoside triP hydrolase domain | 36.72 | 384 | 236 | 7 | 12327 | 13457 |
| ref|ZP_01132472.1| | putative ATP-dependent helicase with nucleoside triP hydrolase domain | 37.68 | 69 | 43 | 1 | 12101 | 12307 |
| ref|NP_102246.1| | hypothetical protein mll0452 [*Mesorhizobium loti* MAFF303099] | 34.04 | 379 | 246 | 5 | 28866 | 27742 |
| ref|NP_102246.1| | hypothetical protein mll0452 [*Mesorhizobium loti* MAFF303099] | 30.65 | 248 | 152 | 11 | 29661 | 28978 |

TABLE 1-continued

| Subject id | Description | % identity | alignment length | Mis matches | gap openings | q. start | q. end |
|---|---|---|---|---|---|---|---|
| ref\|YP_003524538.1\| | phage uncharacterized protein [*Sideroxydans lithotrophicus* ES-1] | 38.89 | 360 | 210 | 8 | 1474 | 425 |
| ref\|YP_003524538.1\| | phage uncharacterized protein [*Sideroxydans lithotrophicus* ES-1] | 51.63 | 184 | 89 | 1 | 2893 | 2342 |
| ref\|YP_003004760.1\| | type III restriction protein res subunit [*Dickeya zeae* Ech1591] | 38.24 | 408 | 241 | 8 | 12315 | 13505 |
| ref\|YP_003004760.1\| | type III restriction protein res subunit [*Dickeya zeae* Ech1591] | 33.73 | 166 | 103 | 3 | 11996 | 12472 |
| ref\|YP_864936.1\| | hypothetical protein Mmc1_1012 [*Magnetococcus* sp. MC-1] | 33.41 | 416 | 256 | 8 | 36990 | 35806 |
| ref\|YP_864936.1\| | hypothetical protein Mmc1_1012 [*Magnetococcus* sp. MC-1] | 29.07 | 172 | 102 | 7 | 35697 | 35242 |
| ref\|ZP_05973724.1\| | putative helicase, ATP-dependent [*Providencia rustigianii* DSM 4541] | 37.16 | 409 | 251 | 8 | 12297 | 13505 |
| ref\|ZP_05973724.1\| | putative helicase, ATP-dependent [*Providencia rustigianii* DSM 4541] | 42.73 | 110 | 63 | 1 | 11996 | 12325 |
| ref\|ZP_05881861.1\| | helicase-related protein [*Vibrio metschnikovii* CIP 69.14] | 36.36 | 407 | 252 | 8 | 12258 | 13457 |
| ref\|ZP_05881861.1\| | helicase-related protein [*Vibrio metschnikovii* CIP 69.14] | 42.20 | 109 | 63 | 1 | 11996 | 12322 |
| ref\|ZP_05716951.1\| | helicase-related protein [*Vibrio mimicus* VM573] | 37.31 | 394 | 240 | 8 | 12297 | 13457 |
| ref\|ZP_05716951.1\| | helicase-related protein [*Vibrio mimicus* VM573] | 40.91 | 110 | 65 | 1 | 11996 | 12325 |
| ref\|ZP_05057345.1\| | Type III restriction enzyme, res subunit family [*Verrucomicrobiae*] | 32.48 | 431 | 281 | 14 | 12315 | 13577 |
| ref\|ZP_05057345.1\| | Type III restriction enzyme, res subunit family [*Verrucomicrobiae*] | 41.67 | 96 | 56 | 1 | 11996 | 12283 |
| ref\|ZP_01739797.1\| | putative ATP-dependent helicase [*Marinobacter* sp. ELB17] | 32.99 | 385 | 243 | 10 | 12327 | 13436 |
| ref\|ZP_01739797.1\| | putative ATP-dependent helicase [*Marinobacter* sp. ELB17] | 38.05 | 113 | 64 | 1 | 11996 | 12316 |
| ref\|ZP_05181869.1\| | hypothetical protein Bru83_11056 [*Brucella* sp. 83/13] | 36.28 | 328 | 207 | 6 | 28875 | 27898 |
| ref\|ZP_05181869.1\| | hypothetical protein Bru83_11056 [*Brucella* sp. 83/13] | 33.94 | 165 | 108 | 4 | 29625 | 29134 |
| ref\|ZP_06361166.1\| | conserved hypothetical protein [*Rhodopseudomonas palustris* DX-1] | 41.96 | 336 | 180 | 5 | 27272 | 26310 |
| ref\|YP_003280885.1\| | pCQ3_36 [*Streptomyces* sp. W9] | 29.10 | 725 | 448 | 21 | 2737 | 761 |
| ref\|YP_769508.1\| | hypothetical protein RL3930 [*Rhizobium leguminosarum* bv. *viciae* 3841] | 29.08 | 612 | 418 | 21 | 29631 | 27844 |

TABLE 1-continued

| Subject id | Description | % identity | alignment length | Mis matches | gap openings | q. start | q. end |
|---|---|---|---|---|---|---|---|
| ref\|ZP_02494554.1\| | ATPases with chaperone activity, ATP-binding subunit [*Burkholderia* | 25.60 | 828 | 539 | 19 | 37122 | 34870 |
| ref\|YP_001063346.1\| | ATPases with chaperone activity, ATP-binding subunit [*Burkholderia* | 25.60 | 828 | 539 | 19 | 37122 | 34870 |
| ref\|YP_002280258.1\| | hypothetical protein Rleg2_0736 [*Rhizobium leguminosarum* bv. *trifolii* | 28.13 | 647 | 442 | 22 | 29673 | 27802 |
| ref\|ZP_06177758.1\| | helicase-related protein [*Vibrio harveyi* 1DA3] | 36.03 | 408 | 258 | 8 | 12363 | 13577 |
| ref\|YP_001327489.1\| | hypothetical protein Smed_1819 [*Sinorhizobium medicae* WSM419] | 33.42 | 377 | 250 | 5 | 28875 | 27748 |
| ref\|YP_001327489.1\| | hypothetical protein Smed_1819 [*Sinorhizobium medicae* WSM419] | 27.54 | 167 | 121 | 4 | 29634 | 29134 |
| ref\|YP_769506.1\| | hypothetical protein RL3928 [*Rhizobium leguminosarum* bv. *viciae* 3841] | 40.24 | 328 | 188 | 3 | 27275 | 26316 |
| ref\|YP_468637.1\| | hypothetical protein RHE_CH01103 [*Rhizobium etli* CFN 42] | 40.56 | 323 | 185 | 3 | 27272 | 26325 |
| ref\|YP_672800.1\| | hypothetical protein Meso_0231 [*Mesorhizobium* sp. BNC1] | 51.30 | 230 | 103 | 1 | 31062 | 30400 |
| ref\|YP_002826409.1\| | hypothetical protein NGR_c18920 [*Rhizobium* sp. NGR234] | 32.63 | 377 | 253 | 5 | 28875 | 27748 |
| ref\|YP_002826409.1\| | hypothetical protein NGR_c18920 [*Rhizobium* sp. NGR234] | 31.45 | 159 | 109 | 3 | 29610 | 29134 |
| ref\|ZP_03522929.1\| | hypothetical protein RetlG_17541 [*Rhizobium etli* GR56] | 39.14 | 327 | 192 | 3 | 27275 | 26316 |
| ref\|ZP_05811994.1\| | protein of unknown function DUF847 [*Mesorhizobium opportunistum* | 56.76 | 185 | 80 | 1 | 21202 | 20648 |
| ref\|YP_002280260.1\| | hypothetical protein Rleg2_0738 [*Rhizobium leguminosarum* bv. *trifolii* | 39.14 | 327 | 192 | 3 | 27275 | 26316 |
| ref\|ZP_03383797.1\| | putative helicase [*Salmonella enterica* subsp. *enterica* serovar Typhi | 38.05 | 339 | 208 | 5 | 12447 | 13457 |
| ref\|NP_102250.1\| | hypothetical protein mll0457 [*Mesorhizobium loti* MAFF303099] | 37.13 | 334 | 208 | 4 | 32487 | 31492 |
| ref\|YP_917849.1\| | hypothetical protein Pden_4087 [*Paracoccus denitrificans* PD1222] | 51.38 | 181 | 88 | 0 | 21202 | 20660 |
| ref\|ZP_03523887.1\| | hypothetical protein RetlG_23247 [*Rhizobium etli* GR56] | 29.60 | 500 | 332 | 18 | 29634 | 28195 |
| ref\|YP_672802.1\| | hypothetical protein Meso_0233 [*Mesorhizobium* sp. BNC1] | 41.03 | 234 | 137 | 2 | 30378 | 29680 |
| ref\|ZP_02494546.1\| | hypothetical protein BpseN_34245 | 27.00 | 600 | 425 | 17 | 29601 | 27841 |

TABLE 1-continued

| Subject id | Description | % identity | alignment length | Mis matches | gap openings | q. start | q. end |
|---|---|---|---|---|---|---|---|
| | [*Burkholderia pseudomallei* NCTC 13177] | | | | | | |
| ref|YP_001063338.1| | hypothetical protein BURPS668_A2344 [*Burkholderia pseudomallei* 668] | 27.00 | 600 | 425 | 17 | 29601 | 27841 |
| ref|YP_672809.1| | microcystin-dependent protein-like [*Mesorhizobium* sp. BNC1] | 40.51 | 274 | 157 | 8 | 22147 | 21344 |
| ref|YP_002601309.1| | putative secretion activating protein [*Desulfobacterium autotrophicum* | 48.80 | 209 | 107 | 3 | 21202 | 20576 |
| ref|YP_002125131.1| | phage uncharacterized protein [*Alteromonas macleodii* 'Deep ecotype'] | 34.24 | 330 | 211 | 6 | 1375 | 404 |
| ref|YP_002125131.1| | phage uncharacterized protein [*Alteromonas macleodii* 'Deep ecotype'] | 30.84 | 107 | 74 | 0 | 2641 | 2321 |
| ref|YP_002497863.1| | protein of unknown function DUF847 [*Methylobacterium nodulans* ORS 2060] | 48.97 | 194 | 98 | 2 | 21181 | 20603 |
| ref|YP_002500190.1| | protein of unknown function DUF847 [*Methylobacterium nodulans* ORS 2060] | 54.07 | 172 | 79 | 2 | 21181 | 20666 |
| ref|YP_002500876.1| | protein of unknown function DUF847 [*Methylobacterium nodulans* ORS 2060] | 52.27 | 176 | 84 | 2 | 21193 | 20666 |
| ref|YP_001353895.1| | hypothetical protein mma_2205 [*Janthinobacterium* sp. Marseille] | 24.66 | 730 | 503 | 16 | 36900 | 34852 |
| ref|YP_002499091.1| | protein of unknown function DUF847 [*Methylobacterium nodulans* ORS 2060] | 46.19 | 197 | 106 | 1 | 21193 | 20603 |
| ref|ZP_00209324.1| | COG3926: Putative secretion activating protein [*Magnetospirillum* | 46.49 | 185 | 99 | 1 | 21193 | 20639 |
| ref|ZP_06361173.1| | conserved hypothetical protein [*Rhodopseudomonas palustris* DX-1] | 37.12 | 326 | 203 | 4 | 32460 | 31489 |
| ref|YP_002495956.1| | protein of unknown function DUF847 [*Methylobacterium nodulans* ORS 2060] | 52.33 | 172 | 82 | 2 | 21181 | 20666 |
| ref|YP_002499477.1| | protein of unknown function DUF847 [*Methylobacterium nodulans* ORS 2060] | 50.29 | 175 | 87 | 1 | 21190 | 20666 |
| ref|YP_002497304.1| | protein of unknown function DUF847 [*Methylobacterium nodulans* ORS 2060] | 51.74 | 172 | 83 | 1 | 21181 | 20666 |
| ref|ZP_06793097.1| | hypothetical protein BAZG_01351 [*Brucella* sp. NVSL 07-0026] | 45.81 | 203 | 110 | 1 | 21190 | 20582 |
| ref|ZP_05168646.1| | hypothetical protein BpinM_07480 [*Brucella pinnipedialis* M163/99/10] | 45.81 | 203 | 110 | 1 | 21190 | 20582 |
| ref|ZP_05163566.1| | hypothetical protein Bsuib55_12901 [*Brucella suis* bv. 5 str. 513] | 45.81 | 203 | 110 | 1 | 21190 | 20582 |
| ref|YP_001592825.1| | hypothetical protein BCAN_A1001 | 45.81 | 203 | 110 | 1 | 21190 | 20582 |

TABLE 1-continued

| Subject id | Description | % identity | alignment length | Mis matches | gap openings | q. start | q. end |
|---|---|---|---|---|---|---|---|
| ref|YP_221702.1| | [*Brucella canis* ATCC 23365] secretion activator protein [*Brucella abortus* bv. 1 str. 9-941] | 45.81 | 203 | 110 | 1 | 21190 | 20582 |
| ref|YP_002497710.1| | protein of unknown function DUF847 [*Methylobacterium nodulans* ORS 2060] | 51.43 | 175 | 85 | 2 | 21190 | 20666 |
| ref|ZP_01870783.1| | helicase-related protein [*Vibrio shilonii* AK1] | 37.90 | 314 | 192 | 7 | 12648 | 13580 |
| ref|YP_003366167.1| | putative prophage DNA methylase [*Citrobacter rodentium* ICC168] | 39.59 | 245 | 142 | 5 | 15941 | 16657 |
| ref|ZP_05451234.1| | hypothetical protein Bneo5_12042 [*Brucella neotomae* 5K33] | 45.32 | 203 | 111 | 1 | 21190 | 20582 |
| ref|YP_224274.1| | putative helicase subunit [*Listonella* phage phiHSIC] | 47.01 | 251 | 130 | 5 | 8623 | 9366 |
| ref|YP_002732723.1| | hypothetical protein BMEA_A1023 [*Brucella melitensis* ATCC 23457] | 45.32 | 203 | 111 | 1 | 21190 | 20582 |
| ref|ZP_01976451.1| | DNA or RNA helicase [*Vibrio cholerae* B33] | 32.60 | 181 | 118 | 2 | 12315 | 12845 |
| ref|ZP_01976451.1| | DNA or RNA helicase [*Vibrio cholerae* B33] | 40.91 | 110 | 65 | 1 | 11996 | 12325 |
| ref|ZP_05457454.1| | hypothetical protein BcetM4_12068 [*Brucella ceti* M490/95/1] | 45.32 | 203 | 111 | 1 | 21190 | 20582 |
| ref|ZP_03349713.1| | putative helicase [*Salmonella enterica* subsp. *enterica* serovar Typhi] | 40.59 | 271 | 159 | 4 | 12651 | 13457 |
| ref|NP_539912.1| | secretion activator protein [*Brucella melitensis* 16M] | 44.55 | 202 | 112 | 1 | 21190 | 20585 |
| ref|ZP_05256839.1| | gp10 [*Bacteroides* sp. 4_3_47FAA] | 36.90 | 271 | 157 | 6 | 15896 | 16666 |
| ref|YP_100085.1| | putative site-specific DNA-methyltransferase [*Bacteroides fragilis*] | 36.90 | 271 | 157 | 6 | 15896 | 16666 |
| ref|YP_865634.1| | hypothetical protein Mmc1_1720 [*Magnetococcus* sp. MC-1] | 34.10 | 346 | 224 | 9 | 28857 | 27832 |
| ref|ZP_04550445.1| | gp10 [Bacteroides sp. 2_2_4] | 36.53 | 271 | 158 | 6 | 15896 | 16666 |
| ref|ZP_05414506.1| | DNA (cytosine-5-)-methyltransferase [*Bacteroides finegoldii* DSM 17565] | 38.02 | 263 | 152 | 6 | 15896 | 16651 |
| ref|NP_203459.1| | virion structural protein [*Myxococcus* phage Mx8] | 27.23 | 459 | 293 | 11 | 37041 | 35788 |
| ref|ZP_03009853.1| | hypothetical protein BACCOP_01715 [*Bacteroides coprocola* DSM 17136] | 37.64 | 263 | 153 | 7 | 15896 | 16651 |
| ref|ZP_03508429.1| | hypothetical protein RetlB5_25766 [*Rhizobium etli* Brasil 5] | 38.61 | 259 | 155 | 2 | 27275 | 26511 |
| ref|NP_958114.1| | gp10 [Burkholderia phage Bcep43] | 38.06 | 247 | 145 | 5 | 15944 | 16660 |
| ref|NP_705636.1| | gp10 [Burkholderia phage Bcep781] | 38.06 | 247 | 145 | 5 | 15944 | 16660 |
| ref|YP_613683.1| | hypothetical protein TM1040_1688 | 46.12 | 219 | 106 | 4 | 10751 | 11371 |

TABLE 1-continued

| Subject id | Description | % identity | alignment length | Mis matches | gap openings | q. start | q. end |
|---|---|---|---|---|---|---|---|
| ref\|YP_002501648.1\| | [*Ruegeria* sp. TM1040] protein of unknown function DUF847 [*Methylobacterium nodulans* ORS 2060] | 46.89 | 177 | 93 | 2 | 21190 | 20663 |
| ref\|ZP_03458262.1\| | hypothetical protein BACEGG_01035 [*Bacteroides eggerthii* DSM 20697] | 36.88 | 263 | 155 | 7 | 15896 | 16651 |
| ref\|ZP_03208869.1\| | hypothetical protein BACPLE_02533 [*Bacteroides plebeius* DSM 17135] | 37.50 | 264 | 153 | 8 | 15896 | 16651 |
| ref\|ZP_05280285.1\| | putative site-specific DNA-methyltransferase [*Bacteroides fragilis* | 36.88 | 263 | 155 | 7 | 15896 | 16651 |
| emb\|CBL19545.1\| | DNA modification methylase [*Ruminococcus* sp. SR1/5] | 35.06 | 251 | 154 | 6 | 15929 | 16654 |
| ref\|YP_003353511.1\| | phage DNA methylase [*Lactococcus lactis* subsp. *lactis* KF147] | 38.08 | 239 | 142 | 5 | 15944 | 16642 |
| ref\|ZP_04822629.1\| | DNA (cytosine-5-)-methyltransferase [*Clostridium botulinum* E1 str. | 36.93 | 241 | 143 | 5 | 15944 | 16639 |
| ref\|YP_672797.1\| | hypothetical protein Meso_0228 [*Mesorhizobium* sp. BNC1] | 37.50 | 304 | 177 | 8 | 33414 | 32542 |
| ref\|ZP_03376876.1\| | putative helicase [*Salmonella enterica* subsp. *enterica* serovar Typhi | 43.40 | 235 | 131 | 4 | 12759 | 13457 |
| ref\|YP_002502352.1\| | protein of unknown function DUF847 [*Methylobacterium nodulans* ORS 2060] | 45.20 | 177 | 96 | 2 | 21190 | 20663 |
| ref\|ZP_04918174.1\| | DNA or RNA helicases of superfamily II [*Vibrio cholerae* RC385] | 31.29 | 163 | 108 | 2 | 12315 | 12791 |
| ref\|ZP_04918174.1\| | DNA or RNA helicases of superfamily II [*Vibrio cholerae* RC385] | 40.91 | 110 | 65 | 1 | 11996 | 12325 |
| ref\|YP_002826407.1\| | hypothetical protein NGR_c18900 [*Rhizobium* sp. NGR234] | 31.10 | 447 | 186 | 10 | 27287 | 26313 |
| ref\|ZP_04680067.1\| | Hypothetical protein, conserved [*Ochrobactrum intermedium* LMG 3301] | 42.41 | 191 | 110 | 1 | 21202 | 20630 |
| ref\|ZP_03528019.1\| | hypothetical protein RetlC8_15010 [*Rhizobium etli* CIAT 894] | 32.06 | 287 | 190 | 6 | 28647 | 27802 |
| ref\|YP_613645.1\| | hypothetical protein TM1040_1650 [*Ruegeria* sp. TM1040] | 44.75 | 181 | 99 | 3 | 21202 | 20663 |
| ref\|YP_613599.1\| | hypothetical protein TM1040_1604 [*Ruegeria* sp. TM1040] | 44.75 | 181 | 99 | 3 | 21202 | 20663 |
| ref\|YP_612821.1\| | hypothetical protein TM1040_0826 [*Ruegeria* sp. TM1040] | 44.75 | 181 | 99 | 3 | 21202 | 20663 |
| ref\|ZP_05854349.1\| | DNA (cytosine-5-)-methyltransferase | 36.49 | 222 | 137 | 3 | 15989 | 16642 |

TABLE 1-continued

| Subject id | Description | % identity | alignment length | Mis matches | gap openings | q. start | q. end |
|---|---|---|---|---|---|---|---|
| | [*Blautia hansenii* DSM 20583] | | | | | | |
| ref\|YP_001592705.1\| | hypothetical protein BCAN_A0869 [*Brucella canis* ATCC 23365] | 41.11 | 180 | 106 | 1 | 21202 | 20663 |
| ref\|ZP_05180771.1\| | hypothetical protein Bru83_05374 [*Brucella* sp. 83/13] | 38.50 | 200 | 115 | 2 | 21202 | 20627 |
| ref\|ZP_05454244.1\| | hypothetical protein Bmelb3E_11717 [*Brucella melitensis* bv. 3 str. | 40.78 | 179 | 106 | 1 | 21202 | 20666 |
| ref\|ZP_05175770.1\| | hypothetical protein BcetM6_11506 [*Brucella ceti* M644/93/1] | 40.78 | 179 | 106 | 1 | 21202 | 20666 |
| ref\|YP_001258831.1\| | hypothetical protein BOV_0848 [*Brucella ovis* ATCC 25840] | 40.78 | 179 | 106 | 1 | 21202 | 20666 |
| ref\|NP_540027.1\| | secretion activator protein [*Brucella melitensis* 16M] | 40.78 | 179 | 106 | 1 | 21202 | 20666 |
| ref\|YP_001353888.1\| | hypothetical protein mma_2198 [*Janthinobacterium* sp. Marseille] | 27.92 | 462 | 328 | 16 | 29199 | 27829 |
| ref\|YP_001353888.1\| | hypothetical protein mma_2198 [*Janthinobacterium* sp. Marseille] | 26.79 | 168 | 122 | 4 | 29634 | 29134 |
| ref\|ZP_03370431.1\| | putative helicase [*Salmonella enterica* subsp. *enterica* serovar Typhi | 42.11 | 228 | 130 | 4 | 12780 | 13457 |
| ref\|YP_001627531.1\| | hypothetical protein BSUIS_A0894 [*Brucella suis* ATCC 23445] | 40.22 | 179 | 107 | 1 | 21202 | 20666 |
| ref\|ZP_05171770.1\| | hypothetical protein BpinB_06732 [*Brucella pinnipedialis* B2/94] | 40.22 | 179 | 107 | 1 | 21202 | 20666 |
| ref\|ZP_04130502.1\| | DNA methylase N-4/N-6 domain protein [*Bacillus thuringiensis* serovar | 37.87 | 235 | 138 | 6 | 15956 | 16636 |
| ref\|ZP_05331980.1\| | DNA methylase N-4/N-6 domain-containing protein [*Clostridium difficile* | 32.64 | 242 | 159 | 4 | 15944 | 16657 |
| ref\|ZP_06792882.1\| | hypothetical protein BAZG_01128 [*Brucella* sp. NVSL 07-0026] | 40.22 | 179 | 107 | 1 | 21202 | 20666 |
| ref\|YP_002826408.1\| | hypothetical protein NGR_c18910 [*Rhizobium* sp. NGR234] | 52.17 | 138 | 63 | 1 | 27706 | 27302 |
| ref\|YP_455251.1\| | putative ATP-dependent helicase [*Sodalis glossinidius* str. 'morsitans'] | 29.83 | 181 | 123 | 2 | 12315 | 12845 |
| ref\|YP_455251.1\| | putative ATP-dependent helicase [*Sodalis glossinidius* str. 'morsitans'] | 39.25 | 107 | 65 | 1 | 11996 | 12316 |
| emb\|CAM75773.1\| | Helicase, C-terminal: Type III restriction enzyme, res subunit: DEAD/DEAH | 31.01 | 287 | 190 | 8 | 12333 | 13169 |
| emb\|CAM75773.1\| | Helicase, C-terminal: Type III restriction enzyme, res subunit: DEAD/DEAH | 34.02 | 97 | 61 | 2 | 11996 | 12277 |
| ref\|YP_419719.1\| | superfamily II DNA/RNA helicase | 31.01 | 287 | 190 | 8 | 12333 | 13169 |

TABLE 1-continued

| Subject id | Description | % identity | alignment length | Mis matches | gap openings | q. start | q. end |
|---|---|---|---|---|---|---|---|
| ref|YP_419719.1| | [*Magnetospirillum magneticum* AMB-1] superfamily II DNA/RNA helicase [*Magnetospirillum magneticum* AMB-1] | 34.02 | 97 | 61 | 2 | 11996 | 12277 |
| ref|ZP_05181861.1| | hypothetical protein Bru83_11004 [*Brucella* sp. 83/13] | 26.61 | 372 | 242 | 6 | 36810 | 35788 |
| ref|ZP_05181861.1| | hypothetical protein Bru83_11004 [*Brucella* sp. 83/13] | 25.41 | 181 | 125 | 5 | 35625 | 35113 |
| ref|ZP_02082641.1| | hypothetical protein CLOBOL_00154 [*Clostridium bolteae* ATCC BAA-613] | 36.13 | 238 | 145 | 5 | 15944 | 16636 |
| ref|YP_414410.1| | secretion activator protein, putative [*Brucella melitensis* biovar | 45.14 | 175 | 96 | 1 | 21106 | 20582 |
| ref|ZP_03149730.1| | phage uncharacterized protein [*Geobacillus* sp. G11MC16] | 33.96 | 318 | 203 | 11 | 1378 | 446 |
| ref|ZP_03149730.1| | phage uncharacterized protein [*Geobacillus* sp. G11MC16] | 35.11 | 131 | 84 | 2 | 2758 | 2369 |
| ref|YP_001418062.1| | hypothetical protein Xaut_3175 [*Xanthobacter autotrophicus* Py2] | 41.76 | 170 | 95 | 3 | 21193 | 20696 |
| ref|ZP_05155418.1| | hypothetical protein Babob3T_02779 [*Brucella abortus* bv. 3 str. Tulya] | 39.11 | 179 | 109 | 1 | 21202 | 20666 |
| ref|NP_697992.1| | secretion activator protein, putative [*Brucella suis* 1330] | 44.57 | 175 | 97 | 1 | 21106 | 20582 |
| ref|ZP_05895246.1| | conserved hypothetical protein [*Brucella abortus* bv. 9 str. C68] | 41.07 | 168 | 99 | 1 | 21169 | 20666 |
| ref|ZP_03148199.1| | phage uncharacterized protein [*Geobacillus* sp. G11MC16] | 32.49 | 317 | 208 | 9 | 1378 | 446 |
| ref|ZP_03148199.1| | phage uncharacterized protein [*Geobacillus* sp. G11MC16] | 35.88 | 131 | 83 | 2 | 2758 | 2369 |
| ref|YP_001370913.1| | hypothetical protein Oant_2370 [*Ochrobactrum anthropi* ATCC 49188] | 39.55 | 177 | 107 | 1 | 21202 | 20672 |
| ref|ZP_03053948.1| | DNA methylase [*Bacillus pumilus* ATCC 7061] | 36.47 | 255 | 146 | 8 | 15920 | 16636 |
| ref|ZP_03053844.1| | DNA methylase [*Bacillus pumilus* ATCC 7061] | 35.39 | 243 | 152 | 4 | 15944 | 16657 |
| ref|YP_001126919.1| | terminase large subunit, putative [*Geobacillus thermodenitrificans* | 32.49 | 317 | 208 | 9 | 1378 | 446 |
| ref|YP_001126919.1| | terminase large subunit, putative [*Geobacillus thermodenitrificans* | 34.35 | 131 | 85 | 2 | 2758 | 2369 |
| ref|ZP_05910454.1| | helicase-related protein [*Vibrio parahaemolyticus* AQ4037] | 39.23 | 260 | 155 | 7 | 12807 | 13577 |
| ref|NP_761655.1| | helicase-like protein [*Vibrio vulnificus* CMCP6] | 41.82 | 220 | 125 | 5 | 12807 | 13457 |
| ref|YP_001235617.1| | phage uncharacterized protein [*Acidiphilium cryptum* JF-5] | 33.44 | 311 | 198 | 11 | 1378 | 473 |
| ref|YP_001235617.1| | phage uncharacterized protein [*Acidiphilium cryptum* JF-5] | 34.96 | 123 | 80 | 1 | 2737 | 2369 |

TABLE 1-continued

| Subject id | Description | % identity | alignment length | Mis matches | gap openings | q. start | q. end |
|---|---|---|---|---|---|---|---|
| ref\|YP_001294846.1\| | DNA methylase [*Burkholderia* phage BcepNY3] | 34.96 | 246 | 154 | 5 | 15923 | 16642 |
| ref\|YP_001110197.1\| | DNA methylase N-4/N-6 domain-containing protein [*Burkholderia*] | 34.18 | 237 | 150 | 5 | 15944 | 16636 |
| ref\|ZP_05807828.1\| | protein of unknown function DUF847 [*Mesorhizobium opportunistum*] | 40.66 | 182 | 102 | 4 | 21187 | 20660 |
| ref\|ZP_03376875.1\| | putative helicase [*Salmonella enterica* subsp. *enterica* serovar Typhi] | 42.73 | 110 | 63 | 1 | 11996 | 12325 |
| ref\|ZP_03376875.1\| | putative helicase [*Salmonella enterica* subsp. *enterica* serovar Typhi] | 30.16 | 126 | 84 | 2 | 12315 | 12680 |
| ref\|YP_866814.1\| | type III restriction enzyme, res subunit [*Magnetococcus* sp. MC-1] | 29.66 | 290 | 196 | 8 | 12333 | 13178 |
| ref\|YP_866814.1\| | type III restriction enzyme, res subunit [*Magnetococcus* sp. MC-1] | 35.05 | 97 | 60 | 2 | 11996 | 12277 |
| ref\|ZP_06243726.1\| | helicase domain protein [*Victivallis vadensis* ATCC BAA-548] | 32.43 | 367 | 225 | 12 | 12324 | 13355 |
| ref\|ZP_06243726.1\| | helicase domain protein [*Victivallis vadensis* ATCC BAA-548] | 28.26 | 184 | 104 | 10 | 11996 | 12463 |
| ref\|ZP_05620789.1\| | bifunctional DNA primase/polymerase domain protein [*Enhydrobacter*] | 23.15 | 691 | 505 | 21 | 5912 | 7906 |
| ref\|YP_745404.1\| | large terminase subunit [*Granulibacter bethesdensis* CGDNIH1] | 33.02 | 318 | 196 | 10 | 1375 | 473 |
| ref\|YP_745404.1\| | large terminase subunit [*Granulibacter bethesdensis* CGDNIH1] | 35.06 | 174 | 110 | 5 | 2881 | 2369 |
| ref\|NP_102244.1\| | hypothetical protein mll0449 [*Mesorhizobium loti* MAFF303099] | 36.73 | 226 | 136 | 4 | 26972 | 26316 |
| ref\|NP_761654.1\| | superfamily II DNA/RNA helicase [*Vibrio vulnificus* CMCP6] | 41.82 | 110 | 64 | 1 | 11996 | 12325 |
| ref\|NP_761654.1\| | superfamily II DNA/RNA helicase [*Vibrio vulnificus* CMCP6] | 24.84 | 153 | 111 | 2 | 12315 | 12761 |
| ref\|NP_108621.1\| | hypothetical protein mlr8547 [*Mesorhizobium loti* MAFF303099] | 41.94 | 186 | 102 | 4 | 21181 | 20642 |
| ref\|ZP_04567784.1\| | DNA methylase N-4/N-6 domain-containing protein [*Fusobacterium*] | 35.08 | 248 | 149 | 5 | 15929 | 16636 |
| ref\|ZP_04215575.1\| | Terminase large subunit [*Bacillus cereus* Rock4-2] | 31.33 | 316 | 201 | 12 | 1378 | 479 |
| ref\|ZP_04215575.1\| | Terminase large subunit [*Bacillus cereus* Rock4-2] | 38.74 | 111 | 67 | 2 | 2671 | 2342 |
| ref\|ZP_05181870.1\| | hypothetical protein Bru83_11061 [*Brucella* sp. 83/13] | 59.82 | 112 | 44 | 1 | 27634 | 27302 |

TABLE 1-continued

| Subject id | Description | % identity | alignment length | Mis matches | gap openings | q. start | q. end |
|---|---|---|---|---|---|---|---|
| ref\|NP_108221.1\| | hypothetical protein mlr8035 [*Mesorhizobium loti* MAFF303099] | 40.96 | 188 | 105 | 4 | 21187 | 20642 |
| ref\|ZP_05786522.1\| | secretion activator protein [*Silicibacter lacuscaerulensis* ITI-1157] | 45.10 | 153 | 83 | 2 | 21157 | 20702 |
| ref\|ZP_05082830.1\| | secretion activator protein [*Pseudovibrio* sp. JE062] | 41.81 | 177 | 101 | 2 | 21202 | 20678 |
| ref\|NP_944318.1\| | gp10 [Burkholderia phage Bcep1] | 35.17 | 236 | 147 | 5 | 15953 | 16642 |
| ref\|YP_003069080.1\| | putative helicase domain protein, DEAD/DEAH motif [*Methylobacterium* | 32.17 | 286 | 186 | 10 | 12333 | 13166 |
| ref\|YP_003069080.1\| | putative helicase domain protein, DEAD/DEAH motif [*Methylobacterium* | 32.73 | 110 | 71 | 2 | 11996 | 12316 |
| emb\|CBL08412.1\| | DNA modification methylase [*Roseburia intestinalis* M50/1] | 35.83 | 240 | 150 | 5 | 15944 | 16651 |
| ref\|ZP_02038948.1\| | hypothetical protein BACCAP_04595 [*Bacteroides capillosus* ATCC 29799] | 34.87 | 238 | 151 | 4 | 15944 | 16645 |
| ref\|ZP_02038963.1\| | hypothetical protein BACCAP_04610 [*Bacteroides capillosus* ATCC 29799] | 34.87 | 238 | 151 | 4 | 15944 | 16645 |
| ref\|YP_001640282.1\| | helicase domain-containing protein [*Methylobacterium extorquens* PA1] | 32.17 | 286 | 186 | 10 | 12333 | 13166 |
| ref\|YP_001640282.1\| | helicase domain-containing protein [*Methylobacterium extorquens* PA1] | 32.73 | 110 | 71 | 2 | 11996 | 12316 |
| ref\|ZP_06361169.1\| | conserved hypothetical protein [*Rhodopseudomonas palustris* DX-1] | 33.64 | 220 | 146 | 1 | 30378 | 29719 |
| ref\|ZP_05378025.1\| | protein of unknown function DUF847 [*Hyphomicrobium denitrificans* ATCC | 40.46 | 173 | 102 | 3 | 21199 | 20684 |
| ref\|ZP_04100574.1\| | Large terminase subunit [*Bacillus thuringiensis* serovar *berliner* ATCC | 28.86 | 343 | 225 | 7 | 1444 | 473 |
| ref\|ZP_04100574.1\| | Large terminase subunit [*Bacillus thuringiensis* serovar *berliner* ATCC | 36.11 | 108 | 68 | 2 | 2662 | 2342 |
| ref\|ZP_03752697.1\| | hypothetical protein ROSEINA2194_01101 [*Roseburia inulinivorans* DSM | 35.42 | 240 | 151 | 5 | 15944 | 16651 |
| ref\|YP_003309616.1\| | phage uncharacterized protein [*Sebaldella termitidis* ATCC 33386] | 29.05 | 327 | 211 | 10 | 1378 | 461 |
| ref\|ZP_01550894.1\| | hypothetical protein SIAM614_21537 [*Stappia aggregata* IAM 12614] | 35.75 | 179 | 115 | 1 | 21199 | 20663 |
| ref\|YP_001925629.1\| | helicase domain protein [*Methylobacterium populi* BJ001] | 30.99 | 313 | 201 | 12 | 12333 | 13226 |
| ref\|YP_001925629.1\| | helicase domain protein [*Methylobacterium populi* BJ001] | 32.73 | 110 | 71 | 2 | 11996 | 12316 |

TABLE 1-continued

| Subject id | Description | % identity | alignment length | Mis matches | gap openings | q. start | q. end |
|---|---|---|---|---|---|---|---|
| ref|ZP_06537032.1| | putative ATP-dependent helicase [*Salmonella enterica* subsp. *enterica* | 42.73 | 110 | 63 | 1 | 11996 | 12325 |
| ref|ZP_06537032.1| | putative ATP-dependent helicase [*Salmonella enterica* subsp. *enterica* | 32.29 | 96 | 61 | 2 | 12315 | 12590 |
| ref|ZP_03356632.1| | putative helicase [*Salmonella enterica* subsp. *enterica* serovar Typhi | 42.73 | 110 | 63 | 1 | 11996 | 12325 |
| ref|ZP_03356632.1| | putative helicase [*Salmonella enterica* subsp. *enterica* serovar Typhi | 32.29 | 96 | 61 | 2 | 12315 | 12590 |
| ref|ZP_00741804.1| | Large terminase subunit [*Bacillus thuringiensis* serovar *israelensis* | 30.13 | 302 | 211 | 5 | 1378 | 473 |
| ref|ZP_00741804.1| | Large terminase subunit [*Bacillus thuringiensis* serovar *israelensis* | 36.11 | 108 | 68 | 2 | 2662 | 2342 |
| ref|ZP_00740989.1| | Large terminase subunit [*Bacillus thuringiensis* serovar *israelensis* | 28.57 | 343 | 226 | 8 | 1444 | 473 |
| ref|ZP_00740989.1| | Large terminase subunit [*Bacillus thuringiensis* serovar *israelensis* | 37.04 | 108 | 67 | 2 | 2662 | 2342 |
| ref|YP_001209644.1| | hypothetical protein DNO_0739 [*Dichelobacter nodosus* VCS1703A] | 39.41 | 170 | 102 | 2 | 21202 | 20696 |
| ref|YP_003504938.1| | uncharacterized phage protein [*Denitrovibrio acetiphilus* DSM 12809] | 31.56 | 320 | 213 | 11 | 1378 | 437 |
| ref|YP_003504938.1| | uncharacterized phage protein [*Denitrovibrio acetiphilus* DSM 12809] | 35.38 | 130 | 84 | 0 | 2731 | 2342 |
| ref|YP_002421814.1| | helicase domain protein [*Methylobacterium chloromethanicum* CM4] | 31.82 | 286 | 187 | 10 | 12333 | 13166 |
| ref|YP_002421814.1| | helicase domain protein [*Methylobacterium chloromethanicum* CM4] | 31.82 | 110 | 72 | 2 | 11996 | 12316 |
| ref|YP_003550691.1| | hypothetical protein SAR116_0364 [alpha proteobacterium IMCC1322] | 38.02 | 192 | 119 | 2 | 21259 | 20684 |
| ref|YP_001368768.1| | HNH endonuclease [*Ochrobactrum anthropi* ATCC 49188] | 37.57 | 173 | 96 | 2 | 11490 | 11972 |
| emb|CBK98006.1| | DNA modification methylase [*Faecalibacterium prausnitzii* L2-6] | 34.84 | 221 | 142 | 3 | 15989 | 16645 |
| ref|ZP_05375895.1| | protein of unknown function DUF847 [*Hyphomicrobium denitrificans* ATCC | 40.46 | 173 | 102 | 3 | 21199 | 20684 |
| ref|ZP_05414485.1| | DNA (cytosine-5-)-methyltransferase [*Bacteroides finegoldii* DSM 17565] | 32.81 | 253 | 153 | 6 | 15944 | 16651 |
| ref|ZP_02067759.1| | hypothetical protein BACOVA_04769 [*Bacteroides ovatus* ATCC 8483] | 33.60 | 253 | 151 | 8 | 15944 | 16651 |

TABLE 1-continued

| Subject id | Description | % identity | alignment length | Mis matches | gap openings | q. start | q. end |
|---|---|---|---|---|---|---|---|
| ref\|XP_001786642.1\| | predicted protein [*Physcomitrella patens* subsp. *patens*] | 39.25 | 186 | 108 | 5 | 1384 | 842 |
| ref\|XP_001786642.1\| | predicted protein [*Physcomitrella patens* subsp. *patens*] | 29.91 | 117 | 76 | 3 | 2674 | 2342 |
| ref\|ZP_04848440.1\| | conserved hypothetical protein [*Bacteroides* sp. 1_1_6] | 33.20 | 253 | 152 | 8 | 15944 | 16651 |
| ref\|YP_002898939.1\| | putative HNH endonuclease [Roseophage EE36P1] | 37.35 | 166 | 101 | 1 | 11484 | 11972 |
| ref\|ZP_03458269.1\| | hypothetical protein BACEGG_01042 [*Bacteroides eggerthii* DSM 20697] | 33.60 | 253 | 151 | 8 | 15944 | 16651 |
| ref\|ZP_04194926.1\| | Terminase large subunit [*Bacillus cereus* AH676] | 30.82 | 305 | 206 | 6 | 1378 | 479 |
| ref\|ZP_04194926.1\| | Terminase large subunit [*Bacillus cereus* AH676] | 36.90 | 84 | 52 | 2 | 2617 | 2369 |
| ref\|ZP_05427405.1\| | DNA (cytosine-5-)-methyltransferase [*Eubacterium saphenum* ATCC 49989] | 34.65 | 228 | 136 | 6 | 15953 | 16597 |
| ref\|ZP_05280292.1\| | DNA methylase N-4/N-6 domain-containing protein [*Bacteroides fragilis*] | 33.20 | 253 | 152 | 8 | 15944 | 16651 |
| ref\|ZP_03208876.1\| | hypothetical protein BACPLE_02540 [*Bacteroides plebeius* DSM 17135] | 33.60 | 253 | 151 | 8 | 15944 | 16651 |
| ref\|ZP_02327823.1\| | hypothetical protein Plarl_09255 [*Paenibacillus larvae* subsp. *larvae*] | 34.18 | 237 | 148 | 6 | 15956 | 16642 |
| ref\|YP_498254.1\| | hypothetical protein Saro_2985 [*Novosphingobium aromaticivorans* DSM] | 40.35 | 171 | 102 | 2 | 21190 | 20678 |
| ref\|YP_917856.1\| | hypothetical protein Pden_4094 [*Paracoccus denitrificans* PD1222] | 39.78 | 186 | 108 | 4 | 24268 | 23723 |
| ref\|YP_001552287.1\| | hypothetical protein BA3_0018 [*Thalassomonas* phage BA3] | 40.00 | 170 | 101 | 2 | 11472 | 11978 |
| ref\|ZP_06744184.1\| | DEAD/DEAH box helicase [*Bacteroides vulgatus* PC510] | 30.22 | 278 | 182 | 9 | 12321 | 13118 |
| ref\|ZP_06744184.1\| | DEAD/DEAH box helicase [*Bacteroides vulgatus* PC510] | 35.14 | 111 | 69 | 4 | 11996 | 12319 |
| ref\|ZP_05257788.1\| | DNA methylase N-4/N-6 domain-containing protein [*Bacteroides* sp.] | 33.86 | 254 | 150 | 9 | 15944 | 16651 |
| ref\|ZP_01787476.1\| | hypothetical protein CGSHi22421_00957 [*Haemophilus influenzae* R3021] | 29.25 | 318 | 208 | 10 | 1375 | 473 |
| ref\|ZP_01787476.1\| | hypothetical protein CGSHi22421_00957 [*Haemophilus influenzae* R3021] | 32.52 | 123 | 72 | 2 | 2704 | 2369 |
| ref\|NP_203462.1\| | major virion structural protein [*Myxococcus* phage Mx8] | 29.36 | 327 | 231 | 4 | 32466 | 31486 |
| ref\|NP_463999.1\| | hypothetical protein lmo0470 [*Listeria monocytogenes* EGD-e] | 34.83 | 201 | 127 | 3 | 16052 | 16642 |

TABLE 1-continued

| Subject id | Description | % identity | alignment length | Mis matches | gap openings | q. start | q. end |
|---|---|---|---|---|---|---|---|
| emb\|CBA73542.1\| | conserved hypothetical phage protein [*Arsenophonus nasoniae*] | 29.08 | 306 | 212 | 8 | 1375 | 473 |
| emb\|CBA73542.1\| | conserved hypothetical phage protein [*Arsenophonus nasoniae*] | 31.71 | 123 | 73 | 2 | 2704 | 2369 |
| ref\|ZP_02494551.1\| | 3-phosphoglycerate kinase [*Burkholderia pseudomallei* NCTC 13177] | 29.15 | 319 | 223 | 6 | 32457 | 31510 |
| ref\|YP_003187049.1\| | phage terminase large subunit TerL [*Acetobacter pasteurianus* IFO | 31.72 | 309 | 202 | 8 | 1375 | 476 |
| ref\|YP_003187049.1\| | phage terminase large subunit TerL [*Acetobacter pasteurianus* IFO | 34.13 | 167 | 109 | 2 | 2878 | 2381 |
| ref\|ZP_04725581.1\| | putative phage associated protein [*Neisseria gonorrhoeae* FA19] | 40.00 | 165 | 91 | 2 | 11484 | 11954 |
| ref\|YP_002001290.1\| | putative phage associated protein [*Neisseria gonorrhoeae* NCCP11945] | 40.00 | 165 | 91 | 2 | 11484 | 11954 |
| ref\|YP_001063342.1\| | 3-phosphoglycerate kinase [*Burkholderia pseudomallei* 668] | 29.15 | 319 | 223 | 6 | 32457 | 31510 |
| ref\|ZP_01788573.1\| | hypothetical protein CGSHi3655_09046 [*Haemophilus influenzae* 3655] | 28.62 | 318 | 210 | 10 | 1375 | 473 |
| ref\|ZP_01788573.1\| | hypothetical protein CGSHi3655_09046 [*Haemophilus influenzae* 3655] | 33.06 | 124 | 71 | 2 | 2704 | 2369 |
| ref\|ZP_03009861.1\| | hypothetical protein BACCOP_01723 [*Bacteroides coprocola* DSM 17136] | 33.20 | 253 | 152 | 8 | 15944 | 16651 |
| ref\|NP_203466.1\| | [hypothetical protein Mx8p52 [*Myxococcus* phage Mx8] | 26.61 | 387 | 274 | 13 | 28872 | 27742 |
| ref\|ZP_05521263.1\| | terminase large subunit, putative [*Streptomyces hygroscopicus* ATCC | 30.87 | 311 | 185 | 9 | 1375 | 533 |
| ref\|ZP_05521263.1\| | terminase large subunit, putative [*Streptomyces hygroscopicus* ATCC | 31.36 | 118 | 79 | 2 | 2737 | 2390 |
| ref\|YP_002117646.1\| | p088 [*Rhizobium* phage 16-3] | 31.30 | 262 | 171 | 8 | 12324 | 13082 |
| ref\|YP_002117646.1\| | p088 [*Rhizobium* phage 16-3] | 31.96 | 97 | 63 | 2 | 11996 | 12277 |
| ref\|ZP_05332310.1\| | putative site-specific DNA-methyltransferase [*Clostridium difficile* | 33.60 | 247 | 150 | 6 | 15944 | 16642 |
| ref\|NP_958672.1\| | Bbp2 [*Bordetella* phage BPP-1] | 40.24 | 169 | 101 | 2 | 21193 | 20687 |
| ref\|ZP_04740538.1\| | putative phage associated protein [*Neisseria gonorrhoeae* SK-93-1035] | 39.39 | 165 | 92 | 2 | 11484 | 11954 |
| ref\|ZP_04440303.1\| | probable site-specific DNA-methyltransferase [*Lactobacillus rhamnosus* | 31.43 | 245 | 159 | 6 | 15962 | 16669 |
| ref\|ZP_03707983.1\| | hypothetical protein CLOSTMETH_02741 [*Clostridium methylpentosum* DSM | 32.35 | 238 | 157 | 4 | 15944 | 16645 |

TABLE 1-continued

| Subject id | Description | % identity | alignment length | Mis matches | gap openings | q. start | q. end |
|---|---|---|---|---|---|---|---|
| ref|ZP_04719195.1| | putative phage associated protein [Neisseria gonorrhoeae 35/02] | 32.40 | 321 | 210 | 10 | 1381 | 440 |
| ref|ZP_04719195.1| | putative phage associated protein [Neisseria gonorrhoeae 35/02] | 29.41 | 119 | 83 | 2 | 2743 | 2390 |
| ref|YP_002117655.1| | p097 [Rhizobium phage 16-3] | 35.80 | 243 | 156 | 9 | 15917 | 16645 |
| ref|YP_001693301.1| | DNA methylase [Clostridium botulinum B1 str. Okra] | 32.08 | 240 | 155 | 4 | 15944 | 16639 |
| ref|NP_471068.1| | hypothetical protein lin1732 [Listeria innocua Clip11262] | 28.94 | 349 | 210 | 12 | 1378 | 446 |
| ref|NP_471068.1| | hypothetical protein lin1732 [Listeria innocua Clip11262] | 28.65 | 185 | 131 | 3 | 2893 | 2342 |
| ref|ZP_02032066.1| | hypothetical protein PARMER_02074 [Parabacteroides merdae ATCC 43184] | 29.37 | 269 | 178 | 8 | 12324 | 13094 |
| ref|ZP_02032066.1| | hypothetical protein PARMER_02074 [Parabacteroides merdae ATCC 43184] | 36.94 | 111 | 67 | 4 | 11993 | 12316 |
| ref|YP_003344808.1| | putative terminase large subunit TerL [Aggregatibacter phage S1249] | 27.99 | 318 | 212 | 11 | 1375 | 473 |
| ref|YP_003344808.1| | putative terminase large subunit TerL [Aggregatibacter phage S1249] | 31.11 | 135 | 78 | 3 | 2728 | 2369 |
| ref|ZP_04720728.1| | putative phage associated protein [Neisseria gonorrhoeae DGI18] | 32.40 | 321 | 210 | 10 | 1381 | 440 |
| ref|ZP_04720728.1| | putative phage associated protein [Neisseria gonorrhoeae DGI18] | 29.41 | 119 | 83 | 2 | 2743 | 2390 |
| ref|ZP_03643400.1| | hypothetical protein BACCOPRO_01768 [Bacteroides coprophilus DSM 18228] | 31.10 | 254 | 159 | 7 | 15944 | 16657 |
| ref|YP_001715839.1| | DNA methylase [Clostridium botulinum A3 str. Loch Maree] | 32.24 | 245 | 153 | 6 | 15944 | 16639 |
| ref|NP_852753.1| | putative terminase large subunit TerL [Haemophilus phage Aaphi23] | 27.99 | 318 | 212 | 11 | 1375 | 473 |
| ref|NP_852753.1| | putative terminase large subunit TerL [Haemophilus phage Aaphi23] | 30.37 | 135 | 79 | 3 | 2728 | 2369 |
| ref|ZP_06643501.1| | phage associated protein [Neisseria gonorrhoeae F62] | 38.79 | 165 | 93 | 2 | 11484 | 11954 |
| emb|CBL41024.1| | DNA modification methylase [Clostridiales sp. SS3/4] | 33.61 | 238 | 154 | 5 | 15944 | 16645 |
| ref|YP_002002065.1| | putative phage associated protein [Neisseria gonorrhoeae NCCP11945] | 32.09 | 321 | 211 | 10 | 1381 | 440 |
| ref|YP_002002065.1| | putative phage associated protein [Neisseria gonorrhoeae NCCP11945] | 29.41 | 119 | 83 | 2 | 2743 | 2390 |

TABLE 1-continued

| Subject id | Description | % identity | alignment length | Mis matches | gap openings | q. start | q. end |
|---|---|---|---|---|---|---|---|
| ref\|YP_001875859.1\| | DNA methylase N-4/N-6 domain-containing protein [*Elusimicrobium minutum* | 34.55 | 246 | 155 | 10 | 15917 | 16636 |
| ref\|YP_208181.1\| | putative phage associated protein [*Neisseria gonorrhoeae* FA 1090] | 38.79 | 165 | 93 | 2 | 11484 | 11954 |
| ref\|YP_207645.1\| | putative phage associated protein [*Neisseria gonorrhoeae* FA 1090] | 32.09 | 321 | 211 | 10 | 1381 | 440 |
| ref\|YP_207645.1\| | putative phage associated protein [*Neisseria gonorrhoeae* FA 1090] | 29.41 | 119 | 83 | 2 | 2743 | 2390 |
| ref\|YP_001302249.1\| | hypothetical protein BDI_0858 [*Parabacteroides distasonis* ATCC 8503] | 29.63 | 270 | 178 | 9 | 12324 | 13097 |
| ref\|YP_001302249.1\| | hypothetical protein BDI_0858 [*Parabacteroides distasonis* ATCC 8503] | 40.00 | 90 | 51 | 3 | 11993 | 12253 |
| ref\|YP_001285555.1\| | EndY [*Enterobacteria phage TLS*] | 49.18 | 122 | 60 | 1 | 11610 | 11969 |
| ref\|ZP_06663130.1\| | endonuclease [*Escherichia coli* B088] | 40.24 | 169 | 99 | 3 | 11472 | 11972 |
| ref\|ZP_04757897.1\| | putative phage protein [*Neisseria flavescens* SK114] | 31.78 | 321 | 212 | 10 | 1381 | 440 |
| ref\|ZP_04757897.1\| | putative phage protein [*Neisseria flavescens* SK114] | 28.81 | 118 | 84 | 1 | 2743 | 2390 |
| ref\|ZP_06628270.1\| | putative terminase, large subunit [*Enterococcus faecalis* R712] | 30.06 | 336 | 211 | 11 | 1378 | 443 |
| ref\|ZP_06628270.1\| | putative terminase, large subunit [*Enterococcus faecalis* R712] | 29.23 | 130 | 86 | 4 | 2740 | 2369 |
| ref\|ZP_03983304.1\| | phage possible protein [*Enterococcus faecalis* HH22] | 29.79 | 339 | 211 | 12 | 1378 | 443 |
| ref\|ZP_03983304.1\| | phage possible protein [*Enterococcus faecalis* HH22] | 29.23 | 130 | 86 | 4 | 2740 | 2369 |
| gb\|ABD63727.1\| | putative terminase large subunit [*Lactococcus* phage ul36.k1t1] | 29.91 | 331 | 205 | 13 | 1384 | 473 |
| gb\|ABD63727.1\| | putative terminase large subunit [*Lactococcus* phage ul36.k1t1] | 28.46 | 123 | 87 | 2 | 2734 | 2369 |
| ref\|NP_815176.1\| | terminase, large subunit, putative [*Enterococcus faecalis* V583] | 29.23 | 349 | 223 | 12 | 1378 | 404 |
| ref\|NP_815176.1\| | terminase, large subunit, putative [*Enterococcus faecalis* V583] | 29.23 | 130 | 86 | 4 | 2740 | 2369 |
| ref\|NP_102245.1\| | hypothetical protein mll0450 [*Mesorhizobium loti* MAFF303099] | 49.11 | 112 | 56 | 1 | 27634 | 27302 |
| ref\|ZP_05579649.1\| | conserved hypothetical protein [Enterococcus faecalis Fly1] | 29.76 | 336 | 212 | 11 | 1378 | 443 |

TABLE 1-continued

| Subject id | Description | % identity | alignment length | Mis matches | gap openings | q. start | q. end |
|---|---|---|---|---|---|---|---|
| ref\|ZP_05579649.1\| | conserved hypothetical protein [*Enterococcus faecalis* Fly1] | 29.23 | 130 | 86 | 4 | 2740 | 2369 |
| ref\|ZP_05854196.1\| | DNA (cytosine-5-)-methyltransferase [*Blautia hansenii* DSM 20583] | 33.19 | 238 | 155 | 5 | 15944 | 16645 |
| ref\|YP_002328249.1\| | predicted endonuclease [*Escherichia coli* O127:H6 str. E2348/69] | 46.34 | 123 | 64 | 1 | 11610 | 11972 |
| emb\|CAJ28416.1\| | terminase larae subunit [Phage PY100] | 30.48 | 315 | 205 | 10 | 1375 | 473 |
| ref\|YP_003169232.1\| | protein of unknown function DUF847 [*Candidatus Accumulibacter* | 36.76 | 185 | 107 | 2 | 21199 | 20675 |
| ref\|YP_003325139.1\| | phage uncharacterized protein [*Xylanimonas cellulosilytica* DSM 15894] | 28.44 | 320 | 211 | 9 | 1378 | 473 |
| ref\|YP_003325139.1\| | phage uncharacterized protein [*Xylanimonas cellulosilytica* DSM 15894] | 29.06 | 117 | 81 | 3 | 2686 | 2342 |
| emb\|CBK77887.1\| | DNA modification methylase [*Clostridium saccharolyticum*-like K10] | 33.61 | 238 | 154 | 5 | 15944 | 16645 |
| gb\|ABP57294.1\| | hypothetical protein bst021 [*Bacteroides uniformis*] | 31.05 | 248 | 159 | 5 | 15944 | 16651 |
| ref\|YP_001562680.1\| | hypothetical protein Daci_1652 [*Delftia acidovorans* SPH-1] | 38.27 | 162 | 100 | 2 | 21190 | 20705 |
| ref\|ZP_05257320.1\| | conserved hypothetical protein [*Bacteroides* sp. 4_3_47FAA] | 30.48 | 269 | 175 | 8 | 12324 | 13094 |
| ref\|ZP_05257320.1\| | conserved hypothetical protein [*Bacteroides* sp. 4_3_47FAA] | 34.82 | 112 | 68 | 5 | 11996 | 12316 |
| ref\|ZP_06349823.1\| | protein of unknown function DUF847 [*Rhodomicrobium vannielii* ATCC | 37.36 | 182 | 113 | 3 | 21193 | 20651 |
| ref\|ZP_05918562.1\| | conserved hypothetical protein [*Prevotella* sp. oral taxon 472 str. | 27.78 | 342 | 228 | 9 | 1438 | 470 |
| ref\|ZP_05918562.1\| | conserved hypothetical protein [*Prevotella* sp. oral taxon 472 str. | 35.48 | 93 | 59 | 1 | 2728 | 2453 |
| ref\|YP_003041966.1\| | hypothetical protein PAU_03136 [*Photorhabdus asymbiotica*] | 35.59 | 222 | 119 | 9 | 10760 | 11353 |
| ref\|ZP_06090627.1\| | conserved hypothetical protein [*Bacteroides* sp. 3_1_33FAA] | 29.35 | 276 | 176 | 9 | 12324 | 13094 |
| ref\|ZP_06090627.1\| | conserved hypothetical protein [*Bacteroides* sp. 3_1_33FAA] | 35.45 | 110 | 68 | 4 | 11996 | 12316 |
| emb\|CBK98101.1\| | DNA modification methylase [*Faecalibacterium prausnitzii* L2-6] | 33.03 | 221 | 146 | 4 | 15989 | 16645 |
| ref\|YP_003065547.1\| | hypothetical protein CLIBASIA_05180 [*Candidatus Liberibacter asiaticus* | 29.67 | 273 | 186 | 5 | 28701 | 27901 |
| ref\|YP_453589.1\| | HNH endonuclease family protein [*Xanthomonas* phage OP1] | 39.61 | 154 | 91 | 3 | 11475 | 11930 |
| ref\|ZP_05907433.1\| | helicase-related protein [*Vibrio* | 40.91 | 110 | 65 | 1 | 11996 | 12325 |

TABLE 1-continued

| Subject id | Description | % identity | alignment length | Mis matches | gap openings | q. start | q. end |
|---|---|---|---|---|---|---|---|
| ref|ZP_05907433.1| | parahaemolyticus Peru-466] helicase-related protein [Vibrio parahaemolyticus Peru-466] | 28.05 | 82 | 55 | 2 | 12315 | 12548 |
| ref|YP_001770241.1| | helicase domain-containing protein [Methylobacterium sp. 4-46] | 32.13 | 249 | 161 | 8 | 112333 | 13055 |
| ref|YP_001770241.1| | helicase domain-containing protein [Methylobacterium sp. 4-46] | 31.63 | 98 | 55 | 5 | 11996 | 12253 |
| ref|ZP_06782195.1| | hypothetical protein A60131_06220 [Acinetobacter. sp 6013113] | 39.76 | 166 | 100 | 2 | 21202 | 20705 |
| ref|YP_001327487.1| | hypothetical protein Smed_1817 [Sinorhizobium medicae WSM419] | 36.87 | 198 | 120 | 6 | 26900 | 26322 |
| ref|YP_001327487.1| | hypothetical protein Smed_1817 [Sinorhizobium medicae WSM419] | 45.61 | 114 | 62 | 0 | 27278 | 26937 |
| ref|ZP_03223900.1| | DNA methylase [Salmonella enterica subsp. enterica serovar 4,[5],12:i:—] | 29.19 | 298 | 148 | 8 | 15941 | 16645 |
| ref|YP_001599091.1| | hypothetical protein NMCC_0954 [Neisseria meningitidis 053442] | 36.75 | 166 | 105 | 2 | 21202 | 20705 |
| ref|YP_001754215.1| | helicase domain-containing protein [Methylobacterium radiotolerans JCM | 31.74 | 293 | 185 | 11 | 12333 | 13166 |
| ref|YP_001754215.1| | helicase domain-containing protein [Methylobacterium radiotolerans JCM | 32.88 | 73 | 46 | 2 | 12065 | 12274 |
| ref|YP_001742088.1| | putative endonuclease protein [Salmonella phage E1] | 44.53 | 128 | 69 | 1 | 11592 | 11969 |
| ref|ZP_02494544.1| | hypothetical protein BpseN_34235 [Burkholderia pseudomallei NCTC 13177] | 29.13 | 381 | 212 | 14 | 27284 | 26316 |
| ref|YP_468632.1| | hypothetical protein RHE_CH01097 [Rhizobium etli CFN 42] | 28.12 | 320 | 229 | 5 | 32466 | 31510 |
| ref|YP_419721.1| | hypothetical protein amb0358 [Magnetospirillum magneticum AMB-1] | 24.62 | 589 | 413 | 21 | 6452 | 8125 |
| ref|ZP_01261287.1| | helicase-related protein [Vibrio alginolyticus 12G01] | 41.82 | 110 | 64 | 1 | 11996 | 12325 |
| ref|ZP_01261287.1| | helicase-relaed protein [Vibrio alginolyticus 12G01] | 29.49 | 78 | 51 | 2 | 12315 | 12536 |
| ref|YP_001063336.1| | hypothetical protein BURPS668_A2342 [Burkholderia pseudomallei 668] | 29.13 | 381 | 212 | 14 | 27284 | 26316 |
| ref|YP_769512.1| | hypothetical protein RL3934 [Rhizobium leguminosarum bv. viciae 3841] | 28.44 | 320 | 228 | 5 | 32466 | 31510 |
| ref|ZP_06787471.1| | hypothetical protein A6014_13049 [Acinetobacter sp. 6014059] | 29.32 | 307 | 212 | 10 | 1381 | 476 |

TABLE 1-continued

| Subject id | Description | % identity | alignment length | Mis matches | gap openings | q. start | q. end |
|---|---|---|---|---|---|---|---|
| ref|ZP_06787471.1| | hypothetical protein A6014_13049 [*Acinetobacter* sp. 6014059] | 27.42 | 124 | 89 | 1 | 2731 | 2363 |
| ref|ZP_05756780.1| | DNA methylase N-4/N-6 domain-containing protein [*Bacteroides* sp. D2] | 30.67 | 238 | 142 | 7 | 15953 | 16597 |
| emb|CBA06915.1| | conserved hypothetical protein [*Neisseria meningitidis* alpha153] | 36.14 | 166 | 106 | 2 | 21202 | 20705 |
| ref|YP_002320044.1| | hypothetical protein AB57_2704 [*Acinetobacter baumannii* AB0057] | 29.32 | 307 | 212 | 10 | 1381 | 476 |
| ref|YP_002320044.1| | hypothetical protein AB57_2704 [*Acinetobacter baumannii* AB0057] | 27.42 | 124 | 89 | 1 | 2731 | 2363 |
| ref|NP_858997.1| | endonuclease of the HNH family with predicted DNA-binding module in the | 38.56 | 153 | 92 | 3 | 11475 | 11927 |
| ref|NP_274047.1| | hypothetical protein NMB1012 [*Neisseria meningitidis* MC58] | 36.14 | 166 | 106 | 2 | 21202 | 20705 |
| ref|YP_001565093.1| | hypothetical protein Daci_4077 [*Delftia acidovorans* SPH-1] | 39.51 | 162 | 98 | 4 | 21193 | 20708 |
| ref|ZP_02426493.1| | hypothetical protein ALIPUT_02660 [*Alistipes putredinis* DSM 17216] | 27.88 | 312 | 215 | 8 | 1375 | 470 |
| ref|ZP_02426493.1| | hypothetical protein ALIPUT_02660 [*Alistipes putredinis* DSM 17216] | 38.78 | 98 | 59 | 1 | 2743 | 2453 |
| ref|YP_003279035.1| | hypothetical protein CtCNB1_2993 [*Comamonas testosteroni* CNB-2] | 33.47 | 248 | 158 | 9 | 24457 | 23735 |
| gb|ABO12457.2| | hypothetical protein putative phage associated protein [*Acinetobacter* | 28.99 | 307 | 213 | 10 | 1381 | 476 |
| gb|ABO12457.2| | hypothetical protein putative phage associated protein [*Acinetobacter* | 27.54 | 138 | 99 | 2 | 2731 | 2321 |
| ref|YP_001085059.1| | putative phage associated protein [*Acinetobacter baumannii* ATCC | 28.99 | 307 | 213 | 10 | 1381 | 476 |
| ref|YP_001085059.1| | putative phage associated protein [*Acinetobacter baumannii* ATCC | 27.54 | 138 | 99 | 2 | 2731 | 2321 |
| ref|ZP_03375127.1| | putative helicase [*Salmonella enterica* subsp. *enterica* serovar Typhi | 32.32 | 164 | 107 | 2 | 12315 | 12794 |
| ref|ZP_03375127.1| | putative helicase [*Salmonella enterica* subsp. *enterica* serovar Typhi | 34.09 | 44 | 29 | 0 | 12194 | 12325 |
| ref|ZP_06788596.1| | hypothetical protein A6014_18731 [*Acinetobacter* sp. 6014059] | 29.51 | 305 | 212 | 10 | 1381 | 476 |
| ref|ZP_06788596.1| | hypothetical protein A6014_18731 [*Acinetobacter* sp. 6014059] | 28.26 | 138 | 98 | 2 | 2731 | 2321 |
| ref|YP_001847402.1| | hypothetical protein ACICU_02743 [*Acinetobacter baumannii* ACICU] | 29.51 | 305 | 212 | 10 | 1381 | 476 |

TABLE 1-continued

| Subject id | Description | % identity | alignment length | Mis matches | gap openings | q. start | q. end |
|---|---|---|---|---|---|---|---|
| ref\|YP_001847402.1\| | hypothetical protein ACICU_02743 [*Acinetobacter baumannii* ACICU] | 28.26 | 138 | 98 | 2 | 2731 | 2321 |
| ref\|YP_975058.1\| | hypothetical protein NMC1002 [*Neisseria meningitidis* FAM18] | 35.54 | 166 | 107 | 2 | 21202 | 20705 |
| ref\|YP_001285722.1\| | p55.1 [*Xanthomonas* phage Xop411] | 38.56 | 153 | 92 | 3 | 11475 | 11927 |
| emb\|CBL04730.1\| | DNA modification methylase [*Gordonibacter pamelaeae* 7-10-1-bT] | 31.47 | 232 | 146 | 6 | 15941 | 16597 |
| ref\|YP_003257431.1\| | hypothetical protein pZL12-67 [*Streptomyces* sp. ZL12] | 38.22 | 191 | 111 | 5 | 1375 | 824 |
| ref\|YP_003923.1\| | putative ATP-dependent helicase [*Enterobacteria* phage T1] | 30.31 | 353 | 215 | 13 | 12522 | 13487 |
| ref\|YP_003923.1\| | putative ATP-dependent helicase [*Enterobacteria* phage T1] | 31.37 | 102 | 70 | 1 | 12002 | 12307 |
| ref\|ZP_06097802.1\| | conserved hypothetical protein [*Brucella* sp. 83/13] | 33.33 | 297 | 107 | 6 | 27287 | 26670 |
| emb\|CBA05974.1\| | conserved hypothetical protein [*Neisseria meningitidis* serogroup W135] | 35.54 | 166 | 107 | 2 | 21202 | 20705 |
| emb\|CAM75771.1\| | primase [*Magnetospirillum gryphiswaldense* MSR-1] | 24.61 | 512 | 359 | 17 | 6452 | 7906 |
| pdb\|2IS5\|A | Chain A, Crystal Structure Of 3 Residues Truncated Version Of Protein | 36.42 | 162 | 103 | 2 | 21190 | 20705 |
| pdb\|2IKB\|A | Chain A, Crystal Structure Of A Protein Of Unknown Function Nmb1012 | 36.42 | 162 | 103 | 2 | 21190 | 20705 |
| ref\|XP_002336241.1\| | predicted protein [*Populus trichocarpa*] | 39.13 | 161 | 98 | 3 | 21190 | 20708 |
| ref\|YP_002440151.1\| | hypothetical protein PLES_25511 [*Pseudomonas aeruginosa* LESB58] | 35.06 | 174 | 101 | 4 | 11484 | 11969 |
| ref\|NP_859005.1\| | endonuclease of the HNH family with predicted DNA-binding module at | 37.91 | 153 | 93 | 3 | 11475 | 11927 |
| ref\|YP_002330023.1\| | predicted HNH endonuclease [*Escherichia coli* O127:H6 str. E2348/69] | 38.78 | 147 | 86 | 2 | 11466 | 11894 |
| ref\|YP_001629579.1\| | hypothetical protein Bpet0976 [*Bordetella petrii* DSM 12804] | 27.68 | 336 | 236 | 11 | 1459 | 473 |
| ref\|YP_001629579.1\| | hypothetical protein Bpet0976 [*Bordetella petrii* DSM 12804] | 30.77 | 117 | 80 | 1 | 2737 | 2390 |
| ref\|ZP_05360494.1\| | secretion activator protein [*Acinetobacter radioresistens* SK82] | 35.54 | 166 | 103 | 2 | 21190 | 20705 |
| ref\|NP_858964.1\| | endonuclease of the HNH family [*Xanthomonas* phage Xp10] | 36.84 | 152 | 95 | 2 | 11475 | 11927 |
| ref\|YP_003060760.1\| | protein of unknown function DUF847 [*Hirschia baltica* ATCC 49814] | 33.33 | 174 | 107 | 5 | 21190 | 20696 |

TABLE 1-continued

| Subject id | Description | % identity | alignment length | Mis matches | gap openings | q. start | q. end |
|---|---|---|---|---|---|---|---|
| ref\|YP_001742082.1\| | putative ATP-dependent helicase [*Salmonella* phage E1] | 27.16 | 416 | 273 | 13 | 12423 | 13580 |
| ref\|YP_001742082.1\| | putative ATP-dependent helicase [*Salmonella* phage E1] | 33.71 | 89 | 59 | 2 | 12059 | 12325 |
| ref\|YP_917855.1\| | hypothetical protein Pden_4093 [*Paracoccus denitrificans* PD1222] | 33.88 | 245 | 156 | 8 | 23153 | 22437 |
| gb\|ADA72691.1\| | HNH endonuclease [*Shigella flexneri* 2002017] | 46.02 | 113 | 59 | 1 | 11640 | 11972 |
| ref\|YP_001467758.1\| | chaperone and heat shock protein 70 [*Campylobacter concisus* 13826] | 27.65 | 311 | 218 | 9 | 1375 | 464 |
| ref\|YP_001467758.1\| | chaperone and heat shock protein 70 [*Campylobacter concisus* 13826] | 29.61 | 179 | 115 | 6 | 2881 | 2378 |
| ref\|ZP_05431357.1\| | HNH endonuclease [*Shigella* sp. D9] | 46.02 | 113 | 59 | 1 | 11640 | 11972 |
| ref\|ZP_04945757.1\| | hypothetical protein BDAG_01666 [*Burkholderia dolosa* AUO158] | 41.67 | 156 | 88 | 4 | 11484 | 11942 |
| emb\|CAX50201.1\| | conserved hypothetical protein [*Neisseria meningitidis* 8013] | 34.94 | 166 | 108 | 2 | 21202 | 20705 |
| ref\|YP_002438405.1\| | EndY [*Pseudomonas aeruginosa* LESB58] | 37.12 | 132 | 83 | 0 | 11577 | 11972 |
| ref\|YP_001789610.1\| | hypothetical protein Lcho_0570 [*Leptothrix cholodnii* SP-6] | 36.20 | 163 | 103 | 2 | 21181 | 20696 |
| ref\|YP_001300123.1\| | putative ATP-dependent helicase [*Bacteroides vulgatus* ATCC 8482] | 28.29 | 258 | 175 | 10 | 12321 | 13064 |
| ref\|YP_001300123.1\| | putative ATP-dependent helicase [*Bacteroides vulgatus* ATCC 8482] | 36.84 | 114 | 70 | 4 | 11984 | 12319 |
| emb\|CBK86224.1\| | AP2 domain. [*Enterobacter cloacae* NCTC 9394] | 39.47 | 152 | 91 | 2 | 11490 | 11942 |
| ref\|ZP_05435815.1\| | hypothetical protein E4_01140 [*Escherichia* sp. 4_1_40B] | 38.27 | 162 | 99 | 4 | 11490 | 11972 |
| ref\|YP_001285711.1\| | p42.1 [*Xanthomonas* phage Xop411] | 37.91 | 153 | 93 | 3 | 11475 | 11927 |
| ref\|ZP_05055011.1\| | hypothetical protein OA307_933 [*Octadecabacter antarcticus* 307] | 50.00 | 104 | 52 | 1 | 3302 | 2991 |
| ref\|ZP_04978507.1\| | hypothetical bacteriophage protein [*Mannheimia haemolytica* PHL213] | 35.12 | 168 | 109 | 2 | 21190 | 20687 |
| ref\|YP_865630.1\| | hypothetical protein Mmc1_1716 [*Magnetococcus* sp. MC-1] | 27.85 | 316 | 228 | 3 | 32457 | 31510 |
| ref\|NP_102247.1\| | hypothetical protein mll0453 [*Mesorhizobium loti* MAFF303099] | 30.87 | 230 | 158 | 2 | 30378 | 29692 |
| ref\|YP_001992359.1\| | protein of unknown function DUF847 [*Rhodopseudomonas palustris* TIE-1] | 34.36 | 195 | 115 | 7 | 21202 | 20657 |
| ref\|YP_001353886.1\| | hypothetical protein mma_2196 [*Janthinobacterium* sp. Marseille] | 33.33 | 276 | 163 | 9 | 27278 | 26514 |

TABLE 1-continued

| Subject id | Description | % identity | alignment length | Mis matches | gap openings | q. start | q. end |
|---|---|---|---|---|---|---|---|
| ref|YP_003937.1| | putative endonuclease [Enterobacteria phage T1] | 37.66 | 154 | 92 | 5 | 11520 | 11969 |
| ref|YP_453670.1| | putative phage helicase [Xanthomonas phage OP2] | 25.94 | 239 | 171 | 6 | 12354 | 13052 |
| ref|YP_453670.1| | putative phage helicase [Xanthomonas phage OP2] | 32.20 | 118 | 73 | 4 | 11984 | 12316 |
| ref|ZP_02682965.1| | HNH endonuclease family protein [Salmonella enterica subsp. enterica | 35.67 | 171 | 108 | 3 | 11466 | 11972 |
| ref|YP_002280254.1| | hypothetical protein Rleg2_0732 [Rhizobium leguminosarum bv. trifolii | 29.46 | 258 | 182 | 3 | 32283 | 31510 |
| ref|ZP_06361170.1| | conserved hypothetical protein [Rhodopseudomonas palustris DX-1] | 29.67 | 246 | 151 | 6 | 31062 | 30391 |
| ref|ZP_06019578.1| | conserved hypothetical protein [Lactobacillus crispatus MV-3A-US] | 27.35 | 373 | 238 | 15 | 1492 | 473 |
| ref|ZP_05361197.1| | conserved hypothetical protein [Acinetobacter radioresistens SK82] | 30.15 | 325 | 219 | 13 | 1378 | 428 |
| ref|ZP_05361197.1| | conserved hypothetical protein [Acinetobacter radioresistens SK82] | 26.96 | 115 | 83 | 1 | 2731 | 2390 |
| ref|YP_001595442.1| | putative HNH endonuclease [Enterobacteria phage phiEcoM-GJ1] | 36.65 | 161 | 102 | 2 | 11484 | 11966 |
| ref|YP_087300.1| | hypothetical protein MS0108 [Mannheimia succiniciproducens MBEL55E] | 33.13 | 163 | 109 | 2 | 21190 | 20702 |
| ref|YP_001784196.1| | hypothetical protein HSM_0864 [Haemophilus somnus 2336] | 33.96 | 212 | 126 | 5 | 10760 | 11353 |
| ref|ZP_05575019.1| | DEAD box family helicase [Enterococcus faecalis E1Sol] | 28.06 | 253 | 179 | 8 | 12327 | 13076 |
| ref|ZP_05575019.1| | DEAD box family helicase [Enterococcus faecalis E1Sol] | 30.39 | 102 | 70 | 2 | 11996 | 12298 |
| ref|ZP_06222047.1| | hypothetical protein HAINFHK1212_1942 [Haemophilus influenzae HK1212] | 37.89 | 161 | 100 | 2 | 21184 | 20702 |
| ref|ZP_06222396.1| | hypothetical protein HAINFHK1212_0139 [Haemophilus influenzae HK1212] | 37.74 | 159 | 99 | 2 | 21178 | 20702 |
| ref|YP_002363335.1| | protein of unknown function DUF847 [Methylocella silvestris BL2] | 34.66 | 176 | 114 | 3 | 21190 | 20666 |
| ref|YP_002287849.1| | secretion activator protein [Oligotropha carboxidovorans OM5] | 33.33 | 180 | 119 | 3 | 21163 | 20627 |
| ref|YP_001603102.1| | DNA methylase N-4/N-6 domain-containing protein [Gluconacetobacter | 30.74 | 231 | 151 | 4 | 15941 | 16606 |
| ref|YP_453616.1| | HNH endonuclease family protein [Xanthomonas phage OP1] | 35.53 | 152 | 97 | 3 | 11475 | 11927 |
| ref|ZP_06016778.1| | conserved hypothetical protein [Klebsiella pneumoniae subsp. | 43.20 | 125 | 69 | 2 | 11610 | 11978 |

TABLE 1-continued

| Subject id | Description | % identity | alignment length | Mis matches | gap openings | q. start | q. end |
|---|---|---|---|---|---|---|---|
| ref|YP_001285569.1| | EndZ [*Enterobacteria* phage TLS] | 39.57 | 139 | 82 | 1 | 11562 | 11972 |
| ref|YP_001285548.1| | HelA [*Enterobacteria* phage TLS] | 27.33 | 439 | 279 | 19 | 12414 | 13610 |
| ref|YP_001285548.1| | HelA [*Enterobacteria* phage TLS] | 30.93 | 97 | 67 | 1 | 12005 | 12295 |
| ref|NP_888770.1| | hypothetical protein BB2226 [*Bordetella bronchiseptica* RB50] | 40.00 | 140 | 82 | 4 | 11490 | 11903 |
| ref|XP_711763.1| | hypothetical protein CaO19.10315 [*Candida albicans* SC5314] | 28.35 | 261 | 176 | 8 | 12303 | 13052 |
| ref|XP_711763.1| | hypothetical protein CaO19.10315 [*Candida albicans* SC5314] | 32.35 | 68 | 46 | 1 | 11996 | 12199 |
| ref|YP_398984.1| | putative HNH endonuclease [*Enterobacteria* phage RTP] | 37.01 | 154 | 94 | 2 | 11517 | 11969 |
| ref|YP_001344507.1| | hypothetical protein Asuc_1210 [*Actinobacillus succinogenes* 130Z] | 35.98 | 214 | 121 | 7 | 10760 | 11353 |
| ref|NP_102251.1| | hypothetical protein mll0458 [*Mesorhizobium loti* MAFF303099] | 25.09 | 275 | 201 | 6 | 33396 | 32587 |
| ref|ZP_04464409.1| | hypothetical protein CGSHi6P18H1_08105 [*Haemophilus influenzae* 6P18H1] | 37.82 | 156 | 97 | 2 | 21169 | 20702 |
| ref|ZP_05122973.1| | DNA methylase [*Rhodobacteraceae bacterium* KLH11] | 32.36 | 275 | 170 | 8 | 15908 | 16684 |
| emb|CAJ28486.1| | NTP dependent helicase [Phage PY100] | 28.35 | 388 | 242 | 19 | 12522 | 13577 |
| ref|ZP_06294764.1| | protein of unknown function DUF847 [*Burkholderia* sp. CCGE1001] | 33.13 | 163 | 109 | 3 | 21193 | 20705 |
| ref|ZP_06222476.1| | poly(A) polymerase [*Haemophilus influenzae* HK1212] | 36.36 | 165 | 105 | 2 | 21196 | 20702 |
| ref|ZP_06222539.1| | hypothetical protein HAINFHK1212_1520 [*Haemophilus influenzae* HK1212] | 36.65 | 161 | 102 | 2 | 21184 | 20702 |
| gb|EEQ42459.1| | conserved hypothetical protein [*Candida albicans* WO-1] | 26.82 | 261 | 180 | 8 | 12303 | 13052 |
| gb|EEQ42459.1| | conserved hypothetical protein [*Candida albicans* WO-1] | 32.35 | 68 | 46 | 1 | 11996 | 12199 |
| ref|ZP_06288708.1| | DEAD/DEAH box helicase [*Prevotella timonensis* CRIS 5C-B1] | 25.77 | 291 | 196 | 12 | 12321 | 13133 |
| ref|ZP_06288708.1| | DEAD/DEAH box helicase [*Prevotella timonensis* CRIS 5C-B1] | 34.21 | 114 | 73 | 4 | 11984 | 12319 |
| ref|YP_001565108.1| | pathogenesis-related transcriptional factor and ERF protein [*Delftia* | 35.54 | 166 | 94 | 5 | 11490 | 11948 |
| ref|YP_575655.1| | HNH endonuclease [*Nitrobacter hamburgensis* X14] | 40.65 | 123 | 71 | 1 | 11610 | 11972 |
| ref|NP_881902.1| | hypothetical protein BP3370 [*Bordetella pertussis* Tohama I] | 39.29 | 140 | 83 | 4 | 11490 | 11903 |
| ref|ZP_06222379.1| | hypothetical protein HAINFHK1212_1590 | 37.82 | 156 | 97 | 2 | 21169 | 20702 |

TABLE 1-continued

| Subject id | Description | % identity | alignment length | Mis matches | gap openings | q. start | q. end |
|---|---|---|---|---|---|---|---|
| ref|ZP_06223216.1| | hypothetical protein HAINFHK1212_0338 [*Haemophilus influenzae* HK1212] | 36.81 | 163 | 103 | 2 | 21190 | 20702 |
| gb|EEQ42458.1| | conserved hypothetical protein [*Candida albicans* WO-1] | 26.64 | 259 | 183 | 7 | 12297 | 13052 |
| gb|EEQ42458.1| | conserved hypothetical protein [*Candida albicans* WO-1] | 35.29 | 68 | 44 | 1 | 11996 | 12199 |
| ref|YP_003608210.1| | protein of unknown function DUF847 [*Burkholderia* sp. CCGE1002] | 32.52 | 163 | 110 | 3 | 21193 | 20705 |
| ref|ZP_05783661.1| | conserved hypothetical protein [*Citreicella* sp. SE45] | 25.09 | 558 | 391 | 23 | 6551 | 8143 |
| ref|XP_711764.1| | hypothetical protein CaO19.10316 [*Candida albicans* SC5314] | 26.64 | 259 | 183 | 7 | 12297 | 13052 |
| ref|XP_711764.1| | hypothetical protein CaO19.10316 [*Candida albicans* SC5314] | 35.29 | 68 | 44 | 1 | 11996 | 12199 |
| gb|ADD96376.1| | hypothetical protein yberc0001_14950 [uncultured organism] | 30.67 | 163 | 111 | 2 | 11451 | 11933 |
| ref|YP_003376236.1| | hypothetical protein of unknown function duf847 [*Xanthomonas*] | 35.16 | 182 | 103 | 6 | 21193 | 20693 |
| ref|ZP_06221712.1| | hypothetical protein HAINFHK1212_1133 [*Haemophilus influenzae* HK1212] | 38.56 | 153 | 94 | 2 | 21160 | 20702 |
| ref|ZP_06221842.1| | hypothetical protein HAINFHK1212_2061 [*Haemophilus influenzae* HK1212] | 38.56 | 153 | 94 | 2 | 21160 | 20702 |
| ref|ZP_06222749.1| | DNA topoisomerase III [*Haemophilus influenzae* HK1212] | 38.56 | 153 | 94 | 2 | 21160 | 20702 |
| ref|ZP_06222012.1| | hypothetical protein HAINFHK1212_1041 [*Haemophilus influenzae* HK1212] | 38.56 | 153 | 94 | 2 | 21160 | 20702 |
| ref|ZP_06222819.1| | hypothetical protein HAINFHK1212_1706 [*Haemophilus influenzae* HK1212] | 38.56 | 153 | 94 | 2 | 21160 | 20702 |
| ref|ZP_05375782.1| | protein of unknown function DUF847 [*Hyphomicrobium denitrificans* ATCC] | 33.17 | 199 | 126 | 5 | 21199 | 20624 |
| ref|ZP_03995517.1| | phage protein [*Lactobacillus crispatus* JV-V01] | 27.75 | 364 | 225 | 15 | 1450 | 473 |
| ref|ZP_04977471.1| | hypothetical protein MHA_0919 [*Mannheimia haemolytica* PHL213] | 33.53 | 170 | 112 | 3 | 21193 | 20687 |
| ref|ZP_04898487.1| | putative conserved hypothetical protein [*Burkholderia pseudomallei* | 27.15 | 372 | 248 | 12 | 1522 | 476 |
| ref|ZP_04898487.1| | putative conserved hypothetical protein [*Burkholderia pseudomallei* | 26.92 | 130 | 91 | 2 | 2731 | 2354 |
| ref|YP_001285701.2| | p31.1 [*Xanthomonas* phage Xop411] | 36.99 | 146 | 89 | 3 | 11499 | 11927 |
| ref|YP_003550710.1| | Microcystin-dependent protein-like protein [alpha proteobacterium | 35.96 | 203 | 128 | 7 | 21955 | 21353 |

TABLE 1-continued

| Subject id | Description | % identity | alignment length | Mis matches | gap openings | q. start | q. end |
|---|---|---|---|---|---|---|---|
| ref|YP_002922896.1| | putative HNH endonuclease [*Enterobacteria* phage WV8] | 35.80 | 162 | 103 | 2 | 11490 | 11972 |
| ref|YP_880745.1| | gp2 protein [*Mycobacterium avium* 104] | 27.60 | 279 | 185 | 9 | 1561 | 776 |
| ref|YP_880745.1| | gp2 protein [*Mycobacterium avium* 104] | 29.69 | 128 | 89 | 2 | 2722 | 2342 |
| ref|ZP_00782397.1| | helicase, putative [*Streptococcus agalactiae* H36B] | 25.10 | 259 | 185 | 7 | 12327 | 13076 |
| ref|ZP_00782397.1| | helicase, putative [*Streptococcus agalactiae* H36B] | 30.39 | 102 | 70 | 2 | 11996 | 12298 |
| ref|ZP_06019826.1| | conserved hypothetical protein [*Lactobacillus crispatus* MV-3A-US] | 25.91 | 359 | 233 | 14 | 1450 | 473 |
| ref|ZP_02883093.1| | protein of unknown function DUF847 [*Burkholderia graminis* C4D1M] | 33.13 | 163 | 109 | 3 | 21193 | 20705 |
| ref|YP_001072155.1| | hypothetical protein Mjls_3888 [*Mycobacterium* sp. JLS] | 27.24 | 279 | 186 | 9 | 1561 | 776 |
| ref|YP_001072155.1| | hypothetical protein Mjls_3888 [*Mycobacterium* sp. JLS] | 29.69 | 128 | 89 | 2 | 2722 | 2342 |
| ref|YP_001006557.1| | hypothetical protein YE2335 [*Yersinia enterocolitica* subsp. | 34.52 | 168 | 102 | 3 | 11466 | 11945 |
| ref|NP_944978.1| | Putative HNH endonuclease [*Enterobacteria* phage Felix 01] | 35.85 | 159 | 100 | 3 | 11502 | 11972 |
| ref|YP_600161.1| | DNA/RNA helicase [*Streptococcus* phage 2096.1] | 25.19 | 266 | 190 | 7 | 12306 | 13076 |
| ref|YP_600161.1| | DNA/RNA helicase [*Streptococcus* phage 2096.1] | 31.37 | 102 | 69 | 2 | 11996 | 12298 |
| ref|NP_268909.1| | DEAD box family helicase [*Streptococcus* phage 370.1] | 25.19 | 266 | 190 | 7 | 12306 | 13076 |
| ref|NP_268909.1| | DEAD box family helicase [*Streptococcus* phage 370.1] | 31.37 | 102 | 69 | 2 | 11996 | 12298 |
| gb|ADF83450.1| | putative DNA methylase [*Lactobacillus* phage LBR48] | 29.18 | 281 | 152 | 11 | 15944 | 16645 |
| ref|XP_002417354.1| | conserved hypothetical protein [*Candida dubliniensis* CD36] | 26.64 | 259 | 183 | 7 | 12297 | 13052 |
| ref|XP_002417354.1| | conserved hypothetical protein [*Candida dubliniensis* CD36] | 33.82 | 68 | 45 | 1 | 11996 | 12199 |
| ref|ZP_06606319.1| | terminase large subunit [*Aeromicrobium marinum* DSM 15272] | 26.99 | 326 | 214 | 13 | 1378 | 473 |
| ref|YP_003084146.1| | large terminase subunit [Cyanophage PSS2] | 24.85 | 330 | 231 | 8 | 1375 | 437 |
| ref|YP_002911899.1| | DNA methylase N-4/N-6 domain protein [*Burkholderia glumae* BGR1] | 29.10 | 244 | 162 | 9 | 15947 | 16645 |
| ref|YP_001887786.1| | protein of unknown function DUF847 [*Burkholderia phytofirmans* PsJN] | 34.36 | 163 | 107 | 4 | 21193 | 20705 |
| ref|YP_554806.1| | hypothetical protein Bxe_B0491 | 33.13 | 163 | 109 | 3 | 21193 | 20705 |

TABLE 1-continued

| Subject id | Description | % identity | alignment length | Mis matches | gap openings | q. start | q. end |
|---|---|---|---|---|---|---|---|
| gb|EFG74825.1| | [Burkholderia xenovorans LB400] gp2 protein [Mycobacterium parascrofulaceum ATCC BAA-614] | 27.24 | 279 | 186 | 9 | 1561 | 776 |
| gb|EFG74825.1| | gp2 protein [Mycobacterium parascrofulaceum ATCC BAA-614] | 29.69 | 128 | 89 | 2 | 2722 | 2342 |
| ref|YP_001469624.1| | HNH endonuclease [Xanthomonas phage Xop411] | 34.81 | 158 | 102 | 3 | 11490 | 11960 |
| ref|YP_001239849.1| | hypothetical protein BBta_3868 [Bradyrhizobium sp. BTAi1] | 30.00 | 190 | 127 | 3 | 21163 | 20612 |
| emb|CBK86236.1| | AP2 domain. [Enterobacter cloacae NCTC 9394] | 37.58 | 149 | 91 | 3 | 11475 | 11915 |
| ref|ZP_06469271.1| | conserved hypothetical protein [Burkholderia sp. CCGE1003] | 34.36 | 163 | 107 | 4 | 21193 | 20705 |
| ref|ZP_06089323.1| | LOW QUALITY PROTEIN: conserved hypothetical protein [Bacteroides sp. | 37.80 | 164 | 94 | 4 | 16184 | 16651 |
| ref|ZP_04752828.1| | hypothetical bacteriophage protein [Actinobacillus minor NM305] | 32.94 | 170 | 113 | 3 | 21193 | 20687 |
| ref|ZP_03800364.1| | hypothetical protein COPCOM_02633 [Coprococcus comes ATCC 27758] | 37.24 | 145 | 83 | 4 | 16226 | 16636 |
| ref|ZP_01791611.1| | hypothetical protein CGSHiAA_00570 [Haemophilus influenzae PittAA] | 37.18 | 156 | 98 | 2 | 21169 | 20702 |
| ref|YP_864938.1| | hypothetical protein Mmc1_1014 [Magnetococcus sp. MC-1] | 28.05 | 353 | 202 | 14 | 27287 | 26385 |
| ref|ZP_02327247.1| | DNA/RNA helicase [Paenibacillus larvae subsp. larvae BRL-230010] | 27.17 | 254 | 182 | 8 | 12324 | 13076 |
| ref|ZP_02327247.1| | DNA/RNA helicase [Paenibacillus larvae subsp. larvae BRL-230010] | 26.73 | 101 | 73 | 2 | 11996 | 12295 |
| ref|ZP_06223211.1| | hypothetical protein HAINFHK1212_0035 [Haemophilus influenzae HK1212] | 38.16 | 152 | 94 | 2 | 21157 | 20702 |
| gb|ACD75432.1| | AMDV4_3 [uncultured virus] | 29.43 | 265 | 163 | 8 | 15941 | 16663 |
| ref|YP_002276802.1| | Tail Collar domain protein [Gluconacetobacter diazotrophicus PAl 5] | 31.25 | 240 | 149 | 8 | 22027 | 21356 |
| gb|ADD81106.1| | TerL [Rhodococcus phage ReqiPine5] | 30.66 | 212 | 143 | 6 | 1378 | 755 |
| ref|YP_002475454.1| | hypothetical bacteriophage protein [Haemophilus parasuis SH0165] | 34.15 | 164 | 108 | 2 | 21193 | 20702 |
| ref|YP_002276931.1| | Tail Collar domain protein [Gluconacetobacter diazotrophicus PAl 5] | 30.51 | 295 | 185 | 12 | 22180 | 21356 |
| ref|YP_001862243.1| | hypothetical protein Bphy_6144 [Burkholderia phymatum STM815] | 34.57 | 162 | 106 | 4 | 21190 | 20705 |

TABLE 1-continued

| Subject id | Description | % identity | alignment length | Mis matches | gap openings | q. start | q. end |
|---|---|---|---|---|---|---|---|
| ref|ZP_05555322.1| | conserved hypothetical protein [*Lactobacillus crispatus* MV-1A-US] | 25.21 | 361 | 235 | 15 | 1450 | 473 |
| ref|ZP_05377878.1| | Pathogenesis-related transcriptional factor and ERF protein | 38.16 | 152 | 89 | 4 | 11490 | 11930 |
| ref|ZP_04601775.1| | hypothetical protein GCWU000324_01248 [*Kingella oralis* ATCC 51147] | 29.45 | 163 | 115 | 2 | 21193 | 20705 |
| ref|ZP_01789655.1| | hypothetical protein CGSHi3655_00165 [*Haemophilus influenzae* 3655] | 34.34 | 166 | 109 | 2 | 21202 | 20705 |
| ref|YP_239069.1| | hypothetical protein RB43ORF093w [*Enterobacteria* phage RB43] | 35.29 | 153 | 98 | 2 | 11517 | 11972 |
| ref|ZP_05346792.1| | DNA/RNA helicase [*Bryantella formatexigens* DSM 14469] | 26.15 | 260 | 189 | 8 | 12306 | 13076 |
| ref|ZP_05346792.1| | DNA/RNA helicase [*Bryantella formatexigens* DSM 14469] | 29.70 | 101 | 70 | 2 | 11996 | 12295 |
| ref|YP_001850249.1| | hypothetical protein MMAR_1945 [*Mycobacterium marinum* M] | 26.77 | 269 | 190 | 7 | 1561 | 776 |
| ref|YP_001850249.1| | hypothetical protein MMAR_1945 [*Mycobacterium marinum* M] | 28.91 | 128 | 90 | 2 | 2722 | 2342 |
| ref|ZP_03009318.1| | hypothetical protein BACCOP_01174 [*Bacteroides coprocola* DSM 17136] | 25.84 | 267 | 190 | 9 | 12297 | 13073 |
| ref|ZP_03009318.1| | hypothetical protein BACCOP_01174 [*Bacteroides coprocola* DSM 17136] | 31.78 | 107 | 68 | 4 | 11996 | 12301 |
| ref|ZP_06342161.1| | DEAD/DEAH box helicase [*Bulleidia extructa* W1219] | 26.82 | 261 | 187 | 8 | 12306 | 13076 |
| ref|ZP_06342161.1| | DEAD/DEAH box helicase [*Bulleidia extructa* W1219] | 32.99 | 97 | 64 | 2 | 11996 | 12283 |
| ref|ZP_06646295.1| | DNA/RNA helicase [*Erysipelotrichaceae bacterium* 5_2_54FAA] | 27.60 | 221 | 158 | 6 | 12420 | 13076 |
| ref|ZP_06646295.1| | DNA/RNA helicase [*Erysipelotrichaceae bacterium* 5_2_54FAA] | 30.00 | 110 | 76 | 3 | 11996 | 12322 |
| ref|YP_398997.1| | putative ATP-dependent helicase [*Enterobacteria* phage RTP] | 24.37 | 435 | 293 | 14 | 12414 | 13610 |
| ref|YP_363378.1| | hypothetical protein XCV1647 [*Xanthomonas campestris* pv. *vesicatoria* | 34.25 | 181 | 105 | 6 | 21193 | 20693 |
| ref|ZP_02328732.1| | DNA/RNA helicase [*Paenibacillus larvae* subsp. *larvae* BRL-230010] | 27.45 | 255 | 181 | 9 | 12324 | 13076 |
| ref|ZP_02328732.1| | DNA/RNA helicase [*Paenibacillus larvae* subsp. *larvae* BRL-230010] | 26.73 | 101 | 73 | 2 | 11996 | 12295 |
| ref|ZP_06704951.1| | conserved hypothetical protein [*Xanthomonas fuscans* subsp. *aurantifolii* | 34.25 | 181 | 105 | 6 | 21193 | 20693 |

TABLE 1-continued

| Subject id | Description | % identity | alignment length | Mis matches | gap openings | q. start | q. end |
|---|---|---|---|---|---|---|---|
| ref|NP_641937.1| | hypothetical protein XAC1605 [*Xanthomonas axonopodis* pv. *citri* str. | 34.25 | 181 | 105 | 6 | 21193 | 20693 |
| ref|ZP_04566003.1| | type III restriction enzyme [*Mollicutes bacterium* D7] | 26.58 | 222 | 161 | 6 | 12417 | 13076 |
| ref|ZP_04566003.1| | type III restriction enzyme [*Mollicutes bacterium* D7] | 31.37 | 102 | 69 | 2 | 11996 | 12298 |
| ref|XP_002492528.1| | Putative protein of unknown function [*Pichia pastoris* GS115] | 25.97 | 258 | 176 | 8 | 12327 | 13055 |
| ref|XP_002492528.1| | Putative protein of unknown function [*Pichia pastoris* GS115] | 25.89 | 112 | 76 | 4 | 11996 | 12310 |
| ref|NP_705681.1| | gp58 [*Burkholderia* phage Bcep781] | 25.38 | 264 | 183 | 8 | 12327 | 13076 |
| ref|NP_705681.1| | gp58 [*Burkholderia* phage Bcep781] | 30.97 | 113 | 71 | 3 | 11999 | 12316 |
| ref|NP_858950.1| | endonuclease of the HNH family [*Xanthomonas* phage Xp10] | 37.50 | 136 | 84 | 3 | 11475 | 11879 |
| ref|YP_001293436.1| | hypothetical protein ORF029 [*Pseudomonas* phage 73] | 26.37 | 292 | 205 | 9 | 12333 | 13178 |
| ref|YP_001293436.1| | hypothetical protein ORF029 [*Pseudomonas* phage 73] | 32.41 | 108 | 69 | 3 | 11999 | 12310 |
| ref|ZP_03385165.1| | putative helicase Salmonella enterica subsp. *enterica* serovar Typhi | 42.73 | 110 | 63 | 1 | 11996 | 12325 |
| ref|YP_001294897.1| | helicase [*Burkholderia* phage BcepNY3] | 25.38 | 264 | 183 | 8 | 12327 | 13076 |
| ref|YP_001294897.1| | helicase [*Burkholderia* phage BcepNY3] | 30.97 | 113 | 71 | 3 | 11999 | 12316 |
| ref|NP_958163.1| | gp57 [*Burkholderia* phage Bcep43] | 25.38 | 264 | 183 | 8 | 12327 | 13076 |
| ref|NP_958163.1| | gp57 [*Burkholderia* phage Bcep43] | 30.97 | 113 | 71 | 3 | 11999 | 12316 |
| ref|NP_944368.1| | gp60 [*Burkholderia* phage Bcep1] | 25.38 | 264 | 183 | 8 | 12327 | 13076 |
| ref|NP_944368.1| | gp60 [*Burkholderia* phage Bcep1] | 30.97 | 113 | 71 | 3 | 11999 | 12316 |
| ref|YP_164394.1| | DEAD box family helicase [*Bacillus* phage BCJA1c] | 25.78 | 256 | 187 | 7 | 12318 | 13076 |
| ref|YP_164394.1| | DEAD box family helicase [*Bacillus* phage BCJA1c] | 25.69 | 109 | 80 | 2 | 11996 | 12319 |
| ref|YP_002911934.1| | P42.1 [*Burkholderia glumae* BGR1] | 38.30 | 141 | 86 | 2 | 11496 | 11915 |
| ref|NP_203468.1| | hypothetical protein Mx8p54 [*Myxococcus* phage Mx8] | 29.24 | 342 | 216 | 12 | 27287 | 26340 |
| ref|ZP_04682609.1| | p077 [*Ochrobactrum intermedium* LMG 3301] | 28.38 | 229 | 159 | 4 | 8671 | 9342 |
| ref|YP_003065546.1| | hypothetical protein CLIBASIA_05175 [*Candidatus Liberibacter asiaticus* | 35.46 | 141 | 84 | 2 | 27703 | 27302 |
| ref|YP_239236.1| | hypothetical protein RB43ORF260w [*Enterobacteria* phage RB43] | 30.18 | 169 | 112 | 4 | 11463 | 11951 |
| ref|ZP_06111909.1| | ferrichrome transport ATP-binding protein FhuC [*Clostridium botulinum* | 37.61 | 117 | 70 | 2 | 15944 | 16285 |

TABLE 1-continued

| Subject id | Description | % identity | alignment length | Mis matches | gap openings | q. start | q. end |
|---|---|---|---|---|---|---|---|
| ref\|ZP_05113457.1\| | hypothetical protein SADFL11_1342 [*Labrenzia alexandrii* DFL-11] | 43.75 | 96 | 54 | 1 | 3278 | 2991 |
| ref\|ZP_03529250.1\| | hypothetical protein RetlC8_22061 [*Rhizobium etli* CIAT 894] | 31.51 | 146 | 100 | 1 | 37125 | 36688 |
| ref\|ZP_05860237.1\| | DNA/RNA helicase [*Jonquetella anthropi* E3_33 E1] | 25.00 | 312 | 223 | 14 | 12327 | 13229 |
| ref\|ZP_05860237.1\| | DNA/RNA helicase [*Jonquetella anthropi* E3_33 E1] | 35.71 | 112 | 69 | 5 | 11996 | 12322 |
| ref\|YP_002564202.1\| | gp6 [*Mycobacterium* phage Phlyer] | 33.98 | 206 | 130 | 8 | 1375 | 776 |
| ref\|YP_002564202.1\| | gp6 [*Mycobacterium* phage Phlyer] | 25.00 | 132 | 85 | 3 | 2722 | 2369 |
| ref\|NP_945017.1\| | Putative HNH endonuclease [*Enterobacteria* phage Felix 01] | 35.22 | 159 | 99 | 4 | 11475 | 11939 |
| ref\|ZP_01054763.1\| | putative DEAD box family helicase, phage associated [*Roseobacter* sp. | 26.95 | 308 | 195 | 12 | 12333 | 13166 |
| ref\|ZP_01054763.1\| | putative DEAD box family helicase, phage associated [*Roseobacter* sp. | 33.33 | 84 | 54 | 3 | 11996 | 12241 |
| ref\|ZP_05377955.1\| | Pathogenesis-related transcriptional factor and ERF protein | 33.55 | 152 | 99 | 3 | 11475 | 11924 |
| ref\|YP_724333.1\| | hypothetical protein Tery_4946 [*Trichodesmium erythraeum* IMS101] | 31.36 | 169 | 114 | 5 | 21211 | 20711 |
| ref\|YP_002014616.1\| | gp5 [*Mycobacterium* phage Phaedrus] | 33.98 | 206 | 130 | 8 | 1375 | 776 |
| ref\|YP_002014616.1\| | gp5 [*Mycobacterium* phage Phaedrus] | 25.00 | 132 | 85 | 3 | 2722 | 2369 |
| ref\|YP_003610365.1\| | protein of unknown function DUF847 [*Burkholderia* sp. CCGE1002] | 32.52 | 163 | 110 | 3 | 21193 | 20705 |
| ref\|ZP_06222216.1\| | hypothetical protein HAINFHK1212_0433 [*Haemophilus influenzae* HK1212] | 37.93 | 145 | 90 | 2 | 21136 | 20702 |
| ref\|ZP_06221530.1\| | hypothetical protein HAINFHK1212_1001 [*Haemophilus influenzae* HK1212] | 37.93 | 145 | 90 | 2 | 21136 | 20702 |
| ref\|ZP_05988809.1\| | putative phage large subunit terminase [*Mannheimia haemolytica* | 28.48 | 309 | 213 | 13 | 1378 | 476 |
| ref\|ZP_05988809.1\| | putative phage large subunit terminase [*Mannheimia haemolytica* | 30.17 | 116 | 81 | 1 | 2737 | 2390 |
| ref\|ZP_05854350.1\| | DNA (cytosine-5-)-methyltransferase [*Blautia hansenii* DSM 20583] | 28.24 | 255 | 168 | 6 | 15935 | 16654 |
| ref\|YP_785834.1\| | phage large subunit terminase [*Bordetella avium* 197N] | 29.36 | 327 | 219 | 14 | 1378 | 434 |
| ref\|YP_785834.1\| | phage large subunit terminase [*Bordetella avium* 197N] | 29.41 | 119 | 83 | 2 | 2743 | 2390 |
| ref\|ZP_01048606.1\| | phage uncharacterized protein [*Nitrobacter* sp. Nb-311A] | 26.00 | 350 | 239 | 13 | 1462 | 473 |
| ref\|ZP_01048606.1\| | phage uncharacterized protein [*Nitrobacter* sp. Nb-311A] | 26.89 | 119 | 86 | 1 | 2677 | 2324 |

TABLE 1-continued

| Subject id | Description | % identity | alignment length | Mis matches | gap openings | q. start | q. end |
|---|---|---|---|---|---|---|---|
| ref|YP_655728.1| | gp48 [*Mycobacterium* phage Qyrzula] | 25.79 | 221 | 160 | 4 | 12402 | 13052 |
| ref|YP_655728.1| | gp48 [*Mycobacterium* phage Qyrzula] | 35.92 | 103 | 63 | 3 | 11996 | 12295 |
| ref|NP_817811.1| | gp50 [*Mycobacterium* phage Rosebush] | 25.79 | 221 | 160 | 4 | 12402 | 13052 |
| ref|NP_817811.1| | gp50 [*Mycobacterium* phage Rosebush] | 35.92 | 103 | 63 | 3 | 11996 | 12295 |
| ref|YP_003429878.1| | putative DEAD box family helicase, phage associated [*Streptococcus*] | 24.71 | 259 | 186 | 7 | 12327 | 13076 |
| ref|YP_003429878.1| | putative DEAD box family helicase, phage associated [*Streptococcus*] | 30.39 | 102 | 70 | 2 | 11996 | 12298 |
| ref|YP_001736109.1| | hypothetical protein SYNPCC7002_C0009 [*Synechococcus* sp. PCC 7002] | 29.15 | 319 | 220 | 12 | 12216 | 13154 |
| ref|YP_001736109.1| | hypothetical protein SYNPCC7002_C0009 [*Synechococcus* sp. PCC 7002] | 30.59 | 85 | 58 | 3 | 11987 | 12238 |
| ref|YP_002501630.1| | phage uncharacterized protein [*Methylobacterium nodulans* ORS 2060] | 28.62 | 318 | 211 | 10 | 1378 | 473 |
| ref|YP_002501630.1| | phage uncharacterized protein [*Methylobacterium nodulans* ORS 2060] | 31.73 | 104 | 65 | 3 | 2677 | 2384 |
| ref|YP_001834420.1| | hypothetical protein Bind_3374 [*Beijerinckia indica* subsp. *indica* ATCC | 32.18 | 174 | 117 | 5 | 21190 | 20672 |
| ref|NP_597900.1| | putative endonuclease [*Enterobacteria* phage HK022] | 30.87 | 149 | 102 | 2 | 11472 | 11915 |
| ref|YP_001950208.1| | HNH endonuclease [*Ralstonia phage* RSL1] | 31.82 | 176 | 107 | 5 | 11481 | 11969 |
| ref|ZP_01724547.1| | hypothetical protein BB14905_13950 [*Bacillus* sp. B14905] | 33.11 | 151 | 98 | 2 | 1378 | 935 |
| ref|ZP_01724547.1| | hypothetical protein BB14905_13950 [*Bacillus* sp. B14905] | 33.87 | 124 | 80 | 3 | 2734 | 2369 |
| ref|YP_277511.1| | hypothetical protein yejH [*Enterobacteria* phage JK06] | 31.90 | 232 | 141 | 7 | 12411 | 13055 |
| ref|YP_277511.1| | hypothetical protein yejH [*Enterobacteria* phage JK06] | 29.46 | 112 | 77 | 2 | 12002 | 12331 |
| ref|NP_936907.1| | hypothetical protein VVA0851 [*Vibrio vulnificus* YJ016] | 30.81 | 172 | 115 | 2 | 21190 | 20687 |
| ref|XP_001485376.1| | hypothetical protein PGUG_03105 [*Pichia guilliermondii* ATCC 6260] | 29.92 | 264 | 170 | 10 | 12306 | 13052 |
| ref|XP_001485376.1| | hypothetical protein PGUG_03105 [*Pichia guilliermondii* ATCC 6260] | 26.42 | 106 | 73 | 2 | 11996 | 12298 |
| ref|ZP_05377917.1| | Pathogenesis-related transcriptional factor and ERF protein | 34.57 | 162 | 105 | 4 | 11490 | 11972 |
| ref|YP_002235510.1| | putative methyltransferase [*Burkholderia cenocepacia* J2315] | 32.66 | 248 | 150 | 11 | 15944 | 16636 |
| ref|ZP_04996124.1| | conserved hypothetical protein [*Streptomyces* sp. Mg1] | 36.36 | 132 | 84 | 4 | 1375 | 980 |
| ref|XP_001528318.1| | hypothetical protein LELG_00838 | 32.70 | 263 | 167 | 10 | 12306 | 13064 |

TABLE 1-continued

| Subject id | Description | % identity | alignment length | Mis matches | gap openings | q. start | q. end |
|---|---|---|---|---|---|---|---|
| ref|YP_676376.1| | [*Lodderomyces elongisporus* NRRL DNA methylase N-4/N-6 [*Mesorhizobium* sp. BNC1] | 26.38 | 254 | 183 | 4 | 15941 | 16690 |
| ref|YP_865217.1| | type III restriction enzyme, res subunit [*Magnetococcus* sp. MC-1] | 25.94 | 293 | 203 | 9 | 12333 | 13169 |
| ref|YP_865217.1| | type III restriction enzyme, res subunit [*Magnetococcus* sp. MC-1] | 27.62 | 105 | 72 | 2 | 11993 | 12295 |
| ref|YP_865981.1| | type III restriction enzyme, res subunit [*Magnetococcus* sp. MC-1] | 25.00 | 296 | 205 | 9 | 12333 | 13169 |
| ref|YP_865981.1| | type III restriction enzyme, res subunit [*Magnetococcus* sp. MC-1] | 27.62 | 105 | 72 | 2 | 11993 | 12295 |
| ref|YP_866555.1| | type III restriction enzyme, res subunit [*Magnetococcus* sp. MC-1] | 25.17 | 286 | 197 | 8 | 12333 | 13139 |
| ref|YP_866555.1| | type III restriction enzyme, res subunit [*Magnetococcus* sp. MC-1] | 27.62 | 105 | 72 | 2 | 11993 | 12295 |
| ref|YP_002922621.1| | P07 [*Xanthomonas* phage phiL7] | 40.21 | 97 | 57 | 1 | 11610 | 11897 |
| ref|ZP_03588245.1| | DNA methylase [*Burkholderia multivorans* CGD1] | 31.51 | 238 | 156 | 8 | 15944 | 16636 |
| ref|ZP_01983885.1| | DNA methylase [*Vibrio cholerae* 623-39] | 28.24 | 262 | 160 | 9 | 15941 | 16642 |
| ref|ZP_06258255.1| | DEAD/DEAH box helicase [*Veillonella parvula* ATCC 17745] | 24.81 | 266 | 191 | 7 | 12306 | 13076 |
| ref|ZP_06258255.1| | DEAD/DEAH box helicase [*Veillonella parvula* ATCC 17745] | 35.37 | 82 | 52 | 3 | 11996 | 12238 |
| ref|ZP_06351481.1| | DNA methylase N-4/N-6 domain protein [*Rhodomicrobium vannielii* ATCC | 29.62 | 260 | 167 | 7 | 15914 | 16645 |
| ref|ZP_06222326.1| | hypothetical protein HAINFHK1212_0129 [*Haemophilus influenzae* HK1212] | 37.76 | 143 | 89 | 2 | 21130 | 20702 |
| ref|ZP_06221926.1| | hypothetical protein HAINFHK1212_0534 [*Haemophilus influenzae* HK1212] | 37.76 | 143 | 89 | 2 | 21130 | 20702 |
| ref|YP_002498769.1| | phage uncharacterized protein [*Methylobacterium nodulans* ORS 2060] | 25.87 | 317 | 220 | 10 | 1378 | 473 |
| ref|ZP_03521690.1| | hypothetical protein RetIG_10420 [*Rhizobium etli* GR56] | 26.10 | 272 | 200 | 4 | 32466 | 31654 |
| ref|YP_001533100.1| | hypothetical protein Dshi_1757 [*Dinoroseobacter shibae* DFL 12] | 34.27 | 178 | 93 | 5 | 21196 | 20735 |
| gb|EDK39007.2| | hypothetical protein PGUG_03105 [*Pichia guilliermondii* ATCC 6260] | 29.55 | 264 | 171 | 10 | 12306 | 13052 |
| gb|EDK39007.2| | hypothetical protein PGUG_03105 [*Pichia guilliermondii* ATCC 6260] | 26.42 | 106 | 73 | 2 | 11996 | 12298 |
| ref|ZP_06393533.1| | protein of unknown function DUF847 | 32.61 | 184 | 110 | 5 | 21202 | 20693 |

TABLE 1-continued

| Subject id | Description | % identity | alignment length | Mis matches | gap openings | q. start | q. end |
|---|---|---|---|---|---|---|---|
| ref\|ZP_03544066.1\| | phage uncharacterized protein [*Comamonas testosteroni* KF-1] [*Dethiosulfovibrio peptidovorans* DSM | 28.35 | 321 | 221 | 13 | 1378 | 443 |
| ref\|ZP_03544066.1\| | phage uncharacterized protein [*Comamonas testosteroni* KF-1] | 27.35 | 117 | 84 | 2 | 2737 | 2390 |
| ref\|YP_001119034.1\| | hypothetical protein Bcep1808_1188 [*Burkholderia vietnamiensis* G4] | 30.06 | 163 | 114 | 3 | 21193 | 20705 |
| ref\|YP_866744.1\| | type III restriction enzyme, res subunit [*Magnetococcus* sp. MC-1] | 25.68 | 296 | 203 | 10 | 12333 | 13169 |
| ref\|YP_866744.1\| | type III restriction enzyme, res subunit [*Magnetococcus* sp. MC-1] | 27.62 | 105 | 72 | 2 | 11993 | 12295 |
| ref\|YP_002898982.1\| | hypothetical protein EE36P1_gp51 [Roseophage EE36P1] | 35.21 | 142 | 91 | 4 | 11475 | 11897 |
| ref\|ZP_01976970.1\| | ATP-dependent RNA helicase, DEAD/DEAH box family [*Vibrio cholerae* B33] | 30.10 | 206 | 143 | 7 | 13041 | 13655 |
| ref\|YP_001899851.1\| | protein of unknown function DUF847 [*Ralstonia pickettii* 12J] | 29.45 | 163 | 115 | 3 | 21193 | 20705 |
| ref\|ZP_06681838.1\| | gp10 [*Enterococcus faecium* E980] | 28.07 | 171 | 117 | 4 | 15941 | 16435 |
| ref\|YP_001600402.1\| | putative DNA methylase N-4/N-6 [*Gluconacetobacter diazotrophicus* PAl 5] | 27.54 | 236 | 167 | 3 | 15941 | 16636 |
| ref\|XP_001390242.1\| | hypothetical protein An03g03600 [*Aspergillus niger*] | 26.07 | 257 | 182 | 7 | 12306 | 13052 |
| ref\|XP_001390242.1\| | hypothetical protein An03g03600 [*Aspergillus niger*] | 28.21 | 78 | 54 | 2 | 11993 | 12220 |
| gb\|EFG84791.1\| | putative DNA methylase N-4/N-6 [*Gluconacetobacter hansenii* ATCC 23769] | 28.23 | 248 | 162 | 5 | 15941 | 16636 |
| ref\|ZP_05843252.1\| | protein of unknown function DUF847 [*Rhodobacter* sp. SW2] | 34.50 | 171 | 88 | 5 | 21175 | 20735 |
| ref\|YP_002274239.1\| | putative HNH endonuclease [Stx2-converting phage 1717] | 30.20 | 149 | 103 | 2 | 11472 | 11915 |
| ref\|ZP_01034820.1\| | hypothetical protein ROS217_23282 [*Roseovarius* sp. 217] | 35.56 | 180 | 91 | 7 | 21175 | 20711 |
| ref\|YP_840552.1\| | DNA methylase N-4/N-6 domain-containing protein [*Burkholderia* | 30.74 | 283 | 179 | 12 | 15839 | 16636 |
| ref\|YP_002964945.1\| | HNH endonuclease family protein [*Methylobacterium extorquens* AM1] | 34.27 | 143 | 93 | 2 | 11490 | 11915 |
| ref\|YP_001110809.1\| | hypothetical protein SPSV3_gp09 [*Salmonella* phage SETP3] | 34.55 | 165 | 103 | 5 | 11490 | 11969 |
| ref\|YP_529251.1\| | XRE family transcriptional regulator [*Saccharophagus degradans* 2-40] | 32.14 | 168 | 104 | 4 | 21169 | 20696 |

TABLE 1-continued

| Subject id | Description | % identity | alignment length | Mis matches | gap openings | q. start | q. end |
|---|---|---|---|---|---|---|---|
| ref\|ZP_06178203.1\| | conserved hypothetical protein [*Vibrio harveyi* 1DA3] | 27.82 | 266 | 178 | 9 | 12321 | 13076 |
| ref\|ZP_06178203.1\| | conserved hypothetical protein [*Vibrio harveyi* 1DA3] | 38.57 | 70 | 43 | 2 | 11993 | 12202 |
| ref\|ZP_06142710.1\| | type III restriction protein res subunit [*Ruminococcus flavefaciens* | 26.75 | 228 | 159 | 7 | 12417 | 13076 |
| ref\|ZP_06142710.1\| | type III restriction protein res subunit [*Ruminococcus flavefaciens* | 31.68 | 101 | 68 | 2 | 11996 | 12295 |
| gb\|EFG69405.1\| | DNA methylase N-4/N-6 domain protein [*Burkholderia* sp. Ch1-1] | 28.05 | 246 | 162 | 9 | 15947 | 16639 |
| ref\|ZP_06542003.1\| | putative helicase [*Salmonella enterica* subsp. *enterica* serovar Typhi | 52.63 | 95 | 43 | 1 | 12741 | 13019 |
| ref\|YP_002502042.1\| | phage uncharacterized protein [*Methylobacterium nodulans* ORS 2060] | 27.86 | 323 | 225 | 12 | 1378 | 434 |
| ref\|ZP_01948157.1\| | conserved hypothetical protein [*Vibrio cholerae* 1587] | 30.23 | 172 | 116 | 2 | 21190 | 20687 |
| ref\|YP_655687.1\| | gp7 [*Mycobacterium* phage Qyrzula] | 30.77 | 208 | 136 | 7 | 1375 | 776 |
| ref\|YP_655687.1\| | gp7 [*Mycobacterium* phage Qyrzula] | 25.56 | 133 | 84 | 3 | 2722 | 2369 |
| gb\|AAY44387.1\| | RB16 HNH(AP2) 2 [*Enterobacteria* phage RB16] | 38.00 | 150 | 92 | 6 | 11493 | 11939 |
| ref\|NP_817768.1\| | gp7 [*Mycobacterium* phage Rosebush] | 30.77 | 208 | 136 | 7 | 1375 | 776 |
| ref\|NP_817768.1\| | gp7 [*Mycobacterium* phage Rosebush] | 26.32 | 133 | 83 | 3 | 2722 | 2369 |
| ref\|ZP_01040991.1\| | primase, putative [*Erythrobacter* sp. NAP1] | 30.42 | 263 | 170 | 10 | 5942 | 6691 |
| ref\|ZP_02192066.1\| | type III restriction enzyme, res subunit [alpha proteobacterium BAL199] | 28.33 | 293 | 195 | 11 | 12333 | 13166 |
| ref\|ZP_02192066.1\| | type III restriction enzyme, res subunit [alpha proteobacterium BAL199] | 31.43 | 105 | 68 | 3 | 11993 | 12295 |
| ref\|ZP_03682448.1\| | hypothetical protein CATMIT_01082 [*Catenibacterium mitsuokai* DSM 15897] | 24.05 | 262 | 194 | 9 | 12306 | 13076 |
| ref\|ZP_03682448.1\| | hypothetical protein CATMIT_01082 [*Catenibacterium mitsuokai* DSM 15897] | 28.57 | 105 | 73 | 3 | 11996 | 12304 |
| ref\|ZP_01878875.1\| | hypothetical protein RTM1035_05155 [*Roseovarius* sp. TM1035] | 35.50 | 169 | 85 | 5 | 21175 | 20741 |
| gb\|AAX12931.1\| | hypothetical protein [*Escherichia blattae* DSM 4481] | 35.81 | 148 | 88 | 4 | 21190 | 20768 |
| ref\|YP_001121090.1\| | type III restriction enzyme, res subunit [*Burkholderia vietnamiensis* | 26.19 | 294 | 202 | 11 | 12333 | 13169 |
| ref\|YP_001121090.1\| | type III restriction enzyme, res subunit [*Burkholderia vietnamiensis* | 29.25 | 106 | 75 | 1 | 11993 | 12310 |

TABLE 1-continued

| Subject id | Description | % identity | alignment length | Mis matches | gap openings | q. start | q. end |
|---|---|---|---|---|---|---|---|
| gb|EFG70468.1| | protein of unknown function DUF847 [*Burkholderia* sp. Ch1-1] | 33.13 | 163 | 109 | 4 | 21193 | 20705 |
| ref|ZP_06050227.1| | secretion activator protein [*Vibrio cholerae* CT 5369-93] | 30.81 | 172 | 115 | 2 | 21190 | 20687 |
| ref|ZP_04683498.1| | Hypothetical protein OINT_3000003 [*Ochrobactrum intermedium* LMG 3301] | 34.84 | 155 | 99 | 4 | 21157 | 20699 |
| ref|ZP_04417624.1| | secretion activator protein [*Vibrio cholerae* 12129(1)] | 30.23 | 172 | 116 | 2 | 21190 | 20687 |
| ref|YP_001241623.1| | putative phage tail Collar domain [*Bradyrhizobium* sp. BTAi1] | 29.25 | 212 | 137 | 5 | 21946 | 21350 |
| ref|ZP_01972132.1| | conserved hypothetical protein [*Vibrio cholerae* NCTC 8457] | 30.23 | 172 | 116 | 2 | 21190 | 20687 |
| ref|YP_317463.1| | DNA methylase N-4/N-6 [*Nitrobacter winogradskyi* Nb-255] | 25.83 | 240 | 174 | 3 | 15929 | 16636 |
| ref|ZP_01075891.1| | hypothetical protein MED121_02105 [*Marinomonas* sp. MED121] | 32.68 | 153 | 103 | 2 | 21163 | 20705 |
| ref|ZP_04629946.1| | hypothetical protein yberc0001_14950 [*Yersinia bercovieri* ATCC 43970] | 32.19 | 146 | 98 | 3 | 11490 | 11924 |
| ref|YP_866508.1| | type III restriction enzyme, res subunit [*Magnetococcus* sp. MC-1] | 27.86 | 280 | 187 | 10 | 12375 | 13169 |
| ref|YP_866508.1| | type III restriction enzyme, res subunit [*Magnetococcus* sp. MC-1] | 25.74 | 101 | 75 | 1 | 11993 | 12295 |
| ref|YP_001371723.1| | DNA methylase N-4/N-6 domain-containing protein [*Ochrobactrum anthropi* | 25.85 | 236 | 171 | 3 | 15941 | 16636 |
| ref|YP_282807.1| | adenine-specific methyltransferase [*Streptococcus pyogenes* MGAS5005] | 30.40 | 250 | 152 | 11 | 15953 | 16636 |
| ref|NP_437108.1| | hypothetical protein SM_b20828 [*Sinorhizobium meliloti* 1021] | 50.00 | 76 | 38 | 0 | 21049 | 20822 |
| ref|YP_917737.1| | hypothetical protein Pden_3975 [*Paracoccus denitrificans* PD1222] | 36.31 | 168 | 83 | 5 | 21172 | 20741 |
| ref|XP_002148691.1| | DEAD/DEAH box helicase, putative [*Penicillium marneffei* ATCC 18224] | 24.80 | 250 | 180 | 8 | 12327 | 13052 |
| ref|XP_002148691.1| | DEAD/DEAH box helicase, putative [*Penicillium marneffei* ATCC 18224] | 32.53 | 83 | 54 | 2 | 11978 | 12220 |
| ref|ZP_06079511.1| | secretion activator protein [*Vibrio* sp. RC586] | 30.23 | 172 | 116 | 2 | 21190 | 20687 |
| ref|ZP_03587372.1| | EF hand domain protein [*Burkholderia multivorans* CGD1] | 28.90 | 173 | 111 | 6 | 21190 | 20708 |
| ref|ZP_03274694.1| | protein of unknown function DUF847 [*Arthrospira maxima* CS-328] | 29.55 | 220 | 141 | 10 | 21199 | 20582 |

TABLE 1-continued

| Subject id | Description | % identity | alignment length | Mis matches | gap openings | q. start | q. end |
|---|---|---|---|---|---|---|---|
| ref|ZP_02139834.1| | hypothetical protein RLO149_03017 [*Roseobacter litoralis* Och 149] | 28.48 | 323 | 210 | 13 | 1378 | 473 |
| ref|ZP_02139834.1| | hypothetical protein RLO149_03017 [*Roseobacter litoralis* Och 149] | 30.09 | 113 | 78 | 1 | 2677 | 2342 |
| ref|YP_001045164.1| | DNA methylase N-4/N-6 domain-containing protein [*Rhodobacter* | 28.57 | 266 | 173 | 7 | 15926 | 16672 |
| ref|ZP_01955098.1| | conserved hypothetical protein [*Vibrio cholerae* MZO-3] | 30.23 | 172 | 116 | 2 | 21190 | 20687 |

As mentioned herein above, the present invention also contemplates isolated polynucleotides which hybridize to the isolated polynucleotides described herein above. Such polynucleotides may be used to monitor *Brucella* phage gene expression, eventually allowing detection of *Brucella* strains (i.e. diagnosing) in a bacterial contaminated environment.

Such polynucleotides typically comprises a region of complementary nucleotide sequence that hybridizes under experimental conditions to at least about 8, 10, 13, 15, 18, 20, 22, 25, 30, 40, 50, 55, 60, 65, 70, 80, 90, 100, 120 (or any other number in-between) or more consecutive nucleotides to the sequence of the *Brucella* phage.

The polynucleotide (or plurality thereof) may be fixed to a solid support (e.g. in an array) and may be used to monitor phage expression in a *Brucella* sample.

Alternatively, the polynucleotide may serve as a primer in a primer pair and may be used in an amplification reaction (e.g. PCR) to identify *Brucella* phage.

The conditions are selected such that hybridization of the polynucleotide to the *Brucella* phage sequence is favored and hybridization to other non *Brucella* phage nucleic acid sequences is minimized.

By way of example, hybridization of short nucleic acids (below 200 bp in length, e.g. 13-50 bp in length) can be effected by the following hybridization protocols depending on the desired stringency: (i) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 1-1.5° C. below the Tm, final wash solution of 3 M TMACI, 0.01 M sodium phosphate (pH 6.8), 1 mM EDTA (pH 7.6), 0.5% SDS at 1-1.5° C. below the Tm (stringent hybridization conditions) (ii) hybridization solution of 6×SSC and 0.1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature of 2-2.5° C. below the Tm, final wash solution of 3 M TMACI, 0.01 M sodium phosphate (pH 6.8), 1 mM EDTA (pH 7.6), 0.5% SDS at 1-1.5° C. below the Tm, final wash solution of 6×SSC, and final wash at 22° C. (stringent to moderate hybridization conditions); and (iii) hybridization solution of 6×SSC and 1% SDS or 3 M TMACI, 0.01 M sodium phosphate (pH 6.8), 1 mM EDTA (pH 7.6), 0.5% SDS, 100 µg/ml denatured salmon sperm DNA and 0.1% nonfat dried milk, hybridization temperature at 2.5-3° C. below the Tm and final wash solution of 6×SSC at 22° C. (moderate hybridization solution).

The polynucleotides may further be labeled with detectable moieties. Methods for labeling nucleic acid molecules are well-known in the art. For a review of labeling protocols, label detection techniques, and recent developments in the field, see, for example, L. J. Kricka, Ann. Clin. Biochem. 2002, 39: 114-129; R. P. van Gijlswijk et al., Expert Rev. Mol. Diagn. 2001, 1: 81-91; and S. Joos et al., J. Biotechnol. 1994, 35: 135-153.

As mentioned, the present inventors have identified a region within the *Brucella* phage genome which serves as a regulatory sequence in *Brucella* and other bacteria—see Table 3 of the Examples section herein below.

Thus, according to another aspect of the present invention there is provided a method of down-regulating expression of a gene of interest in bacteria, the method comprising transforming bacteria with a nucleic acid construct which comprises a *Brucella* phage regulatory sequence, thereby down-regulating expression of the gene of interest.

The phrase "*Brucella* bacteria" as used herein, refers to all strains of *Brucella* including, but not limited to *B. abortus* strain 544, *B. Suis* strain 1330 and *B. melitensis* strain 16M. According to a particular embodiment, the downregulating is effected in the *B. Suis* strain or the *B. melitensis* of *Brucella*.

Examples of bacterial constructs include the pET series of *E. coli* expression vectors [Studier et al. (1990) Methods in Enzymol. 185:60-89). An example of a bacterial construct which allows expression in *Brucella* bacteria is the plasmid pBBR1mcs-4 (Kovach et al., 1995, Gene 1995; 166: 175-176), the contents of which are incorporated herein by reference and the pNSGroE plasmid (Seleem et al., BioTechniques 37:740-744 (November 2004), the contents of which are incorporated by renference herein.

It will be appreciated that the method of this aspect of the present invention may be used to down-regulate expression of a gene which is endogenous to the bacteria or endogenous to a phage which is comprised in the bacteria.

The gene of interest is preferably downregulated by at least 10%. According to one embodiment, the gene of interest is downregulated by about 50%. According to another embodiment, the gene of interest is downregulated by about 90%.

Examples of genes of interest include genes that encode polypeptides important for survival of the bacteria. By downregulating such genes, the method may be used to kill the *brucella* bacteria, thereby treating a *brucella* infection.

The present invention contemplates insertion of transposon sequences on either side of the regulatory region such that it can be randomly inserted via a transposition event into the bacterial genome or site specific designed mutation.

As used herein, the term "transposition event" refers to the movement of a transposon from a donor site to a target site.

As used herein, the term "transposon" refers to a genetic element, including but not limited to segments of DNA or RNA that can move from one chromosomal site to another.

An exemplary transposon sequence is provided in SEQ ID NO: 398 (ME1 transposon sequence) and SEQ ID NO: 399 (ME2 transposon sequence). For directed down-regulation of a particular gene, bacterial sequences may be added on either side of the regulatory region, to facilitate a recombination event.

According to one embodiment, the regulatory region comprises from 100 to all the nucleotides of the nucleic acid sequence as set forth in SEQ ID NO: 396 (19630-18579).

Optionally, the nucleic acid construct comprises additional regulatory regions such as the one set forth in SEQ ID NO: 397 (16509-15500).

According to a particular embodiment, the nucleic acid construct further comprises a heterologous nucleic acid sequence and upstream thereto, a promoter sequence which directs expression of the heterologous nucleic acid sequence. The promoter sequence is selected such that it allows transcription of the heterologous nucleic acid sequence in the bacteria. Thus an exemplary promoter that may be used in *Brucella* is one set forth in SEQ ID NO: 400. Another promoter that may be used to express a heterologous nucleic acid sequence in *Brucella* include the groE promoter [Saleem et al., BioTechniques 37:740-744 (November 2004)]. Additional prokaryotic promoters are also contemplated by the present inventors which are known in the art.

The regulatory region (for example SEQ ID NO: 396) is typically placed immediately downstream to the heterologous sequence in order to down-regulate expression thereof.

An exemplary construct contemplated by the present invention that may be used to show that SEQ ID NO: 396 comprises regulatory activity may comprise as follows:

i. a polynucleotide encoding a gene of interest (e.g. detectable moiety) operationally fused to a *Brucella* promoter; and ii. a *Brucella* phage sequence fused to a 3' end of the gene of interest, the regulatory sequence comprising from 100 nucleotides to all the nucleotides of the nucleic acid sequence as set forth in SEQ ID NO: 396.

Optionally, the construct may also comprise:

iii. a *Brucella* phage sequence fused to a 5' end of the promoter, the sequence comprising from 100 nucleotides to all the nucleotides of the nucleic acid sequence as set forth in SEQ ID NO: 397.

It will be appreciated that when the heterologous nucleic acid sequence encodes a detectable moiety, it may be used to determine a strain of *Brucella*. The present inventors have shown that a plasmid construct comprising SEQ ID NO:396 placed immediately downstream of a detectable moiety can downregulate its expression in a strain specific manner. Thus, expression of the detectable moiety was almost completely down-regulated in *B. suis* and only partially down-regulated in *B. melitensis*. Such a construct can also be used to determine which bacteria are sensitive to the *brucella* phage regulatory region and engineer these bacteria by gene down-regulation. In addition, the construct may be used as a tool to decipher novel factors that modify promoter activity by analysis of the detectable signal.

The detectable moiety is typically comprised in a reporter polypeptide which emits a detectable signal. It may be a fluorescent signal (e.g. green fluorescent protein (GFP) red fluorescent protein (RFP) or yellow fluorescent protein (YFP)); a luminescent signal (e.g. luciferase—LUX) or a color signal (e.g. β-glucuronidase (GUS) and β.-galactosidase). In addition, transcribed RNAs of the polypeptides can be used as reporter products of the system.

According to a specific embodiment of this aspect of the present invention, the heterologous nucleic acid sequence encodes a LUX operon. Such an operon is encoded by the sequence as set forth in SEQ ID NO: 401. Further information regarding LUX operons may be found in Winson M K, Swift S, Hill P J, Sims C M, Griesmayr G, Bycroft B W, Williams P, Stewart GSAB. 1998, Engineering the luxCDABE genes from *Photorhabdus luminescens* to provide a bioluminescent reporter for constitutive and promoter probe plasmids and mini-Tn5 constructs. FEMS Microbiol Letteres 163: 193-202; Craney A Hohenauer T, Xu Y, Navani N K, Li Y, Nodwell J. 2007. A synthetic luxCDABE gene cluster optimized for expression in high-GC bacteria. Nuc Acid Res 35: No. 6 e46, both of which are incorporated herein by reference.

The present inventors identified sequences in the *Brucella* phage genome which were devoid of open reading frames and generated constructs which facilitated insertion of genes of interest (for example, those encoding detectable moieties) into the *Brucella* phage at those positions, so as not to affect the vital life cycle of the phage.

Thus, according to yet another aspect of the present invention there is provided a nucleic acid construct comprising:

i. a polynucleotide encoding a gene of interest operationally fused to a *Brucella* promoter;

ii. a first *Brucella* phage sequence fused to a 5' end of the promoter, the first sequence comprising from 100 nucleotides to all the nucleotides of the nucleic acid sequence as set forth in SEQ ID NO: 394; and iii. a second *Brucella* phage sequence fused to a 3' end of the gene of interest, the second sequence comprising from 100 nucleotides to all the nucleotides of the nucleic acid sequence as set forth in SEQ ID NO: 395.

Since the flanking sequences around the gene of interest (i.e. SEQ ID NO: 394 and SEQ ID NO: 395) are *Brucella* phage sequences, such a construct may be used to insert the gene of interest by recombination into the *Brucella* phage genome.

If a phage is required which may be used to identify *Brucella* bacteria (and diagnose an infection), the gene of interest may encode a detectable moiety. Detectable moieties are further described herein above.

If a phage is required which may be used to kill *Brucella* bacteria, the gene of interest may encode a polypeptide which is lethal to *Brucella* bacteria. Such polypeptides may include anti-bacterial toxins (bacteriocins) and the like. In addition, non-translated sequences may be used to down-regulate important bacterial functions and factors that affect these sequences could be exploited to control bacterial functions.

Examples 3 and 4 of the Example section herein below describe a method of generating *Brucella* bacteria which carry the phage as co-residence of recombinant strains. Such carrier *Brucella* clones provide a means of unlimited chances to achieve direct recombinantional events between harbored foreign DNA and *Brucella* phage.

It will be appreciated that the phage which identifies *Brucella* bacteria by outputting a detectable signal (or carrier *Brucella* clones comprising same) may be used to diagnose a *Brucella* infection in a subject.

According to this aspect of the present invention, the method of diagnosing comprises contacting a sample of the subject with the recombinant *Brucella* phage described herein above. Infection of the *Brucella* bacteria with the recombinant *Brucella* phage would result in an increase in expression of the detectable moiety, thereby providing a signal that the infection is due to *Brucella* bacteria. The subject is typically a mammalian subject, e.g. sheep, cows, goats and humans.

Typically, the sample which is analyzed is a cellular sample derived from blood, urine, faeces, uterine, fetus membranes and placental membranes and fluids, mammary glands, lymph nodes, granuloma, sperm, testes, brain, cardio and renal organs, Cerebrospinal fluid (CSF), milk, dairy products, of the subject. Environmental samples (soil, aerosols, water) are also contemplated.

The terms "comprises", "comprising", "includes", "including", "having" and their conjugates mean "including but not limited to".

The term "consisting of means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

General Materials and Methods

Purification of Phage $Iz_1$ and extracting genome DNA: Phage $Iz_1$ was consecutively propagated on *Brucella abortus* reference strain 544 by inoculating drops of a phage $Iz_1$ suspension at routine test dilution (RTD) concentration on tryptic soy agar plates on which a 0.1 ml aliquot of a *B. abortus* strain 544 suspension was spread. After overnight growth at 37° C. in 5% $CO_2$ atmosphere plaques were collected into tryptic soy broth and enumerated for further preparations of RTD suspensions used in phage typing of *Brucella* isolates.

The same procedure was applied in order to purify phage $Iz_1$ particles for DNA extractions. However, phage suspension was prepared in TMGS buffer and filtered twice, first through 0.45 μm and subsequently through 0.2 μm filters in order to achieve a non-Brucella contaminated phage suspension.

2 ml of phage suspensions were centrifuged per tube using Sorvall RC M100 ultracentrifugation (Du-Pont). Ultracentrifugation was carried out at 10° C., for 4 hours at 60,000 rpm and DNA was extracted from phage pellets using QIAamp DNA Mini Kit, according to manufacturer's instructions (Qiagen GmbH, Hilden, Germany).

Cloning Phage $Iz_1$ HindIII DNA fragments—construction of phage Iz1 HindIII fragment clones in *E. coli* plasmid pBlueScript: Phage $Iz_1$ DNA was digested by HindIII, according to manufacturer's instructions (Fermentas Inc., Maryland, USA). The HindIII digestion profile concurred with previously published data (Rigby et al., Can J Vet Res. 1989; 53: 319-325). The DNA fragments were purified from agarose gel using Wizard® SV Gel system (Promega). Plasmid pBlueScript was digested by HindIII and purified from agarose gel using Wizard® SV Gel system (Promega). The purified pBlueScript plasmid and Phage $Iz_1$ DNA fragments were mixed, ligated and transformed to *E. coli* JM109 (Promega). Plasmid DNAs were extracted using HiYield Plasmid Mini Kit (RBC Bioscience, Taipei County, Taiwan).

DNA-DNA hybridizations: Hybridization was executed using DIG nonradioactive nucleic acid labeling and detection system, according to manufacturer's instructions (Roche Diagnostics GmbH, Mannheim, Germany).

Construction of plasmid pBBR1mcs-4.1-I11053Lux$_{CDABE}$: Plasmid pBBR1mcs-4 1-I11053Lux$_{CDABE}$ was constructed by inserting the *Photorhabdus luminescens* luxCDABE operon (Winson et al., 1998, FEMS Microbiol Letters 1998; 163: 193-202, incorporated herein by reference) into plasmid pBBR1mcs-4 (Kovach et al., 1995, Gene 1995; 166: 175-176).

Construction of plasmids pBBR1mcs-4.1-I11053Lux$_{CDABE}$ (15B-18B and 15A-18A, respectively) Specific Phage $Iz_1$ sequences were used as scaffold of the plasmid constructs. Primers were designed to include both Tn5 mosaic ends, 1 and 2, respectively. The KpnI::PstI sequence was added 5' and PvuII::ME-1::KpnI sequence added to the 3' end of fragment 15500 to 16509 of Phage $Iz_1$ amplicon. The SacI::ME-2::PvuII sequence was added 5' and SalI::SacI added 3' to 18579 to 19630 fragment of Phage $Iz_1$ amplicon (PvuII, KpnI, SacI, SalI are nucleotide sequences of the restriction endonuclease restriction sites of these enzymes; The position of the primers used to generate these constructs is illustrated in FIG. 4.

Phage $Iz_1$ naked DNA was used as the substrate in separate PCR DNA amplification reactions to obtain the desired amplicons. The first fragment [SacI::ME-2::PvuII-Iz(18579-19630)-SalI::SacI] was digested with SacI then ligated into a SacI linerized plasmid pBBR1mcs-4.1-I11053Lux$_{CDABE}$ to generate an intermediate plasmid pBBR1mcs-4,1-I11053Lux$_{CDABE}$::Sack:ME-2::PvuII-Iz(18579-19630)-SalI::SacI, in orientations A and B (FIG. 3B). These plasmids were then used to construct the two complete plasmid structures shown in FIG. 3B by KpnI linearization of these constructs and ligation with fragment [KpnI::PstI-Iz(15500-16509)-Pvuth:ME-1::KpnI] that established the two complete constructs shown in FIG. 3B. Importantly, Plasmid 15A-18A establishes an intact Tn5 transposon construct that includes Phage $Iz_1$ genome sequences flanking pLux. In contrast, plasmid 15B-18B includes pLux as an intact Tn5 transposon and phage $Iz_1$ sequences correctly orientated in the flanking ends of the intact Tn5::pLux construct.

Establishing phage $Iz_1$ pre-infected-electro-competent *Brucella suis* strain 1330 cells: *Brucella suis* strain 1330 was grown at 37° C. in 5% $CO_2$ atmosphere for 2 days on Trypticase soy agar supplemented with Serum-dextrose (Alton G G, Jones L M, Angus R D, Verger J M. Techniques for the brucellosis laboratory. Institute National de la Recherche Agronomique, Paris. 1988). Cells were collected by a plating loop and transferred to 6 ml Tryptic soy broth (TSB) establishing cell suspension at a concentration of around $10^7$-$10^8$ cells/ml. Then, 1 ml of the cell suspension was inoculated into 22 ml of TSB in a 250 ml Erlenmeyer vessel and laid down to chill in the refrigerator for 2 hours. In total, 4 such *Brucella suis* strain 1330 cell suspensions were prepared. Incubation was stopped by taking each vessel out from the incubator to ambient temperature and 1 ml phage $Iz_1$ in TSB at $x10^4$ concentration of the routine test dilution (RTD, Alton et al., 1988) were added to the *Brucella* cell suspension. Taken that *Brucella* complete a single cycle of cells replication by 4 hours *Brucella* phage infection was allowed to a minimal period of 2 hours by incubating the cell suspension at 37° C. in 5% $CO_2$ atmosphere and chilling the cell suspension immediately after by incubation in ice. Then, the 4 cell suspensions were centrifuged for 13 minutes at 6500 rpm, in a fixed angle rotor at 4° C., each in a separate tube. The supernatants were spilled and every two cell pellets were pooled together and resuspended in 12 ml of 10% glycerol solution in double distilled water pre-cooled to 4° C. Washing in the cold (including pre-cooled pipettes and micro-tips) was repeated 4 times, each carried out by resuspending the pellet and repeated centrifugation for 13 minutes at 8000 rpm. The two cell pellets were resuspended and pooled together in 3 ml 10% glycerol and spun down at 8000 rpm for 10 minutes, at 4° C. The final cell pellet was then resuspended in 0.5 ml of pre-cooled 10% glycerol solution and further divided to aliquots of 50 µl each in pre-cooled eppendorf tubes that were immediately cooled to freezing using liquid nitrogen and then stored at −80° C. until use.

Example 1

Deciphering the Complete Phage $Iz_1$ Genome Sequence

Results

The complete genome sequence of phage $Iz_1$ has been deciphered using 454 Life Sciences™ Roche GS-FLX sequencing platform (DYN Labs, LTD, Israel). The largest contig that was identified includes 38,254 bp (SEQ ID NO: 1 and SEQ ID NO: 2). Within this contig, the present data identified two *Brucella* phage $Iz_1$ genome populations differing by an SNP or a heterozygote nucleotide (nucleotide 5546 was recorded as N but in fact it was conclusively identified as C, and the polymorphism was distributed equally in 8 contigs between C or A at nucleotide 5549, respectively (FIG. 1).

To further corroborate the sequence of the phage, 8 HindIII DNA digest segments (1.1, 2.1; 3.1; 4.1, 5.1; 5.2; 5.3; 7.3) from phage $Iz_1$ were sub-cloned into plasmid pBS and sequenced corroborating the established sequences of identical overlapping fragments in phage $Iz_1$ genome. In concordance with these results, whole genomic naked DNA of phage $Iz_1$ hybridized with each of these clones. Two additional clones, e.g., 5.4 and 71_3 and 71_5_I, included partial sequencing (FIG. 2).

The sequence of the phage was analyzed using BLAST ((Basic Local Alignment Search Tool) software.

The results are displayed in Table 2, herein below.

TABLE 2

| Query id | Description | % identity | Alignment length | Mis-matches | gap openings | q. start | q. end |
|---|---|---|---|---|---|---|---|
| contig1 | *Ochrobactrum anthropi* ATCC 49188 chromosome 1, complete sequence | 91.64 | 299 | 25 | 0 | 19140 | 19438 |
| contig1 | *Ochrobactrum anthropi* ATCC 49188 chromosome 1, complete sequence | 100.00 | 46 | 0 | 0 | 17964 | 18009 |
| contig1 | *Ochrobactrum anthropi* ATCC 49188 chromosome 1, complete sequence | 97.62 | 42 | 1 | 0 | 17519 | 17560 |
| contig1 | *Ochrobactrum anthropi* ATCC 49188 chromosome 1, complete sequence | 100.00 | 37 | 0 | 0 | 16687 | 16723 |
| contig1 | *Ochrobactrum anthropi* ATCC 49188 chromosome 1, complete sequence | 100.00 | 35 | 0 | 0 | 17850 | 17884 |
| contig1 | *Ochrobactrum anthropi* ATCC 49188 chromosome 1, complete sequence | 93.33 | 45 | 1 | 2 | 17267 | 17310 |

Results from the analysis of CpG islands show that although the observed/expected ratio>0.60, the actual percent C+percent G>50.00, indicating that the phage comprises sequences other than *Brucella*.

An inverted repeat was found at positions 5088-5179 and 5405-5310 suggesting a putative site of the origin of replication.

Using an internet based promoter finding tool (worldwidewebdotfruitflydotorg/seq_tools/promoter) the present inventors identified 183 potential promoters on the forward strand and 201 potential promoters on the reverse strand. The sequences of these promoters are set forth in SEQ ID NOs: 3-185 for the forward strand and 186-386 for the reverse strand.

Example 2

Regulating *Brucella* Genes by Phage $Iz_1$ Sequences

Plasmid constructs that include selected sequences from Phage $Iz_1$ genome were designed and transformed to *E. coli* JM109 including those indicated in FIG. 3B and Table 3, herein below. The plasmid constructs were then transformed to *E. coli* S17, as this strain supports plasmid transfer to *Brucella* by conjugation, and selecting *Brucella* clones by growth on ampicilin. Trans-conjugant *Brucella* strains with these constructs endowed specific clones with Lux activities that depended on the Phage $Iz_1$ inserts and the specific *Brucella* strain that was transformed with these plasmids. *B. suis* reference strain 1330, *B. melitensis* type strain 16M and *B. abortus* reference strain 544 have shown similar strong constitutive Lux expression, based on the promoter upstream of the Lux operon, when harboring plasmid pBBR1mcs4.1 Il1053Lux$_{CDABE}$/15B-18B (see FIG. 3B). In contrast, plasmid pBBR1mcs4.1 Il1053Lux$_{CDABE}$/15A-18A was lethal to *B. abortus* strain 544 (it was impossible to establish trans-conjugant clones with this construct even if ampicilin was reduced to 25 µg/ml, that is one forth of the normal selective concentration used with *B. suis* strain 1330). The same applied less severely to *B. melitensis* strain 16M that was selected on agar plates with ampicilin at concentration of 50 µg/ml. Only *B. suis* strain 1330 was successfully transformed with the plasmid construct using ampicilin at a concentration of 100 µg/ml. This proves that the Phage $Iz_1$ sequences conferred different lethal activities on *Brucella* species as the same plasmid that does not contain phage sequences could be successfully transformed to each of these *Brucella* strains.

Further, light activity was completely silenced in *B. suis* strain 1330 whereas it was partially expressed in *B. melitensis* strain 16M (Results could not be shown with *B. abortus* as the plasmid was lethal to this strain, as explained above). When arguing for silencing activities by Phage $Iz_1$ sequences this could be demonstrated by adding external n-decanal to *Brucella* suspensions. The pentacistronic Lux operon consists of a luxAB component that encodes for a bacterial luciferase that oxidizes $FMNH_2$ and a long-chain aliphatic aldehyde (n-decanal substrate) in the presence of molecular oxygen to yield a 490-nm optical signature. The aldehyde is subsequently regenerated by a multi-enzyme reductase complex encoded by the luxC, luxD, and luxE genes. Accordingly, the Lux operon is encoding two separate functions, expression of luciferase by genes A and B and the substrate, by genes, C, D and E, respectively. External N-decanal could be used as a substitute for the native substrate. Because the addition of external n-decanal to the cell suspension fully restored light in both *B. suis* strain 1330 pBBR1mcs4.1 Il1053Lux$_{CDABE}$/15A-18A and *B. melitensis* strain 16M pBBR1mcs4.1 Il1053Luxc$_{DABE}$/15A-18A, this indicates that luciferase was present in the reaction mixture at the time, inferring it was fully expressed under the promoter that resides upstream to Phage Iz1 15A and LuxC and Lux D, sequences. It is most likely therefore that gene LuxE, downstream of LuxA and LuxB was under unique regulation from Phage $Iz_1$ 18A sequence under the 3' orientation. This is further supported by the fact that this regulation was exerted at different intensities between *B. suis* strain 1330 (null Lux activity) and *B. melitensis* strain 16M (partial Lux activity). As phage $Iz_1$ fully lyses *B. abortus* and *B. suis* strains but has only partial lysis on *B. melitensis* strains, our data corroborate the historical *Brucella* species phage typing method and support our invention that the 18A Phage $Iz_1$ sequence regulates *Brucella* gene expression.

Table 3, herein below provides additional plasmids comprising phage Iz1 sequences that are capable of down-regulating genes placed immediately downstream thereto in both brucella and other bacteria.

TABLE 3

| Bacterial strain | Plasmid | Max luminescence | Comments | |
|---|---|---|---|---|
| E. coli S17 | pBBR1mcs-4.1-I1053Lux$_{CDABE}$ | 187000 RLU | Lux was affected by strain physiology | |
| B. suis 1330 | pBBR1mcs-4.1-I1053Lux$_{CDABE}$ | Variable, up to $1.5 \times 10^6$ RLU | Lux was affected by strain physiology | |
| B. melitensis Elberg Rev.1 vaccine strain | pBBR1mcs-4.1-I1053Lux$_{CDABE}$ | $7 \times 10^6$ RLU | Plasmid was maintained even under no antibiotic selection for several passages | |
| E. coli JM109 | pBBR1mcs-4.1-I1053Lux$_{CDABE}$/18A | 77 RLU | Background level | |
| E. coli JM109 | pBBR1mcs-4.1-I1053Lux$_{CDABE}$/18B | Variable, up 21000 RLU | | |
| B. suis 1330 | pBBR1mcs-4.1-I1053Lux$_{CDABE}$/18A | Variable, up to 3800 RLU | By adding external n-decanal an over-load RLU was measured | Susceptible to phage Iz$_1$ |
| E. coli JM109 | pBBR1mcs-4.1-I1053Lux$_{CDABE}$/15A-18A | 160 RLU | By adding external n-decanal = 160000 RLU | |
| E. coli JM109 | pBBR1mcs-4.1-I1053Lux$_{CDABE}$/15B-18B | 50000 RLU | By adding external n-decal = 482000 RLU | |
| E. coli S17 | pBBR1mcs-4.1-I1053Lux$_{CDABE}$/15A-18A | 80 | By adding external n-decanal = 149000 RLU | |
| E. coli S17 | pBBR1mcs-4.1-I1053Lux$_{CDABE}$/15B-18B | 12000 RLU | By adding external n-decanal = 195000 RLU | |
| B. suis 1330 | pBBR1mcs-4.1-I1053Lux$_{CDABE}$/15B-18B | Variable, up to $20 \times 10^6$ RLU | | Similar representative results with two clones, 1; 3 |
| B. suis 1330 | pBBR1mcs-4.1-I1053Lux$_{CDABE}$/15A-18A | 217 RLU | By adding external n-decanal = up to $8.7 \times 10^6$ RLU | Similar representative results with two clones, 23; 32 |
| B. melitensis 16M | pBBR1mcs-4.1-I1053Lux$_{CDABE}$/15A-18A/ | 58000 RLU | | Clone 16 |
| B. melitensis 16M | pBBR1mcs-4.1-I1053Lux$_{CDABE}$/15B-18B | $18 \times 10^6$ RLU | | Clone 18 |
| B. abortus 2308 | pBBR1mcs-4.1-I1053Lux$_{CDABE}$/15B-18B | $1-3 \times 10^6$ RLU | | Similar representative results with three clones, 4; 5; 10 | pII1053 is strongly expressed in a constitutive manner in the three Brucella species, B. suis, B. melitensis and B. abortus. This promoter is expressed less intensively in E. coli.

The construct 18A downregulates Lux expression in both E. coli and Brucella, most likely by silencing LuxE.

Example 3

Establishing Phage Iz$_1$ Pre-Infected-Electro-Competent Brucella suis Strain 1330 Cells In this example, the goal was to develop a method that will extend existence of phage Iz$_1$ infection of Brucella to an un-limited period of time in order to enable phage genome engineering at that time by recombinant DNA technology.

Naked phage DNA exists within bacterial cytosol immediately after phage infection following intrusion of the bacterial envelop by the phage DNA. Phage replication further ensues due to controlling bacterial gene expression and gearing the bacterial DNA replication machinery to a phage system. Prevention of DNA packaging into intact phage particles will therefore allow gene engineering of the phage genome by electroporation of the bacterial host during this period with recombinant DNA constructs that facilitate gene transposition or gene recombination. Accordingly, the present inventors hypothesized that phage infection could be arrested by chilling the Brucella host cells immediately after infection, then washing the Brucella cells several times using water-glycerol and freezing the cells at −80° C. until needed for electroporation.

Results

One eppendorf tube that contained phage arrested infection as described above, was taken out from the −80° C. freezer, and the cells were thawed on ice, and diluted to 1 ml by adding 0.95 ml of SOC-B solution (Lai F, Microb Pathog 1990; 9:363-368). Then, 1:10 dilutions of the cell suspension were prepared in cold physiological saline solution, up to $10^{-7}$. Drops of 10 µl were then inoculated on B. abortus strain 544 that was spread (0.1 ml of a TSB heavy cell suspension) on a TSA plate by a bacterial Drigalski spreader.

For comparison, an aliquot of the SOC-B cell suspension was passed through 0.45 µm syringe filter in order to ascertain that free Iz$_1$ phage particles did not exist in the cell suspension. The filtrate was similarly diluted 1:10 in physiological saline solution and 10 µl drops from each dilution were inoculated on B. abortus strain 544 plate (see above).

The two plates were incubated over night at 37° C. in 5% $CO_2$ atmosphere. The next day, plaques were sought in each dilution of whole cell suspension and cell-filtrate. The last dilution of the cell filtrate that yielded phage plaques was $10^{-2}$ in which only two plaques were identified. In agreement with the dilution around 200 plaques were identified at $10^{-1}$ dilution, indicating a minimal presence of free phage particles in the whole cell suspension prior to filtration. In contrast, the last dilution that yielded phage plaques by the whole cell suspension was $10^{-6}$, at which a single plaque was identified. In agreement with the dilutions, 10 plaques were identified at dilution $10^{-5}$ and concentrated plaques were found at $10^{-4}$ and below, indicating existence of close to a 4 logarithmic higher magnitude of phage particles in the cell suspension compared to the cell filtrate. All together, these data support the working hypothesis that despite interfering with phage replication by cooling off the cell suspension, cold washings and freezing at −80° C., the phage infection was fully restored when the cells were thawed and re-cultured. Similar results were achieved when phage infection was stopped after 1 hour and 15 minutes.

Example 4

Development of a *Brucella* Reporter Clone

The present example describes how a pre-phage infection state could be used to develop a recombinant phage $Iz_1$ clone that induces Lux activity in *Brucella* species. Such a recombinant clone could be used as a highly sensitive reporter to indicate presence of living *Brucella* cells in a suspected sample by light measurements in a host, its tissues (such as aborted placenta and fetus membranes and fluids) or milk samples.

Method

The method involves two steps (See FIG. 5). Firstly, a hybrid DNA was established between phage $Iz_1$ genomic DNA and plasmid pBBR1mcs4.1-Il1053Lux$_{CDABE}$/15B-18B. Then, this hybrid DNA was electroporated to electrocompetent phage $Iz_1$ pre-infected *B. suis* strain 1330 cells and the cells were selected for ampicilin resistance. Phage $Iz_1$ carrier clones were identified amongst the growing colonies.

1. Establishing Hybrid DNA

A short denaturation and annealing process between equal amounts of phage $Iz_1$ and plasmid pBBR1mcs4.1-Il1053Lux$_{CDABE}$/15B-18B DNAs was applied, the latter shares homologous sequences with the phage genome (FIGS. 3A-B). The final annealing step was stopped by bringing the reaction to 4° C., in order to establish hybrid DNA molecules between hybridizing single stranded DNAs of the two entities.

DNA denaturation and annealing was carried out in total volume of 25 μl reaction mixture using Biometra, T-Gradient, thermocycler, Germany. The thermocycling reactions were as follows:
Pre-heating: 95° C.-1.30°
6 cycles of: 95° C.-1.15', 55.5° C.-2.00', 72° C.-2.00°
Final annealing at 55.5° C.-7.00°
Stop at 4° C.

2. Electroporation

Electrocompetent pre-phage $Iz_1$ infected *B. suis* cells were used. 40 μl of electrocompetent cells were electroporated by adding 2 μl of the final thermocycling reaction mixture using bacterial mode of MicroPulser™, BIO-RAD, Hercules, Calif., USA (2.49 Kv, 4.9 ms). Immediately after electroporation, cells were suspended in 1 ml SOC-B (see above) and incubated with shaking at 37° C. for 1 hour and 30 min. A 1:10 dilution of the SOC-B electroporated cell suspension was prepared and 10 μl aliquots from both undiluted and 1:10 diluted SOC-B suspensions were inoculated on TSA plates that included 50 μg/ml ampicillin as the selecting antibiotic.

As a control, 10 μl drops of the electroporated cells in SOC-B and 1:10 dilution were inoculated on *B. abortus* strain 544 cells that were pre-spread on TSA agar plate in order to demonstrate phage $Iz_1$ infection of the electroporated *B. suis* strain 1330 cells.

Results

Non-electroporated cell suspension successfully grew on plain TSA plates but did not grow on TSA plates that included 50 μg/ml ampicillin. After electroporation, about 90 colonies grew on selective agar from the non-diluted SOC-B cell suspension and about 9 colonies grew from the 1:10 cell dilution. Four colonies from each dilution were selected for further analysis, each transferred on a TSA plate that included 50 μg/ml ampicillin. Table 4 herein below summarizes the luminescence and phage activity of electroporated clones.

TABLE 4

| Clone No. | Luminescence | Phage activity |
|---|---|---|
| 1 | 338,600 RLU | + |
| 2 | 943,500 RLU | Neg |
| 3 | $1.8 \times 10^6$ RLU | Neg |
| 4 | $3.4 \times 10^6$ RLU | Neg |
| 11 | $1.8 \times 10^6$ RLU | + |
| 12 | $7.2 \times 10^6$ RLU | + |
| 13 | $4.9 \times 10^6$ RLU | + |
| 14 | $5.7 \times 10^6$ RLU | + |

These results indicate the following: 1. Plasmid pBBR1mcs4.1-Il1053Lux$_{CDABE}$ was successfully transformed into these clones. 2. Smooth clones (2, 3, and 4) did not secret phage activity and rough clones were phage carriers (FIG. 5).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated polynucleotide comprising a) at least 100 consecutive nucleotides of the nucleic acid sequence as set forth in SEQ ID NOs: 396, b) a heterologous nucleic acid sequence and c) a heterologous promoter sequence which directs expression of said heterologous nucleic acid sequence, wherein said at least 100 consecutive nucleotides is positioned downstream to said b) heterologous nucleic acid sequence.

2. The isolated polynucleotide of claim 1, comprising the sequence as set forth in SEQ ID NO: 396.

3. The isolated polynucleotide of claim 1 further comprising at a nucleic acid sequence as set forth in SEQ ID NO: 394 in a forward or reverse orientation.

4. A nucleic acid construct comprising the isolated polynucleotide of claim 1.

5. The nucleic acid construct of claim 4 comprising a nucleic acid sequence as set forth in SEQ ID NO: 396.

6. A method of down-regulating expression of a gene of interest in a bacteria, the method comprising transforming bacteria with a nucleic acid construct which comprises a) at least 100 consecutive nucleotides of the nucleic acid sequence as set forth in SEQ ID NOs: 396, b) a heterologous nucleic acid sequence and c) a heterologous promoter sequence which directs expression of said heterologous nucleic acid sequence, wherein said at least 100 consecutive nucleotides is positioned downstream to said b) heterologous nucleic acid sequence, thereby down-regulating expression of the gene of interest.

7. The method of claim 6, wherein said bacteria comprises *Brucella* bacteria.

8. The method of claim 6, wherein the gene is endogenous to the bacteria.

9. The method of claim 6, wherein the gene is endogenous to a phage of the bacteria.

\* \* \* \* \*

SEQUENCE LISTING

<160> NUMBER OF SEQ ID NOS: 427

<210> SEQ ID NO 1
<211> LENGTH: 38255
<212> TYPE: DNA
<213> ORGANISM: Brucella phage Iz1

<400> SEQUENCE: 1

-continued

```
tggacttaac ccactcccac ggcccctttg taaactttgc cccactcata gcgcacctgc    60
tttcttgagt acatttagag cgttatgcca attttcatca ttgttgttat caacaatctt   120
atccagcgcg ctcaccaact catcatgcat gttcacgcac ttgacgatgt gggcggcgtt   180
ggcttcttca aacacattag cgatgcactg atctggcgtc tgaattattg agaagtatcc   240
gtcttcaggc gtgaaaactc cgttcagttg gtcccaaggc gtaggcgtgt gttctttcgt   300
catgattgtt tctccacttc taaacacaca taaacataca attgttatgt agtcaaaccc   360
ttttacgctg cccaggcaac ggagaagcat aaacagcgct ataatccatg cgctcaggct   420
tcttctgcgg cttacctggg gtcatacgat ccataagctg cccaaccaat cctagagcgt   480
caacctgatc gtcatgaaca cctacaggga aactcatcat ctcagacata agagcatcta   540
atcccggcaa gtcgtccctc acatacagcc cagacaaggc aatgcgtcca cggatagact   600
gagcacgtac agacttgtca ccgccacgcg ttgggaactg ctcacgcgcc acatacgaac   660
cagtctcgat catacgcttc acaaggaaag gcccaacacc tgatttgatc tgtcctgttt   720
cctcagccca gccaataggt ttccactttc gcaccagatc gcagaacgaa tctacccacc   780
tgtcagaaga tgcctgttgc ctccatatat ccaatagcca aatacgcccc tcgctatcaa   840
cgccaacgac aacatgaacg gtataatccc cgccattatt cgttacagcg tagtcagacg   900
cgccatagat cgacatggta ttaagaggcg gcacctgtga ggctgataca agctttatcc   960
attctttctt gaagtaatca ccgctatcag gtgcaggtct ctgctggaac aatgcagacc  1020
atgtgcgcgg gttctttcga tgaacctgcc agtgctttc gtcaaaccat tcctcccaca  1080
acatttgacc tatctcgcgc ccaagcgggt cgtcagcacg ttcgcactca gcagcaaggc  1140
aaataacctc ccattcaaac ccatccttgc ccataatcat accggattcg ccggcgtagt  1200
tatctggaag gatacggcct gacaggtcgt cttcatgcca gcgtgtttga atgataataa  1260
tagagcctcc cggcttcaaa cgggtaagaa ccgactcctg atactcatcc catgtcctct  1320
gacggataac ctcggaatca gcgtcttgcc tgcccttgat tgggtcgtca ataatgacgc  1380
agttatgaac tagtattccg ttggcgaaga agttgtggtt cttcgaaact tggatgtcga  1440
agacactggc ttcatcgcca attctctcaa ccgagatgac gtgatctcgc tcggcttccc  1500
acgcaagctc ctgtgggcct ccttgtggca ggctggacaa agggttacca aattcgttga  1560
cgcgttgttc atcggccaat tgtcgatgtg gtgaacgtgt agcttcttgt cgtcctcgca  1620
tatcacgcac atgaagccat ccctctctac gatcagcggc ctcatcaccc tgaacgcgcg  1680
ggctgaatga ggctgttgcc tgagaggcgt agctccatcc ttccacatcg ggttcccctt  1740
ctcgctcata cgccgagaat ggtctatgtc cgcacatgtt cggctgcaat aggcggcaaa  1800
gtcccccacc ttcttgccac gccaaaccgc tttgaaagtc ttgttgcaag tcgggcagtc  1860
gcgggagatt ggcggatgaa tcgcagggcg ccacttcctt agaactggac ggcatgtgtc  1920
gcagaacctg cgcgtcttct tttcgtcgg gttcccgcac ccttcgcact ttctcctgtc  1980
cttgtacgac gcgtgctctt ggctgcaagg aaggcagcaa taatgatccc ttccgcactt  2040
cgcctcccat ttccggtaat cgaatgctgg tttcaccttc tcctttgcgc aattggctca  2100
agagactatc accgggggca agtgaagacg ctttgacgta tccacgcccg gtgtagaatt  2160
gatgatttcc cgtagcttca accactgagc ctctggcagt ggtgaccctg taaatcccaa  2220
ttcccttacg atgggagaaa gcttcaatgt cttggtactc catcatattt aatctgtgat  2280
tgaagcttag cactttaacg gaagcggggc aatgttctat attttcgatg gcgacagggc  2340
cttcactggt ttctatcatg gtaccagcta ccaagcagtc ggctctgtta cccgtaatac  2400
```

```
cagacagaat gccccctgac atgtattcgg acccgttgtc caaggcccac tcgtcggcgg    2460
cggcttgatc tccactcaat gatgttgaaa aagggcacg gtattttgat tgcttaataa     2520
ttgagcgggt tcgacggcca aacttcttag ccatgtctga accataagac acgccgatga    2580 cttttgaaccc tggcttctgc cccatagccc atgatgggac gacaacgctg ccatatgaac   2640
tcttcgcact gcctggtggc ataaaaagca taagccgtcc gtaaggcttt tcaatgcacc    2700
tttgagcggg ttcaagtatc aatatgtgat gtttagctaa ctgcgtctca gcaaaatatt   2760
ctgcttcgtc gctttcctcg tcctgttctt caacaggagc tcccggaacc tcaatgtacc   2820
gggcataatc aaccagattt cgacgagcct tacgtctgtt tagaagctct tgggcggctt   2880
gggctttggt tatggtcacg aggttatttc tcccccgcaa taacctttgc aagatcttcg    2940
tctgtcattt caccgatgga atgtttgtgt tccatagtgc cagtctgatg aacctcttga    3000
cgctccgtgt aatcctcacg gaaacgggcc tccatagact ttttccacac ggctgcatta   3060
aacccacccc cgccaaggaa catgccttca cggcctgctt tttcccacca agcctgacaa    3120
tgaaccttag ctctacttaa cgctgctaaa aactctgggt gatctgatgc ccaattctca   3180
atagtctgtc gtgaaacatc aaagtgagca gccatctgcg ccaggaatc tccttgtttc    3240 ccaagttcaa tgactgtctc acaatattct ggtctgtata aggttggacg accgccagcc   3300
ataactattc atattcctct aaaatcttca cctgacgacg caaatactct gctacttcat    3360
gaattggcat ggtagacgcc ataaggttga ttgctcactc acagaaccac atagactgac   3420
ttgcttgaaa gtcatagact gactggtccg ctatctgctg taaagctttc ttgcctttct   3480
tgctcataca acctccatga tatttctatc atacgccttt ttgtacgaaa tgcttattcc   3540
cttatatcct tcacacttgt acgtatgatg ttcacagtat cgcccttaa acctcaaatg    3600 tccacagaat aaatgcgggc cttctgccgt tagcgggtac atgcatccat cgttatcaat   3660
gagtgatact cctggcaggc gtgacaattc gaaatcatcc agctctgggt cttgatacca   3720
ggctgccttt gaaccagcgt taggattgaa cttagacatt cgattcaccg gatcatttct   3780
aggcgacttc ttcgccttca tcgaacgatt aacccggtga agtgtcaaat ccttttctt    3840 aaggtcccctt ttttgaata actcacgctt tcgttttgta agaccgata cctgaccagg    3900 ggttagtcct gtctccaatg caataatctt gactgatgcg ccttcattcc aaagcgcaac   3960
cgccttatcg atcaatccac gctcaatagc ctgccgcgac gtaataccaa gtttcgggaa   4020
caattcacga taacgatgca tgatcgaaag gactgaattc cgggtcaccc caatctcttc   4080
cgcaatctcc atcgcagact tgccatcttt ccatagcctt gaagcacgat caattacttc   4140
ctgcgtccaa acaaatttca tctcaagcac cacataacga acggagcagc aaccctggca   4200
acgattagat atccgatgaa ggttatcatt ttgcggtttc cttctgatac ttcctgacag    4260
caatgatgag ttcacccatg cactccgccg agtgcttccc atgcttatgc gcttctacct   4320
cacgaatgag aacttccact agatgcttac ggcttccgcc tttgcggctg gcttctgggg    4380
agtaggtcat gttatcctcc aaataataaa acaccacatg gcaaacactg ccaaaataac    4440
aattgtctgg tcactcactt cccataccctc ccatagattg cgcccacatt cgcacagaaa   4500
ccgggcaagg agccgtttct ttggtaaatt gaaccctgct ccatggcagc acggcgaacg    4560
ctctcagtga actcctgtgg cgttttcttg atataggcg ctactacacc aaccaattca    4620
cgcaatgcat cctccggtaa aggcaaacca cagtactgtc ttgccacctc catacggata    4680
attccagtta atgcatccac aggctccagg gcttgcgcgg atgcggggc tgcgaatagg    4740 gcggcagatg ccaggataat tttagcgttg atcatcacac caaccccaca gccagaatta    4800
```

```
cgaacggcac tgcaaacgcc agagccagca ttacacctgc catgatgcag gcccacatat   4860
cctgatttgt catttcactt tccttctcca caagatcgag gtccatcatc agaccatcga   4920
ttgtttttct caacccaaaa atatcagctt ggcttactct ctctgtcgtc attccatttt   4980
ctccacttcg ttgttttgat aacccaccat cccacacctt ttatggcgtg tcaacacata   5040
attgtaagaa agatacaacc tgatacgaaa aattcccaaa aatcattgat cccaaagatc   5100
ccaaactttg ggatcgacta agtaattgaa tttaaagcat tatcccgaat atcccttgat   5160
cccggctttt tggtataagg ggagtgggtg taacagtggg tataagtcat ataattgcta   5220
caactagatg tagcaagata gctaagtata tgatatataa agataaatag tcttttatcc   5280
tatcctcaat ttagggtctc tatattactc ttataccgaa tttcttggga tctagggata   5340
attgaagatt ccttaataat ttcaacaact taattgatcc cagaagcatg ggatctatag   5400
ggatctttgg gatcaaccat tgactgtaaa cattgtgacg ggttgtacaa aatggaaaaa   5460
tatttgactt cattttaatt cgtactatgt taggcccata tgacaaaaat ggagagttga   5520
aatgagtttc gaaataagtc ggcgacccma ttgatggact agaacaatat ggtccaggga   5580 ggcccccaa atcccgttc agggatatgc agattggaga ctgttttcgt ttggggttag   5640
ataatcccag caatgtaaga agctgtgcag catcttatgc cgttcgaaac aacaaaaagt   5700
ttaccgtgcg caaacaagac ggtgaatatt tctgctggcg tatcgcataa aaaaagccgg   5760
ctctacgaaa cggtggagga cgctcggagc cggcttgtgg ttccgacgaa gaaaggcaaa   5820
aacgccagaa catggataat ctaacatgac caacacacat atacaagcct ttgctgagaa   5880
caatcatcgt gttttatgt tggaaagcat tgatggtaat tattgtggtt gcggcaatcc   5940
taaatgcaca gcaataggca agcatcctgt agcttccaac tggcagaata ccccgcaatg   6000
ggatgatgac cagatagaaa acatgtcaat gatggttgac agcatggggc gcggatatgg   6060
cgttctgtgt agcaatctat tggtaattga cgtggacgct aagaacggtg gccttgcttc   6120
atatgcagca ctattagaga aattccctga tattgcgtca gctggcctta tcgtcgagac   6180
aggatcaggt ggtggatcca agcacccttta ttttcattg ccagccgatg ttaaaacggt   6240
tcagacgcat aaagactata aagggcattga tttcaaacac accggtttcg tcgtggggcc   6300
tggatcgccg cataagtctg ggagaaatta taatgttctc tctgggtctg tggatgacat   6360
agaccatgcg ccatctgctc ttgttgagtt ccttaaaaga gaggagcgca ggaagatcga   6420
atatgaaggc agcacgatag atatatctga tagcgtcatt gcagacatgc tgtctcatat   6480
tgattgctac gacgaatatt ccgattggat aaagatcggt atggctatcc atgacgccac   6540
tcacggcaac ggtgtagcgc tgtgggatga atggagcaga cgtagctcta aatacaatcc   6600
agaagccatt gacgcccggt ggcactcatt cggcaagtcg tcaaatcctg ttaccattgg   6660
cacattgatc aaaatggcac aggatggagg gtggacggag aaagtatcgt tcgaggaagt   6720
cgagctgcaa ggatggttcg cgaaggctgt aactggtaat cctgtcactc aaggcattac   6780
caaagaagat attaaagagg taaaaaaccc tatcaagggc tgtcctgtag atatctcaac   6840
aatcgacctg acaatgccgc ctggcttctg cggggaggtg acgcggtgga ttaacacaca   6900
gtgccgttat cctcgtttaa acctgtctgc aatggcttct ctatacgcga ttggcaacat   6960
tgcgggtctt aactacgctg cgaacgacac cagccggaca agggcaaatc ttgccatatt   7020
ctgcgtagct gggtcaggga ctggtaaaga tgctgtgctg gaggccgtta ataatatcat   7080
aatcctcgct ggaatgtctg gggcaaatca cggaaagatt aagtctgaac gtgaaatgta   7140
tcaaaatctg atacatcatc aggcggcaat atataccatt gatgaagttg gagcgcatct   7200
```

-continued

| | |
|---|---|
| tgcaaagatt agcaacgctt ctcgatccgg cgcgtctcac cttgagggtg ttattgaaac | 7260 |
| attcatgagc gtttacacca agtctgaatc tttccacatt gtggggggggg atgataaacg | 7320 |
| cgaactgcaa aagatgatgc gtgataagct ggcttacttc gcgcaaaagg tagaggaaaa | 7380 |
| tgaggataaa gaacattctc aaaagatggt tgatagcctg aaagagcgct gaagacagc | 7440 |
| cgatagactt gttgagccat tcttgtcttt gattgggttt accacaccta cacagctatc | 7500 |
| ccgtatgatg tcattgata acgcggaaag cgggttcctt ggccgtacgg ttatgtgtgt | 7560 |
| agagccagat attaacccctt atccaaatcc agggtttacc aaggaagata tgccatatgg | 7620 |
| catgaaaatg aagattcttg ccctatctgg cgtggatagt agtgaagagt ttgaccggat | 7680 |
| tgagcgtcga gggccgttga aactggttga tatagaacca gaggcaaagg aacttattga | 7740 |
| acggtgtatc aattggactg ttgattataa ccagagcaag attgaaatgg gcttggagcc | 7800 |
| attctctggt ttgtatcgac gtgtgtgcga aaggcgatt aagattgccc ttatccttgg | 7860 |
| cataccagat gggttgataa ctgttgagca tgtaaaatgg gcgatggccg cttctatgcg | 7920 |
| tgatgctgag gaaaaggtaa gcgcaatcac cattgaggat aaatcatttt cgaaggctga | 7980 |
| taagcttctg gcgtctattt acaaagcagt gaaaataag ccggggcaaa catttgcgtg | 8040 |
| gattgcagca agatcaaata tatcaaaata cgggaaagag gaagtagaaa aggcattggc | 8100 |
| gcatatggtg gcacgtggtg atattcgtgt ggaagaagta accaataaaa agaatcttga | 8160 |
| aattttgaaa aggtattatg tgagataacc tggaaggagg tgatgcctaa tggaaccggc | 8220 |
| taaattcgga accatgcaaa aagcccccggc gtaaaaccg gggcgttaat gttaaaggcg | 8280 |
| cattaatatg cataggttaa taaacgtcag gattagattc gcggttatta gtgtttctat | 8340 |
| catccctctc cctcctgcaa tgccctatac tcactaacct ttttaatggt ttcccatgtt | 8400 |
| gggttgatgg tttttcccctac cttgatacga ctcagggact ggtaaatcat ccctgtttcc | 8460 |
| ttcgccattt tatgcagtcc gccataaggc aggctacgta gatattcctg aagctctgga | 8520 |
| cctgtgaggt atttcatatt tttcccttttt gttgaaaatc tatgttgaca atacaattga | 8580 |
| atgatgcgaa aagcaatacg taaattgaag aaaggcaaat aaatgagcat tctacaaaac | 8640 |
| gcaacaaatg acggtggcga gcaggcgttg attgtgacgc tgtttggcac accaggcact | 8700 |
| ggtaaaacat caacagcgct tacattccct aagccgtata tgatccgtac tcagggtgaa | 8760 |
| gcagtgccac gtgacgcccc taataaggcc gtatcattgg ggattacaga tagccctgcc | 8820 |
| aagctgtggg aacagctaac ggcactctgc aaagatgaac acgactttaa gacattgatc | 8880 |
| gttgacagct cgactggcct tgaaggaatg ttcatcaagg acgtgctgga taatgacccct | 8940 |
| aaagcgcgag gaattaacac agcccttggt ggttatggtg caggacgagc agcagttgcc | 9000 |
| gcacaacacg caaactgcg aaagggtgca gagtatttgc ggtctgttcg tgggatgcat | 9060 |
| attgtgttca ttggccatgc tgatattgaa cggattgacc cgccagacag tgaatcgtac | 9120 |
| tctaagtatt cactgcgtct tcatcgtgaa tcaatgaagt catacgttga tgatgttgac | 9180 |
| gtggttggtt ccttcgaca agcaactatc ctacgtggtg aagaagatga gcgcaagaaa | 9240 |
| gccatcacca ctggtgatat tattctaacc actactttgc accctgcctt cgttagcaag | 9300 |
| aaccgtctcg gcatcaagga cgatattgtt gtgcagatgg gtgttaatcc tttgcaggag | 9360 |
| tatttgtgat gagtaaagaa gatggagaag ggacaatttt gcgccaatat acctttttaca | 9420 |
| atgcgcaaga tgttgacgac actgtagcaa ggttaaatag taaaattaga gaacttgaaa | 9480 |
| gctctattga atcgttgcaa agcatgagac ctcattgggc taagggatac acatcagata | 9540 |
| gcatggctgc acagggacaa acagcggcac tatctcagat ttggtcatat cttggcgtag | 9600 |

-continued

```
acaatcaaac ggacgccatg caaaagcttc gtgaacttaa taaggagaac taaacatgtc    9660
attctggaac accagctccg gcgaaagcgc catttctaac gctaccagct tcgagattga    9720
aggcggtggg gatattctgc caattccagc aggtaccaag gtgcttgcga ttatcgagaa    9780
tgtgaagatt gcgaccgtta aagacagcgt tgaacaatac gttgaaatca agtgggggcat   9840 tatcaagccg gaagtctata acaagcgcaa gattttttcag aaggtttggt gctttgacta   9900
tgaccccatg cagaaagacc ctgcaaaggc aaaggccaag aaagacaaag cattgaagat    9960
gttggcggct attgatgcca atgcaggagg aaagcttgct caagcaggcg tagagccgac   10020
agatgaaagc cttgctctgg cgcttaataa caagcccatg gttatcggtc tgaatacttg   10080
ggatgatgca gaaacaaaga agccaaaggg taactgggtt tactacgttg gccccaagaa   10140
tgatccggtg acgaagtta ccaaggagga tgtacaggcg caggaggcta aggcaaggc    10200 gagccagcct gctgcgtcgt ctaactttag tcatgaccta gacgacgaaa tcccattttg   10260
atcccttgtc aaacaaaagg gcggcttcgg tcgccctaaa aggatgcata atgggaaagt   10320
atgaatggaa gccgtttact ttattggtta gtgctgagga agtggagaaa gaagtgttga   10380
agattgaagc cggtaaatat tacaaaacag gtgatggccg taaggttggg cctataaaat   10440
catacgaaga cagatatttt cataaggcaa gttttgcgtg cagagaatgg acttatttag   10500
aaaatggtaa atgggctggt tcattaaata atgataaccg tgacctcatc tccgaatggt   10560
cagaagcacc cattcgcacc gtaacgcgcc gtgagattgt ggagggggtg tatgggagcg   10620
tagatattta tcatgtaacg aaaaaatatg tatgcgtgaa aataaactcc aatatgagtg   10680
gtgaagatct aagggaaacg gctcacctgt ttaatcaatt ggccgaagct ctggaggaga   10740
atggaaaatg acctacacat atttcgacgt agaaacgata ccagaccaat ccgaaggcgc   10800
actagagcgt gccaaggaat cagtaaaggt tcctgctaac tacaagaacc cagataccat   10860
tgcggcatat atcgaagaaa acgctcaaga agcatgggag cgaacggcac tagacggttg   10920
gaagggtcat gttgcttgta ttgtgatgaa tgacatgaaa tggatggttc aagaaacttg   10980
gagagagaaa gagatgctcc aagattttt taatcgtctt aatgaatcaa cccttgtcgg   11040
ccacaacatc atcggctttg acatcccatt cctaaccaaa cgcgcccttg ttcttggtgt   11100
taaactgcca ccggaacata tttggccgcg caatctgaag ccgtgggata accgtgtgtt   11160
tgacaccatg ttgcagcttg gcaatggcaa agagtttatc tcgctggata acctggcgcg   11220
caaccttggc actaaaggca agggcaatac gacgggagca caagttcatt acatgtggca   11280
gaatgggctg catgatgaaa ttgcagaata ctgcgctaat gacgttcgta ttgtgcgtga   11340
gattcatgag cggtttcttg cgtgtaattg gtaatatgat ataataaatt gcgcggcta    11400 atccggccag atgaaaagca gttacgctga ctgcctgccg cgtttacaaa ttagcgaacc   11460
ctagcgaggt tattatggat tacgattgca tatcaaaatt aattaaatat tcacctgagt   11520
caggaaagct tttctgggtc aaagggatg atgtttgtaa aagttggaac acaagatatg    11580
ctgggaaaga ggcattcaca gcaactctaa acggctacaa atatggaaaa attttaggga   11640
aaaattatta cgcgcataga attgcatggt taattatgaa tggcgaattt gccgatgaga   11700
tagaccatat agatggaaac agaagcaata atatttacaa taatttaaga tctgtttctc   11760 atcgaacaa tatgaaaaat ataactatgc agtcaaacaa taactccggt gtagttggag   11820
tgtattggaa tagatcaaga tgtaagtggc atgcgcaaat tggagttaat ggtaaaagcc   11880
accatatagg ttacttttca aatatagatg acgctgtaaa ttcaagaaaa aaatatgaag   11940 atattttttgg ttatcataaa aatcacggga aggggtata ggtttgaaaa cacttctacg   12000
```

```
accctaccaa caagaagcgg ttaatgccgt aattgaatat gtgaaaagct ccataatgcc    12060
atgcatggtg gaagcgccta caggtgcagg aaagagcgtc attattgctg agattgcccg    12120
tattatatac gaaatgacgg gcaagcgtat tttggtgact gcacctagtg cagagttggt    12180
tattcagaac cgagcaaagt tcattgccac tggctatcct gccagcatgt atagtgcaag    12240
cgctggtaag aaaagcacac ggcatcatgt ggttttggt actccattga ccattaaatc     12300
taacatcaag gcttttcaaa aaaactttg ccatggttat ttgcgatgaa tgcgatctca     12360
taactccaac cttgaaaaag attatcgaag ggatgcagga gggcaatcca aacctacgtg    12420
ttgtcggcac aacagcaacc cctatgcgta tgagagaggg atatattttc agggaatggc    12480
ctgatggacg gataaacgac gattcacagt cgttgaaccc gtttaccat aaatgcgtat     12540 atcgcattga agcacgtcat ttgattgaac aagggtatct tacgaagccc gttatcggtc    12600
aaatcaacgc tagtaggtat gatacatctg gtttgcagct taaccgcatg ggcaattaca    12660
cgcccgaaag cctggacaaa gcatttgtag gtatggggag aaagacgcg gcaatcgttg     12720 ctgatattgt tcccagaca cgtaatcgca atgctgtatt gatatttgca gctactgtta     12780
aacacgctga agaagttatg gcatcgttac ctcctgaaat aagcgcaata attacgggtg    12840
atacaaaaga tcgtaaagcg atattggata aggtatcgcg gggtaaaata aaatatgtgg    12900
ttaacgtagg tgttttgacg gtaggtgtgg accttcctat tgtcgataca attgcgctta    12960
tgcgtcaatc tgaatccgtg cgcctattgc agcagattat tggtcgcggg ttgcgcttat    13020
atccgaacaa gactgagtgc ttaatcctgg attttgcct taaccatgag aagcatttcc     13080
ctgatggtga tttgtttgac ccaaaagttg ttgcttccaa acctaaaggc gaagccaaac    13140
cactaatcgc caagtgcccg atttgcgaat tccagaacga attctcctgc atcccagact    13200
acgccgatca cgataaagac gaaaacggat attgcctgga tgtgtttggc aaccagatca    13260
tgacagaata cggaccattg tctggacact atggaaggcg gtgctttggc tatgttccgg    13320
ttggcgctgg cagagtggag cgatgcggat acaggtggag tgggaaggac tgcccagcgt    13380
gcggggagaa aaacgacata gctgcgcgat attgctatgt gtgcaaggca gaacttgtag    13440
accccaatga acggctcgtg ggggagttca agcccacaa aaaagaccct catttgccgc     13500
aatgcgatca ggtcatatca atggatgtga aagaagcgt gtctcaggct ggcaatgcta     13560
ttttgcgtgt ggattgggta acaccttatc gtgctttcac aacttacttt atggttgatg    13620
ggcgcacacc aaggcaacaa gccgagtata acaatttcat gttgacaacc gacaatggga    13680
atgttaagcc tgagacaata tcttatcgca agacagatag taaattcttt gccatccttg    13740
gatacaatca accaaaggat gaagaaccag tgagaggaat ggcggcgtga aattcccaga    13800
taacatcccc ctattcggcg acccatccta tcgcggcaaa tgcccgttag aaagcgtcga    13860
gcagatgagc ctggttaatc agatcaggcg cgtttaccct gatacgttcg gcaagattgt    13920
cttccacccg cgcaatgagg gtctggtttc aaagggccag ttttcgtcta tgcaaagca    13980 taaagctgaa ggcatgacga agggcgctcc agattgcata gtccccggaa atccggcatt    14040
cctttgtgag ataaaagag ccaatccgca acttagcaaa tggcaagatg ggcagataga    14100 ataccctagag gctgcgcaga atgccggggc gtttgtgtgt gtggctctag cgctaaggc    14160 ggcgtgggag gcgtttcaaa cctatgtgga gaagtattat ggaaattcgt gatatttga    14220 atgagcgtga gaagacccat ggtgactata ggtctcatgc agctatcacg caagctttga    14280
aggcagatat gcagtgccaa tcctcatggt catcttgcc tgaacaccag cgcgaatcac     14340
tagacatgat cgctcataag attggtcgta ttctagctgg cgatccagac ttccgcgacc    14400
```

```
attgggccga cattgccgga tatgcaactc tgagcgcaga tagatgtacg aagtgacccc    14460
atatgatgca gtttttgaca tatctgtgca aatgcaaata gaaggatatg agaagtatgc    14520
aagaccagga gagaatagtc gttacgcaca cagaaaatgg gaacaggtac acgcacgagc    14580
cttcaggaaa ggtaatatct gacagaaaac tcaaccaact ggtagtaaat aacatggttg    14640
accctgttta cggagggctt ttcggtgatg acatacagga atatgttttc acaaaaggac    14700
tttgaggatg tcatgtgggg gagggaattc tacgagagcg tcagcagcgc gacaaaagag    14760
gccgttgacc atactcttag aaatgaggct cttaggatat gcaatataga tgatgtttat    14820
tctcgaaggt cagcgatata tgaatgtcct gagattttac gagggtatct aaaggtagag    14880
attgagagaa tttggaaaat aaagattgac cggaaaaggt aaacatgtaa ttgtgattat    14940
gtggagataa atcatgacaa cagttccaat catagcaaaa tcactcggtc acttgatggt    15000
tgatgtggag atggaccgaa agaacctgt taatgcatgg ttcgcagcaa ccggtaacga     15060
actgccctat aaaatgtgga tgaggcttgt taatagccca ttcgacatga tgcaggcaca    15120
ggaagaagtg gagaaatata tgggtaaaa taccggaaga agccgtggag cggcgatag     15180 ccgcgcacaa caaatactac gacgatcttg tcatctaccc ttcggaggag cctacgccgg    15240
aaggagcttt tcacgaggcg ttgaagggcg ctctcccctt cctcccgtg caaggggctg     15300 tgaagaagct ggagtgggaa ctggtatcag gcgaccatta tgcggaaggc gctgccacgc    15360
attacaatat ttatgagacc aaaccgggct tgtggaactc tgtaacggtt aagccgggga    15420
atgtgcgttt ggctactaat gtggatttag aagccgccaa agccgccgca caggccgact    15480
atgaggctcg catcctctcc gcgctggagc cttcctctgc gcgtgaacag gcgttggagg    15540
aagtaacgct agaacgcagc attgaacaat ggcgcaatat gaagccctcg gaagtcatga    15600
agggcagcac cgcgcagatc acatatgcac tggaggacgc cagaaaagac attctgtcgc    15660
tggcccgcgc cctatcctcc ccggaccata ttgccgacgc cggtaaggtc gaggggatg     15720 ggtggcatgt cgagtatgaa gtttacagcg aagatgaatg gcaggccgct tcgacggatt    15780 tagacgcgc gcttgattat gccgtcatgt atgccgccga cggcttcaaa aacatcactg     15840
ttcaggaagt gcgccgccgc actctcccct ctgcactagc ttcggagggc gaggaatgag    15900
caagattgcg taccgccgca aggaagtgat cggcgactgc accctgtatc ttggcgattg    15960
catgaaaatc atgccgacac ttggaaaggt gcaggcggtt ttaacagacc cgccatacg     16020 catgacagac gcttcttggg acaacgcgcc aaatgtcgaa gcaatgtggc gtgaattgaa    16080
actcgaccga acagacgccg tgttcatttt gaacgcttcg cagccgttca ccagcgcagt    16140
tgttcttggg aatatcaagg atttccgcgt ggaatggata tgggaaaaga acgctggctc    16200
caactttgga actgtcaaat ggcagccgat gaaggagcac gaaagcgtct ggtgttttc     16260 atcgcgaacc cctcgctatc tgccaataat ggaacagagg gccgctagcg gagctgcgag    16320
ggtcaagact gttgtcaact acgacagtca accagaagca tattctggaa ttaccggcaa    16380
atccgccagc atgaggccgc aactccgcta tccgcgttcc attcagaagt tcaaccggga    16440
gcgcggtttt catccaaatc agaaaccggt gggattggtg tagtatttcc tcaagactga    16500
cacagaggtt ggggacgtag ttctggaccc gtacatgggt agcggaacta ccgctgtggg    16560
ttgcatcaat ttgggccgtc cattcattgg ggtagagatc gatccgcgct acttcgatat    16620
agcgtgcgag cgcgtccgta atgcctacga aaacagcctt aacatgtttg cgggacaaac    16680
cgccgccacc cacccatcag gaggcgaccg tcatggcgag tgaactggag ccgtgcccgt    16740
tttgcagtaa aaccatgatg ttacgtagtg ctttatggcc ttccgaaggc gatgcggatg    16800
```

```
ccatcatcca tgctgatcct acagattgcc ctatgcttgg ctttagcgac ggatcggctg   16860
atggcagcat aattgaaaaa tggaattgca gtttatccaa cgaggatgac ttcccctctg   16920
atgggtcgtg tgttcgctgc ggttctgtac ctcgcaatgc gaacggcctt tgcaacacgt   16980
gtttggacga agatgcggag cgtatagaga acactcgccc cacccccgtt actccagtat   17040
cgccggatgc tgacggcaag tgcggggagt tggtgacggt gggctacggc tatgtgaata   17100
gccttggcga gttagaatat gctcacgcca ccagttcgga aatgcggaca gaagcgctct   17160
gccgccgatc gcaggccgga tccatcattg ccgagcttca agccaaggct aaggattacc   17220
gggaatattc cgaaagactg gtaaagcgtc ttgaaagcga ggaagccacc cgctcacagg   17280
tcgaggagct attggcggcg gaacgggcgg atcatgataa tacaattgcc acactctcaa   17340
gtctgattga ggacaacgcg cgcgctgactg cgcggattaa ggagttggag cgcgttgaga   17400
cggagctttg cacgtcgatt ggtctgctcg aagacaaact caatgccgcg aacggaaaga   17460
tcgaggcact ggtgcagtct ctggcatacg aaaccgccca cgaggcgacg aaacgcgccg   17520
aagccctcga agccaagctc gcggcggctg aacaggcgct gaaaactgcg cgcccatatg   17580
tcgaagatta cgacactcgg cgccataaca ctggcgttga tgaaacgctc acacagatag   17640
acgcagtgct gggagggaag ccgtcatgaa caagcttctt cctacggtct ggatcatgcg   17700
taccgatgac ggatggtatc caatacagcc gagcgagaaa tgccgccccg aagatcacgg   17760
caatctcaac gatcacgtta tttcaattga ggacgccaac ggcaatgtgc tttggcgcag   17820
ggtgaaacaa tgaccgaatt gattgaccgc ctctccaagc tagacgcgcc tgacagggaa   17880
gtggatgctg tgaccgccgc attcgaacgg tgcgcgaagt ctttcactgg cgatgagcta   17940
actgaactct tgaagttttg cccgccatcg cacttctgat cgccctcttg cgcgcaaagg   18000
aggccagcaa gctatgagca acattcttat catcagcctt atcggcttgt tcactagcgg   18060
cgtggccgtc ggcctgtcct tggccgctgt aatttacctg agcctaaacg caaaggaggc   18120
cagcaatgcc tagtaaggaa cacgaagcac ttgtcgagaa ggtggcaaag gccatcaacg   18180
gacctttcca ccctgtgccg gaaggatcgc tattcacgtt ggaccagctt cgcgatgttc   18240
gctggcaaca gatcaatgac gtggaacgaa gtctgtgctt ggctggtgca aaagccgcca   18300
tctccaccat ccgcgccgct ctacaggagc cgacagagat tatgctgcaa gcgtattggg   18360
acgggagtga agcatcagat agctggggct taatgctcgc cgcatccgca cttggggaga   18420
agagcgatgg gatttaacac cgcacttatg gtcttgaatg accgtctcga tgaaattcgt   18480
aacgatcctc attttggcag gagagtttct gatgctgtca tggaggccag tcgccggaaa   18540
gaaaaacact tcgggtcatt ctctatgctg ccgacgcaac atgccgacac ggtgcaggtt   18600
atttctgtag ggttcaatag cattaatttg ctcggatatg catggtcgga cgacccgag   18660 attatcctac gcgaactggc gaaccggcat ggctaccggc ttgtcaaaaa gcgggaatca   18720 gatgggagc agagcgaatg aagctgacat tcgagaagat attctccatc tacttggcgt   18780
tagcggtact aactttcggt tatattgcat cagaaaccaa gtgtgaacag tcgttcatga   18840
gcgcccagac caatacggaa tgcgctgtag ttagaggcgt agtcggtgga ataacttggc   18900
ctctttactg gacttgggaa ggcttttcta tcggccgcca agtcctgaaa ggcggtgacc   18960
atggctaagc tgacagaagc agaatttgcg caacagtgtg cattcatcgc taagaacgcg   19020
gcagattggg catcgtcaat cttagagatc ggagaagctc taaacgatcc tgctaggtta   19080
acgactgtgt gccgcttcac agatgaaatg cgtcaacggc ttgatcatct cgaccggaag   19140
gcaggccgcg ccgcactacg ggaaagggag tgaggatgta cgaacctgat taccattata   19200
```

```
ttccgtgccg atgcttcagc gcggatcatt tggtccgtgt atgcccggat gaggatatag   19260
acggcacatt gaacgttgaa atcctatcat cacgccaatc gtctttctgg tcgcgtgtca   19320
gatgggcctt gaagcatgta ttcggtcggg atgaccttgt attcgcagac gttattatct   19380
cgcgtgagaa atggctgaaa gcggcgggag aagccgaaag gaagaagtg  ggaaagtgag   19440 tgaggatgaa agaagagttg gcatatatag catcaacaca tggtcttact ctgaaagaca   19500
ttatgaaacc atgtcgcttc ccaaccgtgg ttaaggcaag gaatgatgca atattctttg   19560
tgaggattca gtacggtctt tcattagaga aaatagggaa gatatttaat atgcatcatt   19620
caggtatcgc gtatgccatt actagtcact tgtatgctga ttaggtccag gtcttgatct   19680
acgctgctta gggtcgtcaa tgtcacctgt aaggatacct actcttgacg atagaacctc   19740
aacctgagta gtgaggcggt tgatatcccg cctcattaaa tccatacttg aaataagtgt   19800
gttttgcaaa gagtcagtac gttcattggc tctttgcaga ccaaattcca attggtcaac   19860
gcgataagcc agctttccta tgtctgccgt tgttgccttt aactctgcat tctcctttga   19920
aagggaggat atgctctttt gaatgtcatt aagattggtt ccaacataaa acccaaaccc   19980
tacaattgtt ataattgtag ggagattaac tctaaaccag ttaagggtta ctgttgcgtc   20040
ctgtttcatt tcatccgctg acatttgtag gccccgtatc gcccgcgatg ttgtgctacc   20100
tgttgggcaa agggtctatc attttcaacg atatatcttg ccgtttgttc cgatggtgac   20160
attaacacaa gtacatcaca tgggctagtt agcttggcag tcgatgagca agcaaacaag   20220
accatcgtca tcagcagcat aaacggcagc gtcaactttt tgaccatctt taattacctc   20280
tactctatcg ttagataacc gctgtagaac ggattgcttc ccagcgttat acataaaata   20340
atgcgtacca actaacgcca aggccatagc cccataaaga tatggcttaa gcatcgttca   20400
actcctgacg aatgtctttt attgcttta  caatccagcc acgaagtgca agcccaccaa   20460
gaagaactac tagtgcaacc gcccccaagg ccaaaagctc gcgccaaccg aatcctgcaa   20520
gccccaaagc accgatacct ccgccagaga aaagagttcc tagccaacca gccaacgaaa   20580 acttttctt  tacttcctta tctacggaag taggcatgac aggcttgtca acttctttag   20640
ttacaacaga agggcgctca ggagttggct tcgatgaaag acccaatgca aaatcacgaa   20700
cgccagctac tcgtttggtc catcccttgc cgaaggtggg ccatagtatc ttcttggttt   20760
tcttgtctct ggctctcttc atgaaagcca atcgtgtatc acaaagcttg ttgatgacat   20820
tgcgagaacc catagacttg atagcctcaa gcgtctttgg gcccaccttc ccatcctgtg   20880
atacaccaac cactttctga aggtctttaa ccgctctgga tggcccgcta ttcaccgcat   20940
aatcaaatac cgcaaagtca acgccgtccg gcaactcagc gccatgcacc ttatcccaat   21000
actgacgacg atacacggtt tccaactgtg cgtcagtaat cttgcgaaga tcggcttttg   21060
tcccttttgg attcacaaag gcgcggaaag tagcaatagt tacgcccttc atcgtagcgc   21120
caccagggtc agaaggatgg tctgcccatc ctccctcatg cttcaaaacc tctttgagtg   21180
atactttaaa attacgatcc atcttttttct cgcatatcta tcgccattcg cggcgggttg   21240
gtctgacgta caccgtcagc gccctgatca ataataacag cgtctcccgt tctcagtggg   21300
agtattgcag gcgggaggcc tttagggcga atatcaacca ttagtaagac accttgataa   21360
ttttgttgat tattacggta ggctgcatgt tgttatgagg caagcctcca ccttgtgggc   21420
ttataggatg attatgagtt gaaaatggta tattttcatt tgtaaaacct acttgaccat   21480
ttctactcaa acttaaatta ccagttaagt tcttgagtac atttagtatt gtatagctac   21540
caaccccatt tcctgtactg ccaccgtggt catgattggg aatttgatat attgttagtg   21600
```

```
tactattttg ctcaccacca ttagaaccta tcaaagcccc attaatccca cttccagtgg   21660
tagtaacacg gtttgcagcg ctaccccca tgtcatcctt accagcacct accctgcccc    21720
tcaaatcagg caaaacaata aactgtccag acgtggacct attattagat ggatcagtct   21780
gtgaagtggt tcgatatcca aatcctgccg tggcattgag tgcattacca acatagcaag   21840
ctgctacgaa atcgggatat gctgaaactt cgatcgcttg cccaaagcaa aattgccacg   21900
tattaggcgg gttaacgcca gcataatcaa tgactgcgcc cacaggagta ccagactgaa   21960
actgagacaa tggaactgca tttcccggct gggtagcgtt gcctaatccc gtaacctgaa   22020
acccattcat tgcaagatta gcgcgcatac caccttgccc atcccggcta aggctttgcg   22080
tcatcattgc ataaagatca actaacgctg ggttgtgctg agatggcaga atagtatcgc   22140
cggtttgaac gatagtccct tgcagtggat tggtgttgcc gttgctgtct cttggcatgt   22200
tagttaccac ctatattaga ttgcgctgcc aattgagagc caatcaaagc ttgaattaca   22260
gcatctctta tagcaggatt tgatgcattc ggcaaagtcc ctcctgagcg tgcaagaagt   22320
tctgctacat cagcatttct taatcccata cgagtcgcca gttcccttcc agcaaaacct   22380
gcgcccatag tagaagccgc gcttgcagca ccaaccgctg gccaccaat agcgttacca    22440 atcatgaatg gcacaccgct acccaggccc gcactaacaa ctccagtagg cgcaagtttg   22500
ccgatattac gggccgtatt ctgcatgggg gtgccacgcg acacattgtt aatggcctgt   22560
atctgctcag gcgtccaacc ttgctcttgc cccttgataa tacgccggtc aagatttctg   22620
tattcagtgc gtaaggcatt ctcaaaaccg gaacccgtga actgtcctgc acgcgccccc   22680
gcaagttccc ttgcacgctc caatgttcca gctttaagat aacggcttga aatcttgcgc   22740
gcttcagcca actcagggc gagaggagaa acaaagtcat cgaatgcaga aagcatcttc    22800
ttagcgatac ggccttcttt gccttctgcc ccaaaagcag catccgcaag cgtttcccta   22860
ataacctgca tttgtgttgg gttcatatca tacccggcat aatcgcgcat aagctggagc   22920
gcttctttag cctttgggta tgcttctgcg atccgtcctg taggagtgat gagctcgtta   22980
tcccgtgcga tcttggtaat atcgtcagca agactggttg tcattgccgg atcggccaca   23040
acgccacgtg cttcagcctg tgcgtacaag tcagaagctt gagccttaag gtcatcgata   23100
gatggaacag cttttcagc cgcctgacgc gccgaacggt tagccaatcc tgaaatagcc    23160
gcgccagttc ctaacccacc aattaattca cctgctattt cagcgcctac attgtcagga   23220
gcaatctgtt gagcggttgc gccgccaacc ccgccgccta acccagtggc taatatcgat   23280
gcaacttgtc cagcgctact ggcccctgcc gcaaatggag cggcacccc aacgactgc     23340 gcaacgcgcc ttgcgaactg ttcaccgcct gattggctct caggagagat agccaaacct   23400
tgacgcaatc cagcgcttcc gcccaaaggc gtttgtgaag gctgaatatc cgttccaaac   23460
gcataattga tgccagcggc tgcgggtgca accaatagat tgttaaccaa atctaccgga   23520
gcgcccaaag ctcctgtagc tccttctagc aaaccagaaa atatttgtga cccgtagcct   23580
ccttctggtt gaggctgatc agcgccaccc atccctgaa agcttgcaa agcgctcgct     23640 tcatcaggtc cgtcaacttc gtaaacctgt ccgtctgggc cttgtaattc aaatattgcc   23700
attactgttt tgccctgatt tttacgccat taggaagggt tttccatcct gtatcagatg   23760
acttaccctg atcctgcggc ccatcaataa tatcagcata cgcctgacga acccgcttga   23820
ggttgcgtat aagctgctct tttgtctgcg actgatccaa actgccaata gttgactgaa   23880
gataagtaag ttcacgctca gaaacagcac ccaacgcacc gccggttgga gatgcgtcac   23940
gcatagcctg caatctatca aaaccagcgt ttgccttaat ggtggttatc agctggttga   24000
```

```
cgtcattaga ggctgtacca cctatcttgc ttagggcgct accagcaaca ccagtggttg   24060
tgaaaggaga cttatcaatc aaatcaacgg ctctatcaat gtcttcagta caacttgag    24120 aagtcctatc ctgactgacc tttcccttt caaatgcttc acgttctctc tgggccttaa    24180
taaagtccgg actaccaggg attggggaca tagaaatagg ctggccctgc tcgttgtaat   24240
caactttata accaggggg atgttaccca tctgacgagc atctacagta gtagctccag    24300
cgcgttttac ctgctgctgg taatctgcaa aagaccttg gaaaccattg tttctagcgt    24360
attcataatt ctgaatatct gatgttgggt caccttgtcc ctgaataatt ggctgaccgg   24420
tattggcatc ataaacagtg ttgccaacct ttacagtatt acgattgcgt gtagcctgtt   24480
caatagcggc tttccaagca tccgcatcgc cagcaagagc aggattaata cctaacgtct   24540
gcgctgtggc ctggcgctgc gccatcaaac gctgttgctc ttgtgctgct tgctgctgct   24600
gcaactgctg ccccaaaagc ataccggcaa tctgcctacc ttgatttgaa atataagggc   24660
tggaaagagc ctgaataata acagggttaa ttccgccaga ttgtgattgc gcaggcatct   24720
ggaatggttg agacgtaaca ggcgcacgat ctgcgctagg agcagacggg aacggtccag   24780
acaaagcttg cgccacgggc gaagacccag aaggagacaa agcccgccg agcatttgat    24840 cgttcagcgc caacaagcgc ggatcggcag caggagccga ctctgccgac ataggcgtca   24900
cttctggcac aatattagca gatgcaggaa tcgcctgttc aggcaggata ggagacgtag   24960
cagcacctgc attccagcgg tcgttgaagt tagatggtga ttgaggagat acaagagaat   25020
ttgcaaccga aagatttgga tcagaagcaa agtcataagg agcaacttgt gcagctggga   25080
gtccatcaat tggcgcaacc tgctcaatag cttcctgcgg agtagtagct acacgtgcat   25140
aacgggcggc gcgagcttga cgatgctctg gagcaggacg caggaagtta ttgacgatag   25200
cctgagcagc agttgccgta tctggggcag ataggattga ttttgcagcg ccagcctcgg   25260
aaccttgaag ttcgttcata agaaaatcaa gctgcgcatt cacatcagca gggttgacgc   25320
cacgctgcgc tgcgaacgct tcatactcac ggcggcgcgg acctgtaagc tggtaaagac   25380
cgaaaccgcc acggcttccg gggacaattg ggttttttctc attgatgcct ggattcagac   25440
cgctctcatc ctgaaaatta agaataaacg catccgctat atgcggctga agaccacggt   25500
caatcaatcc ttggcgaatc tcaggggcag aagggatatc aacaggctca ccaactgccg   25560
caacggatgt aggtgaagcc cccgctgcga cggcaggatt aaacccagca ccaccgccaa   25620
ggctaccaag catatcactg ataagcgatt gttccgccgc tgcgttggca gtaatagcat   25680
tgtctgctgc gcgacgatca cggccagact ggaaccctag aagccccttc gtcaatacag   25740
aagcccatcc gccagcgtca gggctggtat ctgtagcgcg cccgatcaac gactgtgcga   25800
cctgctgacg ctgggcgatt tgctcaggtg taagacgctc accgtttggt ccagtgaaaa   25860
tggcgggtat tagttcttga aggtttgcca ttaacgattt ccgcctctta gcccaccgga   25920
cattatactg cctattgctt gttttttac gtctgggata tttgattgca tcatattctg    25980
cgcaatgggg gtttgctgct gttgcggcgt tagagtgtac tgattcccct gattaaatcc   26040
catatttgcc atcatggcac tagatggatt agcggatgca aatggtgaga tattgttcat   26100
gaagctttgg ttgtttacta aaccgctatc aatcaatgcg ccagaagctg gagccatagg   26160
aatttgctga taagcatttg gattatttga cattctattg ccaagattat tataaccgct   26220
tagattattt gcagcgaacg tattaatctg ctggttttgc ataaatggca tttgcccttg    26280
gggcctgaat ccaaaattaa acagcatcac ttcaccttgc tataatcaac acggtaatac   26340
ccatctgcgt cctgagagac cgcttcaggc tgcaattcca gcaagtcctg agccatatac   26400
```

```
ccaatgtgcg taaccggcga gccaatgtat ttgaacttgt aaactggaac acctgaatca   26460
gttttgccaa tgcgctcaat atcttccttc agacgtctat ctgagaatgg caacatagac   26520
gcaacaccgc caaacaaccc gccaagagcc cccattttgc tattatatgc gttcatgtct   26580
gcctggtatt tctgattaac gaggccagaa tagtcaaccc cagcaacctg tgactgaggc   26640
gtttgcgcga atgtgctatt gggtgactga acctgagtac cagacataag cccaatgatt   26700
tcattcaaag gctggttgcg ctgtgcaagc tgctcttgga atgcctgcga acgtccagtt   26760
agcgctaact ggttcaattg gtcagtattg gcgttcgtaa ggcgcgccat ttccgtattg   26820
taagcagaag ttccagggcg ataccagag ttaatcaggc gattctcaag gtctttgcgg   26880
ttctgctcct gctgcggcat aatgcgagac gaagcaagat cataagccca gttttcagca   26940
tcctgattgt taaactcaaa cggagaacta aggtaatcac caagccatgc agaccgatcg   27000
ttcgcaatgt ttgcaagatt accctgcgca gactgagacg catcaaagat agcctgctgc   27060
tcaggagaaa gcgtggtgtt agccgtatag gtaggaacct caacgcgctt accgttcggg   27120
tctgtaatcc atgtcgtacc agtctgttga taatccaaga taccccatgg ggtattctgg   27180
tttaccatgt tcatttgctg ctgctgctgg gccgtgaaag aattccacgc gccttgcgct   27240
gcggctgttt gcgctggatc aggggcttca ggagcgctct tgcccattac tcagaaactc   27300
ccttattata aggcgacttg ctccactcgt cgtcagtcaa agaaaaaata aattcgcctt   27360
catccctgcc gcgaagacga ggaatgtaag tttcactaaa cccgaatttt cttgcaatac   27420
caatcatcgt tttatttctt tcagaaactc tcaatacaac taattgacag cctagacgag   27480
tgaatggcag gaagaacata gcattaatca cggcccttgt cagccaccttt ttgctaacag   27540 atgcagatga tagctcaata acaccgtatt cagggtggta attatggtaa agagtccctg   27600
ctataagatc accatcctcg aatacaccca tgctgcaaaa gtcttttatt gttatatcgg   27660
cttctctgca tacgaaaaac ccaaccgctt cattcgcgga agggttcatt gtcttgctgt   27720
aatacattgt atggatcaag ttacaatctc gcccattgtt aagctgattt ccaaatggac   27780
aatctcaaca tcaagaggaa cagaactacc tgacgtcacc tgatagcagg cagaaacgta   27840
gtaacccgtt cctcctaatg atttccactg tgcattgaaa acattaggat tggttccacc   27900
ccatacagac tgcccccata cacctgtacc ccatgcatta gagccatccg cgctcgatgc   27960
cgttggagca gagcccggat caatatcaaa atcagccttg aagcgaaggc cataagacaa   28020
attagccttt acccttgcta cgccacggcc catcttaggg attttaagat tggctggcga   28080
tccaagatca tcaaacagtg ggatgtaaac gccagtgtaa acagacccat tgtccatgcc   28140
tgttacattg gctttgaaca cttcaccgtt agggccacca aaatacatct ctccctggaa   28200
tacgcacata gcgcgagcgt cccaattggt ataacggcac catgcacctg tttcagaatt   28260
ggaaataaac aaaactggat cataatcacc gattgtaata ggcggagata tgattgccat   28320
cttacgttca ggccaaagca tacaagacca atcctcaagg ccgcgaccgt cgacggcctg   28380
ctgccatgcg tcttgaatgt tgtacgaaac agcggcagga gaaagagccg ttacatcaag   28440
actgatagcc ttggaaagag gaataaggcc aacactagta gcaacagcaa tatcaccgcc   28500
gcctctgaaa tgagcgcgat tgccaagagg ccggccaatt ctgtatgtgc caacatgcga   28560
ccagtcgcct gtagcttctg ggtaacttcc ttgaaatact gcaacctcac cctccgtgga   28620
cgttacaacc atctggtcag acaaaccgcc agcagcacct gttcccatag accatgaatc   28680
gccccacagg acgacccgc caagggttaa tataccaccc ataggtaaa caacaggatc   28740 accgcctaca gcgtctgggg catccatata ccatatgttt aaggattcct tctgggcgaa   28800
```

```
ccaaagacgg ttttaaaatg cccaaacgta agacatgtca gcagttgtta aaccgtctgg   28860
gaacgcaacg cccggcacaa tgtttgatag aacgctagca gcttgggcgc tcccaccttg   28920
gtctccggtt agcatttcat tgtctaaaaa gctcccgcca cttacgttct ttgcgttaac   28980
tatatccttt aggacaagcc ctcctcctgg cagaatctca cttactgtac cttctgcccc   29040
ggaagtatca cccgttatca cttctcctac agaaaaatcc tgtattacat tgtcgtaaga   29100
caaagcccaa accccaccag ggatataagg ataaaaagca ttgccatcat aaatgaagcc   29160
tgtagacgct ccgttaacgc caataaggta tattccgcca gtagtggcaa actgtacagt   29220
aatccaatta ccgcctaatg cgccttcaaa ggcttccata tcttcggtag acgattgacc   29280
aaagtaatca ccgttttcag tgaccagata atcgccattc tctgtcacca gtcggtaatt   29340
ataaggaacg aggatattgg taatatcgta aatggtgttt tcggtagacg cgaacaattt   29400
acgattcaag ccgttaacgt atgtaaacag ggacgttacg ccttcatccc cctggcctag   29460
agtggcataa agctctttac cccttcgaag aatagctgtg gtagacgttg gaaagaagtt   29520
atcaagtaca gcagcacctt gtggcccgcc attttccata ggcgtagaca gattgcggtt   29580
gctaatccac ccgcctgtag gtgcatgaaa ctttttaagg tctgacttac gttgcgccgg   29640
tttcttctgc gcgaggatag ggcgctggta catcaattac cccaattcaa aaggccatgc   29700
caaatgtgta ttaagacgcc tgcttctgga acgtgcacgg taaacgtttg tgcctttatc   29760
cttagcagca agctgatcaa gggccattgt aaattgttct tggtcgcctg tatagtctaa   29820
cttcttattc tcacgccatc gccatataag gccaagggta agaaggtcat tgccgccctt   29880
gatgataaaa tcatctgtat cggcagtgaa ctccggcttt cctgcattat ttgaatcaag   29940
agcgtaatta ttggaaatgt aaggatacgt ggcgctattc tgagcattag gcggcggaaa   30000
gaaatgaatc tgattttggt aaatagtcca cgcaccagga gttagctcaa aattacgcgc   30060
gcgccggtat aggaagtcat tgagattttc aatgtgctca tatccccaaa cccaattatt   30120
caagtcctga atatccgtaa ccaaaagctg acgatcatag tcctcaggaa gatcgaatat   30180
ttcagtaacg ccatcagttg gtacgttata aactttagtc agagcctgcc aatctgcgta   30240
cctgcaaata tccctagcca cttcattgac aagatcaaca atctctagtt caagctgatc   30300
tgatgaagta aaaaagacgg cgggcttttg gcccaccaat ctaattgtag cggattgcat   30360
cgctgacaga attgacattt acattccttt tgcaaggttt accagtgatg catggcttag   30420
tcggccatca ggcttagtgc cagtctttga ttcaatcata tcacgcaatt cagcctctgt   30480
cattgcttcg taaagatctt cttcaacttc tggaataaca gttgatgccg ttcctgccga   30540
ttcaagctct gcaatgcgct ttttaagagc ctcgatctca ttaagagctt tatccgacgc   30600
ggaatgatca gaaatatact tgcgagccaa ctccttaagc gtgttaccca tcatgccaag   30660
cgatttaagc ttgtcaccct caagggtatt aagcgcctca atgctgtaga cacgatggac   30720
acggcagatg gaaagctgct cttcagttac gccataagga cgcagcattt ccaacggtgt   30780
tcccattgcg tgctgcgggt tgccttcttt gaacgtacgg tactggtcgg cccaacgttc   30840
tgcataggta atagatttgt tgccttcgcg ttttccacgt ctgatgagcc ggaaaacagg   30900
cgcgtaatta tttgatcccg caaagcggac ctcaacaact tcatacattt ccatgactgc   30960
gtggcctgcc gtttctgact tgggatatt ctcgacctca atcaccttaa agaaaggcgt   31020
tacgttaagg tcgcgcatgt caatttcaac tactttagtc atttatcgtt ccttgtctga   31080 gaagggtaa agggaggccg ttaagcctcc ccatattgat tagagcgcat acactcgcgc   31140
atgaaaataa gcaccggcag gaacagcaac atcaggggcc tgcaaaacgc cagaagcgtt   31200
agcagtggtt acaaaatcag agtccatgtt aacacgtgcg cttgcggtaa gcgcagttgt   31260
gccgttctga acccagatgt aatcgtaacc atcatcgcca gtttcacgat taccaagctt   31320
ataagaaggc tcagtaatac cggaaacagt agcgccgcct gctccctgaa tgcctgtcag   31380
```

```
cgaacgatta agagcaatgc gctcaataat aggacgtgca gtcgtgctat cccaagtcgt    31920
aaagcccgaa acatcaccgt ttgtaatgtt gaacgtcgag gtgcgccagt ttggaacggt    31980
tgcacgatca atgccgccgt atacgccagt gtttggaatg actggaatag cgccaccaag    32040
gccgataagc tcacgacctc cagcgcccgt gccgtcaccg ataagagcaa cttcaaactc    32100
ttccttaacc gacttttcag ccgcatcaag gtaggtttcc ataaggtcga taacctcttc    32160
ctcaccgcga gtgtacatca gttctgtgcc agtcagagag aacatgctga caacacgcga    32220
ccaattgaac acggcagagt taagaagttc tttcggggtg atttcgatct tgtcatagcc    32280
agtgaaccac tgcgcctgca atttgtcgaa ctgaaccgga atacgaagtt ctgggccacc    32340
agcgcgcttt acgcgaatac ggccctgatc acgcagaatg cgggtaagag gggtcgagtt    32400
ataaacaatg tcctgcacct cacgcgagcg ccgggctacg gctgcggtga aagctggcg    32460 gtaatttcta tcctgaacga tagccatttt agctccttaa gccttcttca gacgcttcaa    32520
ctcgtcttcc agaagttcac gcattgacat tttcttatcc ggttctttga cctctagtac    32580
attccccgga gaagatttga ttgatttgct gccgttgaag tcttcgtcaa cacggctttc    32640
agaactagtc tgctttggtg agaaggatga gacatttgaa gaaggattaa tcctttcagc    32700
catgtcgtac gctgcttcaa gcttctcagc aggactaaga ttagctggga ttttaccaga    32760
ttgtagaaag aaagcaatat cctgttctag ttcatagtat cgtgggtgtt cttttgcgaa    32820
tggctcaata tacataaaag ccgccatctg ttcctgcatc gcttggttct gccgtttcag    32880
cgtttccact tctggattaa tctgcggctg ttgctgcggc tggacctgtg gtgcctgcga    32940
cacgtaagaa ttagggtctg cactaatgtg ctgagcaagc tgctgtggag taacattgaa    33000
agcgcgcaaa atatgagaaa tagcctgttg tggctgcata ttcagattgc taagaagctg    33060
gcggaagcct tcaggtgggg actctgcaaa cttcgctca atccccacat agttatcaag    33120
cgcttgttta acgctaacgc catgctgttt accgagctct tcgtattcct taagctcttc    33180
acggaactga tgagattcac ggtactgctg cacctcagtc tcgtgttcac gtacaaggcg    33240
agaaacttcc gactgcacct cattgggcgt attccgccat agctccttag cacgtggaag    33300
aaagcgagca ggaggctcag gacggtcacg gacctcagac ttccgttcgg tctgctgatc    33360
cttaacctgc tcgcttgcgt caacttcctt ctcaggagtg gcgctctttg cctctgtctt    33420
ggcgacaggc ttgggttctt cctccagctt ttcagcctta acaggttttt caacctttc    33480 cggctcttta gtcttatcaa gctccgcctt cagtgagtcc cgtacagatt cagcctttgc    33540
gggaacttcc ggcttggctt cttcaacagg aggaggagtt attttaccac cgccagatgt    33600
tttaggcgtt acatctgatt caagcgtagt tgaaacgtgt tctgtgactg gtgatggttg    33660
aattacttcg tcggtcattt tatacctcgt ctgagaaggt catagggtta aacttcacta    33720
atagcgcgct tgatatcttc acggcgcttt ttacggtcaa attcaggagc cttgaagtca    33780
ggaaggcttt cattgccaag ctcgatatac cgttcgccct ttgggttttcc agaggggaga    33840 agcgtcttac gatagcttga caatgtatca tgcatcttgc cgtccatacc catgcagggc    33900
tggatagtgt cctgacggaa ataggctta ggcagggaac tagcccccat ccttgcccta    33960
tgttctgcta ccaattcaga gattgatttc attacgtcgc aatgatccct gctgtgcgaa    34020
gtgctgccag gatagcatta accgccgttc ccgccgtggt cccgtctgct tccggggtaa    34080
tgtcggcgat tgccgcgcta gaaagaacac caccgcgttc cgttgtggta ggagtggcaa    34140
gagtgactgg aatagaagca ttcgcagcac ccgtaaaggc cccgctagtt cccgtcgcgc    34200
ctccagtaag ggagatagtg cggccagtcg ccagcgccgt tgcggttgct actggtacgg    34260
```

```
tagcggggaa agtggcgggt ttatccgtaa catcatccca cgatactgcg cccccccgaa   34320
gatgattcaa tctggctacg aacttcttta gcaagttctg gaaccattga aagttctact   34380
agtcgatcta ccggtgtctg tgccattatt attcctcgtc aggttcaggt ggtgtatagc   34440
cctcaataat caaaggcggt gcattgctgg atactacact aatcggaata ccaagtccat   34500
tagttgcaac cgtggccact ggcgcatcac tagttactgc aacaaaaggt gctccgttat   34560
cagaaattac aactggaaat ccgggcatct aaacacccca cgcggcaaat agggcaaaac   34620
caatggcgat atatgataaa gcccttgctg atatccaaga gtatttccag tcatcttgcg   34680
cggcaaattg agataatcct ccaaaaagca atgcgtcaga acgtggcta gtaccattga   34740 acgaaacaca tagtccaaac gccgcaaaca ggattgcacc acatattgca taagttgatt   34800
taggcatcac tccacctctc tttgtgtcaa cgcttgagtt tcattaaact cttgcgaacg   34860
attagcgcgg ttttccgatt caactctaag cgccgtatcc accgtgcgtt gttcagcctc   34920
atttgctgcc ttatactcct caaggtcttg cttgcgaacg tctagaccaa tcttggcaag   34980
aatctccgcg gtctgagcct gcataagatt tgttttggct tccatatcag ccatcttagc   35040
cgcaaactcc tgctcctgtt tggatagctg aagctgcaac ttgccttgct caatctcgaa   35100
ctgcgcagca tccttctggg ccttaagctg caaatcctgc attttacctt gcaactcagc   35160
ctgtttaagc tgcgcatctg cttgcacctt agccatctgc gcttgtgctt tagccatctc   35220
agcttcagca agcttattct gcgcctcaat aagagcctgt tgttctccac cttcttgcgg   35280
tggctggtag ttagaagctt catcgatgaa attatcgata aggccatcaa gctcacgacc   35340
aatacgataa ggcccaagaa caaagttaag cataccgcca gcaagtgctg acccggcagg   35400
ccccatttga gccaatccct gcaatgcctg agatgcacca gagaatgttg tcaagaactc   35460
attgcggctg gccttttcct gaatttcatc agtcaaaata gtgctatcag acgcgatttc   35520
aaaagcaaaa ccacgcgatt tatcattgcg caaaaggtca atgatatcct cgataggaat   35580
ttctgaatta gcctcttgca gcataggcgc atatttctgc aaaatggcct gctgagtttc   35640
cttaaacttt gtctggatat cttgctgtaa ttcaggagga atctgatttt cctggacaaa   35700
cttctctgtc tgtttcttaa ggttttcaag ctccttctca gcagcttctt caatgccttt   35760
tatctgcttc tcaatctgcg ctttttgtaga gattttcatc tgagacattt caaggagagt   35820 atccttgaa aaatgctctg caataatctc agccgaaatg cgaacagcgt cggcagcaat   35880
gcgctgtagc tcatcaatct tctgtcgaac acgaacggaa ccgtactgac ccttgagctg   35940
ctgcgctcct agagtttcat cagcctcagt agcaccgcgc ataatgtcgc taataccaga   36000
caactgatag aagtcatcaa ttagctttgc acgcgcctcg ataagtccag tgatagccgt   36060
tgccacttcc gcaagcggca tccaggcaac catgttggtc acatcgctgc taatcgacgg   36120
aacaaagatt acagtttcat catcttcgct ctggataagc tcgcttaccg cgtctcgaat   36180
atcaccgcta ccggccacaa tgcccttgag cttaaccttt tccagcaaaa ggtaaatacg   36240
cgctgtcagc gtgttaatct tgtcaaaatg aacgctataa cgctcatagt ctggaacagg   36300
gatcaacgaa cgacgcgcca gtgtgccata agctggacgg gggcagggga agaagtcttt   36360
tagcttcagg tgtggctcac cttcatccag taggcgatcg acaccctcag aaacccaata   36420
aaccttatta tcagcgcgat gccagacttc ccaaacgctg cctttcagtg acttatcatc   36480
attgccgcgt tcttcgtctt cacgcttttt ggaaagtttt acgtctttgt aaacatcgcc   36540
ggatgcctta tagaaacgct tacgcaactc cttacgcgtc atccatgcac gacgagctac   36600
ccaaccaacc tcggaccatt tacgggcagg ttcatgcagg aaatccatgc gatcaagatg   36660
```

```
ctcgatacaa acgcgctgtt cgcccttttc tgattcatac gtgagccaca tgacgccgcg    36720
attggtgaaa atcaggtcgt cacggacctc gcacataaca tcgtcaatgt tagagcggtc    36780
aaagttagac acagatacgc gctctaacaa ttcagccgtc tttgacttga ctggatcgcg    36840
atctttgaac tgtgttgaaa ctacaggctt tggaggatgc gcataaacag caggctttag    36900
aatttcatag gaagcccaga atagatcaag ctcaccatct gtccaatttt cactgtatgg    36960
acgcttttca ccctgatatt tgctgtaaac cgtatcaata cggtcgcaaa tattctgcca    37020
ttcgcgaaac ttatccttag cgttctgcaa taccgacaga acaacgcttg aagactttgg    37080
ttcgtctttt aattcaagtg tatcggatgg ctggatttct tcttcgtcca cttaaacggc    37140
ctcatttgca aatgttgtgg caatgtaaca tgcaggagtg caaaagaaaa ggccctccga    37200
agagggcccg taacaagact gcctacagcc atacggataa tatcagaacg cgccgggagg    37260
ttgcgccgac acttatgcct cgacgctttc agcgccgccg ttctgatttc gcgggatatg    37320
ccttaaacct ctcagccata ggacaattaa catgccccag cgggatttga acccgcgtca    37380
ccatttggtg aatatccctt ctcgtagccc tcatgtctca cgctacccgg ataagtgggg    37440
cggtactgca tgagggtgga tttttgccct agtcggcgct cttttgagcc gtctggctac    37500
gaggacttcc ccagacccgt tctccaacca cggctatttt cgctggccgt cagctacatg    37560
cgaggatcgg cgcttgatac gctcgatgtg cgaaacgccc tcgcattcct atatcctact    37620
ccgaacccgg cctaattaca aggctgtctt ccagtctac ggtgccgcgt ttgtaggatt    37680
tgtgtgagtt ggcattggag caaatgtcgt ctaaatccac ccactggtct aaatctttaa    37740
ttgatggtct gtttcgataa aggaaaggaa taccattttc atccctcgcc atatacttaa    37800
actccggcgc aacatgatcc cagttgatgg tgtctggtgt ggaggagggt gcgatgcggt    37860
aggttccggc atcccaatcc caataaggtg tatctttctt tgaccaatag tcataattat    37920
taccgcagaa ctcaacttcc tccccatcca cataagcctg catcacttca atcatgcgct    37980
ttgtgcgttc gatgtggtct ttgttggtca tcaaacttct ccacgtgctt tggcgagcaa    38040
tgcatcgatt tcagcgcaga acgcagcttc ccatgggcct agatcgtctt catccatcca    38100
cttacggact tcctcaagat tgcgataaag ctctggcgcg gcggcgatta ggtgggcgtt    38160
tgcgcggtca atttcatcac caaaggggt accgtcagcg gtatcctttg tgaggatacc    38220
gggcgaaagg tcataagatg accaattgtc gtttt                               38255
```

<210> SEQ ID NO 2
<211> LENGTH: 50
<212> TYPE: DNA
<213> ORGANISM: Brucella phage Iz1

<400> SEQUENCE: 2

```
gagcgttatg ccaattttca tcattgttgt tatcaacaat cttatccagc                50
```

<210> SEQ ID NO 3
<211> LENGTH: 50
<212> TYPE: DNA
<213> ORGANISM: Brucella phage Iz1

<400> SEQUENCE: 3

```
ctcggaatca gcgtcttgcc tgcccttgat tgggtcgtca ataatgacgc                50
```

<210> SEQ ID NO 4
<211> LENGTH: 50
<212> TYPE: DNA
<213> ORGANISM: Brucella phage Iz1

```
<400> SEQUENCE: 4
cctgtgggcc tccttgtggc aggctggaca aagggttacc aaattcgttg         50

<210> SEQ ID NO 5
<211> LENGTH: 50
<212> TYPE: DNA
<213> ORGANISM: Brucella phage Iz1

<400> SEQUENCE: 5
accgctttga aagtcttgtt gcaagtcggg cagtcgcggg agattggcgg         50

<210> SEQ ID NO 6
<211> LENGTH: 50
<212> TYPE: DNA
<213> ORGANISM: Brucella phage Iz1

<400> SEQUENCE: 6
ggggcaagtg aagacgcttt gacgtatcca cgcccggtgt agaattgatg         50

<210> SEQ ID NO 7
<211> LENGTH: 50
<212> TYPE: DNA
<213> ORGANISM: Brucella phage Iz1

<400> SEQUENCE: 7
agcctctggc agtggtgacc ctgtaaatcc caattcccct acgatgggag         50

<210> SEQ ID NO 8
<211> LENGTH: 50
<212> TYPE: DNA
<213> ORGANISM: Brucella phage Iz1

<400> SEQUENCE: 8
attgaagctt agcactttaa cggaagcggg gcaatgttct atattttcga         50

<210> SEQ ID NO 9
<211> LENGTH: 50
<212> TYPE: DNA
<213> ORGANISM: Brucella phage Iz1

<400> SEQUENCE: 9
atcaatatgt gatgtttagc taactgcgtc tcagcaaaat attctgcttc         50

<210> SEQ ID NO 10
<211> LENGTH: 50
<212> TYPE: DNA
<213> ORGANISM: Brucella phage Iz1

<400> SEQUENCE: 10
ttcccaagtt caatgactgt ctcacaatat tctggtctgt ataaggttgg         50

<210> SEQ ID NO 11
<211> LENGTH: 50
<212> TYPE: DNA
<213> ORGANISM: Brucella phage Iz1

<400> SEQUENCE: 11
ggtctgtata aggttggacg accgccagcc ataactattc atattcctct         50

<210> SEQ ID NO 12
<211> LENGTH: 50
<212> TYPE: DNA
<213> ORGANISM: Brucella phage Iz1
```

```
<400> SEQUENCE: 12
tctgctactt catgaattgg catggtagac gccataaggt tgattgctca          50

<210> SEQ ID NO 13
<211> LENGTH: 50
<212> TYPE: DNA
<213> ORGANISM: Brucella phage Iz1

<400> SEQUENCE: 13
tagacgccat aaggttgatt gctcactcac agaaccacat agactgactt          50

<210> SEQ ID NO 14
<211> LENGTH: 50
<212> TYPE: DNA
<213> ORGANISM: Brucella phage Iz1

<400> SEQUENCE: 14
ctatcatacg ccttttgta cgaaatgctt attcccttat atccttcaca           50

<210> SEQ ID NO 15
<211> LENGTH: 50
<212> TYPE: DNA
<213> ORGANISM: Brucella phage Iz1

<400> SEQUENCE: 15
acttgtacgt atgatgttca cagtatcgcc ctttaaacct caaatgtcca          50

<210> SEQ ID NO 16
<211> LENGTH: 50
<212> TYPE: DNA
<213> ORGANISM: Brucella phage Iz1

<400> SEQUENCE: 16
aaccagcgtt aggattgaac ttagacattc gattcaccgg atcatttcta          50

<210> SEQ ID NO 17
<211> LENGTH: 50
<212> TYPE: DNA
<213> ORGANISM: Brucella phage Iz1

<400> SEQUENCE: 17
taaggtccct tttttgaat aactcacgct ttcgttttgt aagacctgat           50

<210> SEQ ID NO 18
<211> LENGTH: 50
<212> TYPE: DNA
<213> ORGANISM: Brucella phage Iz1

<400> SEQUENCE: 18
aataacaatt gtctggtcac tcacttccca tacctcccat agattgcgcc          50

<210> SEQ ID NO 19
<211> LENGTH: 50
<212> TYPE: DNA
<213> ORGANISM: Brucella phage Iz1

<400> SEQUENCE: 19
tctccacttc gttgttttga taacccacca tcccacacct tttatggcgt          50

<210> SEQ ID NO 20
<211> LENGTH: 50
<212> TYPE: DNA
<213> ORGANISM: Brucella phage Iz1
```

```
<400> SEQUENCE: 20
tgtcaacaca taattgtaag aaagatacaa cctgatacga aaaattccca          50

<210> SEQ ID NO 21
<211> LENGTH: 50
<212> TYPE: DNA
<213> ORGANISM: Brucella phage Iz1

<400> SEQUENCE: 21
tcccaaactt tgggatcgac taagtaattg aatttaaagc attatcccga          50

<210> SEQ ID NO 22
<211> LENGTH: 50
<212> TYPE: DNA
<213> ORGANISM: Brucella phage Iz1

<400> SEQUENCE: 22
tggtataagg ggagtgggtg taacagtggg tataagtcat ataattgcta          50

<210> SEQ ID NO 23
<211> LENGTH: 50
<212> TYPE: DNA
<213> ORGANISM: Brucella phage Iz1

<400> SEQUENCE: 23
gggatcaacc attgactgta aacattgtga cgggttgtac aaaatggaaa          50

<210> SEQ ID NO 24
<211> LENGTH: 50
<212> TYPE: DNA
<213> ORGANISM: Brucella phage Iz1

<400> SEQUENCE: 24
ttgactgtaa acattgtgac gggttgtaca aaatggaaaa atatttgact          50

<210> SEQ ID NO 25
<211> LENGTH: 50
<212> TYPE: DNA
<213> ORGANISM: Brucella phage Iz1

<400> SEQUENCE: 25
gtgacgggtt gtacaaaatg gaaaaatatt tgacttcatt ttaattcgta          50

<210> SEQ ID NO 26
<211> LENGTH: 50
<212> TYPE: DNA
<213> ORGANISM: Brucella phage Iz1

<400> SEQUENCE: 26
acaaaatgga aaaatatttg acttcatttt aattcgtact atgttaggcc          50

<210> SEQ ID NO 27
<211> LENGTH: 50
<212> TYPE: DNA
<213> ORGANISM: Brucella phage Iz1

<400> SEQUENCE: 27
atatttgact tcattttaat tcgtactatg ttaggcccat atgacaaaaa          50

<210> SEQ ID NO 28
<211> LENGTH: 50
<212> TYPE: DNA
<213> ORGANISM: Brucella phage Iz1
```

<400> SEQUENCE: 28
agggatatgc agattggaga ctgttttcgt ttggggttag ataatcccag    50

<210> SEQ ID NO 29
<211> LENGTH: 50
<212> TYPE: DNA
<213> ORGANISM: Brucella phage Iz1

<400> SEQUENCE: 29
acatatacaa gcctttgctg agaacaatca tcgtgttttt atgttggaaa    50

<210> SEQ ID NO 30
<211> LENGTH: 50
<212> TYPE: DNA
<213> ORGANISM: Brucella phage Iz1

<400> SEQUENCE: 30
aatcatcgtg tttttatgtt ggaaagcatt gatggtaatt attgtggttg    50

<210> SEQ ID NO 31
<211> LENGTH: 50
<212> TYPE: DNA
<213> ORGANISM: Brucella phage Iz1

<400> SEQUENCE: 31
ttgccagccg atgttaaaac ggttcagacg cataaagact ataagggcat    50

<210> SEQ ID NO 32
<211> LENGTH: 50
<212> TYPE: DNA
<213> ORGANISM: Brucella phage Iz1

<400> SEQUENCE: 32
gtagcgctgt gggatgaatg gagcagacgt agctctaaat acaatccaga    50

<210> SEQ ID NO 33
<211> LENGTH: 50
<212> TYPE: DNA
<213> ORGANISM: Brucella phage Iz1

<400> SEQUENCE: 33
aagattaagt ctgaacgtga aatgtatcaa aatctgatac atcatcaggc    50

<210> SEQ ID NO 34
<211> LENGTH: 50
<212> TYPE: DNA
<213> ORGANISM: Brucella phage Iz1

<400> SEQUENCE: 34
atgcgtgata agctggctta cttcgcgcaa aaggtagagg aaaatgagga    50

<210> SEQ ID NO 35
<211> LENGTH: 50
<212> TYPE: DNA
<213> ORGANISM: Brucella phage Iz1

<400> SEQUENCE: 35
gtctttgatt gggtttacca cacctacaca gctatcccgt atgatggtca    50

<210> SEQ ID NO 36
<211> LENGTH: 50
<212> TYPE: DNA
<213> ORGANISM: Brucella phage Iz1

```
<400> SEQUENCE: 36
gcaaaggaac ttattgaacg gtgtatcaat tggactgttg attataacca          50

<210> SEQ ID NO 37
<211> LENGTH: 50
<212> TYPE: DNA
<213> ORGANISM: Brucella phage Iz1

<400> SEQUENCE: 37
tgaacggtgt atcaattgga ctgttgatta taaccagagc aagattgaaa          50

<210> SEQ ID NO 38
<211> LENGTH: 50
<212> TYPE: DNA
<213> ORGANISM: Brucella phage Iz1

<400> SEQUENCE: 38
attctctggt ttgtatcgac gtgtgtgcga aaggcgatt aagattgccc            50

<210> SEQ ID NO 39
<211> LENGTH: 50
<212> TYPE: DNA
<213> ORGANISM: Brucella phage Iz1

<400> SEQUENCE: 39
gaggataaat cattttcgaa ggctgataag cttctggcgt ctatttacaa          50

<210> SEQ ID NO 40
<211> LENGTH: 50
<212> TYPE: DNA
<213> ORGANISM: Brucella phage Iz1

<400> SEQUENCE: 40
ggcaaacatt tgcgtggatt gcagcaagat caaatatatc aaaatacggg          50

<210> SEQ ID NO 41
<211> LENGTH: 50
<212> TYPE: DNA
<213> ORGANISM: Brucella phage Iz1

<400> SEQUENCE: 41
gaagtagaaa aggcattggc gcatatggtg gcacgtggtg atattcgtgt          50

<210> SEQ ID NO 42
<211> LENGTH: 50
<212> TYPE: DNA
<213> ORGANISM: Brucella phage Iz1

<400> SEQUENCE: 42
gcacgtggtg atattcgtgt ggaagaagat accaataaaa agaatcttga          50

<210> SEQ ID NO 43
<211> LENGTH: 50
<212> TYPE: DNA
<213> ORGANISM: Brucella phage Iz1

<400> SEQUENCE: 43
aaaaagaatc ttgaaatttt gaaaaggtat tatgtgagat aacctggaag          50

<210> SEQ ID NO 44
<211> LENGTH: 50
<212> TYPE: DNA
<213> ORGANISM: Brucella phage Iz1
```

```
<400> SEQUENCE: 44
accggggcgt taatgttaaa ggcgcattaa tatgcatagg ttaataaacg          50

<210> SEQ ID NO 45
<211> LENGTH: 50
<212> TYPE: DNA
<213> ORGANISM: Brucella phage Iz1

<400> SEQUENCE: 45
gatggttttc cctaccttga tacgactcag ggactggtaa atcatccctg          50

<210> SEQ ID NO 46
<211> LENGTH: 50
<212> TYPE: DNA
<213> ORGANISM: Brucella phage Iz1

<400> SEQUENCE: 46
atttttccct tttgttgaaa atctatgttg acaatacaat tgaatgatgc          50

<210> SEQ ID NO 47
<211> LENGTH: 50
<212> TYPE: DNA
<213> ORGANISM: Brucella phage Iz1

<400> SEQUENCE: 47
atgttgacaa tacaattgaa tgatgcgaaa agcaatacgt aaattgaaga          50

<210> SEQ ID NO 48
<211> LENGTH: 50
<212> TYPE: DNA
<213> ORGANISM: Brucella phage Iz1

<400> SEQUENCE: 48
aaagggtgca gagtatttgc ggtctgttcg tgggatgcat attgtgttca          50

<210> SEQ ID NO 49
<211> LENGTH: 50
<212> TYPE: DNA
<213> ORGANISM: Brucella phage Iz1

<400> SEQUENCE: 49
tgatgatgtt gacgtggttg gtttccttcg acaagcaact atcctacgtg          50

<210> SEQ ID NO 50
<211> LENGTH: 50
<212> TYPE: DNA
<213> ORGANISM: Brucella phage Iz1

<400> SEQUENCE: 50
tgcaggagta tttgtgatga gtaaagaaga tggagaaggg acaattttgc          50

<210> SEQ ID NO 51
<211> LENGTH: 50
<212> TYPE: DNA
<213> ORGANISM: Brucella phage Iz1

<400> SEQUENCE: 51
atgagtaaag aagatggaga agggacaatt ttgcgccaat ataccttta           50

<210> SEQ ID NO 52
<211> LENGTH: 50
<212> TYPE: DNA
<213> ORGANISM: Brucella phage Iz1
```

-continued

```
<400> SEQUENCE: 52
tacaatgcgc aagatgttga cgacactgta gcaaggttaa atagtaaaat            50

<210> SEQ ID NO 53
<211> LENGTH: 50
<212> TYPE: DNA
<213> ORGANISM: Brucella phage Iz1

<400> SEQUENCE: 53
aagcatgaga cctcattggg ctaagggata cacatcagat agcatggctg            50

<210> SEQ ID NO 54
<211> LENGTH: 50
<212> TYPE: DNA
<213> ORGANISM: Brucella phage Iz1

<400> SEQUENCE: 54
aacaagcgca agattttca gaaggtttgg tgctttgact atgaccccat             50

<210> SEQ ID NO 55
<211> LENGTH: 50
<212> TYPE: DNA
<213> ORGANISM: Brucella phage Iz1

<400> SEQUENCE: 55
attacaaaac aggtgatggc cgtaaggttg ggcctataaa atcatacgaa            50

<210> SEQ ID NO 56
<211> LENGTH: 50
<212> TYPE: DNA
<213> ORGANISM: Brucella phage Iz1

<400> SEQUENCE: 56
acgaagacag atattttcat aaggcaagtt ttgcgtgcag agaatggact            50

<210> SEQ ID NO 57
<211> LENGTH: 50
<212> TYPE: DNA
<213> ORGANISM: Brucella phage Iz1

<400> SEQUENCE: 57
cataaggcaa gttttgcgtg cagagaatgg acttatttag aaaatggtaa            50

<210> SEQ ID NO 58
<211> LENGTH: 50
<212> TYPE: DNA
<213> ORGANISM: Brucella phage Iz1

<400> SEQUENCE: 58
cagagaatgg acttatttag aaaatggtaa atgggctggt tcattaaata            50

<210> SEQ ID NO 59
<211> LENGTH: 50
<212> TYPE: DNA
<213> ORGANISM: Brucella phage Iz1

<400> SEQUENCE: 59
acgcgccgtg agattgtgga gggggtgtat gggagcgtag atatttatca            50

<210> SEQ ID NO 60
<211> LENGTH: 50
<212> TYPE: DNA
<213> ORGANISM: Brucella phage Iz1
```

-continued

<400> SEQUENCE: 60
cgtagatatt tatcatgtaa cgaaaaaata tgtatgcgtg aaaataaact                50

<210> SEQ ID NO 61
<211> LENGTH: 50
<212> TYPE: DNA
<213> ORGANISM: Brucella phage Iz1

<400> SEQUENCE: 61
acctgtttaa tcaattggcc gaagctctgg aggagaatgg aaaatgacct                50

<210> SEQ ID NO 62
<211> LENGTH: 50
<212> TYPE: DNA
<213> ORGANISM: Brucella phage Iz1

<400> SEQUENCE: 62
aacggcacta gacggttgga agggtcatgt tgcttgtatt gtgatgaatg                50

<210> SEQ ID NO 63
<211> LENGTH: 50
<212> TYPE: DNA
<213> ORGANISM: Brucella phage Iz1

<400> SEQUENCE: 63
gcttgtattg tgatgaatga catgaaatgg atggttcaag aaacttggag                50

<210> SEQ ID NO 64
<211> LENGTH: 50
<212> TYPE: DNA
<213> ORGANISM: Brucella phage Iz1

<400> SEQUENCE: 64
atggttcaag aaacttggag agagaaagag atgctccaag attttttttaa              50

<210> SEQ ID NO 65
<211> LENGTH: 50
<212> TYPE: DNA
<213> ORGANISM: Brucella phage Iz1

<400> SEQUENCE: 65
aaacgcgccc ttgttcttgg tgttaaactg ccaccggaac atatttggcc                50

<210> SEQ ID NO 66
<211> LENGTH: 50
<212> TYPE: DNA
<213> ORGANISM: Brucella phage Iz1

<400> SEQUENCE: 66
ccaccggaac atatttggcc gcgcaatctg aagccgtggg ataaccgtgt                50

<210> SEQ ID NO 67
<211> LENGTH: 50
<212> TYPE: DNA
<213> ORGANISM: Brucella phage Iz1

<400> SEQUENCE: 67
acgggagcac aagttcatta catgtggcag aatgggctgc atgatgaaat                50

<210> SEQ ID NO 68
<211> LENGTH: 50
<212> TYPE: DNA

```
<400> SEQUENCE: 68
atgagcggtt tcttgcgtgt aattggtaat atgatataat aaatttgcgc          50

<210> SEQ ID NO 69
<211> LENGTH: 50
<212> TYPE: DNA
<213> ORGANISM: Brucella phage Iz1

<400> SEQUENCE: 69
gtcaaaaggg atgatgtttg taaaagttgg aacacaagat atgctgggaa          50

<210> SEQ ID NO 70
<211> LENGTH: 50
<212> TYPE: DNA
<213> ORGANISM: Brucella phage Iz1

<400> SEQUENCE: 70
ctaaacggct acaaatatgg aaaaatttta gggaaaaatt attacgcgca          50

<210> SEQ ID NO 71
<211> LENGTH: 50
<212> TYPE: DNA
<213> ORGANISM: Brucella phage Iz1

<400> SEQUENCE: 71
caaatatgga aaaattttag ggaaaaatta ttacgcgcat agaattgcat          50

<210> SEQ ID NO 72
<211> LENGTH: 50
<212> TYPE: DNA
<213> ORGANISM: Brucella phage Iz1

<400> SEQUENCE: 72
gagatagacc atatagatgg aaacagaagc aataatattt acaataattt          50

<210> SEQ ID NO 73
<211> LENGTH: 50
<212> TYPE: DNA
<213> ORGANISM: Brucella phage Iz1

<400> SEQUENCE: 73
aacagaagca ataatattta caataattta agatctgttt ctcatcagaa          50

<210> SEQ ID NO 74
<211> LENGTH: 50
<212> TYPE: DNA
<213> ORGANISM: Brucella phage Iz1

<400> SEQUENCE: 74
taatatttac aataatttaa gatctgtttc tcatcagaac aatatgaaaa          50

<210> SEQ ID NO 75
<211> LENGTH: 50
<212> TYPE: DNA
<213> ORGANISM: Brucella phage Iz1

<400> SEQUENCE: 75
taatttaaga tctgtttctc atcagaacaa tatgaaaaat aaactatgc           50

<210> SEQ ID NO 76
<211> LENGTH: 50
<212> TYPE: DNA
<213> ORGANISM: Brucella phage Iz1
```

```
<400> SEQUENCE: 76
ggtgtagttg gagtgtattg gaatagatca agatgtaagt ggcatgcgca                50

<210> SEQ ID NO 77
<211> LENGTH: 50
<212> TYPE: DNA
<213> ORGANISM: Brucella phage Iz1

<400> SEQUENCE: 77
ggcatgcgca aattggagtt aatggtaaaa gccaccatat aggttacttt                50

<210> SEQ ID NO 78
<211> LENGTH: 50
<212> TYPE: DNA
<213> ORGANISM: Brucella phage Iz1

<400> SEQUENCE: 78
gccaccatat aggttacttt tcaaatatag atgacgctgt aaattcaaga                50

<210> SEQ ID NO 79
<211> LENGTH: 50
<212> TYPE: DNA
<213> ORGANISM: Brucella phage Iz1

<400> SEQUENCE: 79 gttactttc aaatatagat gacgctgtaa attcaagaaa aaatatgaa                  50

<210> SEQ ID NO 80
<211> LENGTH: 50
<212> TYPE: DNA
<213> ORGANISM: Brucella phage Iz1

<400> SEQUENCE: 80
aattcaagaa aaaatatga agatatttt ggttatcata aaaatcacgg                  50

<210> SEQ ID NO 81
<211> LENGTH: 50
<212> TYPE: DNA
<213> ORGANISM: Brucella phage Iz1

<400> SEQUENCE: 81
cgagcaaagt tcattgccac tggctatcct gccagcatgt atagtgcaag                50

<210> SEQ ID NO 82
<211> LENGTH: 50
<212> TYPE: DNA
<213> ORGANISM: Brucella phage Iz1

<400> SEQUENCE: 82
gcatcatgtg gttttggta ctccattgac cattaaatct aacatcaagg                 50

<210> SEQ ID NO 83
<211> LENGTH: 50
<212> TYPE: DNA
<213> ORGANISM: Brucella phage Iz1

<400> SEQUENCE: 83
ggacggataa acgacgattc acagtcgttg aacccgtttt accataaatg                50

<210> SEQ ID NO 84
<211> LENGTH: 50
<212> TYPE: DNA
<213> ORGANISM: Brucella phage Iz1
```

-continued

<400> SEQUENCE: 84
aagcgcaata attacgggtg atacaaaaga tcgtaaagcg atattggata         50

<210> SEQ ID NO 85
<211> LENGTH: 50
<212> TYPE: DNA
<213> ORGANISM: Brucella phage Iz1

<400> SEQUENCE: 85
atcgtaaagc gatattggat aaggtatcgc ggggtaaaat aaaatatgtg         50

<210> SEQ ID NO 86
<211> LENGTH: 50
<212> TYPE: DNA
<213> ORGANISM: Brucella phage Iz1

<400> SEQUENCE: 86
ggttaacgta ggtgttttga cggtaggtgt ggaccttcct attgtcgata         50

<210> SEQ ID NO 87
<211> LENGTH: 50
<212> TYPE: DNA
<213> ORGANISM: Brucella phage Iz1

<400> SEQUENCE: 87
agacgaaaac ggatattgcc tggatgtgtt tggcaaccag atcatgacag         50

<210> SEQ ID NO 88
<211> LENGTH: 50
<212> TYPE: DNA
<213> ORGANISM: Brucella phage Iz1

<400> SEQUENCE: 88
gctggcaatg ctattttgcg tgtggattgg gtaacacctt atcgtgcttt         50

<210> SEQ ID NO 89
<211> LENGTH: 50
<212> TYPE: DNA
<213> ORGANISM: Brucella phage Iz1

<400> SEQUENCE: 89
gcataaagct gaaggcatga cgaagggcgc tccagattgc atagtccccg         50

<210> SEQ ID NO 90
<211> LENGTH: 50
<212> TYPE: DNA
<213> ORGANISM: Brucella phage Iz1

<400> SEQUENCE: 90
cgtgggaggc gtttcaaacc tatgtggaga agtattatgg aaattcgtga         50

<210> SEQ ID NO 91
<211> LENGTH: 50
<212> TYPE: DNA
<213> ORGANISM: Brucella phage Iz1

<400> SEQUENCE: 91
cgtttcaaac ctatgtggag aagtattatg gaaattcgtg atattttgaa         50

<210> SEQ ID NO 92
<211> LENGTH: 50
<212> TYPE: DNA
<213> ORGANISM: Brucella phage Iz1

```
<400> SEQUENCE: 92
attttgaatg agcgtgagaa gacccatggt gactataggt ctcatgcagc              50

<210> SEQ ID NO 93
<211> LENGTH: 50
<212> TYPE: DNA
<213> ORGANISM: Brucella phage Iz1

<400> SEQUENCE: 93
gcgtgagaag acccatggtg actataggtc tcatgcagct atcacgcaag              50

<210> SEQ ID NO 94
<211> LENGTH: 50
<212> TYPE: DNA
<213> ORGANISM: Brucella phage Iz1

<400> SEQUENCE: 94
catatgatgc agttttttgac atatctgtgc aaatgcaaat agaaggatat             50

<210> SEQ ID NO 95
<211> LENGTH: 50
<212> TYPE: DNA
<213> ORGANISM: Brucella phage Iz1

<400> SEQUENCE: 95
atgcaaatag aaggatatga gaagtatgca agaccaggag agaatagtcg              50

<210> SEQ ID NO 96
<211> LENGTH: 50
<212> TYPE: DNA
<213> ORGANISM: Brucella phage Iz1

<400> SEQUENCE: 96
gacatacagg aatatgtttt cacaaaagga ctttgaggat gtcatgtggg              50

<210> SEQ ID NO 97
<211> LENGTH: 50
<212> TYPE: DNA
<213> ORGANISM: Brucella phage Iz1

<400> SEQUENCE: 97
tgtaattgtg attatgtgga gataaatcat gacaacagtt ccaatcatag              50

<210> SEQ ID NO 98
<211> LENGTH: 50
<212> TYPE: DNA
<213> ORGANISM: Brucella phage Iz1

<400> SEQUENCE: 98
ttatgtggag ataaatcatg acaacagttc caatcatagc aaaatcactc              50

<210> SEQ ID NO 99
<211> LENGTH: 50
<212> TYPE: DNA
<213> ORGANISM: Brucella phage Iz1

<400> SEQUENCE: 99
ccgtgcaagg ggctgtgaag aagctggagt gggaactggt atcaggcgac              50

<210> SEQ ID NO 100
<211> LENGTH: 50
<212> TYPE: DNA
<213> ORGANISM: Brucella phage Iz1
```

```
<400> SEQUENCE: 100
gctgtgaaga agctggagtg ggaactggta tcaggcgacc attatgcgga                50

<210> SEQ ID NO 101
<211> LENGTH: 50
<212> TYPE: DNA
<213> ORGANISM: Brucella phage Iz1

<400> SEQUENCE: 101
ccagcgcagt tgttcttggg aatatcaagg atttccgcgt ggaatggata                50

<210> SEQ ID NO 102
<211> LENGTH: 50
<212> TYPE: DNA
<213> ORGANISM: Brucella phage Iz1

<400> SEQUENCE: 102
gggtcaagac tgttgtcaac tacgacagtc aaccagaagc atattctgga                50

<210> SEQ ID NO 103
<211> LENGTH: 50
<212> TYPE: DNA
<213> ORGANISM: Brucella phage Iz1

<400> SEQUENCE: 103
gtgggctacg gctatgtgaa tagccttggc gagttagaat atgctcacgc                50

<210> SEQ ID NO 104
<211> LENGTH: 50
<212> TYPE: DNA
<213> ORGANISM: Brucella phage Iz1

<400> SEQUENCE: 104
caggtcgagg agctattggc ggcggaacgg gcggatcatg ataatacaat                50

<210> SEQ ID NO 105
<211> LENGTH: 50
<212> TYPE: DNA
<213> ORGANISM: Brucella phage Iz1

<400> SEQUENCE: 105
tcgtaacgat cctcattttg gcaggagagt ttctgatgct gtcatggagg                50

<210> SEQ ID NO 106
<211> LENGTH: 50
<212> TYPE: DNA
<213> ORGANISM: Brucella phage Iz1

<400> SEQUENCE: 106
gatggggagc agagcgaatg aagctgacat tcgagaagat attctccatc                50

<210> SEQ ID NO 107
<211> LENGTH: 50
<212> TYPE: DNA
<213> ORGANISM: Brucella phage Iz1

<400> SEQUENCE: 107
ttctccatct acttggcgtt agcggtacta actttcggtt atattgcatc                50

<210> SEQ ID NO 108
<211> LENGTH: 50
<212> TYPE: DNA
<213> ORGANISM: Brucella phage Iz1
```

-continued

<400> SEQUENCE: 108
tgggaaagtg agtgaggatg aaagaagagt tggcatatat agcatcaaca    50

<210> SEQ ID NO 109
<211> LENGTH: 50
<212> TYPE: DNA
<213> ORGANISM: Brucella phage Iz1

<400> SEQUENCE: 109
ctgagtagtg aggcggttga tatcccgcct cattaaatcc atacttgaaa    50

<210> SEQ ID NO 110
<211> LENGTH: 50
<212> TYPE: DNA
<213> ORGANISM: Brucella phage Iz1

<400> SEQUENCE: 110
taactctgca ttctcctttg aaagggagga tatgctcttt tgaatgtcat    50

<210> SEQ ID NO 111
<211> LENGTH: 50
<212> TYPE: DNA
<213> ORGANISM: Brucella phage Iz1

<400> SEQUENCE: 111
gggaggatat gctcttttga atgtcattaa gattggttcc aacataaaac    50

<210> SEQ ID NO 112
<211> LENGTH: 50
<212> TYPE: DNA
<213> ORGANISM: Brucella phage Iz1

<400> SEQUENCE: 112
aatgtcatta agattggttc aacataaaa cccaaaccct acaattgtta    50

<210> SEQ ID NO 113
<211> LENGTH: 50
<212> TYPE: DNA
<213> ORGANISM: Brucella phage Iz1

<400> SEQUENCE: 113
cagcgtcaac ttttttgacca tctttaatta cctctactct atcgttagat    50

<210> SEQ ID NO 114
<211> LENGTH: 50
<212> TYPE: DNA
<213> ORGANISM: Brucella phage Iz1

<400> SEQUENCE: 114
agcatcgttc aactcctgac gaatgtcttt tattgctttt acaatccagc    50

<210> SEQ ID NO 115
<211> LENGTH: 50
<212> TYPE: DNA
<213> ORGANISM: Brucella phage Iz1

<400> SEQUENCE: 115
aagggcgctc aggagttggc ttcgatgaaa gacccaatgc aaaatcacga    50

<210> SEQ ID NO 116
<211> LENGTH: 50
<212> TYPE: DNA
<213> ORGANISM: Brucella phage Iz1

```
<400> SEQUENCE: 116
gtgtatcaca aagcttgttg atgacattgc gagaacccat agacttgata        50

<210> SEQ ID NO 117
<211> LENGTH: 50
<212> TYPE: DNA
<213> ORGANISM: Brucella phage Iz1

<400> SEQUENCE: 117
ttttgtccct tttggattca caaaggcgcg gaaagtagca atagttacgc        50

<210> SEQ ID NO 118
<211> LENGTH: 50
<212> TYPE: DNA
<213> ORGANISM: Brucella phage Iz1

<400> SEQUENCE: 118
atcctccctc atgcttcaaa acctctttga gtgatacttt aaaattacga        50

<210> SEQ ID NO 119
<211> LENGTH: 50
<212> TYPE: DNA
<213> ORGANISM: Brucella phage Iz1

<400> SEQUENCE: 119
ttctcagtgg gagtattgca ggcgggaggc ctttagggcg aatatcaacc        50

<210> SEQ ID NO 120
<211> LENGTH: 50
<212> TYPE: DNA
<213> ORGANISM: Brucella phage Iz1

<400> SEQUENCE: 120
taggatgatt atgagttgaa atggtatat tttcatttgt aaaacctact         50

<210> SEQ ID NO 121
<211> LENGTH: 50
<212> TYPE: DNA
<213> ORGANISM: Brucella phage Iz1

<400> SEQUENCE: 121
aaatggtata ttttcatttg taaaacctac ttgaccattt ctactcaaac        50

<210> SEQ ID NO 122
<211> LENGTH: 50
<212> TYPE: DNA
<213> ORGANISM: Brucella phage Iz1

<400> SEQUENCE: 122
ttcatttgta aaacctactt gaccatttct actcaaactt aaattaccag        50

<210> SEQ ID NO 123
<211> LENGTH: 50
<212> TYPE: DNA
<213> ORGANISM: Brucella phage Iz1

<400> SEQUENCE: 123
atttctactc aaacttaaat taccagttaa gttcttgagt acatttagta        50

<210> SEQ ID NO 124
<211> LENGTH: 50
<212> TYPE: DNA
<213> ORGANISM: Brucella phage Iz1
```

```
<400> SEQUENCE: 124
gccaccgtgg tcatgattgg gaatttgata tattgttagt gtactatttt            50

<210> SEQ ID NO 125
<211> LENGTH: 50
<212> TYPE: DNA
<213> ORGANISM: Brucella phage Iz1

<400> SEQUENCE: 125
gccgttgctg tctcttggca tgttagttac cacctatatt agattgcgct            50

<210> SEQ ID NO 126
<211> LENGTH: 50
<212> TYPE: DNA
<213> ORGANISM: Brucella phage Iz1

<400> SEQUENCE: 126
taataacctg catttgtgtt gggttcatat catacccggc ataatcgcgc            50

<210> SEQ ID NO 127
<211> LENGTH: 50
<212> TYPE: DNA
<213> ORGANISM: Brucella phage Iz1

<400> SEQUENCE: 127
ggttatcagc tggttgacgt cattagaggc tgtaccacct atcttgctta            50

<210> SEQ ID NO 128
<211> LENGTH: 50
<212> TYPE: DNA
<213> ORGANISM: Brucella phage Iz1

<400> SEQUENCE: 128
ttcccttttc aaatgcttca cgttctctct gggccttaat aaagtccgga            50

<210> SEQ ID NO 129
<211> LENGTH: 50
<212> TYPE: DNA
<213> ORGANISM: Brucella phage Iz1

<400> SEQUENCE: 129
ctgcaaaaga cccttggaaa ccattgtttc tagcgtattc ataattctga            50

<210> SEQ ID NO 130
<211> LENGTH: 50
<212> TYPE: DNA
<213> ORGANISM: Brucella phage Iz1

<400> SEQUENCE: 130
gaaatataag ggctggaaag agcctgaata ataacagggt taattccgcc            50

<210> SEQ ID NO 131
<211> LENGTH: 50
<212> TYPE: DNA
<213> ORGANISM: Brucella phage Iz1

<400> SEQUENCE: 131
caattgggtt tttctcattg atgcctggat tcagaccgct ctcatcctga            50

<210> SEQ ID NO 132
<211> LENGTH: 50
<212> TYPE: DNA
<213> ORGANISM: Brucella phage Iz1
```

```
<400> SEQUENCE: 132
gcctattgct tgttttttta cgtctgggat atttgattgc atcatattct            50

<210> SEQ ID NO 133
<211> LENGTH: 50
<212> TYPE: DNA
<213> ORGANISM: Brucella phage Iz1

<400> SEQUENCE: 133
tcatggcact agatggatta gcggatgcaa atggtgagat attgttcatg            50

<210> SEQ ID NO 134
<211> LENGTH: 50
<212> TYPE: DNA
<213> ORGANISM: Brucella phage Iz1

<400> SEQUENCE: 134
gctgataagc atttggatta tttgacattc tattgccaag attattataa            50

<210> SEQ ID NO 135
<211> LENGTH: 50
<212> TYPE: DNA
<213> ORGANISM: Brucella phage Iz1

<400> SEQUENCE: 135
attatttgac attctattgc caagattatt ataaccgctt agattatttg            50

<210> SEQ ID NO 136
<211> LENGTH: 50
<212> TYPE: DNA
<213> ORGANISM: Brucella phage Iz1

<400> SEQUENCE: 136
ggcctgaatc caaaattaaa cagcatcact tcaccttgct ataatcaaca            50

<210> SEQ ID NO 137
<211> LENGTH: 50
<212> TYPE: DNA
<213> ORGANISM: Brucella phage Iz1

<400> SEQUENCE: 137
cgcgaatgtg ctattgggtg actgaacctg agtaccagac ataagcccaa            50

<210> SEQ ID NO 138
<211> LENGTH: 50
<212> TYPE: DNA
<213> ORGANISM: Brucella phage Iz1

<400> SEQUENCE: 138
gcgattctca aggtctttgc ggttctgctc ctgctgcggc ataatgcgag            50

<210> SEQ ID NO 139
<211> LENGTH: 50
<212> TYPE: DNA
<213> ORGANISM: Brucella phage Iz1

<400> SEQUENCE: 139
tttcagcatc ctgattgtta aactcaaacg gagaactaag gtaatcacca            50

<210> SEQ ID NO 140
<211> LENGTH: 50
<212> TYPE: DNA
<213> ORGANISM: Brucella phage Iz1
```

-continued

<400> SEQUENCE: 140
tcgtaccagt ctgttgataa tccaagatac cccatggggt attctggttt          50

<210> SEQ ID NO 141
<211> LENGTH: 50
<212> TYPE: DNA
<213> ORGANISM: Brucella phage Iz1

<400> SEQUENCE: 141
ggtttaccat gttcatttgc tgctgctgct gggccgtgaa agaattccac          50

<210> SEQ ID NO 142
<211> LENGTH: 50
<212> TYPE: DNA
<213> ORGANISM: Brucella phage Iz1

<400> SEQUENCE: 142
gcttcaggag cgctcttgcc cattactcag aaactcccctt attataaggc          50

<210> SEQ ID NO 143
<211> LENGTH: 50
<212> TYPE: DNA
<213> ORGANISM: Brucella phage Iz1

<400> SEQUENCE: 143
cggaagggtt cattgtcttg ctgtaataca ttgtatggat caagttacaa          50

<210> SEQ ID NO 144
<211> LENGTH: 50
<212> TYPE: DNA
<213> ORGANISM: Brucella phage Iz1

<400> SEQUENCE: 144
ccgttcctcc taatgatttc cactgtgcat tgaaaacatt aggattggtt          50

<210> SEQ ID NO 145
<211> LENGTH: 50
<212> TYPE: DNA
<213> ORGANISM: Brucella phage Iz1

<400> SEQUENCE: 145
ccgcgctcga tgccgttgga gcagagcccg gatcaatatc aaaatcagcc          50

<210> SEQ ID NO 146
<211> LENGTH: 50
<212> TYPE: DNA
<213> ORGANISM: Brucella phage Iz1

<400> SEQUENCE: 146
ggcccatctt agggatttta agattggctg gcgatccaag atcatcaaac          50

<210> SEQ ID NO 147
<211> LENGTH: 50
<212> TYPE: DNA
<213> ORGANISM: Brucella phage Iz1

<400> SEQUENCE: 147
ctgttacatt ggctttgaac acttcaccgt tagggccacc aaaatacatc          50

<210> SEQ ID NO 148
<211> LENGTH: 50
<212> TYPE: DNA
<213> ORGANISM: Brucella phage Iz1

<400> SEQUENCE: 148
atgcacctgt tcagaattg gaaataaaca aaactggatc ataatcaccg					50

<210> SEQ ID NO 149
<211> LENGTH: 50
<212> TYPE: DNA
<213> ORGANISM: Brucella phage Iz1

<400> SEQUENCE: 149
ggccaattct gtatgtgcca acatgcgacc agtcgcctgt agcttctggg					50

<210> SEQ ID NO 150
<211> LENGTH: 50
<212> TYPE: DNA
<213> ORGANISM: Brucella phage Iz1

<400> SEQUENCE: 150
taaatgaagc ctgtagacgc tccgttaacg ccaataaggt atattccgcc					50

<210> SEQ ID NO 151
<211> LENGTH: 50
<212> TYPE: DNA
<213> ORGANISM: Brucella phage Iz1

<400> SEQUENCE: 151
gctgatcaag ggccattgta aattgttctt ggtcgcctgt atagtctaac					50

<210> SEQ ID NO 152
<211> LENGTH: 50
<212> TYPE: DNA
<213> ORGANISM: Brucella phage Iz1

<400> SEQUENCE: 152
caagagcgta attattggaa atgtaaggat acgtggcgct attctgagca					50

<210> SEQ ID NO 153
<211> LENGTH: 50
<212> TYPE: DNA
<213> ORGANISM: Brucella phage Iz1

<400> SEQUENCE: 153
ttggcccacc aatctaattg tagcggattg catcgctgac agaattgaca					50

<210> SEQ ID NO 154
<211> LENGTH: 50
<212> TYPE: DNA
<213> ORGANISM: Brucella phage Iz1

<400> SEQUENCE: 154
ctgcataggt aatagatttg ttgccttcgc gtttccacgt ctgatgagcc					50

<210> SEQ ID NO 155
<211> LENGTH: 50
<212> TYPE: DNA
<213> ORGANISM: Brucella phage Iz1

<400> SEQUENCE: 155
agcctcccca tattgattag agcgcataca ctcgcgcatg aaaataagca					50

<210> SEQ ID NO 156
<211> LENGTH: 50
<212> TYPE: DNA
<213> ORGANISM: Brucella phage Iz1

<400> SEQUENCE: 156
ctgtcaggtc ccaatatgga agaccgacaa aaacgtcatt aagctgcggg    50

<210> SEQ ID NO 157
<211> LENGTH: 50
<212> TYPE: DNA
<213> ORGANISM: Brucella phage Iz1

<400> SEQUENCE: 157
accgcatcct ggttgatagg acgcataccg tcccccgggt ggaatggtac    50

<210> SEQ ID NO 158
<211> LENGTH: 50
<212> TYPE: DNA
<213> ORGANISM: Brucella phage Iz1

<400> SEQUENCE: 158
cagtgtttgg aatgactgga atagcgccac caaggccgat aagctcacga    50

<210> SEQ ID NO 159
<211> LENGTH: 50
<212> TYPE: DNA
<213> ORGANISM: Brucella phage Iz1

<400> SEQUENCE: 159
gccaccagcg cgctttacgc gaatacggcc ctgatcacgc agaatgcggg    50

<210> SEQ ID NO 160
<211> LENGTH: 50
<212> TYPE: DNA
<213> ORGANISM: Brucella phage Iz1

<400> SEQUENCE: 160
ttcttatccg gttctttgac ctctagtaca ttccccggag aagatttgat    50

<210> SEQ ID NO 161
<211> LENGTH: 50
<212> TYPE: DNA
<213> ORGANISM: Brucella phage Iz1

<400> SEQUENCE: 161
taagattagc tgggatttta ccagattgta gaaagaaagc aatatcctgt    50

<210> SEQ ID NO 162
<211> LENGTH: 50
<212> TYPE: DNA
<213> ORGANISM: Brucella phage Iz1

<400> SEQUENCE: 162
gggattttac cagattgtag aaagaaagca atatcctgtt ctagttcata    50

<210> SEQ ID NO 163
<211> LENGTH: 50
<212> TYPE: DNA
<213> ORGANISM: Brucella phage Iz1

<400> SEQUENCE: 163
gagcaagctg ctgtggagta acattgaaag cgcgcaaaat atgagaaata    50

<210> SEQ ID NO 164
<211> LENGTH: 50
<212> TYPE: DNA
<213> ORGANISM: Brucella phage Iz1

```
<400> SEQUENCE: 164
gctgtggagt aacattgaaa gcgcgcaaaa tatgagaaat agcctgttgt              50

<210> SEQ ID NO 165
<211> LENGTH: 50
<212> TYPE: DNA
<213> ORGANISM: Brucella phage Iz1

<400> SEQUENCE: 165
gaaagcgcgc aaaatatgag aaatagcctg ttgtggctgc atattcagat              50

<210> SEQ ID NO 166
<211> LENGTH: 50
<212> TYPE: DNA
<213> ORGANISM: Brucella phage Iz1

<400> SEQUENCE: 166
cagccttaac aggttttca acctttccg gctctttagt cttatcaagc                50

<210> SEQ ID NO 167
<211> LENGTH: 50
<212> TYPE: DNA
<213> ORGANISM: Brucella phage Iz1

<400> SEQUENCE: 167
gggaacttcc ggcttggctt cttcaacagg aggaggagtt attttaccac              50

<210> SEQ ID NO 168
<211> LENGTH: 50
<212> TYPE: DNA
<213> ORGANISM: Brucella phage Iz1

<400> SEQUENCE: 168
ctgtgactgg tgatggttga attacttcgt cggtcatttt atacctcgtc              50

<210> SEQ ID NO 169
<211> LENGTH: 50
<212> TYPE: DNA
<213> ORGANISM: Brucella phage Iz1

<400> SEQUENCE: 169
accgttcgcc ctttgggttt ccagagggga gaagcgtctt acgatagctt              50

<210> SEQ ID NO 170
<211> LENGTH: 50
<212> TYPE: DNA
<213> ORGANISM: Brucella phage Iz1

<400> SEQUENCE: 170
atcactccac ctctctttgt gtcaacgctt gagtttcatt aaactcttgc              50

<210> SEQ ID NO 171
<211> LENGTH: 50
<212> TYPE: DNA
<213> ORGANISM: Brucella phage Iz1

<400> SEQUENCE: 171
tgctatcaga cgcgatttca aaagcaaaac cacgcgattt atcattgcgc              50

<210> SEQ ID NO 172
<211> LENGTH: 50
<212> TYPE: DNA
<213> ORGANISM: Brucella phage Iz1
```

<400> SEQUENCE: 172
caaaaccacg cgatttatca ttgcgcaaaa ggtcaatgat atcctcgata                  50

<210> SEQ ID NO 173
<211> LENGTH: 50
<212> TYPE: DNA
<213> ORGANISM: Brucella phage Iz1

<400> SEQUENCE: 173
cgataggaat ttctgaatta gcctcttgca gcataggcgc atatttctgc                  50

<210> SEQ ID NO 174
<211> LENGTH: 50
<212> TYPE: DNA
<213> ORGANISM: Brucella phage Iz1

<400> SEQUENCE: 174
ttctgaatta gcctcttgca gcataggcgc atatttctgc aaaatggcct                  50

<210> SEQ ID NO 175
<211> LENGTH: 50
<212> TYPE: DNA
<213> ORGANISM: Brucella phage Iz1

<400> SEQUENCE: 175
ctgtttctta aggttttcaa gctccttctc agcagcttct tcaatgcctt                  50

<210> SEQ ID NO 176
<211> LENGTH: 50
<212> TYPE: DNA
<213> ORGANISM: Brucella phage Iz1

<400> SEQUENCE: 176
cttttgtaga gattttcatc tgagacattt caaggagagt atcctttgaa                  50

<210> SEQ ID NO 177
<211> LENGTH: 50
<212> TYPE: DNA
<213> ORGANISM: Brucella phage Iz1

<400> SEQUENCE: 177
tcagcgtgtt aatcttgtca aaatgaacgc tataacgctc atagtctgga                  50

<210> SEQ ID NO 178
<211> LENGTH: 50
<212> TYPE: DNA
<213> ORGANISM: Brucella phage Iz1

<400> SEQUENCE: 178
cttcgtcttc acgcttttg gaaagtttta cgtctttgta aacatcgccg                   50

<210> SEQ ID NO 179
<211> LENGTH: 50
<212> TYPE: DNA
<213> ORGANISM: Brucella phage Iz1

<400> SEQUENCE: 179
gaaagtttta cgtctttgta aacatcgccg gatgccttat agaaacgctt                  50

<210> SEQ ID NO 180
<211> LENGTH: 50
<212> TYPE: DNA
<213> ORGANISM: Brucella phage Iz1

<400> SEQUENCE: 180
ataaacagca ggctttagaa tttcatagga agcccagaat agatcaagct                50

<210> SEQ ID NO 181
<211> LENGTH: 50
<212> TYPE: DNA
<213> ORGANISM: Brucella phage Iz1

<400> SEQUENCE: 181
catctgtcca attttcactg tatggacgct tttcaccctg atatttgctg                50

<210> SEQ ID NO 182
<211> LENGTH: 50
<212> TYPE: DNA
<213> ORGANISM: Brucella phage Iz1

<400> SEQUENCE: 182
catgccccag cgggatttga acccgcgtca ccatttggtg aatatccctt                50

<210> SEQ ID NO 183
<211> LENGTH: 50
<212> TYPE: DNA
<213> ORGANISM: Brucella phage Iz1

<400> SEQUENCE: 183
gtaggatttg tgtgagttgg cattggagca aatgtcgtct aaatccaccc                50

<210> SEQ ID NO 184
<211> LENGTH: 50
<212> TYPE: DNA
<213> ORGANISM: Brucella phage Iz1

<400> SEQUENCE: 184
tcagcggtat cctttgtgag gataccgggc gaaaggtcat aagatgacca                50

<210> SEQ ID NO 185
<211> LENGTH: 50
<212> TYPE: DNA
<213> ORGANISM: Brucella phage Iz1

<400> SEQUENCE: 185
acgacaattg gtcatcttat gacctttcgc ccggtatcct cacaaaggat                50

<210> SEQ ID NO 186
<211> LENGTH: 50
<212> TYPE: DNA
<213> ORGANISM: Brucella phage Iz1

<400> SEQUENCE: 186
aattaaagat ttagaccagt gggtggattt agacgacatt tgctccaatg                50

<210> SEQ ID NO 187
<211> LENGTH: 50
<212> TYPE: DNA
<213> ORGANISM: Brucella phage Iz1

<400> SEQUENCE: 187
gaaagacagc cttgtaatta ggccgggttc ggagtaggat ataggaatgc                50

<210> SEQ ID NO 188
<211> LENGTH: 50
<212> TYPE: DNA
<213> ORGANISM: Brucella phage Iz1

```
<400> SEQUENCE: 188
ccgggtagcg tgagacatga gggctacgag aagggatatt caccaaatgg            50

<210> SEQ ID NO 189
<211> LENGTH: 50
<212> TYPE: DNA
<213> ORGANISM: Brucella phage Iz1

<400> SEQUENCE: 189
tacagtgaaa attggacaga tggtgagctt gatctattct gggcttccta            50

<210> SEQ ID NO 190
<211> LENGTH: 50
<212> TYPE: DNA
<213> ORGANISM: Brucella phage Iz1

<400> SEQUENCE: 190
agacggctga attgttagag cgcgtatctg tgtctaactt tgaccgctct            50

<210> SEQ ID NO 191
<211> LENGTH: 50
<212> TYPE: DNA
<213> ORGANISM: Brucella phage Iz1

<400> SEQUENCE: 191
ctgtgtctaa ctttgaccgc tctaacattg acgatgttat gtgcgaggtc            50

<210> SEQ ID NO 192
<211> LENGTH: 50
<212> TYPE: DNA
<213> ORGANISM: Brucella phage Iz1

<400> SEQUENCE: 192
gcagcgtttg ggaagtctgg catcgcgctg ataataaggt ttattgggtt            50

<210> SEQ ID NO 193
<211> LENGTH: 50
<212> TYPE: DNA
<213> ORGANISM: Brucella phage Iz1

<400> SEQUENCE: 193
cgcctactgg atgaaggtga gccacacctg aagctaaaag acttcttccc            50

<210> SEQ ID NO 194
<211> LENGTH: 50
<212> TYPE: DNA
<213> ORGANISM: Brucella phage Iz1

<400> SEQUENCE: 194
tttacctttt gctggaaaag gttaagctca agggcattgt ggccggtagc            50

<210> SEQ ID NO 195
<211> LENGTH: 50
<212> TYPE: DNA
<213> ORGANISM: Brucella phage Iz1

<400> SEQUENCE: 195
caaagctaat tgatgacttc tatcagttgt ctggtattag cgacattatg            50

<210> SEQ ID NO 196
<211> LENGTH: 50
<212> TYPE: DNA
<213> ORGANISM: Brucella phage Iz1
```

<400> SEQUENCE: 196
gtggttttgc ttttgaaatc gcgtctgata gcactatttt gactgatgaa        50

<210> SEQ ID NO 197
<211> LENGTH: 50
<212> TYPE: DNA
<213> ORGANISM: Brucella phage Iz1

<400> SEQUENCE: 197
aagagaggtg gagtgatgcc taaatcaact tatgcaatat gtggtgcaat        50

<210> SEQ ID NO 198
<211> LENGTH: 50
<212> TYPE: DNA
<213> ORGANISM: Brucella phage Iz1

<400> SEQUENCE: 198
actagccacg tttctgacgc attgctttt ggaggattat ctcaatttgc         50

<210> SEQ ID NO 199
<211> LENGTH: 50
<212> TYPE: DNA
<213> ORGANISM: Brucella phage Iz1

<400> SEQUENCE: 199 attgctttt ggaggattat ctcaatttgc cgcgcaagat gactggaaat         50

<210> SEQ ID NO 200
<211> LENGTH: 50
<212> TYPE: DNA
<213> ORGANISM: Brucella phage Iz1

<400> SEQUENCE: 200
attatctcaa tttgccgcgc aagatgactg gaaatactct tggatatcag        50

<210> SEQ ID NO 201
<211> LENGTH: 50
<212> TYPE: DNA
<213> ORGANISM: Brucella phage Iz1

<400> SEQUENCE: 201
gaaatactct tggatatcag caagggcttt atcatatatc gccattggtt        50

<210> SEQ ID NO 202
<211> LENGTH: 50
<212> TYPE: DNA
<213> ORGANISM: Brucella phage Iz1

<400> SEQUENCE: 202
gcgtggggtg tttagatgcc cggatttcca gttgtaattt ctgataacgg        50

<210> SEQ ID NO 203
<211> LENGTH: 50
<212> TYPE: DNA
<213> ORGANISM: Brucella phage Iz1

<400> SEQUENCE: 203
gttgcaacta atggacttgg tattccgatt agtgtagtat ccagcaatgc        50

<210> SEQ ID NO 204
<211> LENGTH: 50
<212> TYPE: DNA
<213> ORGANISM: Brucella phage Iz1

```
<400> SEQUENCE: 204
gttccagaac ttgctaaaga agttcgtagc cagattgaat catcttcggg              50

<210> SEQ ID NO 205
<211> LENGTH: 50
<212> TYPE: DNA
<213> ORGANISM: Brucella phage Iz1

<400> SEQUENCE: 205
gtagccagat tgaatcatct tcggggggc gcagtatcgt gggatgatgt               50

<210> SEQ ID NO 206
<211> LENGTH: 50
<212> TYPE: DNA
<213> ORGANISM: Brucella phage Iz1

<400> SEQUENCE: 206
ttaatgctat cctggcagca cttcgcacag cagggatcat tgcgacgtaa              50

<210> SEQ ID NO 207
<211> LENGTH: 50
<212> TYPE: DNA
<213> ORGANISM: Brucella phage Iz1

<400> SEQUENCE: 207
gcttctcccc tctggaaacc caaagggcga acggtatatc gagcttggca              50

<210> SEQ ID NO 208
<211> LENGTH: 50
<212> TYPE: DNA
<213> ORGANISM: Brucella phage Iz1

<400> SEQUENCE: 208
tagaacagga tattgctttc tttctacaat ctggtaaaat cccagctaat              50

<210> SEQ ID NO 209
<211> LENGTH: 50
<212> TYPE: DNA
<213> ORGANISM: Brucella phage Iz1

<400> SEQUENCE: 209
cagcatgttc tctctgactg gcacagaact gatgtacact cgcggtgagg              50

<210> SEQ ID NO 210
<211> LENGTH: 50
<212> TYPE: DNA
<213> ORGANISM: Brucella phage Iz1

<400> SEQUENCE: 210
gctttacgac ttgggatagc acgactgcac gtcctattat tgagcgcatt              50

<210> SEQ ID NO 211
<211> LENGTH: 50
<212> TYPE: DNA
<213> ORGANISM: Brucella phage Iz1

<400> SEQUENCE: 211
gtctcaccta catgactcct gctggtccgg ttgatatcgt tgcagctggt              50

<210> SEQ ID NO 212
<211> LENGTH: 50
<212> TYPE: DNA
<213> ORGANISM: Brucella phage Iz1
```

```
<400> SEQUENCE: 212
agcttgtgct tgagaacccg ctgttctcgt accgcattat cacggcataa              50

<210> SEQ ID NO 213
<211> LENGTH: 50
<212> TYPE: DNA
<213> ORGANISM: Brucella phage Iz1

<400> SEQUENCE: 213
gccggtgctt attttcatgc gcgagtgtat gcgctctaat caatatgggg              50

<210> SEQ ID NO 214
<211> LENGTH: 50
<212> TYPE: DNA
<213> ORGANISM: Brucella phage Iz1

<400> SEQUENCE: 214
gtatgaagtt gttgaggtcc gctttgcggg atcaaataat tacgcgcctg              50

<210> SEQ ID NO 215
<211> LENGTH: 50
<212> TYPE: DNA
<213> ORGANISM: Brucella phage Iz1

<400> SEQUENCE: 215
ctcatcagac gtggaaacgc gaaggcaaca aatctattac ctatgcagaa              50

<210> SEQ ID NO 216
<211> LENGTH: 50
<212> TYPE: DNA
<213> ORGANISM: Brucella phage Iz1

<400> SEQUENCE: 216 ataccttga aggtgacaag cttaaatcgc ttggcatgat gggtaacacg               50

<210> SEQ ID NO 217
<211> LENGTH: 50
<212> TYPE: DNA
<213> ORGANISM: Brucella phage Iz1

<400> SEQUENCE: 217
tttacgaagc aatgacagag gctgaattgc gtgatatgat tgaatcaaag              50

<210> SEQ ID NO 218
<211> LENGTH: 50
<212> TYPE: DNA
<213> ORGANISM: Brucella phage Iz1

<400> SEQUENCE: 218
ggtacgcaga ttggcaggct ctgactaaag tttataacgt accaactgat              50

<210> SEQ ID NO 219
<211> LENGTH: 50
<212> TYPE: DNA
<213> ORGANISM: Brucella phage Iz1

<400> SEQUENCE: 219
tcgtcagctt ttggttacgg atattcagga cttgaataat tgggtttggg              50

<210> SEQ ID NO 220
<211> LENGTH: 50
<212> TYPE: DNA
<213> ORGANISM: Brucella phage Iz1
```

```
<400> SEQUENCE: 220
cttgaataat tgggtttggg gatatgagca cattgaaaat ctcaatgact              50

<210> SEQ ID NO 221
<211> LENGTH: 50
<212> TYPE: DNA
<213> ORGANISM: Brucella phage Iz1

<400> SEQUENCE: 221
gaaagccgga gttcactgcc gatacagatg attttatcat caagggcggc              50

<210> SEQ ID NO 222
<211> LENGTH: 50
<212> TYPE: DNA
<213> ORGANISM: Brucella phage Iz1

<400> SEQUENCE: 222
cttttgaatt ggggtaattg atgtaccagc gccctatcct cgcgcagaag              50

<210> SEQ ID NO 223
<211> LENGTH: 50
<212> TYPE: DNA
<213> ORGANISM: Brucella phage Iz1

<400> SEQUENCE: 223
cgtccctgtt tacatacgtt aacggcttga atcgtaaatt gttcgcgtct              50

<210> SEQ ID NO 224
<211> LENGTH: 50
<212> TYPE: DNA
<213> ORGANISM: Brucella phage Iz1

<400> SEQUENCE: 224
tcgtaaattg ttcgcgtcta ccgaaaacac catttacgat attaccaata              50

<210> SEQ ID NO 225
<211> LENGTH: 50
<212> TYPE: DNA
<213> ORGANISM: Brucella phage Iz1

<400> SEQUENCE: 225
acaggatttt tctgtaggag aagtgataac gggtgatact tccggggcag              50

<210> SEQ ID NO 226
<211> LENGTH: 50
<212> TYPE: DNA
<213> ORGANISM: Brucella phage Iz1

<400> SEQUENCE: 226
aagtgataac gggtgatact tccggggcag aaggtacagt aagtgagatt              50

<210> SEQ ID NO 227
<211> LENGTH: 50
<212> TYPE: DNA
<213> ORGANISM: Brucella phage Iz1

<400> SEQUENCE: 227
ctactagtgt tggccttatt cctctttcca aggctatcag tcttgatgta              50

<210> SEQ ID NO 228
<211> LENGTH: 50
<212> TYPE: DNA
```

<400> SEQUENCE: 228
ttgaggattg gtcttgtatg ctttggcctg aacgtaagat ggcaatcata                50

<210> SEQ ID NO 229
<211> LENGTH: 50
<212> TYPE: DNA
<213> ORGANISM: Brucella phage Iz1

<400> SEQUENCE: 229
tcttgtatgc tttggcctga acgtaagatg gcaatcatat ctccgcctat                50

<210> SEQ ID NO 230
<211> LENGTH: 50
<212> TYPE: DNA
<213> ORGANISM: Brucella phage Iz1

<400> SEQUENCE: 230
ctgaacgtaa gatggcaatc atatctccgc ctattacaat cggtgattat                50

<210> SEQ ID NO 231
<211> LENGTH: 50
<212> TYPE: DNA
<213> ORGANISM: Brucella phage Iz1

<400> SEQUENCE: 231
tatttccaat tctgaaacag gtgcatggtg ccgttatacc aattgggacg                50

<210> SEQ ID NO 232
<211> LENGTH: 50
<212> TYPE: DNA
<213> ORGANISM: Brucella phage Iz1

<400> SEQUENCE: 232
cggtgaagtg ttcaaagcca atgtaacagg catggacaat gggtctgttt                50

<210> SEQ ID NO 233
<211> LENGTH: 50
<212> TYPE: DNA
<213> ORGANISM: Brucella phage Iz1

<400> SEQUENCE: 233
gattgtccat ttggaaatca gcttaacaat gggcgagatt gtaacttgat                50

<210> SEQ ID NO 234
<211> LENGTH: 50
<212> TYPE: DNA
<213> ORGANISM: Brucella phage Iz1

<400> SEQUENCE: 234
caatgggcga gattgtaact tgatccatac aatgtattac agcaagacaa                50

<210> SEQ ID NO 235
<211> LENGTH: 50
<212> TYPE: DNA
<213> ORGANISM: Brucella phage Iz1

<400> SEQUENCE: 235
attgtaactt gatccataca atgtattaca gcaagacaat gaacccttcc                50

<210> SEQ ID NO 236
<211> LENGTH: 50
<212> TYPE: DNA
<213> ORGANISM: Brucella phage Iz1

-continued

<400> SEQUENCE: 236
gcaaaaggtg gctgacaagg gccgtgatta atgctatgtt cttcctgcca     50

<210> SEQ ID NO 237
<211> LENGTH: 50
<212> TYPE: DNA
<213> ORGANISM: Brucella phage Iz1

<400> SEQUENCE: 237
tagttgtatt gagagtttct gaaagaaata aaacgatgat tggtattgca     50

<210> SEQ ID NO 238
<211> LENGTH: 50
<212> TYPE: DNA
<213> ORGANISM: Brucella phage Iz1

<400> SEQUENCE: 238
taaaacgatg attggtattg caagaaaatt cgggtttagt gaaacttaca     50

<210> SEQ ID NO 239
<211> LENGTH: 50
<212> TYPE: DNA
<213> ORGANISM: Brucella phage Iz1

<400> SEQUENCE: 239
ttctttgact gacgacgagt ggagcaagtc gccttataat aagggagttt     50

<210> SEQ ID NO 240
<211> LENGTH: 50
<212> TYPE: DNA
<213> ORGANISM: Brucella phage Iz1

<400> SEQUENCE: 240
aggctatctt tgatgcgtct cagtctgcgc agggtaatct tgcaaacatt     50

<210> SEQ ID NO 241
<211> LENGTH: 50
<212> TYPE: DNA
<213> ORGANISM: Brucella phage Iz1

<400> SEQUENCE: 241
caaatacatt ggctcgccgg ttacgcacat tgggtatatg gctcaggact     50

<210> SEQ ID NO 242
<211> LENGTH: 50
<212> TYPE: DNA
<213> ORGANISM: Brucella phage Iz1

<400> SEQUENCE: 242
caatagaatg tcaaataatc caaatgctta tcagcaaatt cctatggctc     50

<210> SEQ ID NO 243
<211> LENGTH: 50
<212> TYPE: DNA
<213> ORGANISM: Brucella phage Iz1

<400> SEQUENCE: 243
atagcggttt agtaaacaac caaagcttca tgaacaatat ctcaccattt     50

<210> SEQ ID NO 244
<211> LENGTH: 50
<212> TYPE: DNA
<213> ORGANISM: Brucella phage Iz1

```
<400> SEQUENCE: 244
tctcaccatt tgcatccgct aatccatcta gtgccatgat ggcaaatatg            50

<210> SEQ ID NO 245
<211> LENGTH: 50
<212> TYPE: DNA
<213> ORGANISM: Brucella phage Iz1

<400> SEQUENCE: 245
taatccatct agtgccatga tggcaaatat gggatttaat caggggaatc            50

<210> SEQ ID NO 246
<211> LENGTH: 50
<212> TYPE: DNA
<213> ORGANISM: Brucella phage Iz1

<400> SEQUENCE: 246
gcgcagaata tgatgcaatc aaatatccca gacgtaaaaa acaagcaat             50

<210> SEQ ID NO 247
<211> LENGTH: 50
<212> TYPE: DNA
<213> ORGANISM: Brucella phage Iz1

<400> SEQUENCE: 247
tgatatgctt ggtagccttg gcggtggtgc tgggtttaat cctgccgtcg            50

<210> SEQ ID NO 248
<211> LENGTH: 50
<212> TYPE: DNA
<213> ORGANISM: Brucella phage Iz1

<400> SEQUENCE: 248
gccaaggatt gattgaccgt ggtcttcagc cgcatatagc ggatgcgttt            50

<210> SEQ ID NO 249
<211> LENGTH: 50
<212> TYPE: DNA
<213> ORGANISM: Brucella phage Iz1

<400> SEQUENCE: 249
atgaacgaac ttcaaggttc cgaggctggc gctgcaaaat caatcctatc            50

<210> SEQ ID NO 250
<211> LENGTH: 50
<212> TYPE: DNA
<213> ORGANISM: Brucella phage Iz1

<400> SEQUENCE: 250
ttgcaaattc tcttgtatct cctcaatcac catctaactt caacgaccgc            50

<210> SEQ ID NO 251
<211> LENGTH: 50
<212> TYPE: DNA
<213> ORGANISM: Brucella phage Iz1

<400> SEQUENCE: 251
acgaccgctg gaatgcaggt gctgctacgt ctcctatcct gcctgaacag            50

<210> SEQ ID NO 252
<211> LENGTH: 50
<212> TYPE: DNA
<213> ORGANISM: Brucella phage Iz1
```

```
-continued

<400> SEQUENCE: 252
cttatatttc aaatcaaggt aggcagattg ccggtatgct tttggggcag              50

<210> SEQ ID NO 253
<211> LENGTH: 50
<212> TYPE: DNA
<213> ORGANISM: Brucella phage Iz1

<400> SEQUENCE: 253
ttccaagggt cttttgcaga ttaccagcag caggtaaaac gcgctggagc              50

<210> SEQ ID NO 254
<211> LENGTH: 50
<212> TYPE: DNA
<213> ORGANISM: Brucella phage Iz1

<400> SEQUENCE: 254
ctgatacagg atggaaaacc cttcctaatg gcgtaaaaat cagggcaaaa              50

<210> SEQ ID NO 255
<211> LENGTH: 50
<212> TYPE: DNA
<213> ORGANISM: Brucella phage Iz1

<400> SEQUENCE: 255
caatctattg gttgcacccg cagccgctgg catcaattat gcgtttggaa              50

<210> SEQ ID NO 256
<211> LENGTH: 50
<212> TYPE: DNA
<213> ORGANISM: Brucella phage Iz1

<400> SEQUENCE: 256
ccgatccggc aatgacaacc agtcttgctg acgatattac caagatcgca              50

<210> SEQ ID NO 257
<211> LENGTH: 50
<212> TYPE: DNA
<213> ORGANISM: Brucella phage Iz1

<400> SEQUENCE: 257
gcgcgcaaga tttcaagccg ttatcttaaa gctggaacat tggagcgtgc              50

<210> SEQ ID NO 258
<211> LENGTH: 50
<212> TYPE: DNA
<213> ORGANISM: Brucella phage Iz1

<400> SEQUENCE: 258
caggagggac tttgccgaat gcatcaaatc ctgctataag agatgctgta              50

<210> SEQ ID NO 259
<211> LENGTH: 50
<212> TYPE: DNA
<213> ORGANISM: Brucella phage Iz1

<400> SEQUENCE: 259
tcaagctttg attggctctc aattggcagc gcaatctaat ataggtggta              50

<210> SEQ ID NO 260
<211> LENGTH: 50
<212> TYPE: DNA
<213> ORGANISM: Brucella phage Iz1
```

```
<400> SEQUENCE: 260
gcttgctatg ttggtaatgc actcaatgcc acggcaggat ttggatatcg            50

<210> SEQ ID NO 261
<211> LENGTH: 50
<212> TYPE: DNA
<213> ORGANISM: Brucella phage Iz1

<400> SEQUENCE: 261
actaccactg gaagtgggat taatggggct ttgataggtt ctaatggtgg            50

<210> SEQ ID NO 262
<211> LENGTH: 50
<212> TYPE: DNA
<213> ORGANISM: Brucella phage Iz1

<400> SEQUENCE: 262
taatggggct ttgataggtt ctaatggtgg tgagcaaaat agtacactaa            50

<210> SEQ ID NO 263
<211> LENGTH: 50
<212> TYPE: DNA
<213> ORGANISM: Brucella phage Iz1

<400> SEQUENCE: 263
tctaatggtg gtgagcaaaa tagtacacta acaatatatc aaattcccaa            50

<210> SEQ ID NO 264
<211> LENGTH: 50
<212> TYPE: DNA
<213> ORGANISM: Brucella phage Iz1

<400> SEQUENCE: 264
tactcaagaa cttaactggt aatttaagtt tgagtagaaa tggtcaagta            50

<210> SEQ ID NO 265
<211> LENGTH: 50
<212> TYPE: DNA
<213> ORGANISM: Brucella phage Iz1

<400> SEQUENCE: 265
actggtaatt taagtttgag tagaaatggt caagtaggtt ttacaaatga            50

<210> SEQ ID NO 266
<211> LENGTH: 50
<212> TYPE: DNA
<213> ORGANISM: Brucella phage Iz1

<400> SEQUENCE: 266
aggttttaca aatgaaaata taccattttc aactcataat catcctataa            50

<210> SEQ ID NO 267
<211> LENGTH: 50
<212> TYPE: DNA
<213> ORGANISM: Brucella phage Iz1

<400> SEQUENCE: 267
aatggcgata gatatgcgag aaaaagatgg atcgtaattt taaagtatca            50

<210> SEQ ID NO 268
<211> LENGTH: 50
<212> TYPE: DNA
<213> ORGANISM: Brucella phage Iz1
```

<400> SEQUENCE: 268
tcgcaagatt actgacgcac agttggaaac cgtgtatcgt cgtcagtatt    50

<210> SEQ ID NO 269
<211> LENGTH: 50
<212> TYPE: DNA
<213> ORGANISM: Brucella phage Iz1

<400> SEQUENCE: 269
cttcttggtg ggcttgcact tcgtggctgg attgtaaaag caataaaaga    50

<210> SEQ ID NO 270
<211> LENGTH: 50
<212> TYPE: DNA
<213> ORGANISM: Brucella phage Iz1

<400> SEQUENCE: 270
tggggctatg gccttggcgt tagttggtac gcattatttt atgtataacg    50

<210> SEQ ID NO 271
<211> LENGTH: 50
<212> TYPE: DNA
<213> ORGANISM: Brucella phage Iz1

<400> SEQUENCE: 271
tgtgttaatg tcaccatcgg aacaaacggc aagatatatc gttgaaaatg    50

<210> SEQ ID NO 272
<211> LENGTH: 50
<212> TYPE: DNA
<213> ORGANISM: Brucella phage Iz1

<400> SEQUENCE: 272
cccttaactg gtttagagtt aatctcccta caattataac aattgtaggg    50

<210> SEQ ID NO 273
<211> LENGTH: 50
<212> TYPE: DNA
<213> ORGANISM: Brucella phage Iz1

<400> SEQUENCE: 273
ctactcaggt tgaggttcta tcgtcaagag taggtatcct tacaggtgac    50

<210> SEQ ID NO 274
<211> LENGTH: 50
<212> TYPE: DNA
<213> ORGANISM: Brucella phage Iz1

<400> SEQUENCE: 274
gactagtaat ggcatacgcg atacctgaat gatgcatatt aaatatcttc    50

<210> SEQ ID NO 275
<211> LENGTH: 50
<212> TYPE: DNA
<213> ORGANISM: Brucella phage Iz1

<400> SEQUENCE: 275
gaaagaccgt actgaatcct cacaaagaat attgcatcat tccttgcctt    50

<210> SEQ ID NO 276
<211> LENGTH: 50
<212> TYPE: DNA
<213> ORGANISM: Brucella phage Iz1

-continued

```
<400> SEQUENCE: 276
gatgatagga tttcaacgtt caatgtgccg tctatatcct catccgggca          50

<210> SEQ ID NO 277
<211> LENGTH: 50
<212> TYPE: DNA
<213> ORGANISM: Brucella phage Iz1

<400> SEQUENCE: 277
atgaacgact gttcacactt ggtttctgat gcaatataac cgaaagttag          50

<210> SEQ ID NO 278
<211> LENGTH: 50
<212> TYPE: DNA
<213> ORGANISM: Brucella phage Iz1

<400> SEQUENCE: 278
ctggcctcca tgacagcatc agaaactctc ctgccaaaat gaggatcgtt          50

<210> SEQ ID NO 279
<211> LENGTH: 50
<212> TYPE: DNA
<213> ORGANISM: Brucella phage Iz1

<400> SEQUENCE: 279
ctgatgcttc actcccgtcc caatacgctt gcagcataat ctctgtcggc          50

<210> SEQ ID NO 280
<211> LENGTH: 50
<212> TYPE: DNA
<213> ORGANISM: Brucella phage Iz1

<400> SEQUENCE: 280
tcggctgtat tggataccat ccgtcatcgg tacgcatgat ccagaccgta          50

<210> SEQ ID NO 281
<211> LENGTH: 50
<212> TYPE: DNA
<213> ORGANISM: Brucella phage Iz1

<400> SEQUENCE: 281
tcctcaatca gacttgagag tgtggcaatt gtattatcat gatccgcccg          50

<210> SEQ ID NO 282
<211> LENGTH: 50
<212> TYPE: DNA
<213> ORGANISM: Brucella phage Iz1

<400> SEQUENCE: 282
tcctcgcttt caagacgctt taccagtctt tcggaatatt cccggtaatc          50

<210> SEQ ID NO 283
<211> LENGTH: 50
<212> TYPE: DNA
<213> ORGANISM: Brucella phage Iz1

<400> SEQUENCE: 283
catcctcgtt ggataaactg caattccatt tttcaattat gctgccatca          50

<210> SEQ ID NO 284
<211> LENGTH: 50
<212> TYPE: DNA
<213> ORGANISM: Brucella phage Iz1
```

<400> SEQUENCE: 284
tcataaatat tgtaatgcgt ggcagcgcct tccgcataat ggtcgcctga       50

<210> SEQ ID NO 285
<211> LENGTH: 50
<212> TYPE: DNA
<213> ORGANISM: Brucella phage Iz1

<400> SEQUENCE: 285
gaccgagtga ttttgctatg attggaactg ttgtcatgat ttatctccac       50

<210> SEQ ID NO 286
<211> LENGTH: 50
<212> TYPE: DNA
<213> ORGANISM: Brucella phage Iz1

<400> SEQUENCE: 286
ttggaactgt tgtcatgatt tatctccaca taatcacaat tacatgttta       50

<210> SEQ ID NO 287
<211> LENGTH: 50
<212> TYPE: DNA
<213> ORGANISM: Brucella phage Iz1

<400> SEQUENCE: 287
cacaattaca tgtttacctt ttccggtcaa tctttatttt ccaaattctc       50

<210> SEQ ID NO 288
<211> LENGTH: 50
<212> TYPE: DNA
<213> ORGANISM: Brucella phage Iz1

<400> SEQUENCE: 288
atctctacct ttagataccc tcgtaaaatc tcaggacatt catatatcgc       50

<210> SEQ ID NO 289
<211> LENGTH: 50
<212> TYPE: DNA
<213> ORGANISM: Brucella phage Iz1

<400> SEQUENCE: 289
aacggcctct tttgtcgcgc tgctgacgct ctcgtagaat tccctccccc       50

<210> SEQ ID NO 290
<211> LENGTH: 50
<212> TYPE: DNA
<213> ORGANISM: Brucella phage Iz1

<400> SEQUENCE: 290
tctatttgca tttgcacaga tatgtcaaaa actgcatcat atgggtcac       50

<210> SEQ ID NO 291
<211> LENGTH: 50
<212> TYPE: DNA
<213> ORGANISM: Brucella phage Iz1

<400> SEQUENCE: 291
tcattgcgcg ggtggaagac aatcttgccg aacgtatcag ggtaaacgcg       50

<210> SEQ ID NO 292
<211> LENGTH: 50
<212> TYPE: DNA
<213> ORGANISM: Brucella phage Iz1

```
<400> SEQUENCE: 292
cctttggttg attgtatcca aggatggcaa agaatttact atctgtcttg        50

<210> SEQ ID NO 293
<211> LENGTH: 50
<212> TYPE: DNA
<213> ORGANISM: Brucella phage Iz1

<400> SEQUENCE: 293
tggcaaagaa tttactatct gtcttgcgat aagatattgt ctcaggctta        50

<210> SEQ ID NO 294
<211> LENGTH: 50
<212> TYPE: DNA
<213> ORGANISM: Brucella phage Iz1

<400> SEQUENCE: 294
ctatctgtct tgcgataaga tattgtctca ggcttaacat tcccattgtc        50

<210> SEQ ID NO 295
<211> LENGTH: 50
<212> TYPE: DNA
<213> ORGANISM: Brucella phage Iz1

<400> SEQUENCE: 295
acattcccat tgtcggttgt caacatgaaa ttgttatact cggcttgttg        50

<210> SEQ ID NO 296
<211> LENGTH: 50
<212> TYPE: DNA
<213> ORGANISM: Brucella phage Iz1

<400> SEQUENCE: 296
tcggcttgtt gccttggtgt gcgcccatca accataaagt aagttgtgaa        50

<210> SEQ ID NO 297
<211> LENGTH: 50
<212> TYPE: DNA
<213> ORGANISM: Brucella phage Iz1

<400> SEQUENCE: 297
cacgcttctt ttcacatcca ttgatatgac ctgatcgcat tgcggcaaat        50

<210> SEQ ID NO 298
<211> LENGTH: 50
<212> TYPE: DNA
<213> ORGANISM: Brucella phage Iz1

<400> SEQUENCE: 298
ccacatattt tattttaccc cgcgatacct tatccaatat cgctttacga        50

<210> SEQ ID NO 299
<211> LENGTH: 50
<212> TYPE: DNA
<213> ORGANISM: Brucella phage Iz1

<400> SEQUENCE: 299
ctactagcgt tgatttgacc gataacgggc ttcgtaagat acccttgttc        50

<210> SEQ ID NO 300
<211> LENGTH: 50
<212> TYPE: DNA
<213> ORGANISM: Brucella phage Iz1
```

<400> SEQUENCE: 300
cgtaggtttg gattgccctc ctgcatccct tcgataatct ttttcaaggt          50

<210> SEQ ID NO 301
<211> LENGTH: 50
<212> TYPE: DNA
<213> ORGANISM: Brucella phage Iz1

<400> SEQUENCE: 301
ggcaaagttt tttttgaaaa gccttgatgt tagatttaat ggtcaatgga          50

<210> SEQ ID NO 302
<211> LENGTH: 50
<212> TYPE: DNA
<213> ORGANISM: Brucella phage Iz1

<400> SEQUENCE: 302
tagaagtgtt ttcaaaccta taccccttc ccgtgatttt tatgataacc          50

<210> SEQ ID NO 303
<211> LENGTH: 50
<212> TYPE: DNA
<213> ORGANISM: Brucella phage Iz1

<400> SEQUENCE: 303
cccgtgattt ttatgataac caaaaatatc ttcatatttt tttcttgaat          50

<210> SEQ ID NO 304
<211> LENGTH: 50
<212> TYPE: DNA
<213> ORGANISM: Brucella phage Iz1

<400> SEQUENCE: 304
cttcatattt ttttcttgaa tttacagcgt catctatatt tgaaaagtaa          50

<210> SEQ ID NO 305
<211> LENGTH: 50
<212> TYPE: DNA
<213> ORGANISM: Brucella phage Iz1

<400> SEQUENCE: 305
tcttgaattt acagcgtcat ctatatttga aaagtaacct atatggtggc          50

<210> SEQ ID NO 306
<211> LENGTH: 50
<212> TYPE: DNA
<213> ORGANISM: Brucella phage Iz1

<400> SEQUENCE: 306
tctatatttg aaaagtaacc tatatggtgg cttttaccat taactccaat          50

<210> SEQ ID NO 307
<211> LENGTH: 50
<212> TYPE: DNA
<213> ORGANISM: Brucella phage Iz1

<400> SEQUENCE: 307
taactccaat ttgcgcatgc cacttacatc ttgatctatt ccaatacact          50

<210> SEQ ID NO 308
<211> LENGTH: 50
<212> TYPE: DNA
<213> ORGANISM: Brucella phage Iz1

```
<400> SEQUENCE: 308
cggagttatt gtttgactgc atagttatat ttttcatatt gttctgatga              50

<210> SEQ ID NO 309
<211> LENGTH: 50
<212> TYPE: DNA
<213> ORGANISM: Brucella phage Iz1

<400> SEQUENCE: 309
agttatattt ttcatattgt tctgatgaga aacagatctt aaattattgt              50

<210> SEQ ID NO 310
<211> LENGTH: 50
<212> TYPE: DNA
<213> ORGANISM: Brucella phage Iz1

<400> SEQUENCE: 310
ttcatattgt tctgatgaga aacagatctt aaattattgt aaatattatt              50

<210> SEQ ID NO 311
<211> LENGTH: 50
<212> TYPE: DNA
<213> ORGANISM: Brucella phage Iz1

<400> SEQUENCE: 311
gtttagagtt gctgtgaatg cctctttccc agcatatctt gtgttccaac              50

<210> SEQ ID NO 312
<211> LENGTH: 50
<212> TYPE: DNA
<213> ORGANISM: Brucella phage Iz1

<400> SEQUENCE: 312
agaaaagctt tcctgactca ggtgaatatt taattaattt tgatatgcaa              50

<210> SEQ ID NO 313
<211> LENGTH: 50
<212> TYPE: DNA
<213> ORGANISM: Brucella phage Iz1

<400> SEQUENCE: 313
ttaattaatt ttgatatgca atcgtaatcc ataataacct cgctagggtt              50

<210> SEQ ID NO 314
<211> LENGTH: 50
<212> TYPE: DNA
<213> ORGANISM: Brucella phage Iz1

<400> SEQUENCE: 314
cgtaactgct tttcatctgg ccggattagc cgcgcaaatt tattatatca              50

<210> SEQ ID NO 315
<211> LENGTH: 50
<212> TYPE: DNA
<213> ORGANISM: Brucella phage Iz1

<400> SEQUENCE: 315
gggcgcgttt ggttaggaat gggatgtcaa agccgatgat gttgtggccg              50

<210> SEQ ID NO 316
<211> LENGTH: 50
<212> TYPE: DNA
<213> ORGANISM: Brucella phage Iz1
```

```
<400> SEQUENCE: 316
aagtttcttg aaccatccat ttcatgtcat tcatcacaat acaagcaaca          50

<210> SEQ ID NO 317
<211> LENGTH: 50
<212> TYPE: DNA
<213> ORGANISM: Brucella phage Iz1

<400> SEQUENCE: 317
accatccatt tcatgtcatt catcacaata caagcaacat gacccttcca          50

<210> SEQ ID NO 318
<211> LENGTH: 50
<212> TYPE: DNA
<213> ORGANISM: Brucella phage Iz1

<400> SEQUENCE: 318
accactcata ttggagttta ttttcacgca tacatatttt ttcgttacat          50

<210> SEQ ID NO 319
<211> LENGTH: 50
<212> TYPE: DNA
<213> ORGANISM: Brucella phage Iz1

<400> SEQUENCE: 319
gagtttattt tcacgcatac atatttttc gttacatgat aaatatctac           50

<210> SEQ ID NO 320
<211> LENGTH: 50
<212> TYPE: DNA
<213> ORGANISM: Brucella phage Iz1

<400> SEQUENCE: 320
aacttgcctt atgaaaatat ctgtcttcgt atgattttat aggcccaacc          50

<210> SEQ ID NO 321
<211> LENGTH: 50
<212> TYPE: DNA
<213> ORGANISM: Brucella phage Iz1

<400> SEQUENCE: 321
gcctttgcct ttgcagggtc tttctgcatg gggtcatagt caaagcacca          50

<210> SEQ ID NO 322
<211> LENGTH: 50
<212> TYPE: DNA
<213> ORGANISM: Brucella phage Iz1

<400> SEQUENCE: 322
gcaccaaacc ttctgaaaaa tcttgcgctt gttatagact tccggcttga          50

<210> SEQ ID NO 323
<211> LENGTH: 50
<212> TYPE: DNA
<213> ORGANISM: Brucella phage Iz1

<400> SEQUENCE: 323
cgctgtcttt aacggtcgca atcttcacat tctcgataat cgcaagcacc          50

<210> SEQ ID NO 324
<211> LENGTH: 50
<212> TYPE: DNA
<213> ORGANISM: Brucella phage Iz1
```

<400> SEQUENCE: 324
tacctgctgg aattggcaga atatccccac cgccttcaat ctcgaagctg            50

<210> SEQ ID NO 325
<211> LENGTH: 50
<212> TYPE: DNA
<213> ORGANISM: Brucella phage Iz1

<400> SEQUENCE: 325
ggtgttccag aatgacatgt ttagttctcc ttattaagtt cacgaagctt            50

<210> SEQ ID NO 326
<211> LENGTH: 50
<212> TYPE: DNA
<213> ORGANISM: Brucella phage Iz1

<400> SEQUENCE: 326
ctttgcaacg attcaataga gctttcaagt tctctaattt tactatttaa            50

<210> SEQ ID NO 327
<211> LENGTH: 50
<212> TYPE: DNA
<213> ORGANISM: Brucella phage Iz1

<400> SEQUENCE: 327
tcctgcaaag gattaacacc catctgcaca acaatatcgt ccttgatgcc            50

<210> SEQ ID NO 328
<211> LENGTH: 50
<212> TYPE: DNA
<213> ORGANISM: Brucella phage Iz1

<400> SEQUENCE: 328
atagttgctt gtcgaaggaa accaaccacg tcaacatcat caacgtatga            50

<210> SEQ ID NO 329
<211> LENGTH: 50
<212> TYPE: DNA
<213> ORGANISM: Brucella phage Iz1

<400> SEQUENCE: 329
ccaccgtcat ttgttgcgtt ttgtagaatg ctcatttatt tgcctttctt            50

<210> SEQ ID NO 330
<211> LENGTH: 50
<212> TYPE: DNA
<213> ORGANISM: Brucella phage Iz1

<400> SEQUENCE: 330
atttgccttt cttcaattta cgtattgctt ttcgcatcat tcaattgtat            50

<210> SEQ ID NO 331
<211> LENGTH: 50
<212> TYPE: DNA
<213> ORGANISM: Brucella phage Iz1

<400> SEQUENCE: 331
caatttacgt attgcttttc gcatcattca attgtattgt caacatagat            50

<210> SEQ ID NO 332
<211> LENGTH: 50
<212> TYPE: DNA
<213> ORGANISM: Brucella phage Iz1

<400> SEQUENCE: 332
tgtcaacata gattttcaac aaaagggaaa aatatgaaat acctcacagg            50

<210> SEQ ID NO 333
<211> LENGTH: 50
<212> TYPE: DNA
<213> ORGANISM: Brucella phage Iz1

<400> SEQUENCE: 333
ggagagggat gatagaaaca ctaataaccg cgaatctaat cctgacgttt            50

<210> SEQ ID NO 334
<211> LENGTH: 50
<212> TYPE: DNA
<213> ORGANISM: Brucella phage Iz1

<400> SEQUENCE: 334
agattctttt tattggtatc ttcttccaca cgaatatcac cacgtgccac            50

<210> SEQ ID NO 335
<211> LENGTH: 50
<212> TYPE: DNA
<213> ORGANISM: Brucella phage Iz1

<400> SEQUENCE: 335
tttgtaaata gacgccagaa gcttatcagc cttcgaaaat gatttatcct            50

<210> SEQ ID NO 336
<211> LENGTH: 50
<212> TYPE: DNA
<213> ORGANISM: Brucella phage Iz1

<400> SEQUENCE: 336
tcatcttttg cagttcgcgt ttatcatccc cccccacaat gtggaaagat            50

<210> SEQ ID NO 337
<211> LENGTH: 50
<212> TYPE: DNA
<213> ORGANISM: Brucella phage Iz1

<400> SEQUENCE: 337
tgtatcagat tttgatacat ttcacgttca gacttaatct ttccgtgatt            50

<210> SEQ ID NO 338
<211> LENGTH: 50
<212> TYPE: DNA
<213> ORGANISM: Brucella phage Iz1

<400> SEQUENCE: 338
tctttccgtg atttgcccca gacattccag cgaggattat gatattatta            50

<210> SEQ ID NO 339
<211> LENGTH: 50
<212> TYPE: DNA
<213> ORGANISM: Brucella phage Iz1

<400> SEQUENCE: 339
ggacagccct tgatagggtt ttttacctct ttaatatctt ctttggtaat            50

<210> SEQ ID NO 340
<211> LENGTH: 50
<212> TYPE: DNA
<213> ORGANISM: Brucella phage Iz1

<400> SEQUENCE: 340
caatcaatat gagacagcat gtctgcaatg acgctatcag atatatctat                    50

<210> SEQ ID NO 341
<211> LENGTH: 50
<212> TYPE: DNA
<213> ORGANISM: Brucella phage Iz1

<400> SEQUENCE: 341
gataaggcca gctgacgcaa tatcagggaa tttctctaat agtgctgcat                    50

<210> SEQ ID NO 342
<211> LENGTH: 50
<212> TYPE: DNA
<213> ORGANISM: Brucella phage Iz1

<400> SEQUENCE: 342
ttgcctattg ctgtgcattt aggattgccg caaccacaat aattaccatc                    50

<210> SEQ ID NO 343
<211> LENGTH: 50
<212> TYPE: DNA
<213> ORGANISM: Brucella phage Iz1

<400> SEQUENCE: 343
tcagcaaagg cttgtatatg tgtgttggtc atgttagatt atccatgttc                    50

<210> SEQ ID NO 344
<211> LENGTH: 50
<212> TYPE: DNA
<213> ORGANISM: Brucella phage Iz1

<400> SEQUENCE: 344
agagccggct tttttatgc gatacgccag cagaaatatt caccgtcttg                     50

<210> SEQ ID NO 345
<211> LENGTH: 50
<212> TYPE: DNA
<213> ORGANISM: Brucella phage Iz1

<400> SEQUENCE: 345
cctgaacggg tatttggggg gcctccctgg accatattgt tctagtccat                    50

<210> SEQ ID NO 346
<211> LENGTH: 50
<212> TYPE: DNA
<213> ORGANISM: Brucella phage Iz1

<400> SEQUENCE: 346 tattttcca ttttgtacaa cccgtcacaa tgtttacagt caatggttga                     50

<210> SEQ ID NO 347
<211> LENGTH: 50
<212> TYPE: DNA
<213> ORGANISM: Brucella phage Iz1

<400> SEQUENCE: 347
tcaattaagt tgttgaaatt attaaggaat cttcaattat ccctagatcc                    50

<210> SEQ ID NO 348
<211> LENGTH: 50
<212> TYPE: DNA
<213> ORGANISM: Brucella phage Iz1

<400> SEQUENCE: 348
tattaaggaa tcttcaatta tccctagatc ccaagaaatt cggtataaga          50

<210> SEQ ID NO 349
<211> LENGTH: 50
<212> TYPE: DNA
<213> ORGANISM: Brucella phage Iz1

<400> SEQUENCE: 349
caagaaattc ggtataagag taatatagag accctaaatt gaggatagga          50

<210> SEQ ID NO 350
<211> LENGTH: 50
<212> TYPE: DNA
<213> ORGANISM: Brucella phage Iz1

<400> SEQUENCE: 350
agagtaatat agagaccccta aattgaggat aggataaaag actatttatc          50

<210> SEQ ID NO 351
<211> LENGTH: 50
<212> TYPE: DNA
<213> ORGANISM: Brucella phage Iz1

<400> SEQUENCE: 351
agaccctaaa ttgaggatag gataaaagac tatttatctt tatatatcat          50

<210> SEQ ID NO 352
<211> LENGTH: 50
<212> TYPE: DNA
<213> ORGANISM: Brucella phage Iz1

<400> SEQUENCE: 352
aagactattt atctttatat atcatatact tagctatctt gctacatcta          50

<210> SEQ ID NO 353
<211> LENGTH: 50
<212> TYPE: DNA
<213> ORGANISM: Brucella phage Iz1

<400> SEQUENCE: 353
acttagctat cttgctacat ctagttgtag caattatatg acttataccc          50

<210> SEQ ID NO 354
<211> LENGTH: 50
<212> TYPE: DNA
<213> ORGANISM: Brucella phage Iz1

<400> SEQUENCE: 354
tcaatgattt ttgggaattt ttcgtatcag gttgtatctt tcttacaatt          50

<210> SEQ ID NO 355
<211> LENGTH: 50
<212> TYPE: DNA
<213> ORGANISM: Brucella phage Iz1

<400> SEQUENCE: 355
tttgggaatt tttcgtatca ggttgtatct tcttacaat tatgtgttga          50

<210> SEQ ID NO 356
<211> LENGTH: 50
<212> TYPE: DNA

-continued

<400> SEQUENCE: 356
aacaacgaag tggagaaaat ggaatgacga cagagagagt aagccaagct        50

<210> SEQ ID NO 357
<211> LENGTH: 50
<212> TYPE: DNA
<213> ORGANISM: Brucella phage Iz1

<400> SEQUENCE: 357
aaatggaatg acgacagaga gagtaagcca agctgatatt tttgggttga        50

<210> SEQ ID NO 358
<211> LENGTH: 50
<212> TYPE: DNA
<213> ORGANISM: Brucella phage Iz1

<400> SEQUENCE: 358
ctgatatttt tgggttgaga aaacaatcg atggtctgat gatggacctc         50

<210> SEQ ID NO 359
<211> LENGTH: 50
<212> TYPE: DNA
<213> ORGANISM: Brucella phage Iz1

<400> SEQUENCE: 359
aaagtgaaat gacaaatcag gatatgtggg cctgcatcat ggcaggtgta        50

<210> SEQ ID NO 360
<211> LENGTH: 50
<212> TYPE: DNA
<213> ORGANISM: Brucella phage Iz1

<400> SEQUENCE: 360
gctgtggggt tggtgtgatg atcaacgcta aaattatcct ggcatctgcc        50

<210> SEQ ID NO 361
<211> LENGTH: 50
<212> TYPE: DNA
<213> ORGANISM: Brucella phage Iz1

<400> SEQUENCE: 361
tgcattgcgt gaattggttg gtgtagtagc gccctatatc aagaaaacgc        50

<210> SEQ ID NO 362
<211> LENGTH: 50
<212> TYPE: DNA
<213> ORGANISM: Brucella phage Iz1

<400> SEQUENCE: 362
aattgttatt ttggcagtgt ttgccatgtg gtgttttatt atttggagga        50

<210> SEQ ID NO 363
<211> LENGTH: 50
<212> TYPE: DNA
<213> ORGANISM: Brucella phage Iz1

<400> SEQUENCE: 363
cgtaagcatc tagtggaagt tctcattcgt gaggtagaag cgcataagca        50

<210> SEQ ID NO 364
<211> LENGTH: 50
<212> TYPE: DNA
<213> ORGANISM: Brucella phage Iz1

<210> SEQ ID NO 365
<211> LENGTH: 50
<212> TYPE: DNA
<213> ORGANISM: Brucella phage Iz1

<400> SEQUENCE: 364
atcattgctg tcaggaagta tcagaaggaa accgcaaaat gataaccttc                50

<210> SEQ ID NO 365
<211> LENGTH: 50
<212> TYPE: DNA
<213> ORGANISM: Brucella phage Iz1

<400> SEQUENCE: 365
ttcaaggcta tggaaagatg gcaagtctgc gatggagatt gcggaagaga                50

<210> SEQ ID NO 366
<211> LENGTH: 50
<212> TYPE: DNA
<213> ORGANISM: Brucella phage Iz1

<400> SEQUENCE: 366
aagagattgg ggtgacccgg aattcagtcc tttcgatcat gcatcgttat                50

<210> SEQ ID NO 367
<211> LENGTH: 50
<212> TYPE: DNA
<213> ORGANISM: Brucella phage Iz1

<400> SEQUENCE: 367
tgcatcgtta tcgtgaattg ttcccgaaac ttggtattac gtcgcggcag                50

<210> SEQ ID NO 368
<211> LENGTH: 50
<212> TYPE: DNA
<213> ORGANISM: Brucella phage Iz1

<400> SEQUENCE: 368
cggttgcgct ttggaatgaa ggcgcatcag tcaagattat tgcattggag                50

<210> SEQ ID NO 369
<211> LENGTH: 50
<212> TYPE: DNA
<213> ORGANISM: Brucella phage Iz1

<400> SEQUENCE: 369
attgcattgg agacaggact aacccctggt caggtatcag gtcttacaaa                50

<210> SEQ ID NO 370
<211> LENGTH: 50
<212> TYPE: DNA
<213> ORGANISM: Brucella phage Iz1

<400> SEQUENCE: 370
ctggatgatt tcgaattgtc acgcctgcca ggagtatcac tcattgataa                50

<210> SEQ ID NO 371
<211> LENGTH: 50
<212> TYPE: DNA
<213> ORGANISM: Brucella phage Iz1

<400> SEQUENCE: 371
catttattct gtggacattt gaggtttaaa gggcgatact gtgaacatca                50

<210> SEQ ID NO 372
<211> LENGTH: 50
<212> TYPE: DNA
<213> ORGANISM: Brucella phage Iz1

```
<400> SEQUENCE: 372
tggacatttg aggtttaaag ggcgatactg tgaacatcat acgtacaagt        50

<210> SEQ ID NO 373
<211> LENGTH: 50
<212> TYPE: DNA
<213> ORGANISM: Brucella phage Iz1

<400> SEQUENCE: 373
ggctgctcac tttgatgttt cacgacagac tattgagaat tgggcatcag        50

<210> SEQ ID NO 374
<211> LENGTH: 50
<212> TYPE: DNA
<213> ORGANISM: Brucella phage Iz1

<400> SEQUENCE: 374
gtcaggcttg gtgggaaaaa gcaggccgtg aaggcatgtt ccttggcggg        50

<210> SEQ ID NO 375
<211> LENGTH: 50
<212> TYPE: DNA
<213> ORGANISM: Brucella phage Iz1

<400> SEQUENCE: 375
cgaagatctt gcaaaggtta ttgcggggga gaaataacct cgtgaccata        50

<210> SEQ ID NO 376
<211> LENGTH: 50
<212> TYPE: DNA
<213> ORGANISM: Brucella phage Iz1

<400> SEQUENCE: 376
cagaatattt tgctgagacg cagttagcta aacatcacat attgatactt        50

<210> SEQ ID NO 377
<211> LENGTH: 50
<212> TYPE: DNA
<213> ORGANISM: Brucella phage Iz1

<400> SEQUENCE: 377
ctcaaaggtg cattgaaaag ccttacggac ggcttatgct ttttatgcca        50

<210> SEQ ID NO 378
<211> LENGTH: 50
<212> TYPE: DNA
<213> ORGANISM: Brucella phage Iz1

<400> SEQUENCE: 378
ggtccgaata catgtcaggg ggcattctgt ctggtattac gggtaacaga        50

<210> SEQ ID NO 379
<211> LENGTH: 50
<212> TYPE: DNA
<213> ORGANISM: Brucella phage Iz1

<400> SEQUENCE: 379
ttcttacccg tttgaagccg ggaggctcta ttattatcat tcaaacacgc        50

<210> SEQ ID NO 380
<211> LENGTH: 50
<212> TYPE: DNA
<213> ORGANISM: Brucella phage Iz1
```

```
<400> SEQUENCE: 380
aaacacgctg gcatgaagac gacctgtcag gccgtatcct tccagataac            50

<210> SEQ ID NO 381
<211> LENGTH: 50
<212> TYPE: DNA
<213> ORGANISM: Brucella phage Iz1

<400> SEQUENCE: 381
cgtatttggc tattggatat atggaggcaa caggcatctt ctgacaggtg            50

<210> SEQ ID NO 382
<211> LENGTH: 50
<212> TYPE: DNA
<213> ORGANISM: Brucella phage Iz1

<400> SEQUENCE: 382
aaacctattg gctgggctga ggaaacagga cagatcaaat caggtgttgg            50

<210> SEQ ID NO 383
<211> LENGTH: 50
<212> TYPE: DNA
<213> ORGANISM: Brucella phage Iz1

<400> SEQUENCE: 383
cctgtaggtg ttcatgacga tcaggttgac gctctaggat tggttgggca            50

<210> SEQ ID NO 384
<211> LENGTH: 50
<212> TYPE: DNA
<213> ORGANISM: Brucella phage Iz1

<400> SEQUENCE: 384
acggagtttt cacgcctgaa gacggatact tctcaataat tcagacgcca            50

<210> SEQ ID NO 385
<211> LENGTH: 50
<212> TYPE: DNA
<213> ORGANISM: Brucella phage Iz1

<400> SEQUENCE: 385
taagattgtt gataacaaca atgatgaaaa ttggcataac gctctaaatg            50

<210> SEQ ID NO 386
<211> LENGTH: 50
<212> TYPE: DNA
<213> ORGANISM: Brucella phage Iz1

<400> SEQUENCE: 386
taagattgtt gataacaaca atgatgaaaa ttggcataac gctctaaatg            50

<210> SEQ ID NO 387
<211> LENGTH: 16686
<212> TYPE: DNA
<213> ORGANISM: Brucella phage Iz1

<400> SEQUENCE: 387
tggacttaac ccactcccac ggcccctttg taaactttgc cccactcata gcgcacctgc    60
tttcttgagt acatttagag cgttatgcca attttcatca ttgttgttat caacaatctt   120
atccagcgcg ctcaccaact catcatgcat gttcacgcac ttgacgatgt gggcggcgtt   180
ggcttcttca aacacattag cgatgcactg atctggcgtc tgaattattg agaagtatcc   240
```

```
gtcttcaggc gtgaaaactc cgttcagttg gtcccaaggc gtaggcgtgt gttctttcgt    300
catgattgtt tctccacttc taaacacaca taaacataca attgttatgt agtcaaaccc    360
ttttacgctg cccaggcaac ggagaagcat aaacagcgct ataatccatg cgctcaggct    420
tcttctgcgg cttacctggg gtcatacgat ccataagctg cccaaccaat cctagagcgt    480
caacctgatc gtcatgaaca cctacaggga aactcatcat ctcagacata agagcatcta    540
atcccggcaa gtcgtccctc acatacagcc cagacaaggc aatgcgtcca cggatagact    600
gagcacgtac agacttgtca ccgccacgcg ttgggaactg ctcacgcgcc acatacgaac    660
cagtctcgat catacgcttc acaaggaaag gcccaacacc tgatttgatc tgtcctgttt    720
cctcagccca gccaataggt ttccacttc gcaccagatc gcagaacgaa tctacccacc    780
tgtcagaaga tgcctgttgc ctccatatat ccaatagcca aatacgcccc tcgctatcaa    840
cgccaacgac aacatgaacg gtataatccc cgccattatt cgttacagcg tagtcagacg    900
cgccatagat cgacatggta ttaagaggcg gcacctgtga ggctgataca agctttatcc    960
attctttctt gaagtaatca ccgctatcag gtgcaggtct ctgctggaac aatgcagacc   1020
atgtgcgcgg gttcttttcga tgaacctgcc agtgcttttc gtcaaaccat tcctcccaca   1080
acatttgacc tatctcgcgc ccaagcgggt cgtcagcacg ttcgcactca gcagcaaggc   1140
aaataacctc ccattcaaac ccatccttgc ccataatcat accggattcg ccggcgtagt   1200
tatctggaag gatacggcct gacaggtcgt cttcatgcca gcgtgtttga atgataataa   1260
tagagcctcc cggcttcaaa cgggtaagaa ccgactcctg atactcatcc catgtcctct   1320
gacggataac ctcggaatca gcgtcttgcc tgcccttgat tgggtcgtca ataatgacgc   1380
agttatgaac tagtattccg ttggcgaaga agttgtggtt cttcgaaact tggatgtcga   1440
agacactggc ttcatcgcca attctctcaa ccgagatgac gtgatctcgc tcggcttccc   1500
acgcaagctc ctgtgggcct ccttgtggca ggctggacaa agggttacca aattcgttga   1560
cgcgttgttc atcggccaat tgtcgatgtg gtgaacgtgt agcttcttgt cgtcctcgca   1620
tatcacgcac atgaagccat ccctctctac gatcagcggc ctcatcaccc tgaacgcgcg   1680
ggctgaatga ggctgttgcc tgagaggcgt agctccatcc ttccacatcg ggttcccctt   1740
ctcgctcata cgccgagaat ggtctatgtc cgcacatgtt cggctgcaat aggcggcaaa   1800 gtccccacc ttcttgccac gccaaaccgc tttgaaagtc ttgttgcaag tcgggcagtc   1860 gcggagatt ggcggatgaa tcgcagggcg ccacttcctt agaactggac ggcatgtgtc   1920
gcagaacctg cgcgtcttct tttccgtcgg gttcccgcac ccttcgcact ttctcctgtc   1980
cttgtacgac gcgtgctctt ggctgcaagg aaggcagcaa taatgatccc ttccgcactt   2040
cgcctcccat ttccggtaat cgaatgctgg tttcaccttc tcctttgcgc aattggctca   2100
agagactatc accgggggca agtgaagacg ctttgacgta tccacgcccg gtgtagaatt   2160
gatgatttcc cgtagcttca accactgagc ctctggcagt ggtgaccctg taaatcccaa   2220
ttcccttacg atgggagaaa gcttcaatgt cttggtactc catcatattt aatctgtgat   2280
tgaagcttag cactttaacg gaagcgggc aatgttctat attttcgatg gcgacagggc   2340
cttcactggt ttctatcatg gtaccagcta ccaagcagtc ggctctgtta cccgtaatac   2400
cagacagaat gcccctgac atgtattcgg acccgttgtc caaggccac tcgtcggcgg   2460 cggcttgatc tccactcaat gatgttgaaa aagggcacg gtattttgat tgcttaataa   2520
ttgagcgggt tcgacggcca aacttcttag ccatgtctga accataagac acgccgatga   2580
ctttgaaccc tggcttctgc cccatagccc atgatgggac gacaacgctg ccatatgaac   2640
```

```
tcttcgcact gcctggtggc ataaaaagca taagccgtcc gtaaggcttt tcaatgcacc    2700
tttgagcggc ttcaagtatc aatatgtgat gtttagctaa ctgcgtctca gcaaaatatt    2760
ctgcttcgtc gctttcctcg tcctgttctt caacaggagc tcccggaacc tcaatgtacc    2820
gggcataatc aaccagattt cgacgagcct tacgtctgtt tagaagctct gggcggctt    2880
gggctttggt tatggtcacg aggttatttc tcccccgcaa taacctttgc aagatcttcg    2940
tctgtcattt caccgatgga atgtttgtgt tccatagtgc cagtctgatg aacctcttga    3000
cgctccgtgt aatcctcacg gaaacgggcc tccatagact ttttccacac ggctgcatta    3060
aacccacccc cgccaaggaa catgccttca cggcctgctt tttcccacca gcctgacaa    3120
tgaaccttag ctctacttaa cgctgctaaa actctgggt gatctgatgc ccaattctca    3180
atagtctgtc gtgaaacatc aaagtgagca gccatctgcg ccagggaatc tccttgtttc    3240
ccaagttcaa tgactgtctc acaatattct ggtctgtata aggttggacg accgccagcc    3300
ataactattc atattcctct aaaatcttca cctgacgacg caaatactct gctacttcat    3360
gaattggcat ggtagacgcc ataaggttga ttgctcactc acagaaccac atagactgac    3420
ttgcttgaaa gtcatagact gactggtccg ctatctgctg taaagctttc ttgcctttct    3480
tgctcataca acctccatga tatttctatc atacgccttt ttgtacgaaa tgcttattcc    3540
cttatatcct tcacacttgt acgtatgatg ttcacagtat cgcccttaa acctcaaatg    3600
tccacagaat aaatgcgggc cttctgccgt tagcgggtac atgcatccat cgttatcaat    3660
gagtgatact cctggcaggc gtgacaattc gaaatcatcc agctctgggt cttgatacca    3720
ggctgccttt gaaccagcgt taggattgaa cttagacatt cgattcaccg gatcatttct    3780
aggcgacttc ttcgccttca tcgaacgatt aacccggtga agtgtcaaat cccttttctt    3840
aaggtccctt ttttgaata actcacgctt tcgttttgta agacctgata cctgaccagg    3900
ggttagtcct gtctccaatg caataatctt gactgatgcg ccttcattcc aaagcgcaac    3960
cgccttatcg atcaatccac gctcaatagc ctgccgcgac gtaataccaa gtttcgggaa    4020
caattcacga taacgatgca tgatcgaaag gactgaattc cgggtcaccc caatctcttc    4080
cgcaatctcc atcgcagact tgccatcttt ccatagcctt gaagcacgat caattacttc    4140
ctgcgtccaa acaaatttca tctcaagcac cacataacga acggagcagc aaccctggca    4200
acgattagat atccgatgaa ggttatcatt ttgcggtttc cttctgatac ttcctgacag    4260
caatgatgag ttcacccatg cactccgccg agtgcttccc atgcttatgc gcttctacct    4320
cacgaatgag aacttccact agatgcttac ggcttccgcc tttgcggctg gcttctgggg    4380
agtaggtcat gttatcctcc aaataataaa acaccacatg gcaaacactg ccaaaataac    4440
aattgtctgg tcactcactt cccataccctc ccatagattg cgcccacatt cgcacagaaa    4500
ccgggcaagg agccgtttct ttggtaaatt gaaccctgct ccatggcagc acggcgaacg    4560
ctctcagtga actcctgtgg cgttttcttg atatagggcg ctactacacc aaccaattca    4620
cgcaatgcat cctccggtaa aggcaaacca cagtactgtc ttgccacctc catacggata    4680
attccagtta atgcatccac aggctccagg gcttgcgcgg atgcggggc tgcgaatagg    4740
gcggcagatg ccaggataat tttagcgttg atcatcacac caaccccaca gccagaatta    4800
cgaacggcac tgcaaacgcc agagccagca ttacacctgc catgatgcag gcccacatat    4860
cctgatttgt catttcactt tccttctcca caagatcgag gtccatcatc agaccatcga    4920
ttgttttttct caacccaaaa atatcagctt ggcttactct ctctgtcgtc attccatttt    4980
ctccacttcg ttgttttgat aacccaccat cccacacctt ttatggcgtg tcaacacata    5040
```

```
attgtaagaa agatacaacc tgatacgaaa aattcccaaa aatcattgat cccaaagatc    5100
ccaaactttg ggatcgacta agtaattgaa tttaaagcat tatcccgaat atcccttgat    5160
cccggctttt tggtataagg ggagtgggtg taacagtggg tataagtcat ataattgcta    5220
caactagatg tagcaagata gctaagtata tgatatataa agataaatag tcttttatcc    5280
tatcctcaat ttagggtctc tatattactc ttataccgaa tttcttggga tctagggata    5340
attgaagatt ccttaataat ttcaacaact taattgatcc cagaagcatg ggatctatag    5400
ggatctttgg gatcaaccat tgactgtaaa cattgtgacg ggttgtacaa aatggaaaaa    5460
tatttgactt cattttaatt cgtactatgt taggcccata tgacaaaaat ggagagttga    5520
aatgagtttc gaaataagtc ggcgacccma ttgatggact agaacaatat ggtccaggga    5580
ggcccccaa atacccgttc agggatatgc agattggaga ctgttttcgt ttggggttag     5640
ataatcccag caatgtaaga agctgtgcag catcttatgc cgttcgaaac aacaaaaagt    5700
ttaccgtgcg caaacaagac ggtgaatatt tctgctggcg tatcgcataa aaaaagccgg    5760
ctctacgaaa cggtggagga cgctcggagc cggcttgtgg ttccgacgaa gaaaggcaaa    5820
aacgccagaa catggataat ctaacatgac caacacacat atacaagcct ttgctgagaa    5880
caatcatcgt gtttttatgt tggaaagcat tgatggtaat tattgtggtt gcggcaatcc    5940
taaatgcaca gcaataggca agcatcctgt agcttccaac tggcagaata ccccgcaatg    6000
ggatgatgac cagatagaaa acatgtcaat gatggttgac agcatggggc gcggatatgg    6060
cgttctgtgt agcaatctat tggtaattga cgtggacgct aagaacggtg gccttgcttc    6120
atatgcagca ctattagaga aattccctga tattgcgtca gctggcctta tcgtcgagac    6180
aggatcaggt ggtggatcca agcacccttta tttttcattg ccagccgatg ttaaaacggt    6240
tcagacgcat aaagactata agggcattga tttcaaacac accggtttcg tcgtggggcc    6300
tggatcgccg cataagtctg ggagaaatta taatgttctc tctgggtctg tggatgacat    6360
agaccatgcg ccatctgctc ttgttgagtt ccttaaaaga gaggagcgca ggaagatcga    6420
atatgaaggc agcacgatag atatatctga tagcgtcatt gcagacatgc tgtctcatat    6480
tgattgctac gacgaatatt ccgattggat aaagatcggt atggctatcc atgacgccac    6540
tcacggcaac ggtgtagcgc tgtgggatga atggagcaga cgtagctcta aatacaatcc    6600
agaagccatt gacgcccggt ggcactcatt cggcaagtcg tcaaatcctg ttaccattgg    6660
cacattgatc aaaatggcac aggatggagg gtggacggag aaagtatcgt tcgaggaagt    6720
cgagctgcaa ggatggttcg cgaaggctgt aactggtaat cctgtcactc aaggcattac    6780
caaagaagat attaaagagg taaaaaaccc tatcaagggc tgtcctgtag atatctcaac    6840
aatcgacctg acaatgccgc ctggcttctg cggggaggtg acgcggtgga ttaacacaca    6900
gtgccgttat cctcgtttaa acctgtctgc aatggcttct ctatacgcga ttggcaacat    6960
tgcgggtctt aactacgctg cgaacgacac cagccggaca agggcaaatc ttgccatatt    7020
ctgcgtagct gggtcaggga ctggtaagga tgctgtgctg gaggccgtta ataatatcat    7080
aatcctcgct ggaatgtctg gggcaaatca cggaaagatt aagtctgaac gtgaaatgta    7140
tcaaaatctg atacatcatc aggcggcaat atataccatt gatgaagttg agcgcatct    7200
tgcaaagatt agcaacgctt ctcgatccgg cgcgtctcac cttgagggtg ttattgaaac    7260
attcatgagc gtttacacca agtctgaatc tttccacatt gtgggggggg atgataaacg    7320
cgaactgcaa aagatgatgc gtgataagct ggcttacttc gcgcaaaagg tagaggaaaa    7380
tgaggataaa gaacattctc aaaagatggt tgatagcctg aaagagcgct tgaagacagc    7440
```

```
cgatagactt gttgagccat tcttgtcttt gattgggttt accacaccta cacagctatc   7500
ccgtatgatg gtcattgata acgcggaaag cgggttcctt ggccgtacgg ttatgtgtgt   7560
agagccagat attaaccctt atccaaatcc agggtttacc aaggaagata tgccatatgg   7620
catgaaaatg aagattcttg ccctatctgg cgtggatagt agtgaagagt ttgaccggat   7680
tgagcgtcga gggccgttga aactggttga tatagaacca gaggcaaagg aacttattga   7740
acggtgtatc aattggactg ttgattataa ccagagcaag attgaaatgg gcttggagcc   7800
attctctggt ttgtatcgac gtgtgtgcga gaaggcgatt aagattgccc ttatccttgg   7860
cataccagat gggttgataa ctgttgagca tgtaaaatgg gcgatggccg cttctatgcg   7920
tgatgctgag gaaaaggtaa gcgcaatcac cattgaggat aaatcatttt cgaaggctga   7980
taagcttctg gcgtctattt acaaagcagt gaaaaataag ccggggcaaa catttgcgtg   8040
gattgcagca agatcaaata tatcaaaata cgggaaagag gaagtagaaa aggcattggc   8100
gcatatggtg gcacgtggtg atattcgtgt ggaagaagat accaataaaa agaatcttga   8160
aattttgaaa aggtattatg tgagataacc tggaaggagg tgatgcctaa tggaaccggc   8220
taaattcgga accatgcaaa aagccccggc gtaaaaaccg gggcgttaat gttaaaggcg   8280
cattaatatg cataggttaa taaacgtcag gattagattc gcggttatta gtgtttctat   8340
catccctctc cctcctgcaa tgccctatac tcactaacct ttttaatggt ttcccatgtt   8400
gggttgatgg ttttccctac cttgatacga ctcagggact ggtaaatcat ccctgtttcc   8460
ttcgccattt tatgcagtcc gccataaggc aggctacgta gatattcctg aagctctgga   8520
cctgtgaggt atttcatatt tttccttttt gttgaaaatc tatgttgaca atacaattga   8580
atgatgcgaa aagcaatacg taaattgaag aaaggcaaat aaatgagcat tctacaaaac   8640
gcaacaaatg acggtggcga gcaggcgttg attgtgacgc tgtttggcac accaggcact   8700
ggtaaaacat caacagcgct tacattccct aagccgtata tgatccgtac tcagggtgaa   8760
gcagtgccac gtgacgcccc taataaggcc gtatcattgg ggattacaga tagccctgcc   8820
aagctgtggg aacagctaac ggcactctgc aaagatgaac acgactttaa gacattgatc   8880
gttgacagct cgactggcct tgaaggaatg ttcatcaagg acgtgctgga taatgaccct   8940
aaagcgcgag gaattaacac agcccttggt ggttatggtg caggacgagc agcagttgcc   9000
gcacaacacg caaaactgcg aaagggtgca gagtatttgc ggtctgttcg tgggatgcat   9060
attgtgttca ttggccatgc tgatattgaa cggattgacc cgccagacag tgaatcgtac   9120
tctaagtatt cactgcgtct tcatcgtgaa tcaatgaagt catacgttga tgatgttgac   9180
gtggttggtt tccttcgaca agcaactatc ctacgtggtg aagaagatga gcgcaagaaa   9240
gccatcacca ctggtgatat tattctaacc actactttgc accctgcctt cgttagcaag   9300
aaccgtctcg gcatcaagga cgatattgtt gtgcagatgg gtgttaatcc tttgcaggag   9360
tatttgtgat gagtaaagaa gatggagaag ggacaatttt cgccaatat accttttaca   9420 atgcgcaaga tgttgacgac actgtagcaa ggttaaatag taaaattaga gaacttgaaa   9480
gctctattga atcgttgcaa agcatgagac ctcattgggc taagggatac acatcagata   9540
gcatggctgc acagggacaa acagcggcac tatctcagat ttggtcatat cttggcgtag   9600
acaatcaaac ggacgccatg caaaagcttc gtgaacttaa taaggagaac taaacatgtc   9660
attctggaac accagctccg gcgaaagcgc catttctaac gctaccagct tcgagattga   9720
aggcggtggg gatattctgc caattccagc aggtaccaag gtgcttgcga ttatcgaaa   9780 tgtgaagatt gcgaccgtta aagacagcgt tgaacaatac gttgaaatca agtggggcat   9840
```

```
tatcaagccg gaagtctata acaagcgcaa gattttttcag aaggtttggt gctttgacta   9900
tgaccccatg cagaaagacc ctgcaaaggc aaaggccaag aaagacaaag cattgaagat   9960
gttggcggct attgatgcca atgcaggagg aaagcttgct caagcaggcg tagagccgac  10020
agatgaaagc cttgctctgg cgcttaataa caagcccatg gttatcggtc tgaatacttg  10080
ggatgatgca gaaacaaaga agccaaaggg taactgggtt tactacgttg cccccaagaa  10140
tgatccggtg acggaagtta ccaaggagga tgtacaggcg caggaggcta aggcgaaggc  10200
gagccagcct gctgcgtcgt ctaactttag tcatgaccta gacgacgaaa tcccattttg  10260
atcccttgtc aaacaaaagg gcggcttcgg tcgccctaaa aggatgcata atgggaaagt  10320
atgaatggaa gccgtttact ttattggtta gtgctgagga agtggagaaa gaagtgttga  10380
agattgaagc cggtaaatat tacaaaacag gtgatggccg taaggttggg cctataaaat  10440
catacgaaga cagatatttt cataaggcaa gttttgcgtg cagagaatgg acttatttag  10500
aaaatggtaa atgggctggt tcattaaata atgataaccg tgacctcatc tccgaatggt  10560
cagaagcacc cattcgcacc gtaacgcgcc gtgagattgt ggaggggtg tatgggagcg  10620
tagatattta tcatgtaacg aaaaaatatg tatgcgtgaa aataaactcc aatatgagtg  10680
gtgaagatct aagggaaacg gctcacctgt ttaatcaatt ggccgaagct ctggaggaga  10740
atggaaaatg acctacacat atttcgacgt agaaacgata ccagaccaat ccgaaggcgc  10800
actagagcgt gccaaggaat cagtaaaggt tcctgctaac tacaagaacc cagataccat  10860
tgcggcatat atcgaagaaa acgctcaaga agcatgggag cgaacggcac tagacggttg  10920
gaagggtcat gttgcttgta ttgtgatgaa tgacatgaaa tggatggttc aagaaacttg  10980
gagagagaaa gagatgctcc aagatttttt taatcgtctt aatgaatcaa cccttgtcgg  11040
ccacaacatc atcggctttg acatcccatt cctaaccaaa cgcgcccttg ttcttggtgt  11100
taaactgcca ccggaacata tttggccgcg caatctgaag ccgtgggata accgtgtgtt  11160
tgacaccatg ttgcagcttg gcaatggcaa agagtttatc tcgctggata acctggcgcg  11220
caaccttggc actaaaggca agggcaatac gacgggagca caagttcatt acatgtggca  11280
gaatgggctg catgatgaaa ttgcagaata ctgcgctaat gacgttcgta ttgtgcgtga  11340
gattcatgag cggtttcttg cgtgtaattg gtaaatatgat ataataaatt tgcgcggcta  11400
atccggccag atgaaaagca gttacgctga ctgcctgccg cgtttacaaa ttagcgaacc  11460
ctagcgaggt tattatggat tacgattgca tatcaaaatt aattaaatat tcacctgagt  11520
caggaaagct tttctgggtc aaaagggatg atgtttgtaa aagttggaac acaagatatg  11580
ctgggaaaga ggcattcaca gcaactctaa acgctacaa atatgaaaaa attttaggga  11640
aaaattatta cgcgcataga attgcatggt taattatgaa tggcgaattt gccgatgaga  11700
tagaccatat agatgaaaac agaagcaata atatttacaa taatttaaga tctgtttctc  11760
atcagaacaa tatgaaaaat ataactatgc agtcaaacaa taactccggt gtagttggag  11820
tgtattggaa tagatcaaga tgtaagtggc atgcgcaaat tggagttaat ggtaaaagcc  11880
accatatagg ttacttttca aatatagatg acgctgtaaa ttcaagaaaa aaatatgaag  11940
atatttttgg ttatcataaa aatcacggga aggggtata ggtttgaaaa cacttctacg  12000
accctaccaa caagaagcgg ttaatgccgt aattgaaat gtgaaaagct ccataatgcc  12060
atgcatggtg gaagcgccta caggtgcagg aaagagcgtc attattgctg agattgcccg  12120
tattatatac gaaatgacgg gcaagcgtat tttggtgact gcacctagtg cagagttggt  12180
tattcagaac cgagcaaagt tcattgccac tggctatcct gccagcatgt atagtgcaag  12240
```

```
cgctggtaag aaaagcacac ggcatcatgt ggttttggt actccattga ccattaaatc    12300
taacatcaag gcttttcaaa aaaactttg ccatggttat ttgcgatgaa tgcgatctca    12360
taactccaac cttgaaaaag attatcgaag ggatgcagga gggcaatcca aacctacgtg    12420
ttgtcggcac aacagcaacc cctatgcgta tgagagaggg atatatttc agggaatggc    12480
ctgatggacg gataaacgac gattcacagt cgttgaaccc gttttaccat aaatgcgtat    12540
atcgcattga agcacgtcat ttgattgaac aagggtatct tacgaagccc gttatcggtc    12600
aaatcaacgc tagtaggtat gatacatctg gtttgcagct taaccgcatg gcaattaca    12660
cgcccgaaag cctggacaaa gcatttgtag gtatggggag aaagacggcg gcaatcgttg    12720
ctgatattgt ttcccagaca cgtaatcgca atgctgtatt gatatttgca gctactgtta    12780
aacacgctga agaagttatg gcatcgttac ctcctgaaat aagcgcaata attacgggtg    12840
atacaaaaga tcgtaaagcg atattggata aggtatcgcg gggtaaaata aaatatgtgg    12900
ttaacgtagg tgttttgacg gtaggtgtgg accttcctat tgtcgataca attgcgctta    12960
tgcgtcaatc tgaatccgtg cgcctattgc agcagattat tggtcgcggg ttgcgcttat    13020
atccgaacaa gactgagtgc ttaatcctgg attttttgcct taaccatgag aagcatttcc    13080
ctgatggtga tttgtttgac ccaaaagttg ttgcttccaa acctaaaggc gaagccaaac    13140
cactaatcgc caagtgcccg atttgcgaat tccagaacga attctcctgc atcccagact    13200
acgccgatca cgataaagac gaaaacggat attgcctgga tgtgtttggc aaccagatca    13260
tgacagaata cggaccattg tctggacact atggaaggcg gtgctttggc tatgttccgg    13320
ttggcgctgg cagagtggag cgatgcggat acaggtggag tgggaaggac tgcccagcgt    13380
gcggggagaa aaacgacata gctgcgcgat attgctatgt gtgcaaggca gaacttgtag    13440
accccaatga acggctcgtg ggggagttca aagcccacaa aaaagaccct catttgccgc    13500
aatgcgatca ggtcatatca atggatgtga aagaagcgt gtctcaggct ggcaatgcta    13560
ttttgcgtgt ggattgggta acaccttatc gtgctttcac aacttacttt atggttgatg    13620
ggcgcacacc aaggcaacaa gccgagtata acaatttcat gttgacaacc gacaatggga    13680
atgttaagcc tgagacaata tcttatcgca agacagatag taaattcttt gccatccttg    13740
gatacaatca accaaaggat gaagaaccag tgagaggaat ggcggcgtga aattcccaga    13800
taacatcccc ctattcggcg acccatccta tcgcggcaaa tgcccgttag aaagcgtcga    13860
gcagatgagc ctggttaatc agatcaggcg cgtttaccct gatacgttcg gcaagattgt    13920
cttccacccg cgcaatgagg gtctggtttc aaagggccag ttttcgtcta tggcaaagca    13980
taaagctgaa ggcatgacga agggcgctcc agattgcata gtccccggaa atccggcatt    14040
cctttgtgag ataaaagag ccaatccgca acttagcaaa tggcaagatg gcagataga    14100
atacctagag gctgcgcaga atgccggggc gtttgtgtgt gtggctctag gcgctaaggc    14160
ggcgtgggag gcgtttcaaa cctatgtgga gaagtattat ggaaattcgt gatattttga    14220
atgagcgtga gaagacccat ggtgactata ggtctcatgc agctatcacg caagctttga    14280
aggcagatat gcagtgccaa tcctcatggt catctttgcc tgaacaccag cgcgaatcac    14340
tagacatgat cgctcataag attggtcgta ttctagctgg cgatccagac ttccgcgacc    14400
attgggccga cattgccgga tatgcaactc tgagcgcaga tagatgtacg aagtgacccc    14460
atatgatgca gttttgaca tatctgtgca aatgcaaata gaaggatatg agaagtatgc    14520
aagaccagga gagaatagtc gttacgcaca cagaaaatgg gaacaggtac acgcacgagc    14580
cttcaggaaa ggtaatatct gacagaaaac tcaaccaact ggtagtaaat aacatggttg    14640
```

```
acctgtttta cggagggctt ttcggtgatg acatacagga atatgttttc acaaaaggac   14700
tttgaggatg tcatgtgggg gagggaattc tacgagagcg tcagcagcgc gacaaaagag   14760
gccgttgacc atactcttag aaatgaggct cttaggatat gcaatataga tgatgtttat   14820
tctcgaaggt cagcgatata tgaatgtcct gagattttac gagggtatct aaaggtagag   14880
attgagagaa tttggaaaat aaagattgac cggaaaaggt aaacatgtaa ttgtgattat   14940
gtggagataa atcatgacaa cagttccaat catagcaaaa tcactcggtc acttgatggt   15000
tgatgtggag atggaccgaa agaacctgt aatgcatgg ttcgcagcaa ccggtaacga    15060
actgccctat aaaatgtgga tgaggcttgt taatagccca ttcgacatga tgcaggcaca   15120
ggaagaagtg gagaaatata tgggtaaaa taccggaaga agccgtggag gcggcgatag   15180
ccgcgcacaa caaatactac gacgatcttg tcatctaccc ttcggaggag cctacgccgg   15240
aaggagcttt tcacgaggcg ttgaagggcg ctctcccctt cctcccgtg caaggggctg    15300 tgaagaagct ggagtgggaa ctggtatcag gcgaccatta tgcggaaggc gctgccacgc   15360
attacaatat ttatgagacc aaaccgggct tgtggaactc tgtaacggtt aagccgggga   15420
atgtgcgttt ggctactaat gtggatttag aagccgccaa agccgccgca caggccgact   15480
atgaggctcg catcctctcc gcgctggagc cttcctctgc gcgtgaacag gcgttggagg   15540
aagtaacgct agaacgcagc attgaacaat ggcgcaatat gaagccctcg gaagtcatga   15600
agggcagcac cgcgcagatc acatatgcac tggaggacgc cagaaaagac attctgtcgc   15660
tggcccgcgc cctatcctcc ccggaccata ttgccgacgc cggtaaggtc gaggggatg    15720 ggtggcatgt cgagtatgaa gtttacagcg aagatgaatg gcaggccgct tcgacggatt   15780 tagacgcgc gcttgattat gccgtcatgt atgccgccga cggcttcaaa acatcactg    15840 ttcaggaagt gcgccgccgc actctcccct ctgcactagc ttcggagggc gaggaatgag   15900
caagattgcg taccgccgca aggaagtgat cggcgactgc accctgtatc ttggcgattg   15960
catggaaatc atgccgacac ttggaaaggt gcaggcggtt ttaacagacc cgccatacgg   16020
catgacagac gcttcttggg acaacgcgcc aaatgtcgaa gcaatgtggc gtgaattgaa   16080
actcgaccga acagacgccg tgttcatttt gaacgcttcg cagccgttca ccagcgcagt   16140
tgttcttggg aatatcaagg attccgcgt ggaatggata tgggaaaaga acgctggctc    16200
caactttgga actgtcaaat ggcagccgat gaaggagcac gaaagcgtct ggtgttttc    16260 atcgcgaacc cctcgctatc tgccaataat ggaacagagg gccgctagcg gagctgcgag   16320
ggtcaagact gttgtcaact acgacagtca accagaagca tattctggaa ttaccggcaa   16380
atccgccagc atgaggccgc aactccgcta tccgcgttcc attcagaagt tcaacccggga   16440 gcgcggtttt catccaaatc agaaaccggt gggattggtg tagtatttcc tcaagacgta   16500
cacagaggtt ggggacgtag ttctggaccc gtacatgggt agcggaacta ccgctgtggg   16560
ttgcatcaat ttgggccgtc cattcattgg ggtagagatc gatccgcgct acttcgatat   16620
agcgtgcgag cgcgtccgta atgcctacga aaacagcctt aacatgtttg cgggacaaac   16680
cgccgc                                                              16686
```

<210> SEQ ID NO 388
<211> LENGTH: 543
<212> TYPE: DNA
<213> ORGANISM: Brucella phage Iz1

<400> SEQUENCE: 388

```
actggagccg tgcccgtttt gcagtaaaac catgatgtta cgtagtgctt tatggccttc      60
```

```
cgaaggcgat gcggatgcca tcatccatgc tgatcctaca gattgcccta tgcttggctt    120
tagcgacgga tcggctgatg cagcataat tgaaaaatgg aattgcagtt tatccaacga    180
ggatgacttc ccctctgatg ggtcgtgtgt tcgctgcggt tctgtacctc gcaatgcgaa    240
cggcctttgc aacacgtgtt tggacgaaga tgcggagcgt atagagaaca ctcgccccac    300
ccccgttact ccagtatcgc cggatgctga cggcaagtgc ggggagttgg tgacggtggg    360
ctacggctat gtgaatagcc ttggcgagtt agaatatgct cacgccacca gttcggaaat    420
gcggacagaa gcgctctgcc gccgatcgca ggccggatcc atcattgccg agcttcaagc    480
caaggctaag gattaccggg aatattccga aagactggta aagcgtcttg aaagcgagga    540
agc                                                                 543

<210> SEQ ID NO 389
<211> LENGTH: 208
<212> TYPE: DNA
<213> ORGANISM: Brucella phage Iz1

<400> SEQUENCE: 389
atcatgataa tacaattgcc acactctcaa gtctgattga ggacaacgcg gcgctgactg     60
cgcggattaa ggagttggag cgcgttgaga cggagctttg cacgtcgatt ggtctgctcg    120
aagacaaact caatgccgcg aacggaaaga tcgaggcact ggtgcagtct ctggcatacg    180
aaaccgccca cgaggcgacg aaacgcgc                                      208

<210> SEQ ID NO 390
<211> LENGTH: 289
<212> TYPE: DNA
<213> ORGANISM: Brucella phage Iz1

<400> SEQUENCE: 390
gaaaactgcg cgcccatatg tcgaagatta cgacactcgg cgccataaca ctggcgttga     60
tgaaacgctc acacagatag acgcagtgct gggagggaag ccgtcatgaa caagcttctt    120
cctacggtct ggatcatgcg taccgatgac ggatggtatc caatacagcc gagcgagaaa    180
tgccgccccg aagatcacgg caatctcaac gatcacgtta tttcaattga ggacgccaac    240
ggcaatgtgc tttggcgcag ggtgaaacaa tgaccgaatt gattgaccg                289

<210> SEQ ID NO 391
<211> LENGTH: 79
<212> TYPE: DNA
<213> ORGANISM: Brucella phage Iz1

<400> SEQUENCE: 391
atgctgtgac cgccgcattc gaacggtgcg cgaagtcttt cactggcgat gagctaactg     60
aactcttgaa gttttgccc                                                 79

<210> SEQ ID NO 392
<211> LENGTH: 1130
<212> TYPE: DNA
<213> ORGANISM: Brucella phage Iz1

<400> SEQUENCE: 392
agctatgagc aacattctta tcatcagcct tatcggcttg ttcactagcg gcgtggccgt     60
cggcctgtcc ttggccgctg taattaccct gagcctaaac gcaaggagg ccagcaatgc    120 ctagtaagga acacgaagca cttgtcgaga aggtggcaaa ggccatcaac ggaccttttcc   180 accctgtgcc ggaaggatcg ctattcacgt tggaccagct tcgcgatgtt cgctggcaac    240
```

-continued

```
agatcaatga cgtggaacga agtctgtgct tggctggtgc aaaagccgcc atctccacca    300
tccgcgccgc tctacaggag ccgacagaga ttatgctgca agcgtattgg gacgggagtg    360
aagcatcaga tagctggggc ttaatgctcg ccgcatccgc acttggggag aagagcgatg    420
ggatttaaca ccgcacttat ggtcttgaat gaccgtctcg atgaaattcg taacgatcct    480
cattttggca ggagagtttc tgatgctgtc atggaggcca gtcgccggaa agaaaaacac    540
ttcgggtcat tctctatgct gccgacgcaa catgccgaca cggtgcaggt tatttctgta    600
gggttcaata gcattaattt gctcggatat gcatggtcgg acgacccaga gattatccta    660
cgcgaactgg cgaaccggca tggctaccgg cttgtcaaaa agcgggaatc agatggggag    720
cagagcgaat gaagctgaca ttcgagaaga tattctccat ctacttggcg ttagcggtac    780
taactttcgg ttatattgca tcagaaacca agtgtgaaca gtcgttcatg agcgcccaga    840
ccaatacgga atgcgctgta gttagaggcg tagtcggtgg aataacttgg cctctttact    900
ggacttggga aggcttttct atcggccgcc aagtcctgaa aggcggtgac catggctaag    960
ctgacagaag cagaatttgc gcaacagtgt gcattcatcg ctaagaacgc ggcagattgg   1020
gcatcgtcaa tcttagagat cggagaagct ctaaacgatc ctgctaggtt aacgactgtg   1080
tgccgcttca cagatgaaat gcgtcaacgg cttgatcatc tcgaccggaa              1130
```

<210> SEQ ID NO 393
<211> LENGTH: 18817
<212> TYPE: DNA
<213> ORGANISM: Brucella phage Iz1

<400> SEQUENCE: 393

```
agtgaggatg aaagaagagt tggcatatat agcatcaaca catggtctta ctctgaaaga     60
cattatgaaa ccatgtcgct tcccaaccgt ggttaaggca aggaatgatg caatattctt    120
tgtgaggatt cagtacggtc tttcattaga gaaaataggg aagatattta atatgcatca    180
ttcaggtatc gcgtatgcca ttactagtca cttgtatgct gattaggtcc aggtcttgat    240
ctacgctgct tagggtcgtc aatgtcacct gtaaggatac ctactcttga cgatagaacc    300
tcaacctgag tagtgaggcg gttgatatcc cgcctcatta aatccatact tgaaataagt    360
gtgttttgca aagagtcagt acgttcattg gctctttgca gaccaaattc caattggtca    420
acgcgataag ccagctttcc tatgtctgcc gttgttgcct ttaactctgc attctccttt    480
gaaagggagg atatgctctt tgaatgtca ttaagattgg ttccaacata aaccccaaac     540
cctacaattg ttataattgt agggagatta actctaaacc agttaagggt tactgttgcg    600
tcctgtttca tttcatccgc tgacattgt aggccccgta tcgcccgcga tgttgtgcta    660
cctgttgggc aaagggtcta tcattttcaa cgatatatct tgccgtttgt tccgatggtg    720
acattaacac aagtacatca catgggctag ttagcttggc agtcgatgag caagcaaaca    780
agaccatcgt catcagcagc ataaacggca gcgtcaactt tttgaccatc tttaattacc    840
tctactctat cgttagataa ccgctgtaga acggattgct tcccagcgtt atacataaaa    900
taatgcgtac caactaacgc caaggccata gccccataaa gatatggctt aagcatcgtt    960
caactcctga cgaatgtctt ttattgcttt tacaatccag ccacgaagtg caagcccacc   1020
aagaagaact actagtgcaa ccgccccaa ggccaaaagc tcgcgccaac cgaatcctgc    1080 aagcccaaa gcaccgatac ctccgccaga gaaagagtt cctagccaac cagccaacga    1140
aaactttttc tttacttcct tatctacgga agtaggcatg acaggcttgt caacttcttt   1200
agttacaaca gaagggcgct caggagttgg cttcgatgaa agacccaatg caaaatcacg   1260
```

```
aacgccagct actcgtttgg tccatcccct gccgaaggtg ggccatagta tcttcttggt   1320
tttcttgtct ctggctctct tcatgaaagc caatcgtgta tcacaaagct tgttgatgac   1380
attgcgagaa cccatagact tgatagcctc aagcgtcttt gggcccacct tcccatcctg   1440
tgatacacca accactttct gaaggtcttt aaccgctctg gatggcccgc tattcaccgc   1500
ataatcaaat accgcaaagt caacgccgtc cggcaactca cgccatgca ccttatccca   1560 atactgacga cgatacacgg tttccaactg tgcgtcagta atcttgcgaa gatcggcttt   1620
tgtccctttt ggattcacaa aggcgcggaa agtagcaata gttacgccct tcatcgtagc   1680
gccaccaggg tcagaaggat ggtctgccca tcctccctca tgcttcaaaa cctctttgag   1740
tgatacttta aaattacgat ccatcttttt ctcgcatatc tatcgccatt cgcggcgggt   1800
tggtctgacg tacaccgtca gcgccctgat caataataac agcgtctccc gttctcagtg   1860
ggagtattgc aggcgggagg cctttagggc gaatatcaac cattagtaag acaccttgat   1920
aattttgttg attattacgg taggctgcat gttgttatga ggcaagcctc caccttgtgg   1980
gcttatagga tgattatgag ttgaaaatgg tatattttca tttgtaaaac ctacttgacc   2040
atttctactc aaacttaaat taccagttaa gttcttgagt acatttagta ttgtatagct   2100
accaacccca tttcctgtac tgccaccgtg gtcatgattg ggaatttgat atattgttag   2160
tgtactattt tgctcaccac cattagaacc tatcaaagcc ccattaatcc cacttccagt   2220
ggtagtaaca cggtttgcag cgctaccccc catgtcatcc ttaccagcac ctaccctgcc   2280
cctcaaatca ggcaaaacaa taaactgtcc agacgtggac ctattattag atggatcagt   2340
ctgtgaagtg gttcgatatc caaatcctgc cgtggcattg agtgcattac caacatagca   2400
agctgctacg aaatcgggat atgctgaaac ttcgatcgct tgcccaaagc aaaattgcca   2460
cgtattaggc gggttaacgc cagcataatc aatgactgcg cccacaggag taccagactg   2520
aaactgagac aatggaactg catttcccgg ctgggtagcg ttgcctaatc ccgtaacctg   2580
aaacccattc attgcaagat tagcgcgcat accaccttgc ccatcccggc taaggctttg   2640
cgtcatcatt gcataaagat caactaacgc tgggttgtgc tgagatggca gaatagtatc   2700
gccggtttga acgatagtcc cttgcagtgg attggtgttg ccgttgctgt ctcttggcat   2760
gttagttacc acctatatta gattgcgctg ccaattgaga gccaatcaaa gcttgaatta   2820
cagcatctct tatagcagga tttgatgcat tcggcaaagt ccctcctgag cgtgcaagaa   2880
gttctgctac atcagcattt cttaatccca tacgagtcgc cagttccctt ccagcaaaac   2940
ctgcgcccat agtagaagcc gcgcttgcag caccaaccgc tgggccacca atagcgttac   3000
caatcatgaa tggcacaccg ctacccaggc ccgcactaac aactccagta ggcgcaagtt   3060
tgccgatatt acgggccgta ttctgcatgg gggtgccacg cgacacattg ttaatggcct   3120
gtatctgctc aggcgtccaa ccttgctctt gccccttgat aatacgccgg tcaagatttc   3180
tgtattcagt gcgtaaggca ttctcaaaac cggaacccgt gaactgtcct gcacgcgccc   3240
ccgcaagttc ccttgcacgc tccaatgttc cagctttaag ataacggctt gaaatcttgc   3300
gcgcttcagc caactcaggg gcgagaggag aaacaaagtc atcgaatgca gaaagcatct   3360
tcttagcgat acggccttct ttgccttctg ccccaaaagc agcatccgca agcgtttccc   3420
taataacctg catttgtgtt gggttcatat catacccggc ataatcgcgc ataagctgga   3480
gcgcttcttt agccttgggg tatgcttctg cgatccgtcc tgtaggagtg atgagctcgt   3540
tatcccgtgc gatcttggta atatcgtcag caagactggt tgtcattgcc ggatcggcca   3600
caacgccacg tgcttcagcc tgtgcgtaca agtcagaagc ttgagcctta aggtcatcga   3660
```

```
tagatggaac agcttttca gccgcctgac gcgccgaacg gttagccaat cctgaaatag    3720
ccgcgccagt tcctaaccca ccaattaatt cacctgctat ttcagcgcct acattgtcag   3780
gagcaatctg ttgagcggtt gcgccgccaa ccccgccgcc taacccagtg gctaatatcg   3840
atgcaacttg tccagcgcta ctggcccctg ccgcaaatgg agcggcaccc ccaacggact   3900
gcgcaacgcg ccttgcgaac tgttcaccgc ctgattggct ctcaggagag atagccaaac   3960
cttgacgcaa tccagcgctt ccgcccaaag gcgtttgtga aggctgaata tccgttccaa   4020
acgcataatt gatgccagcg gctgcgggtg caaccaatag attgttaacc aaatctaccg   4080
gagcgcccaa agctcctgta gctccttcta gcaaaccaga aaatatttgt gacccgtagc   4140
ctccttctgg ttgaggctga tcagcgccac ccatcccctg aaaagcttgc aaagcgctcg   4200
cttcatcagg tgcgtcaact tcgtaaacct gtccgtctgg gccttgtaat tcaaatattg   4260
ccattactgt ttttgccctga tttttacgcc attaggaagg gttttccatc ctgtatcaga   4320
tgacttaccc tgatcctgcg gcccatcaat aatatcagca tacgcctgac gaacccgctt   4380
gaggttgcgt ataagctgct cttttgtctg cgactgatcc aaactgccaa tagttgactg   4440
aagataagta agttcacgct cagaaacagc acccaacgca ccgccggttg gagatgcgtc   4500
acgcatagcc tgcaatctat caaaaccagc gtttgcctta atggtggtta tcagctggtt   4560
gacgtcatta gaggctgtac cacctatctt gcttagggcg ctaccagcaa caccagtggt   4620
tgtgaaagga gacttatcaa tcaaatcaac ggctctatca atgtcttcag taacaacttg   4680
agaagtccta tcctgactga ccttttcctt ttcaaatgct tcacgttctc tctgggcctt   4740
aataaagtcc ggactaccag ggattgggga catagaaata ggctggccct gctcgttgta   4800
atcaacttta taaccagggg ggatgttacc catctgacga gcatctacag tagtagctcc   4860
agcgcgtttt acctgctgct ggtaatctgc aaaagaccct tggaaaccat tgtttctagc   4920
gtattcataa ttctgaatat ctgatgttgg gtcaccttgt ccctgaataa ttggctgacc   4980
ggtattggca tcataaacag tgttgccaac ctttacagta ttacgattgc gtgtagcctg   5040
ttcaatagcg gctttccaag catccgcatc gccagcaaga gcaggattaa tacctaacgt   5100
ctgcgctgtg gcctggcgct gcgccatcaa acgctgttgc tcttgtgctg cttgctgctg   5160
ctgcaactgc tgcccaaaaa gcataccggc aatctgccta ccttgatttg aaatataagg   5220
gctggaaaga gcctgaataa taacagggtt aattccgcca gattgtgatt gcgcaggcat   5280
ctggaatggt tgagacgtaa caggcgcacg atctgcgcta ggagcagacg ggaacggtcc   5340
agacaaagct tgcgccacgg gcgaagaccc agaaggagac aaagcccgc cgagcatttg   5400
atcgttcagc gccaacaagc gcggatcggc agcaggagcc gactctgccg acataggcgt   5460
cacttctggc acaatattag cagatgcagg aatcgcctgt tcaggcagga taggagacgt   5520
agcagcacct gcattccagc ggtcgttgaa gttagatggt gattgaggag atacaagaga   5580
atttgcaacc gaaagatttg gatcagaagc aaagtcataa ggagcaactt gtgcagctgg   5640
gagtccatca attggcgcaa cctgctcaat agcttcctgc ggagtagtag ctacacgtgc   5700
ataacgggcg gcgcgagctt gacgatgctc tggagcagga cgcaggaagt tattgacgat   5760
agcctgagca gcagttgccg tatctggggc agataggatt gattttgcag cgccagcctc   5820
ggaaccttga agttcgttca taagaaaatc aagctgcgca ttcacatcag cagggttgac   5880
gccacgctgc gctgcgaacg cttcatactc acggcggcgc ggacctgtaa gctggtaaag   5940
accgaaaccg ccacgcttc cggggacaat tgggtttttc tcattgatgc ctggattcag   6000
accgctctca tcctgaaaat taagaataaa cgcatccgct atatgcggct gaagaccacg   6060
```

```
gtcaatcaat ccttggcgaa tctcaggggc agaagggata tcaacaggct caccaactgc   6120
cgcaacggat gtaggtgaag cccccgctgc gacggcagga ttaaacccag caccaccgcc   6180
aaggctacca agcatatcac tgataagcga ttgttccgcc gctgcgttgg cagtaatagc   6240
attgtctgct gcgcgacgat cacggccaga ctggaaccct agaagcccct tcgtcaatac   6300
agaagcccat ccgccagcgt cagggctggt atctgtagcg cgcccgatca acgactgtgc   6360
gacctgctga cgctgggcga tttgctcagg tgtaagacgc tcaccgtttg gtccagtgaa   6420
aatggcgggt attagttctt gaaggtttgc cattaacgat ttccgcctct tagcccaccg   6480
gacattatac tgcctattgc ttgttttttt acgtctggga tatttgattg catcatattc   6540
tgcgcaatgg gggtttgctg ctgttgcggc gttagagtgt actgattccc ctgattaaat   6600
cccatatttg ccatcatggc actagatgga ttagcggatg caaatggtga gatattgttc   6660
atgaagcttt ggttgtttac taaaccgcta tcaatcaatg cgccagaagc tggagccata   6720
ggaatttgct gataagcatt tggattattt gacattctat tgccaagatt attataaccg   6780
cttagattat ttgcagcgaa cgtattaatc tgctggtttt gcataaatgg catttgccct   6840
tggggcctga atccaaaatt aaacagcatc acttcacctt gctataatca acacggtaat   6900
acccatctgc gtcctgagag accgcttcag gctgcaattc cagcaagtcc tgagccatat   6960
acccaatgtg cgtaaccggc gagccaatgt atttgaactt gtaaactgga cacctgaat   7020 cagttttgcc aatgcgctca atatcttcct tcagacgtct atctgagaat ggcaacatag   7080
acgcaacacc gccaaacaac ccgccaagag cccccatttt gctattatat gcgttcatgt   7140
ctgcctggta tttctgatta acgaggccag aatagtcaac cccagcaacc tgtgactgag   7200
gcgtttgcgc gaatgtgcta ttgggtgact gaacctgagt accagacata gcccaatga   7260 tttcattcaa aggctggttg cgctgtgcaa gctgctcttg gaatgcctgc gaacgtccag   7320
ttagcgctaa ctggttcaat tggtcagtat tggcgttcgt aaggcgcgcc atttccgtat   7380
tgtaagcaga agttccaggg cggataccag agttaatcag gcgattctca aggtctttgc   7440
ggttctgctc ctgctgcggc ataatgcgag acgaagcaag atcataagcc cagttttcag   7500
catcctgatt gttaaactca acggagaaac taaggtaatc accaagccat gcagaccgat   7560
cgttcgcaat gtttgcaaga ttaccctgcg cagactgaga cgcatcaaag atagcctgct   7620
gctcaggaga aagcgtggtg ttagccgtat aggtaggaac ctcaacgcgc ttaccgttcg   7680
ggtctgtaat ccatgtcgta ccagtctgtt gataatccaa gatacccat ggggtattct   7740 ggtttaccat gttcatttgc tgctgctgct gggccgtgaa agaattccac gcgccttgcg   7800
ctgcggctgt ttgcgctgga tcaggggctt caggagcgct cttgcccatt actcagaaac   7860
tcccttatta taaggcgact tgctccactc gtcgtcagtc aaagaaaaaa taaattcgcc   7920
ttcatccctg ccgcgaagac gaggaatgta agtttcacta acccgaatt ttcttgcaat   7980 accaatcatc gttttatttc tttcagaaac tctcaataca actaattgac agcctagacg   8040
agtgaatggc aggaagaaca tagcattaat cacggccctt gtcagccacc ttttgctaac   8100
agatgcagat gatagctcaa taacaccgta ttcagggtgg taattatggt aaagagtccc   8160
tgctataaga tcaccatcct cgaatacacc catgctgcaa aagtcttta ttgttatatc   8220 ggcttctctg catacgaaaa acccaaccgc ttcattcgcg gaagggttca ttgtcttgct   8280 gtaaatacatt gtatggatca agttacaatc tcgcccattg ttaagctgat ttccaaatgg   8340
acaatctcaa catcaagagg aacagaacta cctgacgtca cctgatagca ggcagaaacg   8400
tagtaacccg ttcctcctaa tgatttccac tgtgcattga aaacattagg attggttcca   8460
```

```
ccccatacag actgcccccca tacacctgta ccccatgcat tagagccatc cgcgctcgat   8520
gccgttggag cagagcccgg atcaatatca aaatcagcct tgaagcgaag gccataagac   8580
aaattagcct ttaccccttgc tacgccacgg cccatcttag ggattttaag attggctggc   8640
gatccaagat catcaaacag tgggatgtaa acgccagtgt aaacagaccc attgtccatg   8700
cctgttacat tggctttgaa cacttcaccg ttagggccac caaaatacat ctctccctgg   8760
aatacgcaca tagcgcgagc gtcccaattg gtataacggc accatgcacc tgtttcagaa   8820
ttggaaataa acaaaactgg atcataatca ccgattgtaa taggcggaga tatgattgcc   8880
atcttacgtt caggccaaag catacaagac caatcctcaa ggccgcgacc gtcgacggcc   8940
tgctgccatg cgtcttgaat gttgtacgaa acagcggcag gagaaagagc cgttacatca   9000
agactgatag ccttggaaag aggaataagg ccaacactag tagcaacagc aatatcaccg   9060
ccgcctctga aatgagcgcg attgccaaga ggccggccaa ttctgtatgt gccaacatgc   9120
gaccagtcgc ctgtagcttc tgggtaactt ccttgaaata ctgcaacctc accctccgtg   9180
gacgttacaa ccatctggtc agacaaaccg ccagcagcac ctgttcccat agaccatgaa   9240
tcgccccaca ggacggaccc gccaagggtt aatataccac ccatagggta acaacagga    9300 tcaccgccta cagcgtctgg ggcatccata taccatatgt ttaaggattc cttctgggcg   9360
aaccaaagac ggttttttaaa tgcccaaacg taagacatgt cagcagttgt taaaccgtct   9420
gggaacgcaa cgcccggcac aatgtttgat agaacgctag cagcttgggc gctcccacct   9480
tggtctccgg ttagcatttc attgtctaaa aagctcccgc cacttacgtt ctttgcgtta   9540
actatatcct ttaggacaag ccctcctcct ggcagaatct cacttactgt accttctgcc   9600
ccggaagtat cacccgttat cacttctcct acagaaaaat cctgtattac attgtcgtaa   9660
gacaaagccc aaaccccacc agggatataa ggataaaaag cattgccatc ataaatgaag   9720
cctgtagacg ctccgttaac gccaataagg tatattccgc cagtagtggc aaactgtaca   9780
gtaatccaat taccgcctaa tgcgccttca aaggcttcca tatcttcggt agacgattga   9840
ccaaagtaat caccgttttc agtgaccaga taatcgccat tctctgtcac cagtcggtaa   9900
ttataaggaa cgaggatatt ggtaatatcg taaatggtgt tttcggtaga cgcgaacaat   9960
ttacgattca agccgttaac gtatgtaaac agggacgtta cgccttcatc cccctggcct   10020
agagtggcat aaagctcttt accccttcga agaatagctg tggtagacgt tggaaagaag   10080
ttatcaagta cagcagcacc ttgtggcccg ccattttcca taggcgtaga cagattgcgg   10140
ttgctaatcc acccgcctgt aggtgcatgg aactttttaa ggtctgactt acgttgcgcc   10200
ggtttcttct gcgcgaggat agggcgctgg tacatcaatt accccaattc aaaaggccat   10260
gccaaatgtg tattaagacg cctgcttctg gaacgtgcac ggtaaacgtt tgtgccttta   10320
tccttagcag caagctgatc aagggccatt gtaaattgtt cttggtcgcc tgtatagtct   10380
aacttcttat tctcacgcca tcgccatata aggccaaggg taagaaggtc attgccgccc   10440
ttgatgataa aatcatctgt atcggcagtg aactccggct ttcctgcatt atttgaatca   10500
agagcgtaat tattggaaat gtaaggatac gtggcgctat tctgagcatt aggcggcgga   10560
aagaaatgaa tctgattttg gtaaatagtc cacgcaccag gagttagctc aaaattacgc   10620
gcgcgccggt ataggaagtc attgagattt tcaatgtgct catatcccca aacccaatta   10680
ttcaagtcct gaatatccgt aaccaaaagc tgacgatcat agtcctcagg aagatcgaat   10740
atttcagtaa cgccatcagt tggtacgtta taaactttag tcagagcctg ccaatctgcg   10800
tacctgcaaa tatccctagc cacttcattg acaagatcaa caatctctag ttcaagctga   10860
```

```
tctgatgaag taaaaaagac ggcgggcttt tggcccacca atctaattgt agcggattgc   10920
atcgctgaca gaattgacat ttacattcct tttgcaaggt ttaccagtga tgcatggctt   10980
agtcggccat caggcttagt gccagtcttt gattcaatca tatcacgcaa ttcagcctct   11040
gtcattgctt cgtaaagatc ttcttcaact tctggaataa cagttgatgc cgttcctgcc   11100
gattcaagct ctgcaatgcg cttttttaaga gcctcgatct cattaagagc tttatccgac   11160
gcggaatgat cagaaatata cttgcgagcc aactccttaa gcgtgttacc catcatgcca   11220
agcgatttaa gcttgtcacc ttcaagggta ttaagcgcct caatgctgta gacacgatgg   11280
acacggcaga tggaaagctg ctcttcagtt acgccataag gacgcagcat ttccaacggt   11340
gttcccattg cgtgctgcgg gttgccttct ttgaacgtac ggtactggtc ggcccaacgt   11400
tctgcatagg taatagattt gttgccttcg cgtttccacg tctgatgagc cgggaaaaca   11460
ggcgcgtaat tatttgatcc cgcaaagcgg acctcaacaa cttcatacat ttccatgact   11520
gcgtggcctg ccgtttctga cttggggata ttctcgacct caatcacctt aaagaaaggc   11580
gttacgttaa ggtcgcgcat gtcaatttca actactttag tcatttatcg ttccttgtct   11640
gagaaggggt aaagggaggc cgttaagcct ccccatattg attagagcgc atacactcgc   11700
gcatgaaaat aagcaccggc aggaacagca acatcagggg cctgcaaaac gccagaagcg   11760
ttagcagtgg ttacaaaatc agagtccatg ttaaacgtg cgcttgcggt aagcgcagtt   11820
gtgccgttct gaacccagat gtaatcgtaa ccatcatcgc cagtttcacg attaccaagc   11880
ttataagaag gctcagtaat accggaaaca gtagcgccgc ctgctccctg aatgcctgtc   11940
aggtcccaat atggaagacc gacaaaaacg tcattaagct gcgggcctag ctgcggggta   12000
gtccgaaaag gtacggaatt agccatatct ttttctcctt atgccgtgat aatgcggtac   12060
gagaacagcg ggttctcaag cacaagctga ccggaccata caatgccctg agcaaccgca   12120
tcctggttga taggacgcat accgtccccc gggtggaatg gtacgaatgc ctgatctggg   12180
aactcgtaga tagcaaggcc ctgagtatca atgccgaaga tggtgttagc aggcataacc   12240
gtaccaatgc caccagctgc aacgatatca accggaccag caggagtcat gtaggtgaga   12300
cccgcaaagc ccaaacggcc aaggcgttcc gaaacgatgc gctgatgagc aacgaacgat   12360
gcggagatag cctggtacga aagggaatcc gcaatgagaa gatcagcata acggccatta   12420
cgcgaacgat taagagcaat gcgctcaata ataggacgtg cagtcgtgct atcccaagtc   12480
gtaaagcccg aaacatcacc gtttgtaatg ttgaacgtcg aggtgcgcca gtttggaacg   12540
gttgcacgat caatgccgcc gtatacgcca gtgtttggaa tgactggaat agcgccacca   12600
aggccgataa gctcacgacc tccagcgccc gtgccgtcac cgataagagc aacttcaaac   12660
tcttccttaa ccgactttc agccgcatca aggtaggttt ccataaggtc gataacctct   12720
tcctcaccgc gagtgtacat cagttctgtg ccagtcagag agaacatgct gacaacacgc   12780
gaccaattga acacggcaga gttaagaagt tctttcgggg tgatttcgat cttgtcatag   12840
ccagtgaacc actgcgcctg caatttgtcg aactgaaccg gaatacgaag ttctgggcca   12900
ccagcgcgct ttacgcgaat acggccctga tcacgcagaa tgcgggtaag aggggtcgag   12960
ttataaacaa tgtcctgcac ctcacgcgag cgccgggcta cggctgcggt gagaagctgg   13020
cggtaatttc tatcctgaac gatagccatt ttagctcctt aagccttctt cagacgcttc   13080
aactcgtctt ccagaagttc acgcattgac attttcttat ccggttcttt gacctctagt   13140
acattccccg gagaagattt gattgatttg ctgccgttga agtcttcgtc aacacggctt   13200
tcagaactag tctgctttgg tgagaaggat gagacatttg aagaaggatt aatcctttca   13260
```

```
gccatgtcgt acgctgcttc aagcttctca gcaggactaa gattagctgg gattttacca   13320
gattgtagaa agaaagcaat atcctgttct agttcatagt atcgtgggtg ttcttttgcg   13380
aatggctcaa tatacataaa agccgccatc tgttcctgca tcgcttggtt ctgccgtttc   13440
agcgtttcca cttctggatt aatctgcggc tgttgctgcg gctggacctg tggtgcctgc   13500
gacacgtaag aattagggtc tgcactaatg tgctgagcaa gctgctgtgg agtaacattg   13560
aaagcgcgca aaatatgaga aatagccgtg tgtggctgca tattcagatt gctaagaagc   13620
tggcggaagc cttcaggtgg ggactctgca aactttcgct caatcccac atagttatca    13680
agcgcttgtt taacgctaac gccatgctgt ttaccgagct cttcgtattc cttaagctct   13740
tcacggaact gatgagattc acggtactgc tgcacctcag tctcgtgttc acgtacaagg   13800
cgagaaactt ccgactgcac ctcattgggc gtattccgcc atagctcctt agcacgtgga   13860
agaaagcgag caggaggctc aggacggtca cggacctcag acttccgttc ggtctgctga   13920
tccttaacct gctcgcttgc gtcaacttcc ttctcaggag tggcgctctt tgcctctgtc   13980
ttggcgacag gcttgggttc ttcctccagc ttttcagcct taacaggttt ttcaaccttt   14040
tccggctctt tagtcttatc aagctccgcc ttcagtgagt cccgtacaga ttcagccttt   14100
gcgggaactt ccggcttggc ttcttcaaca ggaggaggag ttattttacc accgccagat   14160
gttttaggcg ttacatctga ttcaagcgta gttgaaacgt gttctgtgac tggtgatggt   14220
tgaattactt cgtcggtcat tttataccte gtctgagaag gtcataggt taaacttcac    14280
taatagcgcg cttgatatct tcacggcgct ttttacggtc aaattcagga gccttgaagt   14340
caggaaggct ttcattgcca agctcgatat accgttcgcc ctttgggttt ccagagggga   14400
gaagcgtctt acgatagctt gacaatgtat catgcatctt gccgtccata cccatgcagg   14460
gctggatagt gtcctgacgg aaatagggct taggcaggga actagccccc atccttgccc   14520
tatgttctgc taccaattca gagattgatt tcattacgtc gcaatgatcc ctgctgtgcg   14580
aagtgctgcc aggatagcat taaccgccgt tcccgccgtg gtcccgtctg cttccggggt   14640
aatgtcggcg attgccgcgc tagaaagaac accaccgcgt tccgttgtgg taggagtggc   14700
aagagtgact ggaatagaag cattcgcagc acccgtaaag gccccgctag ttcccgtcgc   14760
gcctccagta agggagatag tgcggccagt cgccagcgcc gttgcggttg ctactggtac   14820
ggtagcgggg aaagtggcgg gtttatccgt aacatcatcc cacgatactg cgccccccg    14880
aagatgattc aatctggcta cgaacttctt tagcaagttc tggaaccatt gaaagttcta   14940
ctagtcgatc taccggtgtc tgtgccatta ttattcctcg tcaggttcag gtggtgtata   15000
gccctcaata atcaaaggcg gtgcattgct ggatactaca ctaatcggaa taccaagtcc   15060
attagttgca accgtggcca ctggcgcatc actagttact gcaacaaaag gtgctccgtt   15120
atcagaaatt acaactggaa atccgggcat ctaaacaccc cacgcggcaa ataggggcaaa  15180
accaatggcg atatatgata aagcccttgc tgatatccaa gagtatttcc agtcatcttg   15240
cgcggcaaat tgagataatc ctccaaaaag caatgcgtca gaaacgtggc tagtaccatt   15300
gaacgaaaca catagtccaa acgccgcaaa caggattgca ccacatattg cataagttga   15360
tttaggcatc actccacctc tctttgtgtc aacgcttgag tttcattaaa ctcttgcgaa   15420
cgattagcgc ggttttccga ttcaactcta agcgccgtat ccaccgtgcg ttgttcagcc   15480
tcatttgctg ccttatactc ctcaaggtct tgcttgcgaa cgtctagacc aatcttggca   15540
agaatctccg cggtctgagc ctgcataaga tttgttttgg cttccatatc agccatctta   15600
gccgcaaact cctgctcctg tttggatagc tgaagctgca acttgccttg ctcaatctcg   15660
```

```
aactgcgcag catccttctg ggccttaagc tgcaaatcct gcattttacc ttgcaactca  15720
gcctgtttaa gctgcgcatc tgcttgcacc ttagccatct gcgcttgtgc tttagccatc  15780
tcagcttcag caagcttatt ctgcgcctca ataagagcct gttgttctcc accttcttgc  15840
ggtggctggt agttagaagc ttcatcgatg aaattatcga taaggccatc aagctcacga  15900
ccaatacgat aaggcccaag aacaaagtta agcataccgc cagcaagtgc tgacccggca  15960
ggccccattt gagccaatcc ctgcaatgcc tgagatgcac cagagaatgt tgtcaagaac  16020
tcattgcggc tggccttttc ctgaatttca tcagtcaaaa tagtgctatc agacgcgatt  16080
tcaaaagcaa aaccacgcga tttatcattg cgcaaaggt caatgatatc ctcgatagga  16140
atttctgaat tagcctcttg cagcataggc gcatatttct gcaaaatggc ctgctgagtt  16200
tccttaaact ttgtctggat atcttgctgt aattcaggag gaatctgatt ttcctggaca  16260
aacttctctg tctgtttctt aaggttttca agctccttct cagcagcttc ttcaatgcct  16320
tttatctgct tctcaatctg cgcttttgta gagattttca tctgagacat ttcaaggaga  16380
gtatcctttg aaaaatgctc tgcaataatc tcagccgaaa tgcgaacagc gtcggcagca  16440
atgcgctgta gctcatcaat cttctgtcga acacgaacgg aaccgtactg acccttgagc  16500
tgctgcgctc ctagagtttc atcagcctca gtagcaccgc gcataatgtc gctaatacca  16560
gacaactgat agaagtcatc aattagcttt gcacgcgcct cgataagtcc agtgatagcc  16620
gttgccactt ccgcaagcgg catccaggca accatgttgg tcacatcgct gctaatcgac  16680
ggaacaaaga ttacagtttc atcatcttcg ctctggataa gctcgcttac cgcgtctcga  16740
atatcaccgc taccggccac aatgcccttg agcttaacct ttttccagcaa aaggtaaata  16800 cgcgctgtca gcgtgttaat cttgtcaaaa tgaacgctat aacgctcata gtctggaaca  16860
gggatcaacg aacgacgcgc cagtgtgcca taagctggac gcgggcaggg gaagaagtct  16920
tttagcttca ggtgtggctc accttcatcc agtaggcgat cgacaccctc agaaacccaa  16980
taaaccttat tatcagcgcg atgccagact tcccaaacgc tgcctttcag tgacttatca  17040
tcattgccgc gttcttcgtc ttcacgcttt tggaaagtt ttacgtcttt gtaaacatcg  17100
ccggatgcct tatagaaacg cttacgcaac tccttacgcg tcatccatgc acgacgagct  17160
acccaaccaa cctcggacca tttacgggca ggttcatgca ggaaatccat gcgatcaaga  17220
tgctcgatac aaacgcgctg ttcgcccttt tctgattcat acgtgagcca catgacgccg  17280
cgattggtga aaatcaggtc gtcacggacc tcgcacataa catcgtcaat gttagagcgg  17340
tcaaagttag acacagatac gcgctctaac aattcagccg tctttgactt gactggatcg  17400
cgatctttga actgtgttga aactacaggc tttggaggat gcgcataaac agcaggcttt  17460
agaatttcat aggaagccca gaatagatca agctcaccat ctgtccaatt ttcactgtat  17520
ggacgctttt caccctgata tttgctgtaa accgtatcaa tacggtcgca atattctgc  17580 cattcgcgaa acttatcctt agcgttctgc aataccgaca gaacaacgct tgaagacttt  17640
ggttcgtctt ttaattcaag tgtatcggat ggctggattt cttcttcgtc cacttaaacg  17700
gcctcatttg caaatgttgt ggcaatgtaa catgcaggag tgcaaaagaa aaggccctcc  17760
gaagagggcc cgtaacaaga ctgcctacag ccatacggat aatatcagaa cgcgccggga  17820
ggttgcgccg acacttatgc ctcgacgctt tcagcgccgc cgttctgatt tcgcgggata  17880
tgccttaaac ctctcagcca taggacaatt aacatgcccc agcgggattt gaacccgcgt  17940
caccatttgg tgaatatccc ttctcgtagc cctcatgtct cacgctaccc ggataagtgg  18000
ggcggtactg catgagggtg gattttttgcc ctagtcggcg ctctttttgag ccgtctggct  18060
```

```
acgaggactt cccagaccc gttctccaac cacggctatt ttcgctggcc gtcagctaca    18120
tgcgaggatc ggcgcttgat acgctcgatg tgcgaaacgc cctcgcattc ctatatccta    18180
ctccgaaccc ggcctaatta caaggctgtc tttccagtct acggtgccgc gtttgtagga    18240
tttgtgtgag ttggcattgg agcaaatgtc gtctaaatcc acccactggt ctaaatcttt    18300
aattgatggt ctgtttcgat aaaggaaagg aataccattt tcatccctcg ccatatactt    18360
aaactccggc gcaacatgat cccagttgat ggtgtctggt gtggaggagg gtgcgatgcg    18420
gtaggttccg gcatcccaat cccaataagg tgtatctttc tttgaccaat agtcataatt    18480
attaccgcag aactcaactt cctccccatc cacataagcc tgcatcactt caatcatgcg    18540
ctttgtgcgt tcgatgtggt ctttgttggt catcaaactt ctccacgtgc tttggcgagc    18600
aatgcatcga tttcagcgca gaacgcagct cccatgggc ctagatcgtc ttcatccatc    18660
cacttacgga cttcctcaag attgcgataa agctctggcg cggcggcgat taggtgggcg    18720
tttgcgcggt caatttcatc accaaaaggg gtaccgtcag cggtatcctt tgtgaggata    18780
ccgggcgaaa ggtcataaga tgaccaattg tcgtttt                            18817
```

<210> SEQ ID NO 394
<211> LENGTH: 1010
<212> TYPE: DNA
<213> ORGANISM: Brucella phage Iz1

<400> SEQUENCE: 394

```
cgcgctggag ccttcctctg cgcgtgaaca ggcgttggag gaagtaacgc tagaacgcag      60
cattgaacaa tggcgcaata tgaagccctc ggaagtcatg aagggcagca ccgcgcagat     120
cacatatgca ctggaggacg ccagaaaaga cattctgtcg ctggcccgcg ccctatcctc     180
cccggaccat attgccgacg ccggtaaggt cgaggggggat gggtggcatg tcgagtatga     240
agtttacagc gaagatgaat ggcaggccgc ttcgacggat ttagacgcg cgcttgatta     300 tgccgtcatg tatgccgccg acggcttcaa aaacatcact gttcaggaag tgcgccgccg     360
cactctcccc tctgcactag cttcggaggg cgaggaatga gcaagattgc gtaccgccgc     420
aaggaagtga tcggcgactg caccctgtat cttggcgatt gcatggaaat catgccgaca     480
cttgaaaagg tgcaggcggt tttaacagac ccgccatacg gcatgacaga cgcttcttgg     540
gacaacgcgc caaatgtcga agcaatgtgg cgtgaattga aactcgaccg aacagacgcc     600
gtgttcattt tgaacgcttc gcagccgttc accagcgcag ttgttcttgg gaatatcaag     660
gatttccgcg tggaatggat atgggaaaag aacgctggct ccaactttgg aactgtcaaa     720
tggcagccga tgaaggagca cgaaagcgtc ttggtgtttt catcgcgaac ccctcgctat     780
ctgccaataa tggaacagag ggccgctagc ggagctgcga gggtcaagac tgttgtcaac     840
tacgacagtc aaccagaagc atattctgga attaccggca aatccgccag catgaggccg     900
caactccgct atccgcgttc cattcagaag ttcaaccggg agcgcggttt tcatccaaat     960
cagaaaccgg tgggattggt gtagtatttc ctcaagacgt acacagaggt                1010
```

<210> SEQ ID NO 395
<211> LENGTH: 1052
<212> TYPE: DNA
<213> ORGANISM: Brucella phage Iz1

<400> SEQUENCE: 395

```
acatgccgac acggtgcagg ttatttctgt agggttcaat agcattaatt tgctcggata      60
tgcatggtcg gacgacccag agattatcct acgcgaactg gcgaaccggc atggctaccg     120
```

```
gcttgtcaaa aagcgggaat cagatgggga gcagagcgaa tgaagctgac attcgagaag        180
atattctcca tctacttggc gttagcggta ctaactttcg gttatattgc atcagaaacc        240
aagtgtgaac agtcgttcat gagcgcccag accaatacgg aatgcgctgt agttagaggc        300
gtagtcggtg gaataacttg gcctctttac tggacttggg aaggcttttc tatcggccgc        360
caagtcctga aaggcggtga ccatggctaa gctgacagaa gcagaatttg cgcaacagtg        420
tgcattcatc gctaagaacg cggcagattg gcatcgtca  atcttagaga tcggagaagc        480
tctaaacgat cctgctaggt taacgactgt gtgccgcttc acagatgaaa tgcgtcaacg        540
gcttgatcat ctcgaccgga aggcaggccg cgccgcacta cgggaaaggg agtgaggatg        600
tacgaacctg attaccatta tattccgtgc cgatgcttca gcgcggatca tttggtccgt        660
gtatgcccgg atgaggatat agacggcaca ttgaacgttg aaatcctatc atcacgccaa        720
tcgtctttct ggtcgcgtgt cagatgggcc ttgaagcatg tattcggtcg ggatgacctt        780
gtattcgcag acgttattat ctcgcgtgag aaatggctga aagcggcggg agaagccgaa        840
aggaaagaag tgggaaagtg agtgaggatg aaagaagagt tggcatatat agcatcaaca        900
catggtctta ctctgaaaga cattatgaaa ccatgtcgct tcccaaccgt ggttaaggca        960
aggaatgatg caatattctt tgtgaggatt cagtacggtc tttcattaga gaaaataggg       1020
aagatattta atatgcatca ttcaggtatc gc                                     1052

<210> SEQ ID NO 396
<211> LENGTH: 1052
<212> TYPE: DNA
<213> ORGANISM: Brucella phage Iz1

<400> SEQUENCE: 396
gcgatacctg aatgatgcat attaaatatc ttccctattt tctctaatga agaccgtac         60 tgaatcctca caaagaatat tgcatcattc cttgccttaa ccacggttgg gaagcgacat       120
ggtttcataa tgtcttttcag agtaagacca tgtgttgatg ctatatatgc caactcttct     180
ttcatcctca ctcactttcc cacttctttc ctttcggctt ctcccgccgc tttcagccat       240
ttctcacgcg agataataac gtctgcgaat acaaggtcat cccgaccgaa tacatgcttc       300
aaggcccatc tgacacgcga ccagaaagac gattggcgtg atgataggat ttcaacgttc       360
aatgtgccgt ctatatcctc atccgggcat acacggacca aatgatccgc gctgaagcat       420
cggcacggaa tataatggta atcaggttcg tacatcctca ctcccttttcc cgtagtgcgg     480 cgcggcctgc cttccggtcg agatgatcaa gccgttgacg catttcatct gtgaagcggc      540
acacagtcgt taacctagca ggatcgttta gagcttctcc gatctctaag attgacgatg      600
cccaatctgc cgcgttctta gcgatgaatg cacactgttg cgcaaattct gcttctgtca      660
gcttagccat ggtcaccgcc tttcaggact tggcggccga tagaaaagcc ttcccaagtc     720
cagtaaagag gccaagttat tccaccgact acgcctctaa ctacagcgca ttccgtattg      780
gtctgggcgc tcatgaacga ctgttcacac ttggtttctg atgcaatata accgaaagtt    840
agtaccgcta acgccaagta gatggagaat atcttctcga atgtcagctt cattcgctct     900
gctccccatc tgattcccgc tttttgacaa gccggtagcc atgccggttc gccagttcgc      960
gtaggataat ctctgggtcg tccgaccatg catatccgag caaattaatg ctattgaacc     1020
ctacagaaat aacctgcacc gtgtcggcat gt                                   1052

<210> SEQ ID NO 397
<211> LENGTH: 1010
```

```
<212> TYPE: DNA
<213> ORGANISM: Brucella phage Iz1

<400> SEQUENCE: 397
acctctgtgt acgtcttgag gaaatactac accaatccca ccggtttctg atttggatga    60
aaaccgcgct cccggttgaa cttctgaatg gaacgcggat agcggagttg cggcctcatg   120
ctggcggatt tgccggtaat tccagaatat gcttctggtt gactgtcgta gttgacaaca   180
gtcttgaccc tcgcagctcc gctagcggcc ctctgttcca ttattggcag atagcgaggg   240
gttcgcgatg aaaacaccaa gacgctttcg tgctccttca tcggctgcca tttgacagtt   300
ccaaagttgg agccagcgtt cttttcccat atccattcca cgcggaaatc cttgatattc   360
ccaagaacaa ctgcgctggt gaacggctgc gaagcgttca aaatgaacac ggcgtctgtt   420
cggtcgagtt tcaattcacg ccacattgct tcgacatttg gcgcgttgtc caagaagcg    480
tctgtcatgc cgtatggcgg gtctgttaaa accgcctgca cctttccaag tgtcggcatg   540
atttccatgc aatcgccaag atacagggtg cagtcgccga tcacttcctt gcggcggtac   600
gcaatcttgc tcattcctcg ccctccgaag ctagtgcaga ggggagagtg cggcggcgca   660
cttcctgaac agtgatgttt ttgaagccgt cggcggcata catgacgca taatcaagcg    720
cgccgtctaa atccgtcgaa gcggcctgcc attcatcttc gctgtaaact tcatactcga   780
catgccaccc atcccctcg accttaccgg cgtcggcaat atggtccggg gaggatagg    840
cgcgggccag cgacagaatg tcttttctgg cgtcctccag tgcatatgtg atctgcgcgg   900
tgctgccctt catgacttcc gagggcttca tattgcgcca ttgttcaatg ctgcgttcta   960
gcgttacttc ctccaacgcc tgttcacgcg cagaggaagg ctccagcgcg              1010

<210> SEQ ID NO 398
<211> LENGTH: 19
<212> TYPE: DNA
<213> ORGANISM: Artificial sequence
<220> FEATURE:
<223> OTHER INFORMATION: ME1 transposone sequence

<400> SEQUENCE: 398
ctgtctctta tacacatct                                                  19

<210> SEQ ID NO 399
<211> LENGTH: 19
<212> TYPE: DNA
<213> ORGANISM: Artificial sequence
<220> FEATURE:
<223> OTHER INFORMATION: ME2 transposone sequence

<400> SEQUENCE: 399
agatgtgtat aagagacag                                                  19

<210> SEQ ID NO 400
<211> LENGTH: 550
<212> TYPE: DNA
<213> ORGANISM: Artificial sequence
<220> FEATURE:
<223> OTHER INFORMATION: Brucella promoter

<400> SEQUENCE: 400
tatgcaggta ccggactgat cgaatttgtc ggtggcctcg ccattctatt cggtttcaag    60
acccgcattg ctgccgtgat cgtcggcctc ttcaccctcg gcgcaacgct ggtggcccat   120
atggacttcg ccgaaggcat gaacctgctg atagcgcaga gaaccttgc catcgctgga    180
ggtctttttcc ttctcttcct gcatggtgca gggtcactct cgatcgacgc cagacgcggt   240
```
tgaccaccag ttctggactt ccccacaaaa agccgtgcca aaatgcgcgg ctttttcata 300
tttcacatga ctgccacttg tttctccatc gagattttac gaagctggag cggcggcacc 360
acgaagaata tatttgcaat tcttcttata cccactatcg ggggaaaacc ggctgacaac 420
gtcctgaagg attgcatagc gatatcttgt gagataaggc agccccccact tttgacgcaa 480 gctccggccc accgtcgcat cttgtaataa tttagtttgt agagaaatct cgaggatccg 540
gggaattcag 550

<210> SEQ ID NO 401
<211> LENGTH: 5846
<212> TYPE: DNA
<213> ORGANISM: Artificial sequence
<220> FEATURE:
<223> OTHER INFORMATION: Brucella promoter

<400> SEQUENCE: 401
gaattcaggc ttggaggata cgtatgacta aaaaaatttc attcattatt aacggccagg 60
ttgaaatctt tcccgaaagt gatgatttag tgcaatccat taattttggt gataatagtg 120
tttacctgcc aatattgaat gactctcatg taaaaaacat tattgattgt aatggaaata 180
acgaattacg gttgcataac attgtcaatt ttctctatac ggtagggcaa agatggaaaa 240
atgaagaata ctcaagacgc aggacataca ttcgtgactt aaaaaaatat atgggatatt 300
cagaagaaat ggctaagcta gaggccaatt ggatatctat gattttatgt tctaaaggcg 360
gcctttatga tgttgtagaa aatgaacttg gttctcgcca tatcatggat gaatggctac 420
ctcaggatga aagttatgtt cgggcttttc cgaaaggtaa atctgtacat ctgttggcag 480
gtaatgttcc attatctggg atcatgtcta tattacgcgc aattttaact aagaatcagt 540
gtattataaa aacatcgtca accgatcctt ttaccgctaa tgcattagcg ttaagtttta 600
ttgatgtaga ccctaatcat ccgataacgc gctctttatc tgttatatat tggccccacc 660
aaggtgatac atcactcgca aaagaaatta tgcgacatgc ggatgttatt gtcgcttggg 720
gagggccaga tgcgattaat tgggcggtag agcatgcgcc atcttatgct gatgtgatta 780
aatttggttc taaaaagagt ctttgcatta tcgataatcc tgttgatttg acgtccgcag 840
cgacaggtgc ggctcatgat gtttgttttt acgatcagcg agcttgtttt tctgcccaaa 900
acatatatta catgggaaat cattatgagg aatttaagtt agcgttgata gaaaaactta 960
atctatatgc gcatatatta ccgaatgcca aaaaagattt tgatgaaaag gcggcctatt 1020
ctttagttca aaaagaaagc ttgtttgctg gattaaaagt agaggtggat attcatcaac 1080
gttggatgat tattgagtca aatgcaggtg tggaatttaa tcaaccactt ggcagatgtg 1140
tgtaccttca tcacgtcgat aatattgagc aaatattgcc ttatgttcaa aaaaataaga 1200
cgcaaaccat atctattttt ccttgggagt catcatttaa atatcgagat gcgttagcat 1260
taaaaggtgc ggaaaggatt gtagaagcag gaatgaataa catatttcga gttggtggat 1320
ctcatgacgg aatgagaccg ttgcaacgat tagtgacata tatttctcat gaaaggccat 1380
ctaactatac ggctaaggat gttgcggttg aaatagaaca gactcgattc ctggaagaag 1440
ataagttcct tgtatttgtc ccataatagg taaaagtatg gaaaatgaat caaaatataa 1500
aaccatcgac cacgttattt gtgttgaagg aaataaaaaa attcatgttt gggaaacgct 1560
gccagaagaa aacagcccaa agagaaagaa tgccattatt attgcgtctg gttttgcccg 1620
caggatggat cattttgctg gtctggcgga atatttatcg cggaatggat ttcatgtgat 1680
ccgctatgat tcgcttcacc acgttggatt gagttcaggg acaattgatg aatttacaat 1740

```
gtctatagga aagcagagct tgttagcagt ggttgattgg ttaactacac gaaaaataaa   1800
taacttcggt atgttggctt caagcttatc tgcgcggata gcttatgcaa gcctatctga   1860
aatcaatgct tcgtttttaa tcaccgcagt cggtgttgtt aacttaagat attctcttga   1920
aagagcttta gggtttgatt atctcagtct acccattaat gaattgccgg ataatctaga   1980
ttttgaaggc cataaattgg gtgctgaagt ctttgcgaga gattgtcttg attttggttg   2040
ggaagattta gcttctacaa ttaataacat gatgtatctt gatataccgt ttattgcttt   2100
tactgcaaat aacgataatt gggtcaagca agatgaagtt atcacattgt tatcaaatat   2160
tcgtagtaat cgatgcaaga tatattctt gttaggaagt tcgcatgact tgagtgaaaa    2220
tttagtggtc ctgcgcaatt tttatcaatc ggttacgaaa gccgctatcg cgatggataa   2280
tgatcatctg gatattgatg ttgatattac tgaaccgtca tttgaacatt taactattgc   2340
gacagtcaat gaacgccgaa tgagaattga gattgaaaat caagcaattt ctctgtctta   2400
aaatctattg agatattcta tcactcaaat agcaatataa ggactctcta tgaaatttgg   2460 aaacttttg cttacatacc aacctcccca attttctcaa acagaggtaa tgaaacgttt    2520
ggttaaatta ggtcgcatct ctgaggagtg tggttttgat accgtatggt tactggagca   2580
tcatttcacg gagtttggtt tgcttggtaa cccttatgtc gctgctgcat atttacttgg   2640
cgcgactaaa aaattgaatg taggaactgc cgctattgtt cttcccacag cccatccagt   2700
acgccaactt gaagatgtga atttattgga tcaaatgtca aaaggacgat tcggtttgg    2760 tatttgccga gggctttaca acaaggactt tcgcgtattc ggcacagata tgaataacag   2820
tcgcgcctta gcggaatgct ggtacgggct gataaagaat ggcatgacag agggatatat   2880
ggaagctgat aatgaacata tcaagttcca taaggtaaaa gtaaacccccg cggcgtatag  2940 cagaggtggc gcaccggttt atgtggtggc tgaatcagct tcgacgactg agtgggctgc   3000
tcaatttggc ctaccgatga tattaagttg gattataaat actaacgaaa agaaagcaca   3060
acttgagctt tataatgaag tggctcaaga atatgggcac gatattcata atatcgacca   3120
ttgcttatca tatataacat ctgtagatca tgactcaatt aaagcgaaag agatttgccg   3180
gaaatttctg gggcattggt atgattctta tgtgaatgct acgactattt ttgatgattc   3240
agaccaaaca agaggttatg atttcaataa agggcagtgg cgtgactttg tattaaaagg   3300
acataaagat actaatcgcc gtattgatta cagttacgaa atcaatcccg tgggaacgcc   3360
gcaggaatgt attgacataa ttcaaaaaga cattgatgct acaggaatat caaatatttg   3420
ttgtggattt gaagctaatg aacagtaga cgaaattatt gcttccatga agctcttcca    3480
gtctgatgtc atgccatttc ttaaagaaaa acaacgttcg ctattatatt agctaaggag   3540
aaagaaatga atttggatt gttcttcctt aacttcatca attcaacaac tgttcaagaa    3600
caaagtatag ttcgcatgca ggaaataacg gagtatgttg ataagttgaa ttttgaacag   3660 atttagtgt atgaaaatca ttttttcagat aatggtgttg tcggcgctcc tctgactgtt   3720
tctggttttc tgctcggttt aacagagaaa attaaaattg gttcattaaa tcacatcatt   3780
acaactcatc atcctgtcgc catagcggag gaagcttgct tattggatca gttaagtgaa   3840
gggagattta ttttagggtt tagtgattgc gaaaaaaaag atgaaatgca ttttttttaat  3900 cgcccggttg aatatcaaca gcaactattt gaagagtgtt atgaaatcat taacgatgct   3960
ttaacaacag gctattgtaa tccagataac gattttttata gcttccctaa aatatctgta   4020
aatccccatg cttatacgcc aggcggacct cggaaatatg taacagcaac cagtcatcat   4080
attgttgagt gggcggccaa aaaaggtatt cctctcatct ttaagtggga tgattctaat   4140
```

-continued

```
gatgttagat atgaatatgc tgaaagatat aaagccgttg cggataaata tgacgttgac    4200
ctatcagaga tagaccatca gttaatgata ttagttaact ataacgaaga tagtaataaa    4260
gctaaacaag agacgcgtgc atttattagt gattatgttc ttgaaatgca ccctaatgaa    4320
aatttcgaaa ataaacttga agaaataatt gcagaaaacg ctgtcggaaa ttatacggag    4380
tgtataactg cggctaagtt ggcaattgaa aagtgtggtg cgaaaagtgt attgctgtcc    4440
tttgaaccaa tgaatgattt gatgagccaa aaaaatgtaa tcaatattgt tgatgataat    4500
attaagaagt accacatgga atatacctaa tagatttcga gttgcagcga ggcggcaagt    4560
gaacgaatcc ccaggagcat agataactat gtgactgggg tgagtgaaag cagccaacaa    4620
agcagcagct tgaaagatga agggtataaa agagtatgac agcagtgctg ccatactttc    4680
taatattatc ttgaggagta aaacaggtat gacttcatat gttgataaac aagaaattac    4740
agcaagctca gaaattgatg atttgatttt ttcgagcgat ccattagtgt ggtcttacga    4800
cgagcaggaa aaaatcagaa agaaacttgt gcttgatgca tttcgtaatc attataaaca    4860
ttgtcgagaa tatcgtcact actgtcaggc acacaaagta gatgacaata ttacggaaat    4920
tgatgacata cctgtattcc caacatcggt ttttaagttt actcgcttat taacttctca    4980
ggaaaacgag attgaaagtt ggtttaccag tagcggcacg aatggtttaa aaagtcaggt    5040
ggcgcgtgac agattaagta ttgagagact cttaggctct gtgagttatg gcatgaaata    5100
tgttggtagt tggtttgatc atcaaataga attagtcaat ttgggaccag atagatttaa    5160
tgctcataat atttggttta aatatgttat gagtttggtg gaattgttat atcctacgac    5220
atttaccgta acagaagaac gaatagattt tgttaaaaca ttgaatagtc ttgaacgaat    5280
aaaaaatcaa gggaaagatc tttgtcttat tggttcgcca tactttattt atttactctg    5340
ccattatatg aaagataaaa aaatctcatt ttctggagat aaaagccttt atatcataac    5400
cggaggcggc tggaaaagtt acgaaaaaga atctctgaaa cgtgatgatt tcaatcatct    5460
tttatttgat actttcaatc tcagtgatat tagtcagatc cgagatatat ttaatcaagt    5520
tgaactcaac acttgtttct ttgaggatga aatgcagcgt aaacatgttc cgccgtgggt    5580
atatgcgcga gcgcttgatc ctgaaacgtt gaaacctgta cctgatggaa cgccggggtt    5640
gatgagttat atggatgcgt cagcaaccag ttatccagca tttattgtta ccgatgatgt    5700
cgggataatt agcagagaat atggtaagta tcccggcgtg ctcgttgaaa ttttacgtcg    5760
cgtcaatacg aggacgcaga aagggtgtgc tttaagctta accgaagcgt ttgatagttg    5820
atgcggccgc caccgcggtg gagctc                                         5846
```

<210> SEQ ID NO 402
<211> LENGTH: 88
<212> TYPE: DNA
<213> ORGANISM: Artificial sequence
<220> FEATURE:
<223> OTHER INFORMATION: Brucella phage Iz1 sequenced fragment
<220> FEATURE:
<221> NAME/KEY: misc_feature
<222> LOCATION: (41)..(41)
<223> OTHER INFORMATION: n is a, c, g, or t

<400> SEQUENCE: 402

```
aaaatggaga gttgaaatga gtttcgaaat aagtcggcga ncccattgat ggactagaac    60
aatatggtcc agggaggccc cccaaata                                       88
```

<210> SEQ ID NO 403
<211> LENGTH: 13

```
<212> TYPE: DNA
<213> ORGANISM: Artificial sequence
<220> FEATURE:
<223> OTHER INFORMATION: Brucella phage Iz1 sequenced fragment
<220> FEATURE:
<221> NAME/KEY: misc_feature
<222> LOCATION: (7)..(7)
<223> OTHER INFORMATION: n is a, c, g, or t

<400> SEQUENCE: 403
aaatagngga gtt                                                          13

<210> SEQ ID NO 404
<211> LENGTH: 13
<212> TYPE: DNA
<213> ORGANISM: Artificial sequence
<220> FEATURE:
<223> OTHER INFORMATION: Brucella phage Iz1 sequenced fragment

<400> SEQUENCE: 404
aaaatggaga gtt                                                          13

<210> SEQ ID NO 405
<211> LENGTH: 19
<212> TYPE: DNA
<213> ORGANISM: Artificial sequence
<220> FEATURE:
<223> OTHER INFORMATION: Brucella phage Iz1 sequenced fragment

<400> SEQUENCE: 405
aaaataggag agttgaaat                                                    19

<210> SEQ ID NO 406
<211> LENGTH: 20
<212> TYPE: DNA
<213> ORGANISM: Artificial sequence
<220> FEATURE:
<223> OTHER INFORMATION: Brucella phage Iz1 sequenced fragment

<400> SEQUENCE: 406
aaaatggaga gttgaaatga                                                   20

<210> SEQ ID NO 407
<211> LENGTH: 26
<212> TYPE: DNA
<213> ORGANISM: Artificial sequence
<220> FEATURE:
<223> OTHER INFORMATION: Brucella phage Iz1 sequenced fragment

<400> SEQUENCE: 407
aaaatggaga gttgaaatga gtttcg                                            26

<210> SEQ ID NO 408
<211> LENGTH: 32
<212> TYPE: DNA
<213> ORGANISM: Artificial sequence
<220> FEATURE:
<223> OTHER INFORMATION: Brucella phage Iz1 sequenced fragment

<400> SEQUENCE: 408
aaaataggag agttgaaatg agttcgaata ag                                     32

<210> SEQ ID NO 409
<211> LENGTH: 41
<212> TYPE: DNA
<213> ORGANISM: Artificial sequence
<220> FEATURE:
<223> OTHER INFORMATION: Brucella phage Iz1 sequenced fragment
```

<400> SEQUENCE: 409
aaaataggag gagttgaaat agagttcgta aataagtacg g         41

<210> SEQ ID NO 410
<211> LENGTH: 65
<212> TYPE: DNA
<213> ORGANISM: Artificial sequence
<220> FEATURE:
<223> OTHER INFORMATION: Brucella phage Iz1 sequenced fragment

<400> SEQUENCE: 410
aaaatggaga gttgaaatga gtttcgaaat aagtcggcga ccccttgatg gactagaaca    60
atatg                                                                65

<210> SEQ ID NO 411
<211> LENGTH: 85
<212> TYPE: DNA
<213> ORGANISM: Artificial sequence
<220> FEATURE:
<223> OTHER INFORMATION: Brucella phage Iz1 sequenced fragment

<400> SEQUENCE: 411
aaaatggaga gttgaaatga gtttcgaaat aagtcggcga ccccttgatg gactagaaca    60
atatggtcca ggaggccccc caata                                          85

<210> SEQ ID NO 412
<211> LENGTH: 52
<212> TYPE: DNA
<213> ORGANISM: Artificial sequence
<220> FEATURE:
<223> OTHER INFORMATION: Brucella phage Iz1 sequenced fragment

<400> SEQUENCE: 412
aaaatggaga gttgaaatga gtttcgaaat aagtcggcga ccccttgatg ga            52

<210> SEQ ID NO 413
<211> LENGTH: 87
<212> TYPE: DNA
<213> ORGANISM: Artificial sequence
<220> FEATURE:
<223> OTHER INFORMATION: Brucella phage Iz1 sequenced fragment

<400> SEQUENCE: 413
aaaatggaga gttgaaatga gtttcgaaat aagtcggcga cccattgatg gactagaaca    60
atatggtcca gggaggcccc ccaaata                                        87

<210> SEQ ID NO 414
<211> LENGTH: 87
<212> TYPE: DNA
<213> ORGANISM: Artificial sequence
<220> FEATURE:
<223> OTHER INFORMATION: Brucella phage Iz1 sequenced fragment

<400> SEQUENCE: 414
aaaatggaga gttgaaatga gtttcgaaat aaagtcggcg acccattgat ggactagaac    60
aatatggtcc agggaggccc ccaaata                                        87

<210> SEQ ID NO 415
<211> LENGTH: 87
<212> TYPE: DNA
<213> ORGANISM: Artificial sequence
<220> FEATURE:
<223> OTHER INFORMATION: Brucella phage Iz1 sequenced fragment

```
<400> SEQUENCE: 415
aaaatggaga gttgaaatga gtttcgaaat aagtcggcga cccattgatg gactagaaca    60
atatggtcca gggaggcccc ccaaata                                        87

<210> SEQ ID NO 416
<211> LENGTH: 87
<212> TYPE: DNA
<213> ORGANISM: Artificial sequence
<220> FEATURE:
<223> OTHER INFORMATION: Brucella phage Iz1 sequenced fragment

<400> SEQUENCE: 416
aaaatggaga gttgaaatga gtttcgaaat aagtcggcga cccattgatg gactagaaca    60
atatggtcca gggaggcccc ccaaata                                        87

<210> SEQ ID NO 417
<211> LENGTH: 86
<212> TYPE: DNA
<213> ORGANISM: Artificial sequence
<220> FEATURE:
<223> OTHER INFORMATION: Brucella phage Iz1 sequenced fragment

<400> SEQUENCE: 417
aaatggagag ttgaaatgag tttcgaaata agtcggcgac cccttgatgg actagaacaa    60
tatggtccag ggaggccccc caaata                                         86

<210> SEQ ID NO 418
<211> LENGTH: 88
<212> TYPE: DNA
<213> ORGANISM: Artificial sequence
<220> FEATURE:
<223> OTHER INFORMATION: Brucella phage Iz1 sequenced fragment

<400> SEQUENCE: 418
aaaataggag agttgaaatg agtttcgaaa taagtcggcg accccttgat ggactagaac    60
aatatggtcc agggaggccc cccaaata                                       88

<210> SEQ ID NO 419
<211> LENGTH: 86
<212> TYPE: DNA
<213> ORGANISM: Artificial sequence
<220> FEATURE:
<223> OTHER INFORMATION: Brucella phage Iz1 sequenced fragment

<400> SEQUENCE: 419
aaatggagag ttgaaatgag tttcgaaata agtcggcgac ccattgatgg actagaacaa    60
tatggtccag ggaggccccc caaata                                         86

<210> SEQ ID NO 420
<211> LENGTH: 80
<212> TYPE: DNA
<213> ORGANISM: Artificial sequence
<220> FEATURE:
<223> OTHER INFORMATION: Brucella phage Iz1 sequenced fragment

<400> SEQUENCE: 420
agagttgaaa tgagtttcga ataagtcggc gaccccttg atggactaga acaatatggt     60
ccagggaggc ccccaaata                                                 80

<210> SEQ ID NO 421
<211> LENGTH: 78
```

-continued

```
<212> TYPE: DNA
<213> ORGANISM: Artificial sequence
<220> FEATURE:
<223> OTHER INFORMATION: Brucella phage Iz1 sequenced fragment

<400> SEQUENCE: 421
agttgaaatg agtttcgaaa taagtcggcg acccattgat ggactagaac aatatggtcc    60
agggaggccc cccaaata                                                  78

<210> SEQ ID NO 422
<211> LENGTH: 65
<212> TYPE: DNA
<213> ORGANISM: Artificial sequence
<220> FEATURE:
<223> OTHER INFORMATION: Brucella phage Iz1 sequenced fragment

<400> SEQUENCE: 422
tttcgaaata agtcggcgac cccttgatgg actagaacaa tatggtccag ggaggccccc    60
aaata                                                                65

<210> SEQ ID NO 423
<211> LENGTH: 61
<212> TYPE: DNA
<213> ORGANISM: Artificial sequence
<220> FEATURE:
<223> OTHER INFORMATION: Brucella phage Iz1 sequenced fragment

<400> SEQUENCE: 423
aaataagtcg gcgacccatt gatggactag aacaatatgg tccagggagg cccccaaat    60 a                                                                    61

<210> SEQ ID NO 424
<211> LENGTH: 56
<212> TYPE: DNA
<213> ORGANISM: Artificial sequence
<220> FEATURE:
<223> OTHER INFORMATION: Brucella phage Iz1 sequenced fragment

<400> SEQUENCE: 424
agtcggcgac cccttgatgg actagaacaa tatggtccag ggaggccccc caaata        56

<210> SEQ ID NO 425
<211> LENGTH: 49
<212> TYPE: DNA
<213> ORGANISM: Artificial sequence
<220> FEATURE:
<223> OTHER INFORMATION: Brucella phage Iz1 sequenced fragment

<400> SEQUENCE: 425
acccattgat ggactagaac aatatggtcc agggacggcc ccccaaata                49

<210> SEQ ID NO 426
<211> LENGTH: 41
<212> TYPE: DNA
<213> ORGANISM: Artificial sequence
<220> FEATURE:
<223> OTHER INFORMATION: Brucella phage Iz1 sequenced fragment

<400> SEQUENCE: 426
gatggactag aacaatatgg tccagggagg cccccaaat a                         41

<210> SEQ ID NO 427
<211> LENGTH: 35
<212> TYPE: DNA
<213> ORGANISM: Artificial sequence
```

```
<220> FEATURE:
<223> OTHER INFORMATION: Brucella phage Iz1 sequenced fragment

<400> SEQUENCE: 427
tagaacaata tggtccaggg aggcccccca aacta                                       35
```